(12) United States Patent
Chandran

(10) Patent No.: US 8,173,840 B2
(45) Date of Patent: May 8, 2012

(54) COMPOUNDS WITH HIGH THERAPEUTIC INDEX

(75) Inventor: V. Ravi Chandran, Allen, TX (US)

(73) Assignee: Signature R&D Holdings, LLC, Allen, TX (US)

(*) Notice: Subject to any disclaimer, the term of this patent is extended or adjusted under 35 U.S.C. 154(b) by 455 days.

(21) Appl. No.: 11/343,557

(22) Filed: Jan. 30, 2006

(65) Prior Publication Data

US 2006/0241017 A1    Oct. 26, 2006

Related U.S. Application Data

(63) Continuation-in-part of application No. PCT/US2004/024901, filed on Jul. 29, 2004.

(60) Provisional application No. 60/491,331, filed on Jul. 29, 2003.

(51) Int. Cl.
*C07K 229/00* (2006.01)

(52) U.S. Cl. .......................... 562/567; 562/444; 514/506

(58) Field of Classification Search .................. 562/567, 562/553, 444; 514/506
See application file for complete search history.

(56) References Cited

U.S. PATENT DOCUMENTS

| | | | | | |
|---|---|---|---|---|---|
| 3,983,099 | A | * | 9/1976 | Niswender | 560/39 |
| 4,091,087 | A | * | 5/1978 | Barrett et al. | 436/505 |
| 4,184,037 | A | * | 1/1980 | Wilkinson | 536/6.1 |
| 4,601,979 | A | | 7/1986 | Andresen et al. | |
| 4,650,803 | A | | 3/1987 | Stella | |
| 4,692,522 | A | | 9/1987 | Parsons et al. | |
| 4,816,484 | A | * | 3/1989 | Toyoshima et al. | 514/563 |
| 5,411,947 | A | | 5/1995 | Hostetler et al. | |
| 5,432,183 | A | | 7/1995 | Schulte | |
| 5,543,414 | A | | 8/1996 | Nestor et al. | |
| 5,800,804 | A | | 9/1998 | Laney | |
| 5,804,595 | A | | 9/1998 | Portoghese et al. | |
| 5,972,379 | A | * | 10/1999 | Guo et al. | 424/450 |
| 6,083,953 | A | | 7/2000 | Nestor et al. | |
| 6,686,336 | B2 | * | 2/2004 | Nagasawa | 514/19 |
| 6,706,892 | B1 | | 3/2004 | Ezrin et al. | |
| 7,420,002 | B2 | * | 9/2008 | Gallop et al. | 514/564 |
| 2002/0099013 | A1 | | 7/2002 | Piccariello et al. | |
| 2003/0087803 | A1 | | 5/2003 | Yatvin et al. | |
| 2006/0287244 | A1 | | 12/2006 | Chandran | |

FOREIGN PATENT DOCUMENTS

| | | |
|---|---|---|
| EP | 0 360 258 | 3/1990 |
| WO | WO 93/25703 | 12/1993 |
| WO | WO 93/25704 | 12/1993 |
| WO | WO 03/084550 | 10/2003 |
| WO | WO 2005/046575 | 5/2005 |

OTHER PUBLICATIONS

Search report for PCT/US04/24901, issued Aug. 1, 2007.*
Fisher, George H. [Advances in Experimental Medicine and Biology (1986), 198A (Kinins 4, Pt. A), 405-10].*
Chun Yang et al., "Chemical Stability, Enzymatic Hydrolysis, and Nasal Uptake of Amino Acid Este Prodrugs of Acyclovir", Journal of Pharmaceutical Sciences, vol. 90 , No. 5, pp. 617-624 (2001).
Jung, Yun Jin, et al. Synthesis and in vitro/in vivo evaluation of 5-aminosalicyl-glycine as a colon-specific prodrug of 5-aminosalicylic acid. Journal of Pharmaceutical Sciences, 2001 89(5), 594-602.
Hutchinson, I. et al., "Antitumor Benzothiazoles. 16. Synthesis and Pharmaceutical Properties of Antitumor 2-(4-Aminophenyl)benzothiazole Amino Acid Prodrugs", Journal of Medicinal Chemistry, 2002, vol. 45, No. 3, p. 744-747.
Han, Hyo-kyung et al., "5'-Amino Acid Esters of Antiviral Nucleosides, Acyclovir, and AZT Are Absorbed by the Intestinal PEPT1 Peptide Transporter", Pharmaceutical Research, 1998, vol. 15, No. 8, p. 1154-1159.
Han, Hyo-kyung et al., "Cellular Uptake Mechanism of Amino Acid Ester Prodrugs in Caco-2/hPEPT1 Cells Overexpressing a Human Peptide Transporter", Pharmaceutical Research, 1998, vol. 15, No. 9, p. 1382-1386.
Friedrichsen, G. M. et al., "Synthesis of analogs of L-valacyclovir and determination of their substrate activity for the oligopeptide transporter in Caco-2 cells", European Journal of Pharmaceutical Sciences, 2002, vol. 16, p. 1-13.
Fleisher, D. et al., "Improved oral drug delivery: solubility limitations overcome by the use of prodrugs", Advanced Drug Delivery Reviews, 1996, vol. 19, p. 115-130.
English language translation of Chinese Office Action dated Mar. 23, 2010 for Chinese Application No. 200480028222.9.

* cited by examiner

*Primary Examiner* — David Lukton
(74) *Attorney, Agent, or Firm* — Scully, Scott, Murphy & Presser, P.C.

(57) ABSTRACT

The present invention is directed to novel therapeutic compounds comprised of an amino acid bonded to a medicament or drug having a hydroxy, amino, carboxy or acylating derivative thereon. These high therapeutic index derivatives have the same utility as the drug from which they are made, and they have enhanced pharmacological and pharmaceutical properties. In fact, the novel drug derivatives of the present invention enhance at least one therapeutic quality, as defined herein. The present invention is also directed to pharmaceutical compositions containing same.

3 Claims, 10 Drawing Sheets

(1 of 10 Drawing Sheet(s) Filed in Color)

COMPOUNDS WITH HIGH THERAPEUTIC INDEX

RELATED APPLICATION

This is a continuation-in-part of PCT Application No. PCT/US04/24901 filed Jul. 29, 2004 which claims benefit of provisional application No. 60/491,331 filed on Jul. 29, 2003.

SCOPE OF THE INVENTION

The invention relates to amino acid derivatives of pharmaceutical compounds, methods of treating particular ailments, which are ameliorated by the administration of these drugs and pharmaceutical compositions containing these drugs. The current invention involves improving many physicochemical, biopharmaceutical, and clinical efficacy of various drugs using amino acids as covalently bonded carriers for these drugs.

BACKGROUND OF THE INVENTION

The development of chemical compounds for the treatment of disorders, maladies and diseases has become increasingly difficult and costly. The probability of success for such development is often discouragingly low. Further, the time for development can approach or exceed ten years, leaving large numbers of patients without remedy for an extended period of time.

Even in cases in which effective pharmaceutical compounds have been developed, there are often disadvantages associated with their administration. These disadvantages can include aesthetic, and pharmacokinetic barriers affecting the effectiveness of some existing pharmaceutical compounds, For example, unpleasant taste or smell of a pharmaceutical compound or composition can be a significant barrier to patient compliance with respect to the administration regimen. The undesirable solubility characteristics of a pharmaceutical compound can lead to difficulty in formulation of a homogeneous composition. Other disadvantages associated with known pharmaceutical compounds include: poor absorption of orally administered formulations; poor bioavailability of the pharmaceutical compounds in oral and other non-intravenous formulations; lack of dose proportionality; low stability of pharmaceutical compounds in vitro and in vivo; poor penetration of the blood/brain barrier; excessive first-pass metabolism of pharmaceutical compounds as they pass through the liver; excessive enterohepatic recirculation; low absorption rates from various sites, including skin, rectal, oral and buccal administration; ineffective compound release at the site of action; excessive irritation, for example, gastrointestinal irritability and/or ulceration; painful injection of parenterally administered pharmaceutical compounds and compositions; excessively high dosages required for some pharmaceutical compounds and compositions, and other undesirable characteristics. Some pharmaceutical compounds are processed by the body to produce toxic by-products with harmful effects.

The art is continually seeking new chemical compounds for the treatment of a wide variety of disorders, with improved properties to overcome the disadvantages of known pharmaceutical compounds mentioned above.

The present invention has overcome many problems associated with currently marketed drugs by making amino acid derivatives. The concept of such derivative chemistry is well known, and there are a number of examples of such derivatives enumerated in the literature and there and even a few such derivatives are available in the market, including such diverse groups as statin drugs, ACE inhibitors, antiviral drugs such as Acyclovir and the like.

SUMMARY OF THE PRESENT INVENTION

The present invention, however, uses amino acids as the moiety to make such derivatives. The inventor has found that the novel drug derivatives of the present invention have a number of advantages. For example, when the amino acid derivatives of the present invention are administered by a number of routes such as oral, IV, rectal or other such methods, the inventor has found that generally these derivatives are not broken down in vivo; rather the amino acid derivatives themselves possess the therapeutic activity.

In many cases, the inventor found that the current amino acid derivatives do not dissociate into the drug from which the amino acid derivative is derived, since there appears to be no active drug in the systemic circulation. Instead, what was found in the systemic circulation was the amino acid derivative is active and less toxic than the corresponding drug and possesses high therapeutic index. A significant advantage of the amino acid derivative of the present invention is that it is non-toxic, and hence either assimilated into the body or safely excreted. This is quite unlike the characteristics exhibited by a number of other drug derivatives available in the market, where the promoiety itself is toxic, as is the case with statin drugs, Enalapril, Benazapril and the like group of ACE inhibitors, and a number of antibiotics such as pivoxil, Axetil, Cilexetil and the like groups, which are highly toxic, thereby reducing the therapeutic index of the active drug.

On the other hand, the amino acid derivatives of the present invention also impart a number of advantages as shown herein below.

The present invention is directed to pharmaceutically active drugs, having an amino acid covalently bonded thereto to form said amino acid derivative, which is administered in this form to the subject, such as a mammal.

The amino acid is an ideal model to be used as a derivative, because it is capable of forming various types of linkages between itself and the drug. By definition, an amino acid has at least two functionalities thereon, an amino group ($NH_2$) and a carboxy group (COOH). For example, the α-amino acids have the well known structure

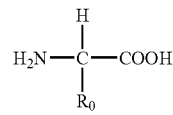

wherever $R_0$ is the side group or chain of the amino acid. The

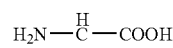

as defined herein, is the main chain of the amino acid. Thus, for example, in addition to the amino group and the carboxyl group on the main chain, the side chain may have other functional groups thereon such as SH or OH or $NH_2$ and the like. The functional groups on the amino acid moiety permit the covalent linkage to occur between the amino acid and the drug.

As defined herein, the drug or medicament useful in the present invention contains functional groups thereon that permit the drug to react with and form a covalent bond with the amino acid. Examples of functional groups present on the drugs include $NH_2$, OH, COOH or acylating derivatives (acid derivatives) thereof, such as esters, amides, anhydrides and the like.

The mode of attachment between the pharmaceutical compound and the amino acid can be via:

1) An ester bond (—CO—O—) arising from condensation of a carboxylic acid and an alcohol or phenolic hydroxyl group, or through transesterification, for example:
   a) Where the pharmaceutical compound has an aliphatic or aromatic hydroxyl group, an ester bond can be formed with the backbone carboxylic acid group of the amino group under esterification conditions; or
   b) Where the pharmaceutical compound has an aliphatic or aromatic hydroxyl group and the amino acid has a side chain carboxylic acid group, an ester bond can be formed therebetween under esterification conditions; or
   c) Where the pharmaceutical compound has a carboxylic acid group and the amino acid has a side chain aliphatic or aromatic hydroxyl group, an ester bond can be formed therebetween under esterification condition; or
   d) Where the pharmaceutical compound has an ester group with substituted or unsubstituted acyloxy (e.g., carbonylalkoxy or arylalkoxycarbonyl, or aryloxycarbonyl) substituent (compound-O—CO-substituent) and the amino acid has a backbone carboxylic acid group, an ester bond can be formed therebetween through transesterification; or
   e) Where the pharmaceutical compound has an ester group with a substituted or unsubstituted acyloxy (e.g., alkoxycarbonyl or arylalkoxycarbonyl, or aryloxy carbonyl) substituent (compound-O—CO-substituent) and the amino acid has a side chain carboxylic acid group, an ester bond can be formed therebetween through transesterification; or
   f) Where the pharmaceutical compound has an ester group with a substituted or unsubstituted alkoxycarbonyl or arylalkoxycarbonyl or aryloxy carbonyl substituent (compound-CO—O-Substituent) and the amino acid has a side chain aliphatic or aromatic hydroxyl group, an ester bond can form therebetween though transesterification; or
   g) The alcohol and carboxylic acid moieties may be on the same molecule such they can form an internal ester. For example, certain compounds like Gabapentin can form an internal ester under ester forming conditions, and is also included within the scope of the present invention.

2) An amide bond (—CO—NH—) arising from condensation of a carboxylic acid and an amine, for example:
   a) Where the pharmaceutical compound has an amino group and the amino acid has a backbone carboxylic acid group, an amide can be formed under amide forming conditions; or
   b) Where the pharmaceutical compound has an amino group and the amino acid has a side chain carboxylic acid group, an amide bond can form therebetween under amide forming conditions; or
   c) Where the pharmaceutical compound has a carboxylic acid group and the amino acid has a backbone amino group, an amide bond can form therebetween under amide forming conditions; or
   d) Where the pharmaceutical compound has a carboxylic acid group and the amino acid has a side chain amino group, an amide bond can be formed therebetween under amide forming conditions.

Thus, the present invention is directed to the amino acid derivatives thus formed. As shown hereinbelow, the amino acid derivatives described herein have advantages not realized relative to the drug without the amino acid attached thereto. For example, it can improve bioavailability, efficacy, be less toxic, exhibit greater solubility in water and/or improve the ability of the drug to pass into the cell membrane or through blood brain barrier, exhibit less side effects, such as gastrointestinal irritability, enhanced therapeutic index and the like.

Thus, the present invention is directed to a method of improving the therapeutic quality of a drug wherein the improvement in the therapeutic quality is selected from the group consisting of improved efficacy, enhanced therapeutic index, increased solubility in the mammal's internal fluid, improved passage through the cell membrane, improved passage through the blood brain barrier, decreased side effects, such as significantly decreased irritation and/or ulcerations, less toxicity, enhanced absorption ratio and the like relative to the corresponding drug administered to the patient in the derivatized form, said method comprising reacting the drug with an amino acid to form a covalent bond therebetween and administering the product thereof (hereinafter "derivative") to a patient. The amino acid derivatives of the present invention have at least one improved quality. In fact, they exhibit preferably at least one of the improved qualities cited hereinabove, and more preferably, at least two of the qualities described herein. Other advantages of the derivative include the wide availability of the amino acids and the ease in which the reactions take place. The reaction to form the amide and esters are generally efficient and yields are very high, presumably above about 60% and more preferably above about 75% and most preferably above about 90%.

BRIEF DESCRIPTION OF THE DRAWINGS

The file of this patent application contains at least one drawings executed in color. Copies of this patent application with color drawing(s) will be provided by the United States Patent and Trademark Office upon request of the necessary fee.

DETAILED DESCRIPTION OF THE PRESENT INVENTION

Figure 1:
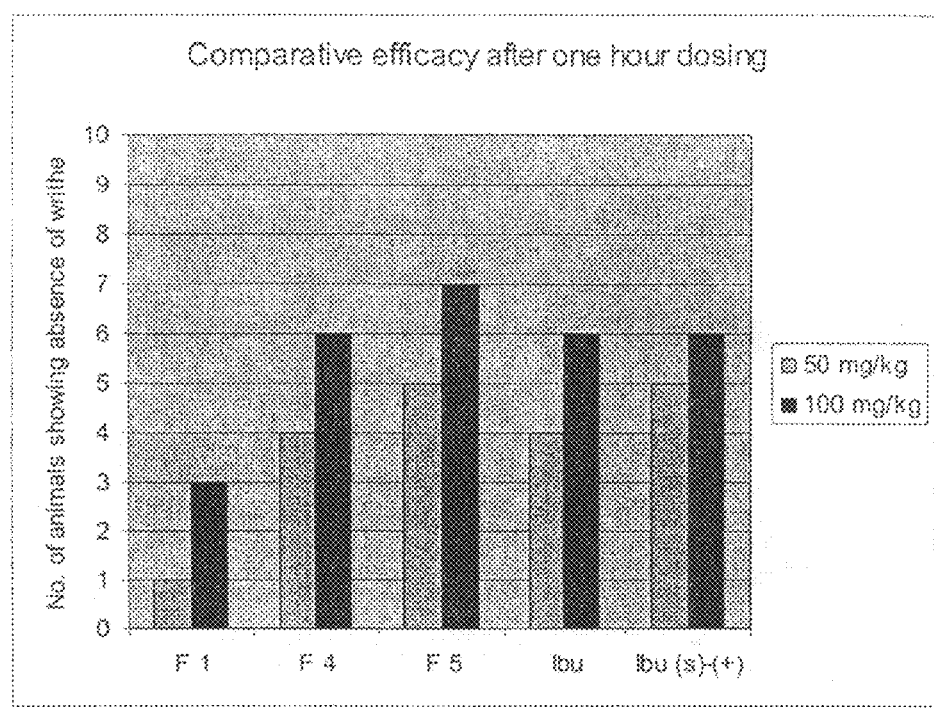
FIG. 1 graphically compares the efficacy of L-serine ester of (±) Ibuprofen (F1), L-threonine ester (±) Ibuprofen (F2) and L-hydroxyproline ester of (±) Ibuprofen (F3), (±) Ibuprofen (i.e., the racemic mixture) and Ibuprofen (S)(+), after one hour dosing, based on the antagonizing property of Acetylcholine induced writhes in Albino mice.

As used here, the terms "drug", "medicament", and "pharmaceutical" and "active agent" are being used interchangeably and refer to the active compound that is administered to the patient without attachment of the amino acid thereto. Moreover, as used herein, the drug contains a functional group thereon capable of reacting with the amino acid, such as $NH_2$, OH, COOH or acylating derivatives thereof (e.g., ester, anhydride, amide, and the like) and the like. When the drug is linked to an amino acid, the term "amino acid derivative" or "derivative of the present invention" or synonym thereto is utilized.

A wide variety of therapeutically active agents can be used with the present invention. Examples include antacids; anti-inflammatory substances; coronary dilators; cerebaldilators; peripheral vasodilators; anti-invectives; psychotropics; anti-manics; stimulants; anti-histamines; laxatives; decongestants; vitamins; gastrointestinal sedatives; anti-diarreal preparations; anti-anginal drugs; vasodilators; anti-arrhythmics; anti-hypertensive drugs; analgesics; anti-pyretics; hypnotics; sedatives; anti-emetics; anti-nauseants; anti-convulsants; neuromuscular drugs; hyper- and hypoglycemic agents; thyroid and anti-thyroid preparations; diuretics, anti-spasmodics; uterine relaxants; mineral and nutritional additives; anti-obesity drugs; anabolic drugs; erythropoietic drugs; anti-asthmatics; bronchodilators; expectorants; cough suppressants; mucolytics anti-uricemic drugs; drugs useful for inhibiting organ transplant rejection; drugs useful for treatment rheumatoid arthritis; antiviral agents; antibiotics; drugs useful for treating asthma; drugs useful for treating urinary spasms or infections; calcium channel blockers; drugs useful for treating malaria; drugs useful for treating skin diseases; anti-hyperlipidemics; drugs useful for treating psychological diseases, such as, attention deficient disorders, schizophrenia, and other psychoses, and the like; drugs useful for treating tuberculosis; antidiabetics; anti cancer drugs; drugs useful for treating gastric hyperacidity; drugs useful for treating eye diseases; and the like. However, the drug utilized must be capable of bonding to the amino acid. Consquently, it must have a hydroxy group, an amino group or a carboxy group or an acylating derivative thereof. By acylating derivative it is meant that the drug contains a carboxy group or a carboxylic acid derivative thereof, which has an acyl group thereon, and which can be hydrolyzed to the acid or salt thereof, such as an amide, ester, anhydride, and the like.

The amino acids useful for reacting with the drugs are those containing the free amino and/or carboxylic acid groups present in all conventional amino acids. The preferred amino acids are described in more detail hereinbelow. They are preferably α-amino acids. In addition, they are preferably L-amino acids and more preferably L-α-amino acids as described hereinbelow. Of those, some preferred embodiments include those amino acids having relatively high solubility in aqueous media, for example, in deionized water at unbuffered aqueous solution at 25° C., of at least 100 g/L, and more preferably, at least 250 g/L, and even more preferably at least 500 g/L. For example, glycine and proline have solubilities in deionized water at 25° C. of approximately 250 g/L and 1620 g/L, respectively, other preferred amino acids contain basic amino side chains, such as lysine. For example, lysine has solubility in deionized water at 25° C. of approximately 700 g/L. Other preferred amino acids are those containing hydroxyl side chains, such as hydroxyproline, serine, and threonine. For example, threonine, hydroxyproline and serine have solubilities in deionized water at 25° C. of approximately 100 g/L, 369 g/L and 420 g/L, respectively. Other preferred embodiments include those amino acids with relatively low solubility in aqueous media, for example, in deionized water at 25° C. of at most 10 g/L, or for example, at most 2 g/L, or for example at most 0.6 g/L. For example, the solubility of tyrosine in deionized water at 25° C. is approximately 0.5 g/L. Such derivatives could be used to produce formulations with extended release characteristics, due to the limited solubility of the derivatives.

Additional preferred amino acids are those containing carboxylic acid side chains, such as glutamic acid and aspartic acid. However, non-essential amino acids, and the non-naturally occurring amino acids can also be bonded to the drug, in accordance with the present invention.

The following reaction schemes depict the reactions discussed hereinabove with respect to the of hydroxyl, carboxyl and amine containing drugs with various amino acids. In the schemes below, R is the drug less the functional OH, COOH or $NH_2$ group whichever is present, and $R_1$ is

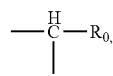

wherein $R_0$ is the side chain of the amino acid listed hereinbelow:

Reaction Scheme A: Where the hydroxyl group of the drug is reacted with the carboxyl group of an amino acid to form the ester derivative

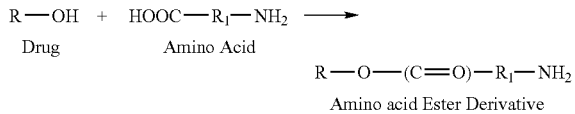

Reaction Scheme B: Where the carboxyl group of the drug is reacted with the hydroxyl group of a hydroxy amino acid wherein the hydroxy group is on the side chain to form the ester derivative.

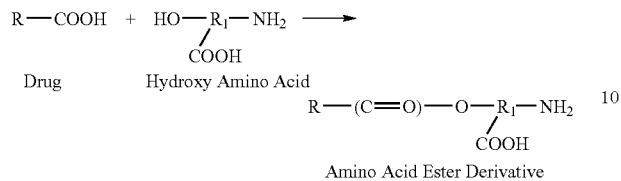

Reaction Scheme C: Where the amino group of the drug is reacted with the carboxyl group of the amino acid to from the amide derivative

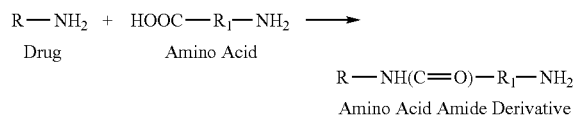

Reaction Scheme D: Where the carboxyl group of the drug is reacted with the carboxyl group of the amino acid to form the anhydride derivative.

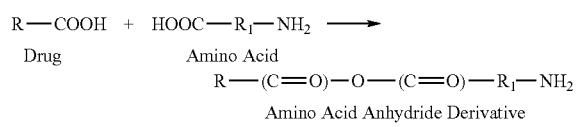

Reaction Scheme E: Where the amino group of the drug is reacted with the amino group of the amino acid to form the azo derivative derivative.

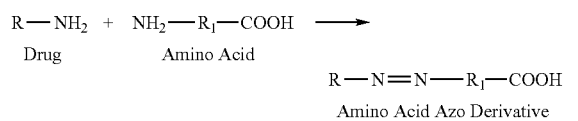

Reaction Scheme F: Where the carboxyl group of the drug is reacted with amino group of the amino acid to form the amide derivative.

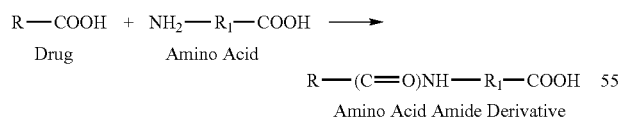

In the above schemes A-F, the preferred amino acids used are shown hereinbelow:

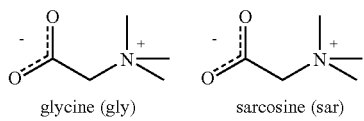

glycine (gly)   sarcosine (sar)

-continued

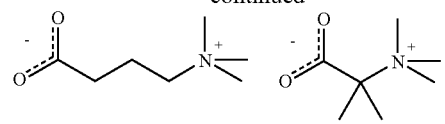

GABA   alanine (ala)

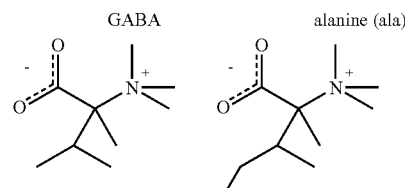

valine (val)   isoleucine (ile)

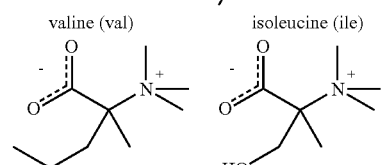

leucine (leu)   serine (ser)

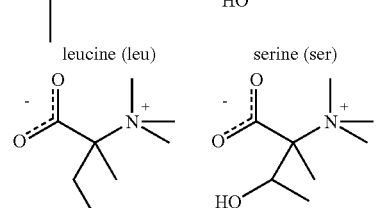

homoserine   threonine (thr)

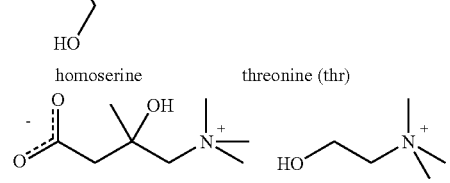

carnitine   choline

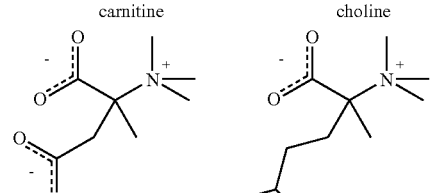

aspartate (asp)   glutamate (glu)

ornithine   lysine (lys)

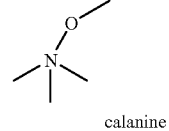

calanine

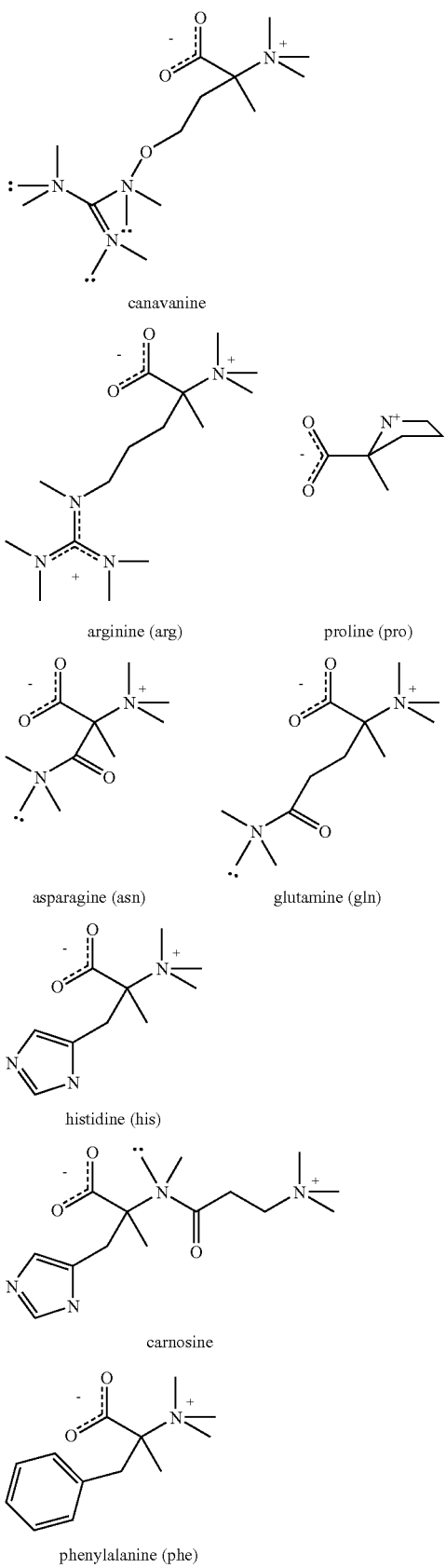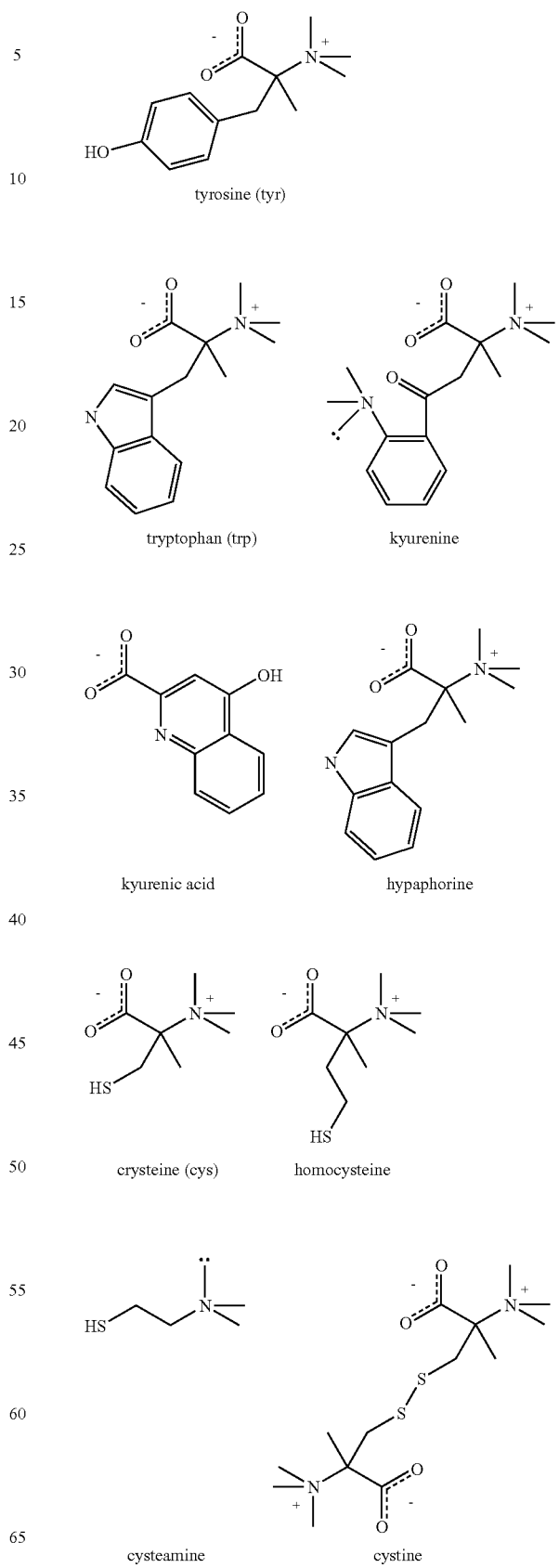

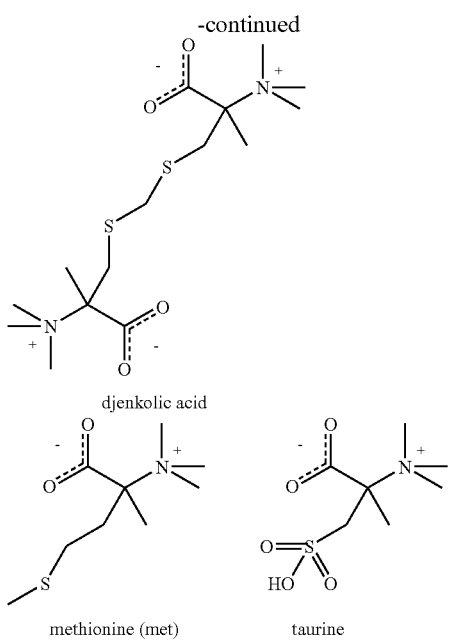

As used herein the term "amino acid" refers to an organic compound having therein a carboxyl group (COOH) and an amino group ($NH_2$) or salts thereof. In solution, at neutral pH, these two terminal groups, ionize to form a double ionized, through overall neutral entity identified as zwitterions. The amine donates an electron to the carboxyl group and the ionic ends are stabilized in aqueous solution by polar water molecules.

As used herein, "AA" refers to an amino acid residue, i.e., the amino acid without either a hydrogen atom or hydroxy group or amino group, depending on the linkage to the drug. For example, "OAA" refers to the amino acid forming an ester linkage with the oxygen atom of the drug. Thus, in this case, the amino acid is without a hydroxy group. However, the designation includes the ester being formed from the bond between the carboxy group of the amino acid with the hydroxy group of the drug. However, if the amino acid has a carboxy group on the side chain, such as glutamic acid or aspartic acid, this also refers to the ester being formed from the carboxy group on the side chain and the hydroxy group of the drug. When aspartic or glutamic acid is the amino acid, the term OAA refers to an ester linkage between the drug and the amino acid from the carboxy group on the main chain or on the side chain. Alternatively, OAA refers to the amino acid forming an ester linkage from the oxygen atom of the side chain of a hydroxy containing amino acid, and the carboxylic acid functionality of the drug. However, the definition should be made clear by the context. For example, the nomenclature, especially in the claims, is accompanied by language reciting that the bond is being formed from a group, such as amino or OH group of the amino acid. Thus, for example, if the term is OAA, and if it is meant to refer to a ester bond between the OH group on the side chain and the acyl group of the drug, the term would be accompanied by a statement that the amino acid is without the hydroxy group of the side chain and that the ester is formed via the hydroxy on the side chain. Alternatively, if the OAA refers to the ester linkage between the carboxy group of the amino acid and the oxygen atom of the drug, the term should be accompanied by a statement that the amino acid is without the hydroxy group and that the ester linkage is through the acyl group of the amino acid. Further, if the structure of the drug to which the amino acid is bonded is identified or provided, the meaning will be apparent to the skilled artisan without explanation.

The term NHAA refers to an amino acid residue (an amino acid less an OH group on the carboxy group) bonded through its acyl group to the amino group of the drug, thereby forming an amide linkage therebetween. Further, it should be noted that if the side chain of the amino acid has a carboxy group thereon, another amide bond may occur linking the carboxy group of the side chain and the amino group of the drug. Thus, the NHAA refers to the amide linkage between a carboxy group on the amino acid and the amino group on the drug. Thus, the term NHAA refers to the amide bond formed between the carboxy group of the drug and the amino group of the amino acid, either in the main chain or on the side chain. Alternatively, it can refer to the amide linkage between the amino group of the amino acid and the carboxy group or acylating derivative of the drug. Again, the term will be accompanied by language in the claims to identify the meaning, if it is not clear from context. However, if the structure is given, the meaning will be apparent to the skilled artisan without explanation.

If there is a bond between the hydroxy group on the side chain of the amino acid, such as hydroxyproline, theonine, tyrosine, serine and the like, then the nomerclature C(O) AA will be utilized, signifying that the linkage is between the carboxy group on the drug and the OH group on the amino acid side chain.

The term

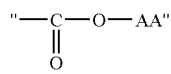

is used to denote that an acid anhydride is formed from the reaction of the carboxyl group of the drug and the carboxyl group of the amino acid, whether it be on the main chain or side chain of the amino acid, to form an carboxylic acid anhydride.

The term

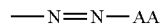

is used to denote the azo bond formed from the reaction of the amino group from the drug and the amino group of the amino acid.

It is the side groups that distinguish the amino acids from each other. Some amino acids, such as lysine, have amino groups on the side chain; other amino acids have side chains containing hydroxy groups, such as threonine, serine, hydroxyproline, and tyrosine; some amino acids have carboxy groups on the side chain, such as glutamic acid or aspartic acid. These functional groups on the side chain also can form a covalent bond with the drug, such as esters, amides, and the like. When these side groups become involved in these linkages, such as hydroxy group, the bond may be depicted as OAA, wherein AA is an amino acid residue having a side chain with a hydroxy group, but without the hydroxy group. Thus, AA by this definition, refers to the amino acid without the hydroxy side group since the hydroxy moiety took part in the reaction in forming the ester. Moreover, when an ester is formed between the hydroxy group of the amino acid and the carboxy group of the drug, the hydroxy group on the carboxy group forms a byproduct with the hydrogen of the hydroxy group, thus, the resulting product does not have the OH group on the carboxy group, but just the acyl moiety. When the bond is depicted as C(=O)—NHAA, this means that the amino acid forms as an amide bond between the carboxy group on the drug and the amino group of the amino acid. However, as written, since the NH from the amide bond comes from the amino acid, AA is the amino acid without the amino group.

The preferred amino acids are the naturally occurring amino acids. It is more preferred that the amino acids are the α-amino acids. It is also preferred that the amino acids are in the L-configuration. The preferred amino acids include the twenty essential amino acids. The preferred amino acids are Lysine (Lys), Leucine (Leu), Isoleucine (Ile), Glycine (Gly), Aspartic Acid (Asp), Glutamic Acid (Glu), Methionine (Met), Alanine (Ala), Valine (Val), Proline (Pro), Histidine (His), Tyrosine (Tyr), Serine (Ser), Norleucine (Nor), Arginine (Arg), Phenylalanine (Phe), Tryptophan (Trp), Hydroxyproline (Hyp), Homoserine (Hsr), Carnitine (Car), Ornithine (Ort), Canavanine (Cav), Asparagine (Asn), Glutamine (Gln), Carnosine (Can), Taurine (Tau), djenkolic Acid (Djk), γ-aminobutyric Acid (GABA), Cysteine (Cys) Cystine (Dcy), Sarcosine (Sar), Threonine (Thr) and the like. The even more preferred amino acids are the twenty essential amino acids, Lys, Leu, Ile, Gly, Asp, Glu, Met, Ala, Val, Pro, His, Tyr, Thr, Arg, Phe, Trp, Gln, Asn, Cys and Ser. The most preferred amino acids are those having a hydroxy group on the side chain, preferably Hyp, Thr, Ser and Tyr and most preferably L-Hyp, L-Tyr, L-Ser and L-Thr. The most preferred amino acids are L-Hyp and L-Thr, and especially L-Thr.

The derivatives are prepared from a drug having a group thereon which can react with the amino acid.

The preferred drugs that are reacted with amino acids in accordance with various schemes are as follows. The drugs and their reaction schemes stated here are not exhaustive, and are typical examples only.

| Drug | Reaction Schemes | | | | | |
|---|---|---|---|---|---|---|
| | A | B | C | D | E | F |
| Abacavir | YES | | YES | | YES | |
| Acarbose | YES | | | | | |
| Acebutolol | YES | | YES | | | |
| Adefovir | YES | | | | | |
| Albuterol | YES | | YES | | | |
| Amlodipine[1] | | | YES | | | |
| Amphotericin B | YES | YES | | YES | | YES |
| Amprenavir | YES | | YES | | YES | |
| Atenolol | YES | | YES | | YES | |
| Atorvastatin | YES | YES | | YES | | YES |
| Atropine | YES | | | | | |
| Baclofen | | YES | YES | YES | YES | YES |
| Benazeprilat | | YES | YES | YES | | YES |
| Betaxolol | YES | | YES | | | |
| Bicalutamide | YES | | YES | | | |
| Biotin | | YES | YES | YES | | YES |
| Biperiden | YES | | | | | |
| Bisoprolol | YES | | YES | | | |
| Bitolterol | YES | | YES | | | |
| Brinzolamide | | | YES | | YES | |
| Bupivacaine | | | YES | | | |
| Buprenorphine | YES | | | | | |
| Bupropion | | | YES | | | |
| Butorphanol | YES | | | | | |
| Capacitabine | | | YES | | | |
| Captopril | | YES | YES | YES | | YES |
| Carbidopa | YES | YES | YES | YES | YES | YES |
| Carnitine | YES | YES | | YES | | YES |
| Carteolol | YES | | YES | | | |
| Cefditoren | | YES | YES | YES | YES | YES |

-continued

| Drug | Reaction Schemes | | | | | |
|---|---|---|---|---|---|---|
| | A | B | C | D | E | F |
| Cerivastatin | YES | YES | | YES | | YES |
| Chloramphenicol | YES | | | | | |
| Cisapride | | | YES | | YES | |
| Clopidogrel Acid | | YES | | YES | | YES |
| Clorazepic Acid | | YES | YES | YES | | YES |
| Cycloserine | | | YES | | YES | |
| Cytarabine | YES | | YES | | YES | |
| Danazol | YES | | | | | |
| Dextroamphetamine | | YES | | YES | | |
| Diclofenac | | YES | YES | YES | | YES |
| Didanosine | YES | | YES | | | |
| Digoxin | YES | | | | | |
| Divalproex | | YES | | YES | | YES |
| Docetaxel | YES | | YES | | | |
| Dorzolamide | | | YES | | YES | |
| Dyphylline | YES | | | | | |
| Dysopyramide | | | YES | | YES | |
| Efavirenz | | YES | | | | |
| Enalaprilat | | YES | YES | YES | | YES |
| Ephedrine | YES | | YES | | | |
| Eplerenone | | YES | | YES | | YES |
| Eprosartan | | YES | | YES | | YES |
| Esmolol | YES | | YES | | | |
| Estramustine | YES | | | | | |
| Ethambutol | YES | | YES | | | |
| Ethchlorvynol | YES | | | | | |
| Ethosuximide | | | YES | | | |
| Ethotoin | | | YES | | | |
| Etidocaine | | | YES | | | |
| Etoposide | YES | | | | | |
| Ezetimibe | YES | | | | | |
| Fenofibrate | | YES | | YES | | YES |
| Fenoprofen | | YES | | YES | | YES |
| Fexofenadine | YES | YES | | YES | | YES |
| Finasteride | | | YES | | | |
| Fluoxetine | | | YES | | | |
| Fluticasone | YES | | | | | |
| Fluvastatin | YES | YES | | YES | | YES |
| Folic Acid | | YES | YES | YES | YES | YES |
| Fosinoprilat | | YES | | YES | | |
| Frovatriptan | | | YES | | YES | |
| Fulvestrant | YES | | | | | |
| Gabapentin* | | YES | YES | YES | YES | YES |
| Ganciclovir | YES | | | | | |
| Glimepiride | | | YES | | | |
| Goserelin | YES | | | | | |
| Hydroxychloroquine | YES | | | | | |
| Hydroxyzine | YES | | | | | |
| Hyoscyamine | YES | | | | | |
| Ibuprofen | | YES | | YES | | YES |
| Ibutilide | YES | | YES | | | |
| Indapamide | | | YES | | YES | |
| Indinavir | YES | | YES | | | |
| Ipratropium | YES | | | | | |
| Irinotecan | YES | | | | | |
| Isosorbide | YES | | | | | |
| Isradipine[5] | | | YES | | | |
| Ketoprofen | | YES | | YES | | YES |
| Ketorolac | | YES | | YES | | YES |
| Labetalol | YES | | YES | | | |
| Lamivudine | YES | | YES | | YES | |
| Lamivudine | YES | | YES | | YES | |
| Lansoprazole | | | YES | | | |
| Latanoprost Acid | YES | YES | | YES | | YES |
| Leuprolide | YES | | | | | |
| Levobunolol | YES | | YES | | YES | |
| Levodopa | YES | YES | YES | YES | YES | YES |
| Levorphanol | YES | | | | | |
| Liothyronine | YES | YES | YES | YES | YES | YES |
| Lisinopril | | YES | YES | YES | YES | YES |
| Lopinavir | YES | | YES | | | |
| Lorazepam | | | YES | | | |
| Lovastatin | YES | YES | | YES | | YES |
| Medroxyprogesterone | YES | | | | | |
| Mefloquine | YES | | YES | | | |
| Megestrol | YES | | | | | |

-continued

| Drug | A | B | C | D | E | F |
|---|---|---|---|---|---|---|
| Mephobarbital | | | YES | | | |
| Mepivacaine | | | YES | | | |
| Metaproterenol | YES | | YES | | | |
| Metformin | | | YES | | YES | |
| Methamphetamine | | | YES | | | |
| Methohexital | YES | | | | | |
| Methotrexate | | YES | | YES | | YES |
| Methylphenidate | | YES | YES | YES | | YES |
| Methylphenidate[6] | | | YES | | | |
| Methylprednisolone | YES | | | | | |
| Metolazone | | | YES | | YES | |
| Metoprolol | YES | | YES | | | |
| Mexiletine | | | YES | | YES | |
| Miglitol | YES | | | | | |
| Miglitol | YES | | | | | |
| Moexiprilat | | YES | YES | YES | | YES |
| Mometasone | YES | | | | | |
| Montelukast | YES | YES | | YES | | YES |
| Nadolol | YES | | YES | | | |
| Nalbuphine | YES | | | | | |
| Naproxen | | YES | | YES | | YES |
| Naratriptan | | | YES | | YES | |
| Nateglinide | | YES | YES | YES | | YES |
| Nelfinavir | YES | | YES | | | |
| Niacin | | YES | | YES | | YES |
| Nicardipine[3] | | | YES | | | |
| Nimidipine[4] | | | YES | | | |
| Nisoldipine[2] | | | YES | | | |
| Norgestimate | YES | | | | | |
| Octreotide | YES | | YES | | | |
| Ofloxacin | | YES | | YES | | YES |
| Olmesartan | | YES | | YES | | YES |
| Omeprazole | | | YES | | YES | |
| Paclitaxel | YES | | YES | | | |
| Pantothenic Acid | YES | YES | YES | YES | | YES |
| Paroxetine | | | YES | | YES | |
| Paroxetine | | | YES | | | |
| Pemoline | | | YES | | YES | |
| Penbutolol | YES | | YES | | | |
| Penicillamine | | YES | YES | YES | YES | YES |
| Pentazocine | YES | | | | | |
| Pentobarbital | | | YES | | | |
| Perindoprilat | | YES | YES | YES | | YES |
| Phenylephrine | YES | | YES | | | |
| Phenylpropanolamine | YES | | YES | | YES | |
| Pindolol | YES | | YES | | | |
| Pioglitazone | | | YES | | | |
| Pirbuterol | YES | | | | | |
| Pramipexole | | | YES | | YES | |
| Pravastatin | YES | YES | | YES | | YES |
| Propafenone | YES | | YES | | | |
| Propranolol | YES | | YES | | | |
| Pseudoephedrine | YES | | YES | | | |
| Quinacrine | | | YES | | | |
| Quinaprilat | | YES | YES | YES | | YES |
| Quinethazone | | | YES | | YES | |
| Quinidine | YES | | | | | |
| Quinine | YES | | | | | |
| Ramiprilat | | YES | YES | YES | | YES |
| Reboxetine | | | YES | | | |
| Repaglinide | | YES | YES | YES | | YES |
| Repaglinide | | YES | YES | YES | YES | YES |
| Ribavirin | YES | | YES | | YES | |
| Ritonavir | YES | | YES | | | |
| Ropivacaine | | | YES | | | |
| Rosiglitazone | | | YES | | | |
| Rosuvastatin | YES | YES | | YES | | YES |
| Salmeterol | YES | | YES | | | |
| Sertraline | | | YES | | | |
| Simavastatin | YES | YES | | YES | | YES |
| Sirolimus | YES | | | | | |
| Sotalol | YES | | YES | | | |
| Sulfa Drugs | | | YES | | YES | |
| Sulfasalazine | | | | | YES | |
| Sumitriptan | | | YES | | YES | |
| Tacrolimus | YES | | | | | |
| Tazorotene | | YES | | YES | | YES |
| Telmesartan | | YES | | YES | | YES |
| Tenofovir | YES | | | | | |
| Terbutaline | YES | | YES | | | |
| Thyroxine | | YES | YES | YES | YES | YES |
| Tiagabine | | YES | | YES | | YES |
| Timolol | YES | | YES | | | |
| Tirofiban | | YES | YES | YES | | YES |
| Tocainide | | | YES | | YES | |
| Tramadol | YES | | | | | |
| Trandolaprilat | | YES | YES | YES | | YES |
| Tranylcypromine | | | YES | | YES | |
| Treprostinil | YES | YES | | YES | | YES |
| Triamcinolone | YES | | | | | |
| Troglitazone | YES | | YES | | | |
| Unoprostone | | YES | | YES | | YES |
| Valsartan | | YES | | YES | | YES |
| Venlafaxine | YES | | | | | |
| Vidarabine | YES | | YES | | YES | |
| Warfarin | YES | | | | | |
| Zalcitabine | YES | | YES | | YES | |
| Zidovudine | YES | | YES | | | |
| Zolmitriptan | | | YES | | YES | |

[1]In case of Amlodipine, one can replace 5-methyl ester moiety with an amino acid resulting in better therapeutic index. In case of intact Amlodipine molecule, biotransformation results in generation of methanol due to solvolysis of 5-methyl ester, which is highly toxic, and replacement of this with a non-toxic naturally occurring amino acid with much less toxicity. In addition, the amino acid can form an amide bond with the primary and secondary amine groups on the Amlodipine. Moreover, an amino acid can form an amide or ester bond at the 3 position of the ring. This same argument goes for rest of the products in this category stated below:

[2]In case of Nisoldipine, replace 5-methyl ester with an amino acid for better therapeutic index, and no loss of activity. Also an amide linkage may form between the amino group of the Nisoldipine and the amino acid. In addition, an amide linkage or ester linkage can form between the 3 isobutyl ester and the amino acid.

[3]For Nicardipine, replace 5-methyl ester with an amino acid for better therapeutic index. In addition, the ester at the 3-position of the ring can form an ester linkage with the OH group on the side chain. Further, the amino group can form an amide bond with a carboxy group or acylating derivative thereof of the amino acid.

[4]For Nimodipine, one could replace 5 (1-methyl)ethyl ester with an amino acid for better therapeutic index. In addition, an amide can form between the amine group of the ring and the amino acid. In addition, the 3 position of Nimodipine can form an amide bond or an ester bond with an amino acid.

[5]For Isradipine, replace 5 methyl ester with an amino acid. The methyl ester is the active, and apparently the carboxylic acid derivative is not active.

[6]An amide linkage can be formed between the secondary nitrogen atom in the ring and an amino acid. Moreover, the 3-position of the ring can form an amide or ester linkage with an amino acid. Replacing the methoxy group with amino acid will still maintain activity, but none of the toxicity of methylphenidate. In addition, an amide bond can form between the nitrogen atom of the pyridine and the amino acids.

The amino acid derivative of the present invention contains amino groups and as such are basic in nature. They are capable of forming a wide variety of pharmaceutically acceptable salts with various inorganic and organic acids. These acids that may be used to prepare pharmaceutically acceptable acid addition salts of such basic compounds are those that form non-toxic acid addition salts, i.e., salts containing pharmaceutically acceptable anions, such as the hydrochloride, hydrobromide, hydroiodide, nitride, sulfate, bisulfate, phosphate, formate, acetate, citrate, tartate, lactate, and the like. The amino acid derivative of the present invention can form pharmaceutically acceptable salts with acids.

As indicated herein, in one embodiment, the present invention is directed to a derivative wherein the derivative comprises a drug, e.g., cyclosporine of the formula

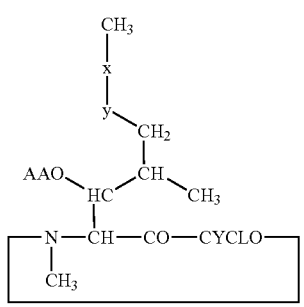

I and an amino acid esterified to the MeBmt (x-y=CH=CH) or dihydro MeBmt portion, (wherein x-y=CH$_2$CH$_2$). The amino acid is attached to the cyclosporine and to the other other drugs by a covalent bond.

The compounds of the present invention are prepared by art recognized techniques. For example, if the drug contains an OH group, said as cyclosporin, then an amino acid or an acylating derivatives thereof, such as the acid halide, e.g., amino acid fluoride, amino acid chloride, or an amino acid alkyl ester wherein alkyl group contains 1-6 carbon atoms is reacted with the carboxy group of the drug, e.g., cyclosporine under esterification condition. Preferably, the reaction is conducted in the presence of an acid, such as hydrochloric acid, hydrobromic acid, p-toluenesulfonic acid and the like. Alternatively, as described hereinabove, if the drug has an amino group thereon, then the amino acid may be reacted with the drug under amide forming conditions to form an amide as the covalent bond. Or if the drug has a carboxy group or acylating derivative thereon, it may be reacted with the amino group of the amino acid to form an amide under amide forming conditions to form an amide bond between the amino acid and the drug. Additionally if the drug has a carboxy group thereon, the hydroxy group of the side chain of the amino acid may be reacted with the carboxy group or acylating derivative thereon under esterification conditions to form the ester linkage between the amino acid and the drug, as described hereinabove.

If the amino acid has a group thereon which is reactive under the reaction conditions it is protected by a protecting group known in the art. After the completion of the reaction, the protecting group is removed. Examples of protecting groups that could be used are described in the book entitled, "Protective Group in Organic Synthesis" by Theodora W. Greene, John Wiley & Sons, 1981, the contents of which are incorporated by reference.

For example, if amino acids with carboxylic groups in their side chains, for example, aspartic acid and glutamic acid, are used in the aforementioned syntheses, these will generally require protection of the side chain carboxylic acid. Suitable protecting groups can be esters, such as cyclohexyl esters, t-butyl esters, benzyl esters, allyl esters, 9-fluorophenyl-methyl groups or adamantyl groups, such as 1- or 2-adamantyl which can be removed after the esterfication reaction is completed using techniques known to one of ordinary skill in the art.

If amino acids with hydroxyl groups in their side chains, for example, serine, threonine, hydroxyproline, and the like and amino acids with phenolic groups in their side chains, for example, tyrosine, and the like are used in the aforementioned esterification reactions, they will desirably require protection of the chain hydroxyl or phenolic group. Suitable protecting groups for the hydroxyl side chain groups can be ethers, such as benzyl ether or t-butyl ether and the like. Removal of the benzyl ether can be effected by liquid hydrogen fluoride, while the t-butyl ether can be removed by treatment with trifluoroacetic acid. Suitable protecting groups for the phenolic side chain groups can be ethers, as above, including benzyl or t-butyl ether or 2,6-dichlorobenzyl, 2-bromobenzyloxycarbonyl, 2,4-dintrophenyl and the like.

Moreover, the products can be purified to be made substantially pure by techniques known to one of ordinary skill in the art, such as by chromatography, e.g., HPLC, crystallization and the like. By substantially "pure" it is meant that the product contains no more than about 10% impurity therein.

The amino acid derivatives of the present invention encompass pharmaceutical acceptable salts, pharmaceutical acceptable solvates, enantiomers, diastereomers, N-Oxides, and polymorphs thereof, as described herein, and they can be associated along with a pharmaceutical acceptable carrier, and optionally but desirably pharmaceutically acceptable excipients and made into pharmaceutical composition using techniques known to one of ordinary skill in the art.

All the various stereoisomers of the amino acid derivatives, such as enantiomers and dieastercomers are comtemplated to be within the scope of the present invention. However, if the preferred drug has a preferred steroisomeric form, it is also preferred in the present invention. Moreover, the preferred amino acid derivatives of the present invention has the asymmetric carbon atom on the group adjacent to the amino and carboxy group from the amino acid moiety in the L configuration.

The amino acid derivatives described herein have the same utility as that drug without the amino acid moiety bonded thereto. The amino acid derivatives are used in therapeutically effective amounts.

The physician will determine the dosage of the derivatives of the present invention which will be most suitable and it will vary with the form of administration and the particular compound chosen, and furthermore, it will vary depending upon various factors, including but not limited to the patient under treatment and the age of the patient, the severity of the condition being treated and the like and the identify of the derivative administered. He will generally wish to initiate treatment with small dosages, substantially less than the optimum dose of the compound, and increase the dosage by small increments until the optimum effect under the circumstances is reached. It will generally be found that when the composition is administered orally, larger quantities of the compounds of the present invention will be required to produce the same effect as a smaller quantity given parenterally. The amino acid derivatives of the present invention have the same utility as the corresponding drug in the non amino acid derivatized form and the dosage level is generally no greater than that is generally employed with these other therapeutic agents. When given parenterally, the compounds are administered generally in dosages of, for example, about 0.001 to about 10,000 mg/kg/day, also depending upon the host and the severity of the condition being treated and the compound utilized.

In a preferred embodiment, the compounds of the present invention utilized are orally administered in amounts ranging from about 0.01 mg to about 1000 mg per kilogram of body weight per day, depending upon the particular mammalian host or the disease to be treated, more preferably from about 0.1 to about 500 mg/kg body weight per day. This dosage regimen may be adjusted by the physician to provide the optimum therapeutic response. For example, several divided doses may be administered daily or the dose may be proportionally reduced as indicated by the exigencies of the therapeutic situation.

The amino acid derivative of the present invention may be administered in any convenient manner, such as by oral, intravenous, intramuscular or subcutaneous routes.

The amino acid derivative of the present invention may be orally administered, for example, with an inert diluent or with an assimilable edible carrier, or it may be enclosed in hard or soft shell gelatin capsules, or it may be compressed into tablets, or it may be incorporated directly into the food of the diet. For oral therapeutic administration, the amino acid derivative of the present invention may be incorporated with excipients and used in the form of ingestible tablets, buccal tablets, troches, capsules, elixirs, suspensions, syrups, wafers, and the like. Such compositions and preparations should contain at least 1% of the derivative. The percentage of the compositions and preparations may, of course, be varied and may conveniently be between about 5 to about 80% of the weight of the unit. The amount of the amino acid derivative used in such therapeutic compositions is such that a suitable dosage will be obtained. Preferred compositions or preparations according to the present invention contain between about 200 mg and about 4000 mg of amino acid derivative. The tablets, troches, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier.

Various other materials may be present as coatings or otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations. For example, sustained release dosage forms are contemplated wherein the active ingredient is bound to an ion exchange resin which, optionally, can be coated with a diffusion barrier coating to modify the release properties of the resin or wherein the derivative of the present invention is associated with a sustained release polymer known in the art, such as hydroxypropylmethylcellulose and the like.

The amino acid derivative may also be administered parenterally or intraperitoneally. It is especially advantageous to formulate parenteral compositions in dosage unit form for ease of administration and uniformity of dosage. Dispersions can also be prepared in glycerol, liquid polyethylene glycols, e.g., PEG 100, PEG 200, PEG 300, PEG 400, and the like, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form is usually sterile and must be fluid to the extent that syringability exists. It must be stable under the conditions of manufacture and storage and usually must be preserved against the contaminating action of microorganisms such as bacteria and fungi. The carrier can be a solvent or dispersion medium containing, for example, water, ethanol, polyol (for example, glycerol, propylene glycol, and one or more liquid polyethylene glycol, e.g. as disclosed herein and the like), suitable mixtures thereof, and vegetable oils. The proper fluidity can be maintained, for example, by the use of a coating such as lecithin, by the maintenance of the required particle size in the case of dispersions and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the amino acid derivative of the present invention in the required amount in the appropriate solvent with various of the other ingredients enumerated above, as required, followed by filtered sterilization. Generally, dispersions are prepared by incorporating the various sterilized amino acid derivative of the present invention into a sterile vehicle which contains the basic dispersion medium and the required other ingredients from those enumerated above. In the case of sterile powders, the above solutions are vacuum dried or freeze-dried, as necessary.

The amino acid derivative of the present invention can also be applied topically, as e.g., through a patch using techniques known to one of ordinary skill in the art.

The amino acid derivative of the present invention can be administered buccally by preparing a suitable formulation of the derivative of the present invention and utilizing procedures well known to those skilled in the art. These formulations are prepared with suitable non-toxic pharmaceutically acceptable ingredients. These ingredients are known to those skilled in the preparation of buccal dosage forms. Some of these ingredients can be found in Remington's Pharmaceutical Sciences, $17^{th}$ edition, 1985, a standard reference in the field. The choice of suitable carriers is highly dependent upon the exact nature of the buccal dosage form desired, e.g., tablets, lozenges, gels, patches and the like. All of these buccal dosage forms are contemplated to be within the scope of the present invention and they are formulated in a conventional manner.

The formulation of the pharmaceutical compositions may be prepared using conventional methods using one or more physiologically and/or pharmaceutically acceptable carriers or excipients. Thus, the amino acid derivatives and their pharmaceutically acceptable salts and solvates may be formulated for administration by inhalation or insufflation (either through the mouth or the nose) or oral, buccal, parenteral, or rectal administration. For oral administration, the pharmaceutical compositions may take the form of, for example, tablets or capsules prepared by conventional means with pharmaceutically acceptable excipients such as binding agents (for example, pregelatinized maize starch, polyvinylpyrrolidone, or hydroxypropylmethyl cellulose); fillers (for example, lactose, microcrystalline cellulose or calcium hydrogen phosphate); lubricants (for example, magnesium stearate, talc, or silica); disintegrants (for example, potato starch, or sodium starch glycolate); or wetting agents (for example, sodium lauryl sulfate). The tablets may be coated by methods well known in the art.

Liquid preparations for oral administration may take the form of, for example, solutions, syrups, or suspensions, or they may be presented as a dry product for constitution with water or other suitable vehicles before use. Such liquid preparations may be prepared by conventional means with pharmaceutically acceptable additives, such as suspending agents (for example, sorbitol syrup, corn syrup, cellulose derivatives or hydrogenated edible oils and fats); emulsifying agents (for example, lecithin or acacia); non-aqueous vehicles (for example, almond oil, oily esters, ethyl alcohol or fractionated vegetable oils); and preservatives (for example, methyl or propyl p-hydroxybenzoates or sorbic acid). The preparations may also contain buffer salts, flavoring, coloring and sweetening agents as appropriate. Preparations for oral administration may be suitably formulated to give controlled release of the amino acid derivative of the present invention.

The amino acid derivative of the present invention may be formulated for parenteral administration by injection, for example, by bolus injection or continuous infusion. Formulations for injection may be presented in unit dosage form, for example, in ampoules, or in multi-dose containers, with an added preservative. The compositions may take such forms as suspension, solutions or emulsions in oily or aqueous vehicles, and may contain formulation agents such as suspending, stabilizing and/or dispersing agents. Alternatively, the amino acid derivative may be in the powder form for constitution with a suitable vehicle, for example, sterile pyrogen-free water, before use.

The amino acid derivatives of the present invention may also be formulated in rectal compositions such as suppositories or retention enemas, for example, containing conventional suppository bases such as cocoa butter or other glycerides.

In addition to the formulations described previously, the amino acid derivative of the present invention may also be formulated as a depot preparation. Such long acting formulations may be administered by implantation (for example, subcutaneously or intramuscularly) or by intramuscular injection. Thus, for example, the amino acid derivatives may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions containing the amino acid derivatives of the present invention may, if desired, be presented in a pack or dispenser device which may contain one or more unit dosage forms containing the active ingredients. The pack may for example comprise metal or plastic foil, such as blister pack. The pack or dispenser device may be accompanied by instructions for administration.

In tablet form, it is desirable to include a lubricant which facilitates the process of manufacturing the dosage units; lubricants may also optimize erosion rate and drug flux. If a lubricant is present, it will be present on the order of 0.01 wt. % to about 2 wt. %, preferably about 0.01 wt. % to 0.5 wt, %, of the dosage unit. Suitable lubricants include, but are not limited to, magnesium stearate, calcium stearate, stearic acid, sodium stearylfumarate, talc, hydrogenated vegetable oils and polyethylene glycol. As will be appreciated by those skilled in the art, however, modulating the particle size of the components in the dosage unit and/or the density of the unit can provide a similar effect—i.e., improved manufacturability and optimization of erosion rate and drug flux—without addition of a lubricant.

Other components may also optionally be incorporated into the dosage unit. Such additional optional components include, for example, one or more disintegrants, diluents, binders, enhancers, or the like. Examples of disintegrants that may be used include, but are not limited to, crosslinked polyvinylpyrrolidones, such as crospovidone (e.g., Polyplasdone® XL, which may be obtained from GAF), cross-linked carboxylic methylcelluloses, such as croscanmelose (e.g., Ac-di-sol®, which may be obtained from FMC), alginic acid, and sodium carboxymethyl starches (e.g., Explotab®, which may be obtained from Edward Medell Co., Inc.), agar bentonite and alginic acid. Suitable diluents are those which are generally useful in pharmaceutical formulations prepared using compression techniques, e.g., dicalcium phosphate dihydrate (e.g., Di-Tab®, which may be obtained from Stauffer), sugars that have been processed by crystallization with dextrin (e.g., co-crystallized sucrose and dextrin such as Di-Pak®, which may be obtained from Amstar), calcium phosphate, cellulose, kaolin, mannitol, sodium chloride, dry starch, powdered sugar and the like. Binders, if used, are those that enhance adhesion. Examples of such binders include, but are not limited to, starch, gelatin and sugars such as sucrose, dextrose, molasses, and lactose. Permeation enhancers may also be present in the novel dosage units in order to increase the rate at which the active agents pass through the buccal mucosa. Examples of permeation enhancers include, but are not limited to, dimethylsulfoxide ("DMSO"), dimethyl formamide ("DMF"), N,N-dimethylacetamide ("DMA"), decylmethylsulfoxide ("$C_{10}$MSO"), polyethylene glycol monolaurate ("PEGML"), glycerol monolaurate, lecithin, the 1-substituted azacycloheptan-2-ones, particularly 1-n-dodecylcyclazacycloheptan-2-one (available under the trademark Azone® from Nelson Research & Development Co., Irvine, Calif.), lower alkanols (e.g., ethanol), SEPA® (available from Macrochem Co., Lexington, Mass.), cholic acid, taurocholic acid, bile salt type enhancers, and surfactants such as Tergitol®, Nonoxynol-9® and TWEEN-80®.

Flavorings may be optionally included in the various pharmaceutical formulations. Any suitable flavoring may be used, e.g., mannitol, lactose or artificial sweeteners such as aspartame. Coloring agents may be added, although again, such agents are not required. Examples of coloring agents include any of the water soluble FD&C dyes, mixtures of the same, or their corresponding lakes.

In addition, if desired, the present dosage units may be formulated with one or more preservatives or bacteriostatic agents, e.g., methyl hydroxybenzoate, propyl hydroxybenzoate, chlorocresol, benzalkonium chloride, or the like.

As used herein, "pharmaceutically acceptable carrier" includes any and all solvents, dispersion media, coatings, antibacterial and antifungal agents, isotonic and absorption delaying agents well known in the art that are associated with drugs, medicaments, or active agents. Except insofar as any conventional media or agent is incompatible with the amino acid derivative, the use of these solvents, dispersion media, coatings and various isotonic and delaying agents and antibacterical and antifungal agents in the therapeutic compositions of the present invention is contemplated. Supplementary active ingredients can also be incorporated into the compositions.

Dosage unit form as used herein refers to physically discrete units suited as unitary dosages for the subjects to be treated, each unit containing a predetermined quantity of amino acid derivative calculated to produce the desired therapeutic effect in association with the required pharmaceutical carrier.

The amino acid derivative is compounded for convenient and effective administration in effective amounts with a suitable pharmaceutically acceptable carrier in dosage unit form as hereinbefore described. A unit dosage, for example, contains the amino acid derivative of the present invention in amounts ranging from about 10 mg e.g. in humans, or as low as 1 mg (for small animals) to about 2000 mg. If placed in solution, the concentration of the amino acids derivative preferably ranges from about 10 mg/mL to about 250 mg/mL. In the case of compositions containing supplementary active ingredients, the dosages are determined by reference to the usual dose and manner of administration of the said ingredients. In the case of buccal administration, the amino acid derivatives are preferably in the buccal unit dosage form present in an amount ranging from about 10 to about 50 mg.

The amino acid derivatives of the present invention are effective in treating disease or conditions in which the corresponding drug (without the amino acid derivative of the present invention) normally are used.

As used herein the term "treating" refers to reversing, alleviating or inhibiting the progress of a disease, disorder or condition, or one or more symptoms of such disease, disorder or condition, to which such term applies. As used herein, "treating" may also refer to decreasing the probability or incidence of the occurrence of a disease, disorder or condition in a mammal as compared to an untreated control population, or as compared to the same mammal prior to treatment. For example, as used herein, "treating" may refer to preventing a disease, disorder or condition, and may include delaying or preventing the onset of a disease, disorder or condition, or delaying or preventing the symptoms associated with a disease, disorder or condition. As used herein, "treating" may also refer to reducing the severity of a disease, disorder or condition or symptoms associated with such disease, disorder or condition prior to a mammal's affliction with the disease, disorder or condition. Such prevention or reduction of the severity of a disease, disorder or condition prior to affliction relates to the administration of the composition of the present invention, as described herein, to a subject that is not at the time of administration afflicted with the disease, disorder or condition. As used herein "treating" may also refer to preventing the recurrence of a disease, disorder or condition or of one or more symptoms associated with such disease, disorder or condition. The terms "treatment" and "therapeutically," as used herein, refer to the act of treating, as "treating" is defined above.

Prophylaxis or preventing, or any like term, refers to decreasing the probability or incidence of the occurrence of a disease, disorder or condition in a mammal. It also includes delaying or preventing the onset of a disease, disorder or condition or delaying the symptoms associated with a disease, disorder or condition. In addition, it also refers to retarding the occurrence of a disease, disorder or condition in a mammal.

As used herein the term "patient" or "subject" refers to a warm blooded animal, and preferably mammals, such as, for example, cats, dogs, horses, cows, pigs, mice, rats and primates, including humans. The preferred patient is humans.

The amino acid derivatives of the present invention exhibit the same utility as the corresponding drug without the amino acid linkage. The amino acid derivative of the present invention exhibits an enhanced therapeutic quality. That is, they exhibit at least one and more preferably at least two enhanced therapeutic qualities relative to the drug which has not been transformed to the derivative of the present invention prior to administration. These include, but are not limited to
  a. Improved taste, smell
  b. Desired octanol/water partition coefficient (i.e., solubility in water/fat)

The various amino acids have different solubility in aqueous solutions. By selecting a particular amino acid, the octanol water partition coefficient can be affected. For example, many drugs in the following list are highly hydrophobic. The amino acids are highly hydrophilic. For example, assume propofol is the drug and lysine is the amino acid. Propofol is completely insoluble in water, while lysine is soluble to the extent of 700 mg/ml. When these two diverse molecules are esterified via an ester bond, the resulting lysine ester of propfol has a solubility in water in excess of 250 mg/ml.

On the other hand, cromolyn sodium is highly water soluble. For all practical purposes, it is not absorbed when administered orally. By affecting its water solubility one could improve absorption. In this case, one would look for conditions opposite to that of propofol, i.e., the goal is to decrease water solubility. By choosing the appropriate low water soluble amino acids, such as tyrosine, one can achieve proper hydrophilic/lipophilic balance.
  c. Improved stability in-vitro and in-vivo
  d. Enhanced penetration of blood-brain barrier
  e. Elimination of first-pass effect in liver, i.e., the drug not metabolized in liver and therefore more drug in system circulation
  f. Reduction of entero-hepatic recirculation (this improves bio-availability)
  g. Painless injections with parenteral formulations
  h. Improved bio-availability
  i. Improved changes in the rate of absorption (increase vs lack thereof)
  j. Reduced side effects
  k. Dose proportionality A dose proportionality claim requires that when the drug is administered in escalating doses, proportionally escalating amounts of active drug is delivered into the blood stream. This is measured by determining the area under the plasma concentration vs. time curve obtained after administering a drug via any route other than IV route and measuring the same in the plasma/blood. A simple mathematical procedure is as follows:

For example, a drug is administered at e.g., 3 different doses, 10, 100 and 1000 mg, orally to a patient; the area under the plasma concentration time curve (AUC) is measured. Then each total AUC is divided by the dose, and the result should be the same for all three doses. If it is the case, then there is dose proportionality. Lack of dose proportionality indicates any one or more of the pharmacokinetic/pharmacological mechanisms are saturable, including absorption, metabolism or the number of receptor sites available for pharmacological response.

For example in the above study, assume the AUC values of 100, 1000 and 10,000 are obtained, in this case the dose proportionality is inappropriate. When there is lack of dose proportionality, there is either more or less amount of drug in the plasma, depending upon which mechanism is saturable. The following are the possibilities: Saturable Absorption. If this is the case, as the dose is increased, proportionally less and less of the drug is absorbed, hence overall AUC will decrease as the dose is increased.

Saturable metabolism of elimination. If thus is the case, then more and more of the drug will be circulating in the blood, and the AUC will increase with increasing dose.

Saturable pharmacological receptor sites: In this case, since all the receptor sites will eventually be occupied by the drug, any additional drug will not increase the response. Thus, increasing dose will not result in increasing response.

Dose proportionality is an excellent response profile, since one can predict accurately the pharmacological response and curative power at all doses. Thus dose proportionality is a desirable quality for any drug. Furthermore, achievement of dose proportionality is also dependent upon the formulation, and fed/fasted differences.

l. Selective hydrolysis of the derivative at site of action
m. Controlled release properties
n. Targeted drug delivery
o. Reduction in toxicity, hence, improved therapeutic ratio
p. Reduced dose
q. Alteration of metabolic pathway to deliver more drug at the site of action
r. Increased solubility in aqueous solution
s. Enhanced efficacy The amino acid derivatives are available in various dosage forms and they are prepared by conventional methods:

i. Oral liquid dosage (Controlled release and immediate release liquids containing sugar and sugar free, dye and dye free, alcohol and alcohol free formulations, including chewable tablets)
ii. Oral solid dosage (Controlled release and immediate release tablets, capsules and caplets
iii. Intravenous (Injections, both ready to use and lyophilized powders)
iv. Intramuscular (Injections, both ready to use and lyophilized powders)
v. Subcutaneous (Injections, both ready to use and lyophilized powders)
vi. Transdermal (Mainly patches)
vii. Nasal (Sprays, formulations for nebulizer treatments)
viii. Topical (Creams, ointments)
ix. Rectal (Creams, ointments and suppositories)
x. Vaginal (Creams, ointments and pessaries)
xi. Ocular (Drops and ointments)
xii. Buccal (Chewable and now chewable tables)

Many drugs discussed herein, especially in the table hereinbelow are characteristically highly hydrophobic and readily precipitate in the presence of even very minor amounts of water, e.g., on contact with the body (e.g., stomach fluids). It is accordingly extremely difficult to provide, e.g., oral formulations which are acceptable to the patient in terms of form and taste, which are stable on storage and which can be administered on a regular basis to provide suitable and controlling patient dosing.

Proposed liquid formulations, e.g., for oral administration of a number of drugs shown herein in the table have heretofore been based primarily on the use of ethanol and oils or similar excipient as carrier media. Thus, the commercially available drink-solutions of a number of drugs employ ethanol and olive oil or corn oil as carrier medium in conjunction with solvent systems comprising e.g., ethanol and LABRIFIL and equivalent excipient as carrier media. For example, the commercially available Cyclosporin drink solution employs ethanol and olive oil or corn oil as carrier medium in conjunctions with a Labroid as a surfactant. See e.g., U.S. Pat. No. 4,388,307. Use of the drink solution and similar composition as proposed in the art is however accompanied by a variety of difficulties.

Further, the palatability of the known oil based system has proved problematic. The taste of the known drink-solution of several drugs is, in particular, unpleasant. Admixture with an appropriate flavored drink, for example, chocolate drink preparation, at high dilution immediately prior to ingestion has generally been practiced in order to make regular therapy at all acceptable. Adoption of oil-based systems has also required the use of high ethanol concentrations which is itself inherently undesirable, in particular where administration to children is foreseen. In addition, evaporation of the ethanol, e.g., from capsules (adopted in large part, to meet problems of palatability, as discussed or other forms (e.g., when opened)) results in the development of a drug precipitate.

Where such compositions are presented in, for example, soft gelatin encapsulated form, this particular difficulty necessitates packaging of the encapsulated product in an airtight component, for example, an air-tight blister or aluminum-foil blister package. This in turn renders the product both bulky and more expensive to produce. The storage characteristics of the aforesaid formulations are, in addition, far from ideal.

Bioavailability levels achieved using existing oral dosage system for a number of drugs described herein are also low and exhibit wide variation between individuals, individual patient types and even for single individuals at different times during the course of therapy. Reports in the literature indicate that currently available therapy employing the commercially available drug drink solution provides an average absolute bioavailability of approximately 10-30% only, with a marked variation between individual groups, e.g., between liver (relatively low bioavailability) and bone-marrow (relatively high bioavailability) transplant recipients. Reported variation in bioavailability between subjects has varied from one or a few percent for some patients, to as much as 90% or more for others. And as already noted, marked change in bioavailability for individuals with time is frequently observed. Thus, there is a need for a more uniform and high bioavailability of a number drugs in patients.

Use of dosage forms of existing drugs is also characterized by extreme variation in required patient dosing. To achieve effective therapy, drug blood or blood serum levels have to be maintained within a specified range. This required range can in turn, vary, depending on the particular condition being treated, e.g., whether therapy is to prevent one or more pharmacological actions of a specific drug and when alternative therapy is employed concomitantly with principal therapy. Because of the wide variations in bioavailability levels achieved with conventional dosage forms, daily dosages needed to achieve required blood serum levels will also vary considerably from individual to individual and even for a single individual. For this reason it may be necessary to monitor blood/blood-serum levels of patients receiving drug therapy at regular and frequent intervals. Monitoring of blood/blood-serum levels has to be carried out on a regular basis. This is inevitably time consuming and inconvenient and adds substantially to the overall cost of therapy.

It is also the case that blood/blood serum levels of a number of drugs without the amino acid linkage described herein achieved using available dosage systems exhibit extreme variation between peak and trough levels. That is, for each patient, effective drug levels in the blood vary widely between administrations of individual dosages.

There is also a need for providing a number of drugs described herein, especially the beta-lactum antibiotics, Cyclosporin, cephalosporins, steroids, quinolone antibiotics and the like, in a water-soluble form for injection. It is well known that Cremaphore L® (CreL) used in current formulations of a number of drugs described hereinbelow is a polyoxyethylated derivative of castor oil and is a toxic vehicle. There have been a number of incidences of anaphylaxis due to the castor oil component. At present there is no formulation that would allow many of these drugs to be in aqueous solution at the concentrations needed due to poor water solubility of the drug.

Beyond all these very evident practical difficulties lies the occurrence of undesirable side reactions already alluded to, observed employing available oral dosage forms.

Several proposals to meet these various problems have been suggested in the art, including both solid and liquid oral dosage forms. An overriding difficulty which has however remained is the inherent insolubility of the several of the drugs without the amino acid linkage shown in the table hereinbelow in aqueous media, hence preventing the use of a dosage form which can contain the drugs in sufficiently high concentration to permit convenient use and yet meet the required criteria in terms of bioavailability, e.g. enabling effective absorption from the stomach or gut lumen and achievement of consistent and appropriately high blood/blood-serum levels, is needed.

The particular difficulties encountered in relation to oral dosing with these drugs have inevitably led to restrictions in the use of specific drug therapy for the treatment of relatively less severe or endangering disease conditions. For example, taking Cyclosporin as a test drug, a particular area of difficulty in this respect has been the adoption of Cyclosporin therapy in the treatment of autoimmune diseases and other conditions affecting the skin, for example for the treatment of atopic dermatitis and psoriasis and, as also widely proposed in the art, for hair growth stimulation, e.g. in the treatment of alopecia due to ageing or disease.

Thus while oral Cyclosporin therapy has shown that the drug is of considerable potential benefit to patients suffering e.g. from psoriasis, the risk of side-reaction following oral therapy has prevented common use. Various proposals have been made in the art for application of Cyclosporins, e.g. Cyclosporin, in topical form and a number of topical delivery systems have been described. Attempts at topical application have however failed to provide any demonstrably effective therapy.

However, the present invention overcomes the problems described hereinabove. More specifically, the amino acid derivative of the present invention significantly enhances its solubility in aqueous solutions relative to the non-derivative form of the pharmaceutical, thereby avoiding the need to utilize a carrier, such as ethanol or castor oil when administered as a solution. Moreover, the amino acid derivatives of these drugs, in accordance with the present invention, do not exhibit the side effects of the prior art formulations. Further, it has been found that when many of the drugs in the table hereinbelow is administered in its amino acid derivative form in accordance with the present invention, there is enhanced oral absorption, thereby enhancing significantly its bioavailability and its efficacy.

The preferred drugs used in combination with the amino acids forming derivatives are listed hereinbelow in the following table and the benefits found are as listed in the penultimate column of the table. In the table, the key is as follows:

a) Improved taste smell
b) Desired Octanol/water partition coefficient (i.e. solubility in water)
c) Improved stability in vitro and in vivo
d) Penetration of blood-brain barrier
e) Elimination of first pass effect in liver
f) Reduction of enterohepatic recirculation
g) Painless injections with parenteral formulations
h) Improved bioavailability
i) Increased rate of absorption
j) Reduced side effects
k) Dose proportionability
l) Selective hydrolysis of the derivative at site of actions
m) Controlled release properties
n) Targeted drug delivery
o) Reduction in toxicity, hence improved therapeutic ratio
p) Reduced dose
q) Alteration of metabolic pathway to deliver more drug at site of action.

Moreover, the table indicates the utility of the derivative. The utility of the derivative is the same as the corresponding drug (without the amino acid moiety attached). The utility is described in the literature such as in the Physicians Desk Reference, 2004 edition, the contents of which are incorporated by reference.

TABLE 1

| Amino Acid Derivatives of | Applicable Dose Range | Preferred Dose Range | Most Preferred Dose Range | Amino Acids that can be reacted with the drug to form the ester/amide/azo/anhydride derivatives | Preferred Amino Acids | Most Preferred Amino Acids | Improvements with derivatives utility immuno | Utility |
|---|---|---|---|---|---|---|---|---|
| Cyclosporin Preferred Forms | | All doses expressed as drug base | | Lys, Leu, Ile, Gly, Asp, Glu, Met, Ala, Val, Pro, His, Tyr, Ser, Nor, Arg, Phe, Trp, Thr, Arg, Phe, Trp, Gln, Asn, Cys and Ser, Hyp, Sar or dipeptides of combination of any two amino acids especially AA-Gly, where Gly is a spacer attached to cyclosporin and AA is the above-cited amino acids. | Lys, Leu, Ile, Gly, Asp, Glu, Met, Ala, Val, Pro, His, Tyr, Thr, Arg, Phe, Trp, Gln, Asn, Cys, Tau, Djk, GABA, Cys, Dcy, Thr, and Sar or dipeptide of combination of any two amino acids especially AA-Gly, where Gly is a spacer attached to cyclosporin and AA is the above-cited amino acids. | Lys, Pro, & Gly and dipeptides of Lys-Gly, Pro-Gly, Gly-Gly | b, e, f, g, h, k, l, o, and p | prophylaxis of organ rejection, e.g., kidney, liver and heart allogenic transplants, treatment of rheumatoid arthritis and psoriosis |
| Oral Tab/Cap | 5-1000 mg | 20-250 mg | 25-100 mg | | | | | |
| Oral Liquid | 1-25 mg/ml | 5-15 mg/ml | 10 mg/ml | | | | | |
| IV Injections | 10-250 mg per 5 ml | 25-100 mg per 5 ml | 50 mg/5 ml | | | | | |
| Lopinavir Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Pro, Gly, & Ala | b, h, j, k, and o | treatment of HIV infections, e.g., AIDS |
| Oral Tab/Cap | 0.1-1 gm | 200-800 mg | 400-500 mg | | | | | |
| Oral Liquid | 0.1-1 gm/5 ml | 0.2-0.8 g/5 ml | 400 mg/5 ml | | | | | |
| Cefdinir Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Tyr, & Thr | a, b, e, f, h, i, o, and p | antibiotic treatment of diseases caused by Haemophilus influenzae, including B-lactamase producing strains, e.g., Haemophilus parainfluenzae (including β-lactosamase producing strains) and moraxella catarihalis (including β-lactamase producing strains), and streptococcus pyogenes; such as pneumonia, bronchitis and sinusitis, pharyngitis and tonsillitis |
| Oral Tab/Cap | 0.1-1 gm | 0.2-0.5 gm | 200-400 mg | | | | | |
| Oral Liquid | 0.1-1 gm/5 ml | 0.2-0.5 gm/5 ml | 0.2-0.4 gm/5 ml | | | | | |
| IV Infusions | 0.01-1 gm/100 ml | 20-500 mg/100 ml | 50-150 mg/100 ml | | | | | |
| Zileuton Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Sar, Ala, Pro | b, h, i, j, k, o, p | treatment of asthma |
| Oral Tab/Cap | 200-1200 mg | 200-800 mg | 300-400 mg | | | | | |
| Oral Liquid | 200-1200 mg/5 ml | 200-800 mg/5 ml | 200-400 mg/5 ml | | | | | |
| Nelfinavir Preferred | | All Doses expressed as drug base | | Lys, Leu, Ile, Gly, Asp, Glu, Met, Ala, | Lys, Leu, Ile, Gly, Asp, Glu, Met, Ala, | Gly, Lys, Sar, Ala, | b, h, i, j, k, o, p | treatment of HIV, infected patients, e.g., AIDS |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| forms | | | | | | | | |
| Oral Tab/Cap | 0.05-1 gm | 0.1-0.5 gm | 0.2-0.4 gm | Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | | Pro | | |
| Oral Powder | 10-250 mg/gm | 20-200 mg/gm | 40-100 mg/gm | | | | | |
| IV Formulation | 10-250 mg/100 ml | 20-200 mg/100 ml | 40-100 mg/100 ml | | | | | |
| Flavoxate Preferred Forms | All doses expressed as drug base | | | | | | | treatment of urinary spasms |
| Oral Tab/Cap | 10-1000 mg | 20-500 mg | 50-250 mg | Lys, Leu, Ile, Gly, Asp, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Tyr, & Thr | b, h, i, j, k, l, o, & p | |
| Oral Liquid | 10-1000 mg/5 ml | 20-500 mg/5 ml | 50-250 mg/5 ml | | | | | |
| Candesarten Preferred Forms | All doses expressed as drug base | | | | | | | treatment of hypertension |
| Oral Tab/Cap | 1-100 mg | 2-75 mg | 4-50 | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Tyr, & Thr | b, c, e, f, h, i, j, k, l, o, p, q | |
| Oral Liquid | 1-100 mg/5 ml | 2-75 mg/5 ml | 4-50 mg/5 ml | | | | | |
| Propofol Preferred Forms | | | | | | | | provides central nervous system anesthesia |
| IV Infusions | 1-25 mg/ml | 2.0-20 mg/ml | 5-15 mg/ml | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Sar, Pro, Ala, & Val | b, c, d, g, h, j, k, l, m, n, o, p, q | |
| Nisoldipine Preferred Forms | All doses expressed as drug base | | | | | | | calcium channel blocker, treatment of hypertension |
| Oral Tab/Cap | 2-100 mg | 2.5-75 mg | 5-50 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Ser, & Hyp | b, e, h, i, j, o | |
| Oral Liquid | 2-100 mg/5 ml | 2.5-75 mg/5 ml | 5-50 mg/5 ml | | | | | |
| Amlodipine Preferred forms | All Doses expressed as drug base | | | | | | | calcium channel blocker, treatment of hypertension |
| Oral Tab/Cap | IV 0.1-20 mg | 1-10 mg | 2.5-5 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Ser, & Hyp | b, e, h, i, j, o | |
| Oral Liquid | 0.1-20 mg/5 ml | 1-10 mg/5 ml | 2.5-5 mg/5 ml | | | | | |
| Ciprofloxacin | All doses expressed as drug base | | | Lys, Leu, Ile, Gly, | Lys, Leu, Ile, Gly, | Hyp, Ser, | a, b, c, g, | Antibiotic; inhibits various |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| Preferred Forms | | | | | | | | |
| Oral Tab/Cap | 0.1-1.5 gm | 0.1-1.0 gm | 0.2-0.8 gm | Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Asp, Glu, Met, Ala, Val, Pro, His, Tyr, Thr, Arg, Phe, Trp, Gln, Asn, Cys and Ser, Hyp, Sar | Thr, Gly, & Lys | h, i, j, k, o, p | bacteria, e.g., pseudomonas aeruginosa, staphylococcus aureus or proteus mirabilis; treatment of corneal ulcers, conjunctivitis, acute otitis externa, |
| Oral Liquid | 0.05-1 gm/5 ml | 0.08-1 gm/5 ml | 0.12-1 g/5 ml | | | | | |
| IV Bulk (Sterile) | 2-25 mg/ml | 3-20 mg/ml | 5-15 mg/ml | | | | | |
| Ramipril Preferred Forms | All doses expressed as drug base | | | | | | | |
| Oral Tab/Cap | 0.1-20 mg | 0.5-12 mg | 1-10 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Thr, Gly & Lys | j, o | treatment of hypertension |
| Oral Liquid | 0.1-20 mg/5 ml | 0.5-12 mg/5 ml | 1-10 mg/5 ml | | | | | |
| Trandolapril Preferred Forms | All doses expressed as drug base | | | | | | | |
| Oral Tab/Cap | 0.1-10 mg | 0.5-7.5 mg | 1-4 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly & Lys | j, o | treatment of hypertension |
| Oral Liquid | 0.1-10 mg/5 ml | 0.5-7.5 mg/5 ml | 1-4 mg/5 ml | | | | | |
| Fosinopril Preferred Forms | All doses expressed as drug base | | | | | | | |
| Oral Tab/Cap | 1-100 mg | 2-75 mg | 5-50 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly, & Lys | j, o | treatment of hypertension |
| Oral Liquid | 1-100 mg/5 ml | 2-75 mg/5 ml | 5-50 mg/5 ml | | | | | |
| Enalapril Preferred forms | All doses expressed as drug base | | | | | | | |
| Oral Tab/Cap | 0.5-100 mg | 1-50 mg | 2-25 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly & Lys | j, o | treatment of hypertension |
| Oral Liquid | 0.5-100 mg/5 ml | 1-50 mg/5 ml | 2-25 mg/5 ml | | | | | |
| Benazepril Preferred Forms | All doses expressed as drug base | | | | | | | |
| Oral Tab/Cap | 1-100 mg | 2-75 mg | 2.5-50 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Thr, Gly, & Lys | j, o | treatment of hypertension |
| Oral Liquid | 1-100 mg/5 ml | 2-75 mg/5 ml | 2.5-50 mg/5 ml | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| Perindopril Preferred Forms | | All doses expressed as drug base | | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Thr, Gly, & Lys | j, o | treatment of hypertension |
| Oral Tab/Cap | 0.1-20 mg | 0.5-15 mg | 1-10 mg | | | | | |
| Oral Liquid | 0.1-20 mg/ 5 ml | 0.5-15 mg/5 ml | 1-10 mg/ 5 ml | | | | | |
| Moexipril Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly & Lys | j, o | treatment of hypertension |
| Oral Tab/Cap | 1-30 mg | 2-20 mg | 5-15 mg | | | | | |
| Oral Liquid | 1-30 mg/5 ml | 2-20 mg/5 ml | 5-15 mg/ 5 ml | | | | | |
| Cromolyn Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, & Pro | b, c, h, i, j, k, l, n, o, p, q | inhibits release of histamine and leukotrienes from mast cell; treatment of mastocytosis, asthma |
| Oral Tab/Cap | 10-200 mg | 20-100 mg | 20-50 mg | | | | | |
| Oral Liquid | 10-200 mg/ 5 ml | 20-100 mg/ 5 ml | 20-50 mg/ 5 ml | | | | | |
| Amoxicillin Preferred forms | | All Doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly & Lys | a, b, c, h, i, j, k, l, o, p | antibiotic effective against β-lactamase negative strains causing infections of ear, nose, throat, e.g., streptococcus, staphylococcus or H influenzae; treatment of infections of genitourinary tract due to E. coli, P. mirabilis, E. faecalis, infections of skin due to streptococcus, staphylococcus or E. coli, infections of lower respiratory tract due to streptococcus, staphyloccus or H. influenzae, and gonorrhea |
| Oral Tab/Cap* | 0.1-1.5 gm | 0.2-1.2 gm | 0.25-1 gm | | | | | |
| Oral Liquid | 0.1-1.5 gm/ 5 ml | 0.2-1.2 gm/ 5 ml | 0.25-1 gm/ 5 ml | | | | | |
| Oral Powder (*also chewable) | 0.1-0.75 gm | 0.1-0.6 gm | 0.125-0.5 gm | | | | | |
| Cefuroxime Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, | Lys, Leu, Ile, Gly, Asp, Glu, Met, Ala, Val, Pro, His, Tyr, Thr, Arg, Phe, Trp, Gln, Asn, Cys and | Hyp, Ser, Thr, Gly, & Lys | b, c, e, f, h, i, j, k, o, p | antibiotic; treatment of pharyngitis/tonsillitis caused by streptococcus, acute bacterialotitis media caused by streptococcus, H |
| Oral Tab/Cap | 10-1000 mg | 50-750 mg | 100-600 mg | | | | | |
| Oral Liquid | 10-1000 mg/ 5 ml | 50-750 mg/ 5 ml | 100-600 mg/ 5 ml | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| | | | | Tau, Djk, GABA, Cys, Dcy, Thr, and Sar | Ser, Hyp, Sar | | | influenzae, moraxella catarrhalis or streptococcus, urinary tract infections caused by E. coli or Klebsiella pneumonia, gonorrhea, skin infections cause by staphylococcus or streptococcus |
| Ceftazidime Preferred Forms | All doses expressed as drug base | | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Thr, Gly, & Lys | a, b, c, g, h, i, j, k, l, o, p, q | antibiotic, treatment of lower respiratory tract infections, including pneumonia caused by pseudomonas, H. influenzae, Klebsiella, Enterbacter, E. coli; proteus mirabilis, streptococcus, staphylococcus; skin and skin structure infections, caused by pseudomonas aeruginosa, Klebsiella, E. coli, Proteus enterbacter, proteus, staphylococcus, streptococcus, urinary tract infections caused by pseudomonas aeruginosa, enterbacter, proteus, Klebsiella, E. coli; bone and joint infections caused by pseudomonas, eruginosa, Klebsiella, Enterbacter, or staphylococcus; gynecologic infections including endometritis, pelvic cellulits and infections of the female genital tract caused by E. coli, intra-abdominal infections and central nervous system infections, including meningitis |
| Powder for IV | 0.1-5 gm | 0.25-4 gm | 0.5-2 gm | | | | | |
| Oral Tab/Cap | 0.1-1 gm | 0.25-1 gm | 0.5-1 gm | | | | | |
| Oral Liquid | 0.1-2.5 gm/ 5 ml | 0.25-2 gm/ 5 ml | 0.5-1 gm/ 5 ml | | | | | |
| Cefpodoxime Preferred Forms | All doses expressed as drug base | | | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly & Lys | a, b, c, g, h, i, j, k, l, o, p, q | antibiotic especially against streptococcus, H. influenzae, moraxella catarrhalis; treatment of acute otis media, pharyngitis, tonsillitis, pneumonia, |
| Oral Tab/Cap | 10-500 mg | 25-350 mg | 50-250 mg | | | | | |
| Oral Liquid | 10-500 mg/ 5 ml | 25-350 mg/ 5 ml | 50-250 mg/ 5 ml | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| | | | | | | | | bronchitis, gonorrhea, and rectal infections in women |
| Atovaquone | | All doses expressed as drug base | | | | | | treatment of malaria caused by plasmodium parasite |
| Preferred Forms | | | | | | | | |
| Oral Tab/Cap | 50-1000 mg | 100-500 mg | 200-300 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Sar, Ala, Pro & Ser | a, b, h, i, j, k, o, p | |
| Oral Liquid | 50-1000 mg above/5 ml | 100-500 mg above/5 ml | 200-300 mg above/5 ml | | | | | |
| For Pediatric Use | 10-150 mg/ 5 ml | 25-100 mg/ 5 ml | 50-75 mg/ 5 ml | | | | | |
| Acyclovir | | All Doses expressed as drug base | | | | | | treatment of human cytomegalovirus (HCMV) |
| Preferred forms | | | | | | | | |
| Oral Tab/Cap | 50-1000 mg | 100-750 ml | 150-500 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Sar, Hyp Pro & Ser | b, c, h, i, j, k, o, p | |
| Oral Liquid | 50-1000 mg/ 5 ml | 100-750 mg/ 5 ml | 150-500 mg/ 5 ml | | | | | |
| Ganciclovir | | All doses expressed as drug base | | | | | | treatment of human cytomegalo virus (HCMV) |
| Preferred Forms | | | | | | | | |
| Oral Tab/Cap | 0.1-1 gm | 0.2-0.8 gm | 0.2-0.6 gm | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Thr, Gly, & Lys | b, c, e, f, h, i, j, k, o, p | |
| Oral Liquid | 0.1-1 gm/5 ml | 0.2-0.8 gm/ 5 ml | 0.2-0.6 mg/ 5 ml | | | | | |
| IV Infusions | 10-200 mg/ml | 25-100 mg/ml | 30-60 mg/ml | | | | | |
| Penciclovir | | All Doses expressed as drug base | | | | | | treatment of human cytomegalovirus (HCMV) |
| Preferred Forms | | | | | | | | |
| Powder for IV | 10-1000 mg/ml | 25-750 mg/ml | 50-500 mg/ml | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Thr, Gly, & Lys | b, c, e, f, h, i, j, k, o, p | |
| Topical Cream | 0.1-5% | 0.25-3% | 0.5-2.5% | | | | | |
| Oral Cap/Tab | 10-500 mg | 20-300 mg | 25-250 mg | | | | | |
| Niacin ER | | All doses expressed as drug base | | | | | | lipid management |
| Preferred Forms | | | | | | | | |
| Oral Tab/Cap | 0.2-2 gm | 0.25-1.5 gm | 0.5-1 gm | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Tyr, Gly & Lys | a, b, h, i, j, l, m, n, o, p, q | |
| Oral Liquid | 0.2-2 gm/5 ml | 0.25-1 gm/ 5 ml | 0.5-1 gm/ 5 ml | | | | | |
| Bexarotene | | All doses expressed as drug base | | | | | | treatment of skin conditions, especially those requiring activation of retinoid X receptors |
| Preferred Forms | | | | | | | | |
| Oral Tab/Cap | 10-500 mg | 25-250 mg | 50-100 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly, & Lys | b, c, h, i, j, k, l, o, p | |
| Oral Liquid | 10-500 mg above/5 ml | 25-250 mg above/5 m | 50-100 mg above/5 ml | | | | | |
| Topical Gel | 0.1-5% | 0.25-2.5% | 0.5-1.5% l | | | | | |
| Propoxyphene | | All Doses expressed as drug base | | Lys, Leu, Ile, Gly, Asp, Glu, Met, Ala, Val, Pro, | Lys, Leu, Ile, Gly, Asp, Glu, Met, Ala, | Ser, Hyp, Thr, Gly, & Lys | a, b, c, h, i, j, k, l, o, p | treatment of pain |
| Preferred forms | | | | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| Oral Tab/Cap | 20-400 mg | 25-250 mg | 30-150 mg | His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Val, Pro, His, Tyr, Thr, Arg, Phe, Trp, Gln, Asn, Cys and Ser, Hyp, Sar | | | |
| Oral Liquid | 20-400 mg/5 ml | 25-250 mg/5 ml | 30-150 mg/5 ml | | | | | |
| Salsalate Preferred Forms | | All doses expressed as drug base | | | | | | |
| Oral Tab/Cap | 0.2-2 gm | 0.25-1.5 gm | 0.3-1 gm | Lys, Leu, Ile, Gly, Asp, Glu, Met, Ala, Val, Pro, His, Tyr, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Thr, Gly, & Lys | b, c, h, i, j, k, o, p | treatment of inflammatory conditions |
| Oral Liquid | 0.2-2 gm/5 ml | 0.25-1.5 gm/5 ml | 0.3-1 gm/5 ml | | | | | |
| Acetaminophen Preferred Forms | | All doses expressed as drug base | | | | | | |
| Oral Tab/Cap | 20-1000 mg | 50-800 mg | 100-600 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Sar, Gly, & Lys | a, b, c, e, h, i, j, k, o, p | treatment of pain or fever |
| Oral Liquid | 20-1000 mg/5 ml | 50-800 mg/5 ml | 100-600 mg/5 ml | | | | | |
| Ibuprofen Preferred Forms | | All doses expressed as drug base | | | | | | |
| Oral Tab/Cap | 20-1000 mg | 50-800 mg | 100-600 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly, Gly, & Lys | a, b, h, i, j, l, m, n, o, p, q | treatment of pain, fever or inflammation |
| Oral Liquid | 20-1000 mg/5 ml | 50-800 mg/5 ml | 100-600 mg/5 ml | | | | | |
| Lovastatin Preferred Forms | | All doses expressed as drug base | | | | | | |
| Oral Tab/Cap | 1-100 mg | 2-80 mg | 5-50 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly, & Lys | b, c, e, f, h, i, j, k, l, o, p | lowers cholesterol concentration; inhibits HMG-CoA reductase |
| Oral Liquid | 1-100 mg/5 ml | 2-80 mg/5 ml | 5-50 mg/5 ml | | | | | |
| Simavastatin Preferred forms | | All doses expressed as drug base | | | | | | |
| Oral Tab/Cap | 1-200 mg | 2-150 mg | 2.5-100 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly, & Lys | b, c, e, f, h, i, j, k, l, o, p | lowers cholesterol concentration; inhibits HMG-CoA reductase |
| Oral Liquid | 1-200 mg/5 ml | 2-150 mg/5 ml | 2.5-100 mg/5 ml | | | | | |
| Atorvastatin Preferred Forms | | All doses expressed as drug base | | | | | | |
| Oral Tab/Cap | 1-250 mg | 2-125 mg | 5-100 mg | Lys, Leu, Ile, Gly, Asp, Glu, Met, Ala, Val, Pro, His, Tyr, His, Tyr, Ser, Nor, Arg, Phe, Trp, Hyp, Hsr, Car, Ort, Cav, Asn, | Lys, Leu, Ile, Gly, Asp, Glu, Met, Ala, Val, Pro, His, Tyr, Thr, Arg, Phe, Trp, Gln, Asn, Cys and | Ser, Hyp, Thr, Gly, & Lys | b, c, e, f, h, i, j, k, l, o, p | lowers cholesterol concentration; inhibits HMG-CoA reductase |
| Oral Liquid | 1-250 mg/5 ml | 2-125 mg/5 ml | 5-100 mg/5 ml | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| | | | | Gln, Can, Tau, Djk, GABA, Cys, Dcy, Thr, and Sar | Ser, Hyp, Sar | | | |
| Pravastatin Preferred Forms | | All doses expressed as drug base | | | | | | lowers choloesterol concentration; inhibits HMG-CoA reductase |
| Oral Tab/Cap | 1-250 mg | 2-125 mg | 5-75 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly, & Lys | b, c, e, f, h, i, j, k, l, o, p | |
| Oral Liquid | 1-250 mg/5 ml | 2-125 mg/5 ml | 5-75 mg/5 ml | | | | | |
| Fluvastatin Preferred Forms | | All doses expressed as drug base | | | | | | lowers choloesterol concentration; inhibits HMG-CoA reductase |
| Oral Tab/Cap | 1-250 mg | 2-125 mg | 5-75 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Tyr, Gly & Lys | b, c, e, f, h, i, j, k, l, o, p | |
| Oral Liquid | 1-250 mg/5 ml | 2-125 mg/5 ml | 5-75 mg/5 ml | | | | | |
| Nadolol Preferred Forms | | All doses expressed as drug base | | | | | | treatment of angina pectoris and hypertension; β-adrenergic receptor antagonist |
| Oral Tab/Cap | 1-250 mg | 5-225 mg | 10-200 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Sar, Ser, & Pro | b, h, i, j, k, l, o, p | |
| Oral Liquid | 1-250 mg/5 ml | 5-225 mg/5 ml | 10-200 mg/5 ml | | | | | |
| Valsartan Preferred forms | | All Doses expressed as drug base | | | | | | treating hypertension, angiotension II antagonist |
| Oral Tab/Cap | 10-500 mg | 25-250 mg | 50-200 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Ser, Thr, Lys, Gly & Sar | b, f, i, j, k, l, o, p | |
| Oral Liquid | 10-500 mg/5 ml | 25-250 mg/5 ml | 50-200 mg/5 ml | | | | | |
| Methylphenidate Preferred Forms | | All doses expressed as drug base | | | | | | treatment of attention deficit disorders and narcolepsy |
| Oral Tab/Cap | 1-50 mg | 2-40 mg | 2.5-25 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Hyp, Sar, & Ser | a, b, c, h, j, k, l, o, p | |
| Oral Liquid | 1-50 mg/5 ml | 2-40 mg/5 ml | 2.5-25 mg/5 ml | | | | | |
| Trovafloxacin Preferred Forms | | All doses expressed as drug base | | | | | | antibiotic; inhibits bacteria such as E. coli, pseudomonas, aeruginosa, H. influenzae, |
| Oral Tab/Cap | 10-500 mg | 50-300 mg | 80-250 mg | Lys, Leu, Ile, Gly, Asp, Glu, Met, Ala, Val, Pro, His, Tyr, Ser, Nor, Arg, Phe, Trp, Hyp, Hsr, Car, | Lys, Leu, Ile, Gly, Asp, Glu, Met, Ala, Val, Pro, His, Tyr, Thr, Arg, Phe, Trp, | Lys, Gly, Ser, Pro, Hyp & Thr | a, b, e, h, j, k, o, p | |
| Oral Liquid | 10-500 mg/5 ml | 50-300 mg/5 ml | 80-250 mg/5 ml | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| | 5 ml | 5 ml | 5 ml | Ort, Cav, Asn, Gln, Can, Tau, Djk, GABA, Cys, Dcy, Thr, and Sar | Gln, Asn, Cys and Ser, Hyp, Sar | | | streptooccous, Klebsiella, staphylococcus, mycoplasma pneumoniae, peptostreptoccocus, prevotella; treatment of pneumonia, postsurgical infections; gynecolgic and pelvic infections, such as endomyometritis, parametritis, septic abortions, and post-partum infections; skin infections, e.g., diabetic foot infections |
| 5-AS* Preferred Forms | | All doses expressed as drug base | | | | | | treatment of tuberculosis |
| Oral Tab/Cap | 1-200 mg | 5-150 mg | 10-125 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Glu, Gly, Tyr & Lys | b, c, i, j, l, m, n, o, p, q | |
| Oral Liquid (* 5-Amino-Salicylic acid) | 1-200 mg/5 ml | 5-150 mg/ 5 ml | 10-125 mg/ 5 ml | | | | | |
| Methylprednisolone Preferred Forms | | All doses expressed as drug base | | | | | | treatment of inflammation especially from infections, tissue damage, allergy and auto-immune disease |
| IM Injection | 2-200 mg/ml | 5-150 mg/ml | 10-100 mg/ml | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Pro, Sar & Ser | b, c, g, j, l, m, n, o, p, q | |
| Topical Cream | 0.001-5% | 0.01-2.5% | 0.1-2% | | | | | |
| MedroxyProgesterone Preferred forms | | All Doses expressed as drug base | | | | | | providing contraception |
| IM Injections | 1 mg-4 gm/ml | 10 mg-2 gm/ml | 40 mg-1 gm/ml | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Pro, Sar & Ser | b, c, g, j, l, m, n, o, p, q | |
| Estramustine Preferred Forms | | All doses expressed as drug base | | | | | | treatment of cancer especially treatment of metastatic or progressive carcinoma of prostate |
| Oral Tab/Cap | 10-500 mg | 25-250 mg | 50-200 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, | Lys, Leu, Ile, Gly, Asp, Glu, Met, Ala, Val, Pro, His, Tyr, Thr, Arg, Phe, Trp, Gln, Asn, Cys and Ser, Hyp, Sar, | Gly, Lys, Pro, Ala, Sar & Val | b, c, h, i, j, k, l, o, p | |
| Oral Liquid | 10-500 mg/ 5 ml | 25-250 mg/ 5 ml | 50-200 mg/ 5 ml | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| Miglitol Preferred Forms | | All doses expressed as drug base | | Dcy, Thr, and Sar | | | | treatment of type II diabetes |
| Oral Tab/Cap | 1-250 mg | 2-150 mg | 10-125 mg | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Sar, Pro, & Ser | b, c, i, j, n, q | |
| Oral Liquid | 1-250 mg/5 ml | 2-150 mg/5 ml | 10-125 mg/5 ml | Dcy, Thr, and Sar | | | | |
| Mefloquine Preferred Forms | | All doses expressed as drug base | | | | | | treatment of malaria |
| Oral Tab/Cap | 10-500 mg | 100-400 mg | 150-300 mg | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Sar, Pro, Val, Ala | a, b, c, h, i, j, k, l, o, p, q | |
| Oral Liquid | 10-500 mg/5 ml | 25-400 mg/5 ml | 150-300 mg/5 ml | Dcy, Thr, and Sar | | | | |
| Danazol Preferred Forms | | All doses expressed as drug base | | | | | | treatment of endometriosis and fibrostatic breast disease |
| Oral Tab/Cap | 2-500 mg | 10-350 mg | 25-250 mg | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Hyp, Pro, Ala, Val, Ser & Thr | a, b, c, e, f, g, h, i, j, k, l, n, o, p, q | |
| Oral Liquid | 2-500 mg/5 ml | 10-350 mg/5 ml | 25-250 mg/5 ml | Dcy, Thr, and Sar | | | | |
| Eprosartan Preferred Forms | | All doses expressed as drug base | | | | | | ACE inhibitors, treatment of hypertension |
| Oral Tab/Cap | 0.1-1 gm | 200-800 mg | 300-750 mg | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, Gly & Val | b, c, h, i, j, k, l, o, p | |
| Oral Liquid | 0.1-1 gm/5 ml | 200-800 mg/5 ml | 300-750 mg/5 ml | Dcy, Thr, and Sar | | | | |
| Divalproex Na Preferred Forms | | All doses expressed as drug base | | | | | | treatment of epilepsy |
| Oral Tab/Cap | 50-800 mg | 75-750 mg | 100-600 mg | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, Gly, & Val | a, b, c, f, h, i, j, k, l, o, p | |
| Oral Liquid | 50-800 mg/5 ml | 75-750 mg/5 ml | 100-60 mg/5 ml | Dcy, Thr, and Sar | | | | |
| Fenofibrate Preferred Forms | | All doses expressed as drug base | | | | | | treatment of hypercholestemia |
| Oral Tab/Cap | 10-800 mg | 20-750 mg | 100-600 mg | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, Gly, & Ala | b, c, h, i, j, k, l, o, p, q | |
| Oral Liquid | 10-800 mg/5 ml | 20-750 mg/5 ml | 100-600 mg/5 ml | Dcy, Thr, and Sar | | | | |
| Gabapentin Preferred Forms | | All Doses expressed as drug base | | | | | | treatment of convulsions |
| Oral Tab/Cap | 10-800 mg | 25-750 mg | 50-500 mg | Lys, Leu, Ile, Gly, Asp, Glu, Met, Ala, Val, Pro, His, Tyr, Thr, Arg, Phe, Trp, | Lys, Leu, Ile, Gly, Asp, Glu, Met, Ala, Val, Pro, His, Tyr, Thr, Arg, Phe, Trp, | Cyclic Deriv. & Tyr | b, c, d, e, f, h, i, j, k, l, n, o, p, p | |
| Oral Liquid | 10-800 mg/5 ml | 25-750 mg/5 ml | 50-500 mg/5 ml | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
|  | 5 ml | 5 ml | 5 ml | Ort, Cav, Asn, Gln, Can, Tau, Djk, GABA, Cys, Dcy, Thr, and Sar | Gln, Asn, Cys and Ser, Hyp, Sar |  |  |  |
| Lansoprazole Preferred Forms |  | All doses expressed as drug base |  |  |  |  |  | suppression of gastric acid secretion by inhibition of (H+, K+) ATP-ase enzyme system at the secretory surface of the gastric parietal cell; treatment of gastric hyperacidity |
| Oral Tab/Cap | 1-60 mg | 2-50 mg | 10-40 mg | Lys, Leu, Ile, Gly, Asp, Glu, Met, Ala, Val, Pro, His, Tyr, Ser, Nor, Arg, Phe, Trp, Hyp, Hsr, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Pro, Sar, Ser & Val | b, e, f, h, i, j, k, l, o, p |  |
| Oral Liquid | 1-6-mg/5 ml | 2-50 mg/5 ml | 10-40 mg/5 ml |  |  |  |  |  |
| Omeprazole Preferred Forms |  | All doses expressed as drug base |  |  |  |  |  | suppression of gastric acid secretion by inhibition of (H+, K+) ATP-ase enzyme system at the secretory surface of the gastric parietal cell, treatment of gastric hyperacidity |
| Oral Tab/Cap | 1-200 mg | 2-100 mg | 5-60 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Val, Pro & Sar | b, e, f, h, i, j, k, l, o, p |  |
| Oral Liquid | 1-200 mg/5 ml | 2-100 mg/5 ml | 5-60 mg/5 ml |  |  |  |  |  |
| Megestrol Preferred Forms |  | All doses expressed as drug base |  |  |  |  |  | treatment of anorexia; improving appetite in anorexic and patients suffering from AIDS |
| Oral Tab/Cap | 2-100 mg | 4-80 mg | 20-60 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Sar, Pro, Ser & Ala | b, c, h, i, j, k, l, n, o, p |  |
| Oral Liquid | 2-100 mg/5 ml | 4-80 mg/5 ml | 20-60 mg/5 ml |  |  |  |  |  |
| Metformin Preferred Forms |  | All doses expressed as drug base |  |  |  |  |  | treatment of hyperglycemia; aids insulin to improve transport of glucose into cells |
| Oral Tab/Cap | 0.2-3 gm | 0.25-1.5 gm | 0.5-1 gm | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Asp, Glu, Lys & Azo dimer | o, p |  |
| Oral Liquid | 0.2-1 gm/5 ml | 0.25-1.5 mg/5 ml | 0.5-1 gm/5 ml |  |  |  |  |  |
| Tazarotene Preferred Forms |  | All doses expressed as drug base |  |  |  |  |  | treatment of psoriasis and acne especially those caused by pathogenic microorganisms, allergy and inflammation |
| Topical Gel | 0.01-0.3% | 0.02-0.25% | 0.025-0.125% | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, & Gly | B, c, h, I, j, k, l, o, p |  |
| Sumatriptan Preferred Forms |  | All Doses expressed as drug base |  |  |  |  |  | 5 HT subtype receptor agonist, treatment of migraine headaches |
| Oral Tab/Cap | 5-250 mg | 10-200 mg | 20-125 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Ala, Pro, Sar & Val | b, c, d, g, h, i, j, k, l, n, o, p, q |  |
| Oral Liquid | 5-250 mg/5 ml | 10-200 mg/5 ml | 20-125 mg/5 ml |  |  |  |  |  |
| IM Injections | 1-36 mg/ml | 2-24 mg/ml | 4-20 mg/ml |  |  |  |  |  |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| Naratriptan Preferred Forms | | All doses expressed as drug base | | | | | | 5 HT subtype receptor agonist; treatment of migraine headaches |
| Oral Tab/Cap | 0.1-10 mg | 0.25-5 mg | 0.5-4 mg | Lys, Leu, Ile, Gly, Asp, Glu, Met, Ala, Val, Pro, His, Tyr, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Sar, Val, Ala, & Pro | b, h, i, j, k, l, o, p | |
| Oral Liquid | 0.1-10 mg/ 5 ml | 0.25-5 mg/ 5 ml | 0.5-4 mg/ 5 ml | | | | | |
| Zolmitriptan Preferred Forms | | All doses expressed as drug base | | | | | | 5 HT subtype receptor agonist; treatment of migraine headaches |
| Oral Tab/Cap | 0.1-12 mg | 0.5-10 mg | 1-7.5 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Sar, Val, Ala, & Pro | b, h, i, j, k, l, o, p | |
| Oral Liquid | 1-12 mg/ 5 ml | 0.5-10 mg/ 5 ml | 1-7.5 mg/ 5 ml | | | | | |
| Aspirin Preferred Forms | | All doses expressed as drug base | | | | | | antipyretic, anti-inflammatory, analgesic, thrombolytic; treatment of hyperthermia, myocardial infarction and thrombolysis |
| Oral Tab/Cap | 10-1000 mg | 20-800 mg | 25-600 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, Gly, & Ala | a, b, c, e, f, g, h, j, k, l, m, n, o, p, q | |
| Oral Liquid | 10-1000 mg/ml | 20-800 mg/ml | 25-600 mg/ml | | | | | |
| Olmesartan Preferred Forms | | All doses expressed as drug base | | | | | | ACE inhibitor, treatment of hypertension |
| Oral Tab/Cap | 1-100 mg | 2-80 mg | 4-50 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, Gly, & Ala | b, h, i, j, k, l, o, p | |
| Oral Liquid | 1-100 mg/ 5 ml | 2-80 mg/ 5 ml | 4-50 mg/5 ml | | | | | |
| Sirolimus Preferred Forms | | All Doses expressed as drug base | | | | | | immunosuppressant in surgical human patients with transplants; antibiotic; treating vitiligo psoriasis, acne |
| Oral Tab/Cap | 0.1-20 mg | 0.5-10 mg | 1-8 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, Gly, & Ala | b, h, i, j, k, l, o, p | |
| Oral Liquid | 0.1-20 mg/ 5 ml | 0.5-10 mg/ 5 ml | 1-8 mg/5 ml | | | | | |
| IM Injections | | | | | | | | |
| Tacrolimus Preferred Forms | | All doses expressed as drug base | | | | | | immunosuppressant in surgical human patients with transplants; antibiotic; treating vitiligo psoriasis, acne |
| Oral Tab/Cap | 0.1-20 mg above/5 ml | 0.2-15 mg above/5 ml | 0.25-10 mg above/5 ml | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Ala, Thr, Sar & Pro | b, c, g, h, i, j, k, l, o, p | |
| Oral Liquid | | | | | | | | |
| IV Infusions | 1-20 mg/ml | 2-15 mg/ml | 2.5-8 mg/ml | | | | | |
| Pimecrolimus Preferred Forms | | All doses expressed as drug base | | | | | | immunosuppressant in surgical human patients with |
| Oral Tab/Cap | 0.1-20 mg | 0.2-15 mg | 0.25-10 mg | Lys, Leu, Ile, Gly, Asp, Glu, Met, Ala, Val, Pro, His, Tyr, Ser, Nor, Arg, | Lys, Leu, Ile, Gly, Asp, Glu, Met, Ala, Val, Pro, His, Tyr, | Lys, Gly, Ala, Thr, Sar & Pro | b, c, g, h, i, j, k, l, o, p | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| Oral Liquid | above/5 ml | above/5 ml | above/5 ml | Phe, Trp, Hyp, Hsr, Car, Orf, Cav, Asn, Gln, Can, Tau, Djk, GABA, Cys, Dcy, Thr, and Sar | Thr, Arg, Phe, Trp, Gln, Asn, Cys and Ser, Hyp, Sar | | | transplants; antibiotic treating |
| Ointment Cream | 0.01-10% | 0.1-5% | 0.5-2% | | | | | vitiligo psoriass, acne |
| Clopidogrel Preferred Forms | | All doses expressed as drug base | | | | | | treatment of myocardial infections |
| Oral Tab/Cap | 10-250 mg | 20-125 mg | 25-100 mg | | 25-100 mg | Ser, Hyp, Thr, Lys, Ala, & Gly | b, c, h, i, j, k, l, m, o, p, q | |
| Oral Liquid | 10-250 mg/ 5 ml | 20-125 mg/ 5 ml | 25-100 mg/ 5 ml | | 25-100 mg/5 ml | | | |
| Amphotericin B Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Orf, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, Ala, & Gly | b, c, g, i, j, l, m, n, o, p, q | treatment of fungus, especially those acting on cell membrane changing its permeability |
| IV Infusion | 0.5-20 mg/kg day | 1-15 mg/kg/ day | 2-10 mg/kg/ day | | | | | |
| Topical Cream | 0.01-10% | 0.1-5% | 0.5-2% | | | | | |
| Tenofovir Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Orf, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Ala, Pro, Ser & Sar | b, c, h, i, j, k, l, n, o, p | inhibitor of HIV virus, treatment of AIDS infections |
| Oral Tab/Cap | 10-900 mg | 50-750 mg | 100-500 mg | | | | | |
| Oral Liquid | 10-900 mg/ 5 ml | 50-750 mg/ 5 ml | 100-500 mg/ 5 ml | | | | | |
| Unoprostone Preferred Forms | | All Doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Orf, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Tyr, Pro, & Lys | b, c, h, i, j, k, l, n, o, p, q | treatment of glaucoma, especially caused by age; lowers intraocular pressure |
| Ocular Drops | 0.01-1% | 0.05-0.5% | 0.01-0.25% | | | | | |
| Fulvestrant Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Orf, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Pro, Ala, Val & Sar | B, c, g, j, l, o, p | treating cancer, especially breast cancer |
| IM Injection | 2-1250 mg/ 5 ml | 10-1000 mg/ 5 ml | 20-500 mg/ 5 ml | | | | | |
| Cefditoren Preferred Forms | | All doses expressed as drug base | | Lys, Leu, Ile, Gly, Asp, Glu, Met, Ala, Val, Pro, His, Tyr, Ser, Nor, Arg, Phe, Trp, Hyp, Hsr, Car, Orf, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Gly, Lys & Ala | b, c, h, i, j, k, l, o, p | antibiotics, especially inhibits H. influenzae; Haemophilus para-influenzae, streptoccoccus, Maraxella catarrhalis; treatment of bronchitis, |
| Oral Tab/Cap | 20-500 mg | 100-400 mg | 150-300 mg | | | | | |
| Oral Liquid | 20-500 mg/ 5 ml | 100-400 mg/ 5 ml | 150-300 mg/ 5 ml | | | | | |

TABLE 1-continued

| Amino Acid Derivatives of | Applicable Dose Range | Preferred Dose Range | Most Preferred Dose Range | Amino Acids that can be reacted with the drug to form the ster/amide/azo/anhydride derivatives | Preferred Amino Acids | Most Preferred Amino Acids | Improvements with derivatives utility immuno | Utility |
|---|---|---|---|---|---|---|---|---|
| Efavirenz Preferred Forms | | All doses expressed as drug base | | | | | | pharyngitis, tonsillitis, skin infections |
| Oral Tab/Cap | 0.2-1.2 gm | 300-800 mg | 400-750 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Pro, Ala, Sar, & Val | b, c, h, i, j, k, l, o, p | inhibitor of HIV-1 specific, non-nucleoside, reverse transcriptase; treatment of AIDS infections |
| Oral Liquid | 0.2-1.2 gm/ 5 ml | 300-800 mg/ 5 ml | 400-750 mg/ 5 ml | | | | | |
| Eplerenone Preferred Forms | | All doses expressed as drug base | | | | | | treatment of hypertension, blocks binding of aldosterone to mineralo-corticoid receptors |
| Oral Tab/Cap | 10-250 mg | 15-200 mg | 20-150 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Ser, Hyp, Thr, Lys, Gly & Val | b, c, h, i, j, k, l, o, p | |
| Oral Liquid | 10-250 mg/ 5 ml | 15-200 mg/ 5 ml | 20-150 mg/ 5 ml | | | | | |
| Treprostinil Preferred Forms | | All Doses expressed as drug base | | | | | | Inhibits platelet aggregation and vasodilation of systemic and pulmonary vascular bed, treatment of cardiovascular related conditions |
| SC infusion | 0.1-100 mg/ml | 0.2-50 mg/ml | 0.5-20 mg/ml | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Gly, Lys, Val, Hyp, Thr & Ser | b, c, g, h, i, j, k, l, o, p | |
| Oral Tab/Cap | 10-1000 mg | 20-800 mg | 25-500 mg | | | | | |
| Adefovir Preferred Forms | | All doses expressed as drug base | | | | | | HIV reverse transcriptase inhibitors; treatment of HIV infections and AIDS |
| Oral Tab/Cap | 1-100 mg | 2-50 mg | 5-20 mg | Lys, Leu, Ile, Gly, Asp, Glu, Met, Ala, Val, Pro, His, Tyr, Ser, Nor, Arg, Phe, Trp, Hyp, Hsr, Car, Ort, Cav, Asn, Gln, Can, Tau, Djk, GABA, Cys, Dcy, Thr, and Sar | Lys, Leu, Ile, Gly, Asp, Glu, Met, Ala, Val, Pro, His, Tyr, Thr, Arg, Phe, Trp, Gln, Asn, Cys and Ser, Hyp, Sar | Lys, Gly, Val, Ser, Hyp, & Pro | b, c, h, i, j, k, l, o, p | |
| Oral Liquid | 1-100 mg/ 5 ml | 2-50 mg/ 5 ml | 5-20 mg/ 5 ml | | | | | |

Above table is not exhaustive, and not final. Inventor has given examples of certain drugs and proposed compostions and dosages, and route of administration. However, above table is typical and does not constraint the scope of this invention.

As used herein, the term "amino acid derivative" or "drug derivative" and like terms refer to the drug bonded to an amino acid residue. In addition, as used herein, the term L-amino acid refers to an amino acid wherein the asymmetric carbon atom attached to the amino and the carboxy group is in the L-configuration. For purpose of this specification, it also includes glycine.

As indicated hereinabove, the amino acid derivatives of the present invention have the same utility as the underlying drug which is not bonded to the amino acid moiety. The amino acid derivative of the present invention possesses at least one enhanced quality identified hereinabove relative to the same drug without the amino acid linkage.

Without wishing to be bound it is believe that the amino acid derivatives of the present invention is the active agent in vivo. Alternatively, the amino acid moiety may be cleaved off in vivo, thereby making the active agent the drug itself in vivo. Alternatively, a combination of both may occur in vivo. However, whichever happens in vivo, when the amino acid derivative of the present invention is administered to a patient, at least one of the improved qualities enumerated hereinabove relative to the drug without the amino acid linkage is realized.

The following non-limiting examples further illustrate the invention:
Synthesis of Various Amino Acid Derivatives of Selected Drugs
I. Propofol Derivatives Propofol (2,6-diisopropylphenol) is a low molecular weight phenol which widely used as a central nervous system anesthetic, and posses sedative and hypnotic activities. It is administered intravenously in the induction and maintenance of anesthesia and/or sedation in mammals. The major advantages of Propofol are that it can induce anesthesia rapidly, minimal side effects and upon withdrawal, the patient recovers quickly without prolonged sedation.

Propofol

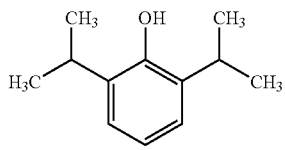

Propofol has been shown to have a large number of therapeutic applications, which are quite varying and somewhat surprising. For example, it has been shown to be an effective antioxidant, anti-emetic, anti-pruritic, anti-epileptic, anti-inflammatory, and even seems to possess anti-cancer properties.
Mechanism of Action:

The mechanism of action of Propofol has been extensively studied. Its central nervous system anesthetic activity has been shown to be related its high affinity for a specific sub-class of GABA receptors (Collins G. G. S., 1988, Br. J. Pharmacology. 542, 225-232). However, there are a number of different receptors in the brain which are substrates for propofol, hence its varied activities.

Propofol also has significant biological effect as an antioxidant. Because of this generalized activity of propofol, it is theoretically useful in the treatment of a number of inflammatory processes where oxidation is an important factor. For example, cyclooxygenase mediated prostaglandin synthesis results in inflammation. By inhibiting oxidation in the respiratory tract, one could use propofol in the treatment of acid aspiration, adult/infant respiratory distress syndrome, airway obstructive diseases, asthma, cancer and a number of other similar pathological conditions.

Since oxidative tissue damage is a very common occurrence, it has been suggested that propofol is useful in the treatment of Parkinson's disease, Alzheimer disease, Friedrich's disease, Huntington's disease, multiple sclerosis, amyotrophic lateral sclerosis, spinal chord injuries, and various other neurodegenerative diseases.

Propofol is currently available in the US market as an intravenous emulsion marketed by Astra Zenaca under the brand name Diprivan®. It is one the most widely used short acting central nervous system anesthetics in the market. The concentration of propofol is 10 mg/mL in non-pyrogenic sterile emulsion and the formula contains soybean oil, glycerol, egg lecithin, disodium edetate and sodium hydroxide.

A significant disadvantage of Propofol is that it is completely insoluble in water. Even at very low concentrations of 10 mg/mL, the drug precipitates out of an aqueous solution in room temperature. Therefore, manufacturers of this formulation use heroic methods to emulsify this product in water using extraordinarily complex and toxic emulsifying agents. For example, manufacturers of the IV formulations use egg lecithin, Cremaphor L®, castor oil, and other similar emulsifiers.

However, use of such emulsifiers is associated with number of problems. It is well known that various types of Cremaphor L® emulsifiers can precipitate allergic reactions. Egg lecithin and castor oil have been shown to produce anaphylactic shock in some patients. Furthermore, maintenance of stability of propofol in these emulsions is short lived and more expensive. Moreover, the presence of egg lecithin and castor oil make the emulsion prone to microbial growth. It may be possible to dissolve propofol in water by complexing it with cyclodextrin, but cyclodextrin has not been approved by the FDA for use in intravenous therapy.

Heretofore, no one has made a safe derivative of propofol. The British patents 1,102,011, and 1,160,468 and U.S. Pat. No. 3,389,138 describe the various phenol esters of amino acids, wherein the propofol is attached to a number of side chains which when released in the body produce toxic effects.

U.S. Pat. No. 6,451,854 describe a number of substituted alpha amino acetic acid esters of propofol, wherein propofol and the side chain were substituted with a number of different chemical groups. All the N,N-disubstituted glycine esters of propofol have not shown to be non-toxic and many of the compounds described are derivative of propofol. Thus when released in the body after the cleavage of ester by the enzymes, many of the active drugs released are not propofol, and hence they do not possesses any toxicity data and are entirely new molecules with unknown therapeutic efficacy in man.

In a published paper on the water soluble salts of amino acid esters of the anesthetic agent propofol, (Int. J. Pharmaceutics, 175[2]: 195-204, 1998) authors have synthesized a number of water soluble derivatives of propofol. However, when these derivatives are cleaved by esterase enzymes, substituted non-natural amino acids with unknown toxicity profile are released in the body.

Until now there has been no pharmaceutical preparation available in the market that can deliver propofol without harmful side effects. The present inventor has produced a number of water soluble, non-toxic derivatives of propofol which are suitable for delivering propofol in the body without any harmful side effects and without the needs for toxic and expensive additives, solubilizers and emulsifiers.

Accordingly, in one aspect, the present invention is directed to a class of derivatives of Propofol. The derivative consists of the carboxyl group of an amino acid esterified to the free hydroxyl group present on the propofol molecules.

More specifically, one aspect of the present invention is directed to, the compounds of the formula:

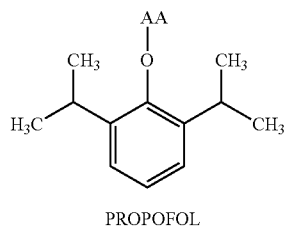

PROPOFOL or pharmaceutically acceptable salts thereof; wherein AA is an amino acid, in which the carboxyl group of AA is reacted with the hydroxyl group of the Propofol.

In another aspect, the present invention is also directed to a pharmaceutical composition comprising a therapeutically effective amount of the various Propofol amino acid derivatives especially Proline Ester drugs and a pharmaceutical carrier therefor. Preferred amino acid derivatives are indicated in Table I.

In another embodiment, the present invention is directed to a method of treating a patient in need of propofol therapy, which method comprises administering to said patient an effective amount of the Propofol.

In a further embodiment, the present invention is directed to a method of enhancing the solubility of propofol in an aqueous solution comprising reacting the hydroxyl functionality of the Propofol with a amino acid, especially a naturally occurring amino acid, and isolating the product thereof.

In a still further embodiment, the present invention is directed to a method of substantially and in a therapeutically efficacious manner, reducing or eliminating the potential toxic side effects of current formulations containing toxic excipients when administered to a patient which comprises reacting the hydroxyl functionality of the propofol molecule with carboxyl function of the amino acid, especially the preferred and most preferred amino acids depicted in Table I, to form an ester covalent bond respectively and isolating the product thereof and administering said product to the patient.

Moreover, the inventor has discovered that when unsubstituted naturally occurring amino acids are esterified to propofol, the resulting derivatives are highly water soluble, (>200 mg/L in water), release non-toxic amino acids upon cleavage in the body and require none of the toxic emulsifier, additives and other excipients.

Furthermore, the inventor has found that the amino acid derivatives of propofol of the present invention are highly effective central nervous system anesthetics. Thus the current amino acid derivatives are effective central nervous system anesthetics, with or without releasing the active parent drug.

The amino acid esters of the present invention are at least 10 times more soluble that propofol in water in room temperature. Especially the glycine, proline and lysine esters of propofol are soluble at the range of more than 100 mg/ml, and in case of lysine it is greater than 250 mg/mL.

The amino acid derivatives of the present invention are not expected to possess any antioxidant activity due to blockage of the phenolic group responsible for such; however the present inventor has found that the amino acid derivatives of propofol are effective anesthetics with or without releasing propofol. Further, the Propofol Proline Ester drugs described, when administered in vivo, maintains its pharmacological and anti-oxidant properties.

The amino acid derivative of propofol of the present invention clearly provides a number of advantages over propofol, for example, all of the side chains cleaved from these derivatives are naturally occurring essential amino acids and hence are non-toxic. This results in high therapeutic index. Secondly the derivatives are readily cleaved in the body to release propofol, however, if not cleaved the amino acid derivatives exhibit the same utility. Furthermore, due to their high water solubility, they can be easily administered by either forming an in-situ solution just before IV administration using lyophilized sterile powder or providing the drug in solution in prefilled syringe or bottles for infusion. The amino acid esters are more stable than propofol since OH group in propofol is blocked thereby prevents oxidation. For example, the Propofol Proline Ester drugs of the present invention are more effective then propofol itself without the toxicity and other pharmaceutical problems associated with current marketed formulations.

The amino acid derivatives of propofol of the present invention possess anti-inflammatory, anti-oxidant, anti-cancer, anti-convulsive, anti-emetic and anti-pruritic properties.

These derivatives of propofol of the present invention are effective in treating diseases or conditions in which Propofol normally are used. The derivatives disclosed herein may or may not be transformed within the body to release the active compound, and can enhance the therapeutic benefits of the Propofol moiety by reducing or eliminating biopharmaceutical and pharmacokenetic barriers associated with each of them. However it should be noted that these derivatives themselves will have sufficient activity without releasing any active drug in the mammals. Since the derivatives are more soluble in water then Propofol, it does not need to be associated with a carrier vehicle, such as alcohol or castor oil which may be toxic or produce unwanted side reactions. Moreover, oral formulations containing the derivatives of Propofol are absorbed into the blood and are quite effective.

Thus, the amino acid derivative of the present invention, e.g., the amino acid derivative of propofol, enhances the therapeutic benefits by removing biopharmaceutical and pharmacokenetic barriers of existing drugs.

Furthermore, the amino acid derivatives, e.g., the amino acid derivatives of propofol, are easily synthesized in high yields using reagents which are readily and commercially available.

Overview:

The procedure for the synthesis of the glycine, L-proline, and L-lysine esters of Propofol is depicted hereinbelow. However, these are exemplary and any amino acid derivative thereof can be prepared using the following methodology. The complete procedure and analytical data is given in the Experimental Section. In general, as shown in the following scheme Propofol (10 g) was coupled with the N-Boc protected amino acid (1 equivalent) in the presence of 1-(3-dimethylaminopropyl)-3-ethylcarbodiimide, hydrochloride (EDC) in the presence of a catalytic amount of 4-(N,N-dimethyamino)-pyridine (DMAP). The EDC was removed by extraction with water. After drying over sodium sulfate, filtration, and concentration thereof, the crude protected amino acid ester of Propofol was purified by flash chromatography to generate the protected esters in 50-60% yield. The protecting groups were then removed by stirring the protected esters in diethyl ether saturated with hydrochloric acid (gas) at room temperature. Yields for the deprotection step were generally 60-95%. After filtration and drying the hydrochloride salts of the glycine and L-proline esters of Propofol did not require additional purification. The hydrochloride salt of the L-lysine-Propofol ester was crystallized once from ethanol to remove a trace of mono-protected L-lysine-Propofol ester.

Synthetic Sequence:

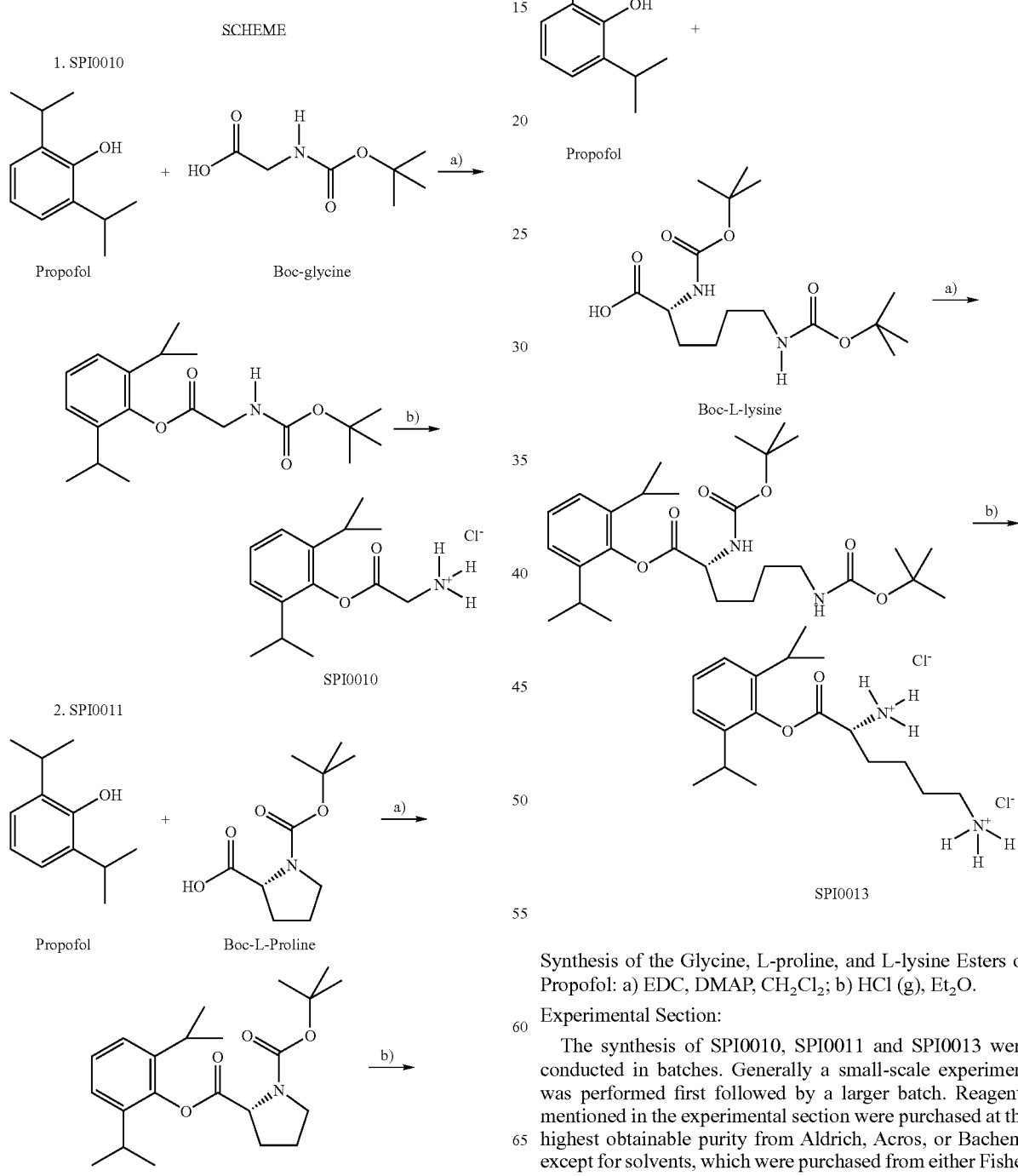

Synthesis of the Glycine, L-proline, and L-lysine Esters of Propofol: a) EDC, DMAP, $CH_2Cl_2$; b) HCl (g), $Et_2O$.

Experimental Section:

The synthesis of SPI0010, SPI0011 and SPI0013 were conducted in batches. Generally a small-scale experiment was performed first followed by a larger batch. Reagents mentioned in the experimental section were purchased at the highest obtainable purity from Aldrich, Acros, or Bachem, except for solvents, which were purchased from either Fisher Scientific or Mallinkrodt.

1) SPI0010

Propofol (9.98 g, 55.97 mmole) was dissolved in dichloromethane (200 mL) at room temperature, under an argon atmosphere. N-t-Butyloxocarbonyl-glycine (11.2 g, 63.91 mmole) was added along with 1-(3-dimethylaminopropyl)-3-ethylcarbodiimide, hydrochloride (EDC, 11.1 g, 57.9 mmole) and 4-(N,N-dimethylamino)-pyridine (DMAP, 1.5 g, 12.27 mmole). After stirring for 21 hours under an argon atmosphere at room temperature, water (200 mL) was added and the layers were separated. The dichloromethane layer was washed with water (200 mL) and dried for 1 hour over sodium sulfate (5 g). After filtration and concentration under reduced pressure, the remaining oil was purified by flash chromatography on silica gel (250 g), eluting with hexanes/ethyl acetate (10:1). The procedure generated the protected N—BOC protected glycine ester of Propofol as a white solid (11.34 g, 60% yield).

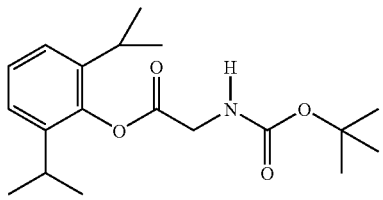

tert-Butoxycarbonylamino-acetic acid
2,6-diisopropylphenyl ester $^1$H NMR (300 MHz, CDCl$_3$): δ=7.25-7.13 (m, 3H), 5.18 (br s, 1H), 4.22 (d, 2H, J=5.7 Hz), 2.89 (m, 2H), 1.46 (s, 9H), 1.18 (d, 12H, J=6.9 Hz).

$^{13}$C NMR (75 MHz, CDCl$_3$): δ=169.35, 155.75, 145.22, 140.35, 126.90, 124.14, 80.32, 42.66, 28.54, 27.79, 23.57.

The Propofol-Boc-glycine ester (11.28 g, 33.6 mmole) was dissolved in anhydrous diethyl ether (200 mL) at room temperature. Hydrochloric acid (gas) was passed through the solution for 45 minutes while stirring. The mixture was allowed to stir at room temperature for 48 hours under an argon atmosphere. After 48 hours hexanes (200 mL) were added and the precipitate was filtered. The white solid was dried under high vacuum for 5 hours at 88° C. The experiment produced SPI0010 (8.73 g, 95% yield, purity 99.9% by HPLC) as a white solid.

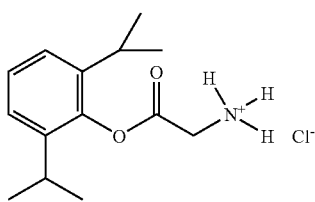

SPI0010

Amino-acetic acid 2,6-diisopropyl-phenyl ester, hydrochloride $^1$H NMR (300 MHz, CDCl$_3$): δ=8.77 (br s, 3H), 7.20-7.08 (m, 3H), 4.14 (m, 2H), 2.87 (m, 2H), 1.11 (d, 12H, J=7 Hz).

$^{13}$C NMR (75 MHz, CDCl$_3$): δ=166.42, 144.84, 140.42, 127.10, 124.06, 40.47, 27.61, 23.55.

CHN Analysis:
calc.: C, 61.87; H, 8.16; N, 5.15. found: C, 61.14; H, 8.20; N, 5.14.

2) SPI0011

Propofol (10.03 g, 56.23 mmole) was dissolved in dichloromethane (100 mL) at room temperature, under an argon atmosphere. N-t-Butyloxocarbonyl-L-proline (14.04 g, 65.22 mmole) was added along with 1-(3-dimethylaminopropyl)-3-ethylcarbodiimide, hydrochloride (EDC, 11.95 g, 62.33 mmole) and 4-(N,N-dimethylamino)-pyridine (DMAP, 1.1 g, 9.0 mmole). After stirring for 3 hours under an argon atmosphere at room temperature, water (100 mL) was added and the layers were separated. The dichloromethane layer was washed again with water (100 mL) and dried for 1 hour over sodium sulfate (5 g). After filtration and concentration under reduced pressure, the remaining oil was purified by flash chromatography on silica gel (250 g), eluting with hexanes/ethyl acetate (10:1). The procedure generated the protected N—BOC protected L-proline ester of Propofol as a clear oil (11.34 g, 66% yield) that solidified on standing in the freezer.

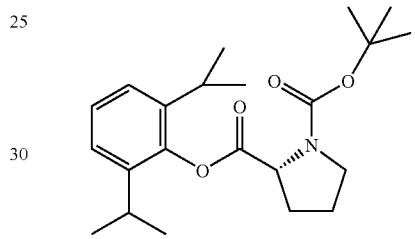

Pyrrolidine-1,2-dicarboxylic acid 1-tert-butyl ester
2-(2,6-diisopropyl-phenyl)ester $^1$H NMR (300 MHz, CDCl$_3$): δ=7.31-7.20 (m, 3H), 4.73 (m, 1H), 3.70-3.50 (m, 2H), 3.20-2.94 (m, 2H), 2.46-2.20 (m, 2H), 2.20-2.0 (m, 2H), 1.55 (m, 9H), 1.25 (m, 12H).

$^{13}$C NMR (75 MHz, CDCl$_3$): δ=171.87, 171.01, 154.34, 153.93, 145.35 145.23, 140.06, 140.21, 126.69, 126.53, 123.95, 80.28, 79.89, 59.14, 46.67, 46.42, 31.10, 30.17, 28.61, 28.56, 28.56, 27.44, 27.18, 23.47.

The Propofol-Boc-L-proline ester (13.95 g, 37.14 mmole) was dissolved in anhydrous diethyl ether (100 mL) at room temperature. Hydrochloric acid (gas) was passed through the solution for 60 minutes while stirring. The mixture was allowed to stir at room temperature for 22 hours under an argon atmosphere. After 22 hours, hexane (50 mL) was added and the precipitate was filtered. The white solid was dried under high vacuum for 5 hours at 88° C. The experiment produced SPI0011 (9.1 g, 81% yield, purity 99.1% by HPLC) as a white solid.

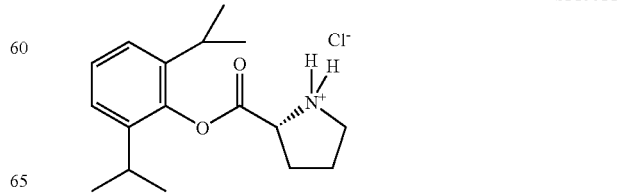

SPI0011

Pyrrolidine-2(S)-carboxylic acid 2,6-diisopropyl-phenyl ester, hydrochloride $^1$H NMR (300 MHz, CDCl$_3$): δ=10.15 (br s, 2H), 7.27-7.14 (m, 3H), 4.78 (t, 1H, J=7.8 Hz), 3.56 (m, 2H), 2.85 (m, 2H), 2.64 (m, 1H), 2.40 (m, 1H), 2.20 (m, 1H), 2.05 (m, 1H), 1.18 (m, 12H).

$^{13}$C NMR (75 MHz, CDCl$_3$): δ=168.30, 144.23, 139.74, 126.98, 123.96, 51.58, 38.21, 29.32, 26.64, 26.18, 23.71, 23.02, 21.67.

CHN Analysis:
calc.: C, 65.48; H, 8.40; N, 4.49. found: C, 65.50; H, 8.43; N, 4.50.

3) SPI0013

The dicyclohexylamine salt of di-N-boc-L-lysine (23.62 g, 0.0447 mole) was added to diethyl ether (200 mL) and potassium hydrogen sulfate (9.14 g) in water (200 mL) that was cooled in an ice/water bath. After stirring for 20 minutes, the layers were separated. The ether layer was extracted three times with cold water (100 mL). The ether layer was then dried over sodium sulfate (15 g) for one hour, filtered, and concentrated under reduced pressure. The procedure generated the free acid of N,N'-di-boc-L-lysine (15.5 g, 100% recovery).

Propofol (8.0 g, 45 mmole) was dissolved in dichloromethane (100 mL) at room temperature, under an argon atmosphere. N,N'-di-t-Butyloxocarbonyl-L-lysine (15.5 g, 44.7 mmole) was added along with 1-(3-dimethylaminopropyl)-3-ethylcarbodiimide, hydrochloride (EDC, 8.62 g, 45 mmole) and 4-(N,N-dimethylamino)-pyridine (DMAP, 0.55 g, 4.5 mmole). After stirring for 3 hours under an argon atmosphere, water (100 mL) was added and the layers were separated. The dichloromethane layer was washed again with water (100 mL) and dried for 1 hour over sodium sulfate (5 g). After filtration and concentration under reduced pressure, the remaining oil was purified by flash chromatography on silica gel (250 g), eluting with hexanes/ethyl acetate (9:1). The procedure generated the protected N—BOC protected L-lysine ester of Propofol as a white foam (12.42 g, 55% yield).

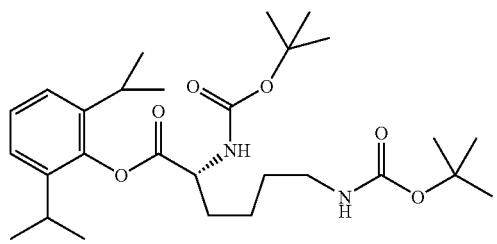

2(S),6-Bis-t-butoxycarbonylamino-hexanoic acid 2,6-diisopropyl-phenyl ester $^1$H NMR (300 MHz, CDCl$_3$): δ=7.28-7.15 (m, 3H), 5.22 (d, 1H, J=8.4 Hz), 4.70 (m, 1H), 4.59 (m, 1H), 3.17 (m, 2H), 2.93 (m, 2H), 2.09 (m, 1H), 1.86 (m, 1H), 1.67-1.54 (m, 4H), 1.48 (s, 9H), 1.46 (s, 9H), 1.20 (m, 12H).

$^{13}$C NMR (75 MHz, CDCl$_3$): δ=171.82, 156.10, 155.65, 145.25, 140.30, 126.80, 124.03, 80.14, 79.28, 53.76, 40.29, 32.09, 28.66, 28.54, 27.48, 23.91, 23.10.

The Propofol-di-Boc-L-lysine ester (12.34 g, 24.37 mmole) was dissolved in anhydrous diethyl ether (250 mL) at room temperature. Hydrochloric acid (gas) was passed through the solution for 60 minutes while stirring and cooling in an ice/water bath. The mixture was allowed to stir at room temperature for 48 hours under an argon atmosphere. After 48 hours the precipitate was filtered and crystallized from ethanol (100 mL). The white solid was dried under high vacuum for 4 hours at 90° C. The experiment produced SPI0013 (5.5 g, 60% yield, purity 98.6% by HPLC) as a white solid.

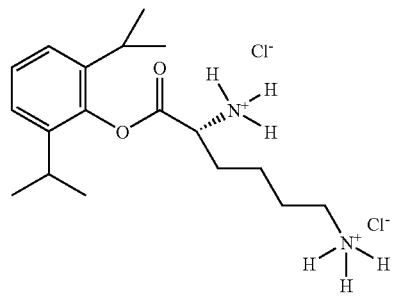

SPI0013

2(S),6-Diamino-hexanoic acid 2,6-diisopropyl-phenyl ester, dihydrochloride $^1$H NMR (300 MHz, CDCl$_3$): δ=9.05 (br s, 3H), 8.35 (br s, 3H), 7.26-7.13 (m, 3H), 4.43 (t, 1H, J=6 Hz), 3.0-2.6 (m, 4H), 2.09 (m, 2H), 1.80-1.50 (m, 4H), 1.10 (d, 12H, J=7 Hz).

$^{13}$C NMR (75 MHz, CDCl$_3$): δ=168.30, 144.23, 139.74, 126.98, 123.96, 51.58, 38.21, 29.32, 26.64, 23.71, 23.02, 21.67.

CHN Analysis:
calc.: C, 56.99; H, 8.50; N, 7.38. found: C, 56.48; H, 8.56; N, 7.30.

Anasthetic Effect in Male Albino Mice for Derivatives of Propofol

The present study was conducted to evaluate the efficacy of new formulations of propofol injection using righting reflex as an index in albino mouse. Propofol injection served as reference control. Male albino mice were exposed to propofol injection and to 3 new formulations of propofol at 3 dose levels—low, intermediate and high dose levels. However the doses of low, intermediate and high for different formulations and reference control were different.

The different doses for each formulation and reference control were selected based on the recommendation of Sponsor. All the doses were expressed as propofol molar equivalents. The doses used for the main experiment for different formulations and reference control were presented below.

TABLE 2

| Test Item | Low Dose (mg/kg) | Intermediate Dose (mg/kg) | High Dose (mg/kg) |
|---|---|---|---|
| Propofol Lysine Ester | 40.0 | 45.0 | 50.0 |
| Propofol Glycine Ester | 30.0 | 35.0 | 40.0 |
| Propofol Proline Ester | 25.0 | 30.0 | 35.0 |
| Propofol Injection (Reference control) | 10.0 | 15.0 | 20.0 |

Efficacy (Anesthetic Property)

The efficacy in terms of time required to regain the righting reflex at different dose levels—low, intermediate and high dose for different formulations and propofol injection are presented below.

TABLE 3

|  | Low Dose | Intermediate Dose | High Dose |
|---|---|---|---|
| Formulation 1 | 0.00 ± 0.00 | 0.00 ± 0.00 | 546.00 ± 0.00 |
| Formulation 2 | 532.10 ± 217.61 | 299.80 ± 211.32 | 641.00 ± 137.86 |
| Formulation 3 | 282.00 ± 162.09 | 421.70 ± 112.92 | 237.25 ± 197.47 |
| Propofol injection (Reference control) | 20.20 ± 43.42 | 123.40 ± 33.70 | 177.70 ± 70.31 |

All doses produced statistically significant results at $p < 0.05$.

Low Dose

Propofol Glycine Esterl was found to be more effective followed by formulation 3 and reference control. Formulation 1 did not show any anesthetic effect.

No mortality was observed at low dose level with different formulations or propofol injection.

Intermediate Dose

Propofol Proline Ester ester was found to be more effective followed by Propofol Glycine Esterl and reference control. Propofol lysine ester did not show any anesthetic effect.

High Dose

Propofol Glycine Esterl was found to be more effective followed by propofol lysine ester, Propofol Proline Esterraline ester and reference control.

Dose Response Relation

Propofol Lysine Ester

The statistical analysis showed a significant improvement at 5% significance level in the relative efficacy for the high dose when compared to low dose group.

Propofol Glycine Ester

The responses to the dose levels were not statistically evident from the analysis, though the comparisons showed significance at 5% level for mid dose to low dose.

Propofol Proline Ester

No significant dose—response effects were evident from the statistical analysis.

Propofol Injection (Reference Control)

For reference control group, the dose response effect were statistically significant and clearly evident.

In conclusion, it was observed that based on the time required to regain the righting reflex, Propofol Glycine Ester and the lysine ester have relatively better efficacy than the other two derivatives (Propofol Proline ester and the drug) in inducing anesthesia in albino mice.

14-Day Chronic Toxicity Studies in Albino Mice Using Propofol Glycine Ester and Proline Ester:

The present study was conducted to evaluate the relative safety of the two new formulations of Propofol injection Propofol Glycine Ester Propofol Proline Ester by conducting a 14 day repeated dose toxicity study through intravenous route using albino mice as test system. Propofol injection served as reference control.

Propofol and its derivatives above were administered to albino mice (Swiss strain), through intravenous route daily for a period of 14 days using sterile sodium chloride solution as vehicle. The study was conducted at one dose level only along with a vehicle control group as per the recommendation of the Sponsor.

The doses used in the present study for the two amino acid ester and Propofol injection were different and presented below. The doses were selected as per the recommendation of the Sponsor. The test doses are expressed as Propofol molar equivalents.

TABLE 4

| Test Item | Group | Dose [in terms of Propofol] (mg/kg) | Equivalent weight of the Test item [mg/kg] |
|---|---|---|---|
| Vehicle | Vehicle Control | 0.0 | 0.0 |
| (Propofol Glycine Ester) | Test Group 1 | 30.0 | 45.60 |
| (Propofol Proline Ester) | Test group 2 | 25.0 | 43.75 |
| Propofol injection | Reference Control | 15.0 | 15.00 |

The salient features of the study are as follows:

1. All the animals of control and the test group 1 (Propofol Glycine Ester), test group 2 (Propofol Proline Ester) and reference control group (Propofol Injection) survived through the dosing period of 14 days.
2. None of the animals of the vehicle control and the test group 1 (Propofol Glycine Ester), test group 2 (Propofol Proline Ester) and Reference Control (Propofol Injection) group exhibited any clinical symptoms of toxicity. However animals dosed with the amino acid esters of Propofol or reference control showed anesthetic effect immediately after dosing. This effect was attributed to the pharmacological property of the amino acid esters or reference control.
3. Body weight gain of animals of test group 2 (Propofol Proline Ester) and reference control (Propofol Injection) was found to be normal and comparable to that of vehicle control group of animals. However, the body weight gain was reduced in both the sexes of test group 1 (Propofol Glycine Ester). Males and females of test group 1 (Propofol Glycine Ester) showed a reduced body weight gain of 25.87% and 26.94% respectively compared to vehicle control group animals.
4. Feed intake of the animals of test group 1 (Propofol Glycine Ester), test group 2 (Propofol Proline Ester) and reference control (Propofol injection) was found to be normal and comparable to that of vehicle control group.
5. Results of hematological analysis revealed the following changes in the animals of different groups when compared to reference control.

Propofol Glycine Ester

The granulocytes counts significantly increased [$p<0.05$] in female animals of Propofol Glycine Ester when compared to the female animals of Propofol injection (RC).

The MCV significantly decreased [$p<0.05$] in female animals of Propofol Glycine Ester when compared to the female animals of Propofol injection (RC).

Propofol Proline Ester

The granulocytes significantly decreased [$p<0.05$] in male animals of Propofol Proline Ester when compared to the male animals of Propofol injection (RC).

The lymphocytes counts significantly increased [$p<0.05$] in male animals of Propofol Proline Ester when compared to the male animals of Propofol injection (RC).

The MCV significantly decreased [$p<0.05$] in female animals of Propofol Proline Ester when compared to the female animals of Propofol injection (RC).

Vehicle Control

The lymphocytes counts significantly increased [$p<0.05$] in male and female animals of vehicle control when compared to the male and female animals of Propofol injection (RC).

6. Results of clinical chemistry analysis revealed the following changes in the animals of different groups when compared to reference control.

Propofol Proline Ester

The level of urea significantly decreased [p<0.05] in female animals of Propofol Proline Ester when compared to the female animals of Propofol injection (RC).

The level of sodium significantly increased [p<0.05] in male animals of Propofol Proline Ester when compared to the male animals of Propofol injection (RC).

Vehicle Control

The cholesterol level significantly decreased [p<0.05] in female animals of vehicle control when compared to the female animals of Propofol injection (RC).

Thus the results the present study showed that the behavior of animals, body weight gain (except in male and female animals of Propofol Glycine Ester)

feed consumption,

Organ weights (absolute and relative)

histopathology of different organs of the animals treated with Propofol Glycine Ester and Propofol Proline Ester were found to be normal and comparable to that of the animals of the reference group.

II. Amino Acid Derivatives of Non-Steroidal Anti-Inflammatory Drugs (NSAIDs)

The NSAIDs comprise a class of structurally distinctive carboxylic acid moiety attached to a planar aromatic functionality. Examples include: acetyl salicyclic acid, salicyclic acid, diflunisal, ibuprofen, fenoprofen, carprofen, flurbiprofen, ketoprofen, naproxen, sulindac, indomethacin, etodolac, tolmetin, ketorolac, diclofenac, and meclofenarnate. The NSADIs posess anti-inflammatory, analgesic, antipyretic and anti-clotting activity.

Examples of the chemical structures of this uniques class of compounds showing wide variety of pharmacological activities are shown below.

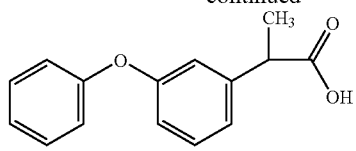

Salicylic Acid     Acetylsalicylic Acid

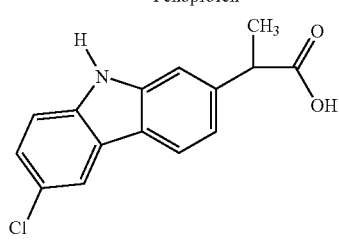

Diflunisal

Ibuprofen

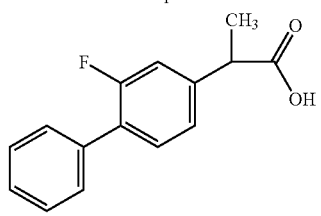

Fenoprofen

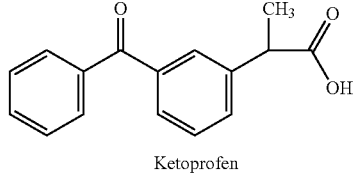

Carprofen

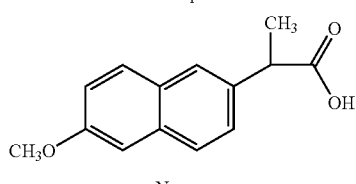

Flurbiprofen

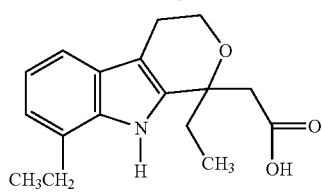

Ketoprofen

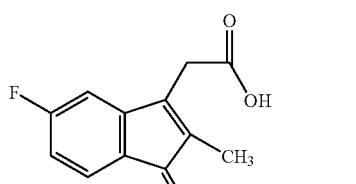

Naproxen

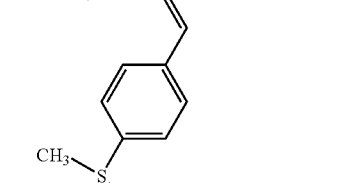

Etodolac

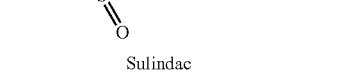

Sulindac

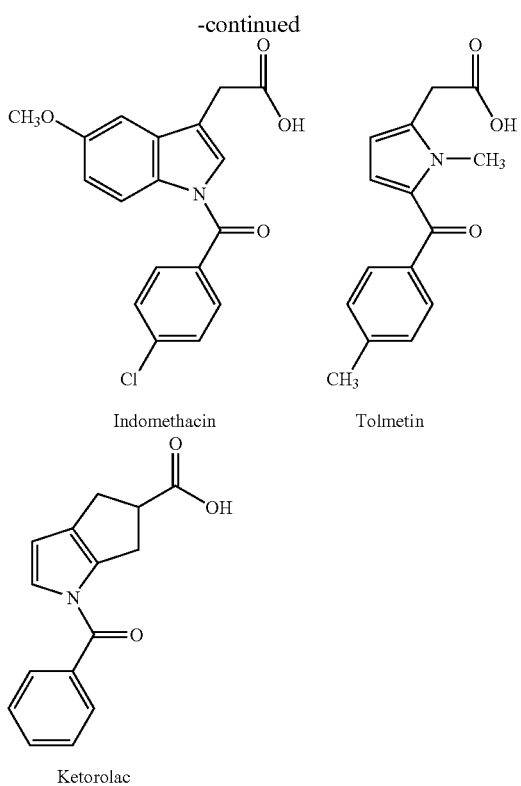

Indomethacin   Tolmetin

Ketorolac

NSAIDs are widely used for the treatment of acute and chronic pain, management of edema, tissue damage resulting from inflammatory joint diseases and also, effective anti-clotting agents in the treatment of myocardial infraction. A number of the agents also possess antipyretic activity in addition to analgesic and anti-inflammatory action, thus useful in reducing fever.

Some drugs in the above group have also been prescribed for Rheumatoid Arthritis, Osteoarthritis, acute gout, ankolysing spondylitis, and dysmenorrhea.

Mechanism of Action:

The major mechanism by which the NSAIDs produce their therapeutic effect is via inhibition of prostaglandin synthesis. Specifically NSAIDs inhibit cyclooxygenases, such as COX-1 and COX-2 enzymes, where these two enzymes are responsible for synthesis of prostaglandins. While COX-1 enzyme is important for the regulation of platelet aggregation, regulation of blood flow in kidney and stomach, and regulation of gastric acid secretion, COX-2 enzyme plays an important role in the pain and inflammatory processes. NSAIDs significantly increase clotting time and can be used for prophylaxis of thromboembolism and myocardial infarction.

All NSAIDs are relatively medium to strong organic acids with pKa's in the 3-6 range. Most of them are carboxylic acid derivatives. Acidic group is essential for COX inhibitory activity and in physiological pH, all the NSAIDs are ionized. All of them have quite varying hydrophilic lipophilic balance, and these are functions of their aromatic and aliphatic side chains and other heterocyclic variations in their structures. Most of the NSAIDs are highly bound to plasma proteins and often competitively replace other drugs which have similar affinity for plasma proteins. Hence concomitant administration of NSAIDs with other therapeutic class of drugs must be carefully evaluated to prevent drug interactions. Most of the drugs, due to their acidic carboxyl group, are metabolized by the mammals in vivo. The major pathway of metabolic clearance of a number of NSAIDs is glucuronidation followed by renal elimination.

Use of acetylsalicylic acid (aspirin) in the prophylaxis of coronary heart diseases is now well known, and this drug has proved to be a lifesaver for a number of patients with myocardial infarction (Heart Attacks). Several additional uses have already been documented for aspirin, for example, it was recently reported in the medical journal Lancet (Vol 349, p 1641) that aspirin reduces the risk of stroke in patients with early warning signs of transient ischemic heart attacks. Pre-eclampsia and fetal growth retardation, both caused by blockages of the blood vessels of the placenta, are two of the commonest complications of pregnancy—there are millions of cases of pre-eclampsia in the world each year. In a trial involving more than 9000 women in 16 countries, a daily dose of 60 mg aspirin reduced the risk of pre-eclampsia by 13 percent. (Aspirin Foundation website). Aspirin has also been shown to be effective in some studies to prevent colon cancer, lung cancer and pancreatic cancer in post-menopausal women. Since aspirin can improve blood flow, its usefulness in the treatment of diabetes and certain forms of dementia such as Alzheimer's disease are becoming increasingly clear.

Because of their unique pharmaceutical potential, the NSAIDs have attracted considerable attention in the press. The primary area of clinical investigation for the above drugs has been as non-steroidal anti-inflammatory agents, in particular in relation to their application to treat patients suffering from pain, arthritis, (Rheumatoid and Osteo) other inflammatory reactions, fever and for the prophylaxis of coronary heart diseases. These drugs are also used in the treatment of migraine headaches, menstrual syndromes, back pain and gout.

Despite the very major contribution which NSAIDs have made, difficulties have been encountered in providing more effective and convenient means of administration (e.g., galenic formulations, for example, oral dosage form, which are both convenient and for the patient as well as providing appropriate bioavailability and allowing dosaging at an appropriate and controlled dosage rate). In addition, there are reported occurrences of undesirable in vivo side reactions associated with NSAIDs; in particular severe gastric and duodenal ulcers, mucosal erythema, and edema, erosions, perforations, blood in stool, ulcerative colitis have been obvious serious impediments to their wider use or application. The dual injury theory involves NSAID-mediated direct damage, followed by a systemic effect in which prostaglandin synthesis is inhibited. Topical injury may also occur as a result of the biliary excretion of active hepatic metabolites and subsequent duodenogastric reflux. (Arthritis and Rheumatism 1995; 38 (1):5-18) The effects are additive; either topical or systemic mechanisms alone are sufficient to produce gastro duodenal mucosal damage. Recently, many of the COX-2 inhibitory NSAIDs such as Vioxx® and Celebrex® have been removed from the market due to their undesirable and life threatening side effects.

Moreover, the above mentioned NSAIDs are characteristically highly hydrophobic and readily precipitate in the presence of even very minor amounts of water, e.g., on contact with the body (e.g., stomach fluids). It is accordingly extremely difficult to provide e.g., oral formulations which are acceptable to the patient in terms of form and taste, which are stable on storage and which can be administered on a regular basis to provide suitable and controlling patient dosaging.

Proposed liquid formulations, e.g., for oral administration of NSAIDs, have heretofore been based primarily on the use of natural gums, like Xanthan, cellulose, citric acid, and lime flavor etc. See e.g., U.S. Pat. No. 5,780,046. Commercially available NSAIDs drink-solution employs incompatible orange color and berry flavor, citric acid, Xanthan Gum, polysorbate 80, pregelatinized starch, glycerin, sodium benzoate, and additional artificial colors and flavors. Use of the drink solution and similar composition as proposed in the art is however accompanied by a variety of difficulties.

Further, the palatability of the known oil based system has proved problematic. The taste of the known drink-solution is, in particular, unpleasant. Admixture with an appropriate flavored drink, for example, chocolate drink preparation, at high dilution immediately prior to ingestion has generally been practiced in order to make regular therapy at all acceptable. Adoption of oil based systems has also required the use of high ethanol concentrations which in and of itself is inherently undesirable, in particular where administration to children is forseen. In addition, evaporation of the ethanol, e.g., from capsules (adopted in large part, to meet problems of palatability, as discussed or other forms (e.g., when opened) results in the development of a NSAID precipitate. Where such compositions are presented in, for example, soft gelatin encapsulated form presents particular difficulty which necessitates packaging of the encapsulated product in an air-tight component, for example, an air-tight blister or aluminum-foil blister package. This in turn renders the product both bulky and more expensive to produce. The storage characteristics of the aforesaid formulations are, in addition, far from ideal.

Gastric irritability of the NSAIDs has been a topic of great concern to the practicing physicians as well as patients. Acute uses of aspirin, fenoprofen, flurbiprofen, indomethacin, ketorolac, meclofenamate, mefanamic acid, and piroxicam produce serious GI side effects. Even Ibuprofen has been shown to cause severe gastric lesions upon long term use. Gastrointestinal toxicity is the most frequently encountered side effect associated with NSAIDs and presents considerable concern. Approximately one half of all hospital admissions for a bleeding ulcer are attributed to the use of NSAIDs, aspirin, or the two taken in combination during the week prior to admission. (Faulkner G, Prichard P, Somerville K, et al. Aspirin and bleeding peptic ulcers in the elderly. Br Med J. 1988; 297:1311-1313). A survey of Tennessee Medicaid patients who were hospitalized with GI complications showed that patients who used NSAIDs had approximately a fourfold greater risk for developing GI hemorrhage or peptic ulcer disease than patients not taking NSAIDs. (Griffin M R, Piper J M, Daugherty J R, et al. Nonsteroidal anti-inflammatory drug use and increased risk for peptic ulcer disease in elderly persons. Ann Intern Med. 1991; 114:257-263). Serious GI events, according to the FDA, occur in as many as 2% to 4% of patients per year who are taking continuous NSAID therapy for rheumatoid arthritis. The relative risk of gastric ulcer (4.725), duodenal ulcer (1.1 to 1.6), bleeding (3.8), perforation, and death are all increased by NSAID use when such patients are compared to those who do not take these products. In 1989, patients with rheumatoid arthritis had approximately 20,000 hospitalizations per year with an estimated cost of $ 10,000 per stay. (Fries J F, Miller S R, Spitz P W, et al. Toward an epidemiology of gastropathy associated with nonsteroidal anti-inflammatory drug use. J Gastroenterology. 1989; 96:647-655).

There is also a need for providing some of the NSAIDs in a water soluble form for injection. It is well known that high concentrations of alcohol and tromethamine used to form a salt in the current formulations of Ketorolac are toxic. At present there is no formulation that would allow the NSAIDs to be in aqueous solution at the concentrations needed due to poor water solubility of the drug.

Beyond all these very evident practical difficulties lies the occurrence of undesirable side reactions already alluded to, observed employing available oral dosage forms.

Several proposals to meet these various problems have been suggested in the art, including both solid and liquid oral dosage forms. An overriding difficulty which has however remained is the inherent insolubility of the NSAIDs in aqueous media, hence preventing the use of a dosage form which can contain NSAIDs in sufficiently high concentration to permit convenient use and yet meet the required criteria in terms of bioavailability, e.g. enabling effective resorption from the stomach or gut lumen and achievement of consistent and appropriately high blood/blood-serum levels.

The present derivatives of NSAIDs overcome the problems described hereinabove. More specifically, an embodiment of the present invention is directed to a derivative of NSAID which significantly enhances its solubility in aqueous solutions, thereby avoiding the need to utilize a carrier, such as ethanol or castor oil when administered as a solution. Moreover, the derivatives of NSAID, in accordance with the present invention, do not exhibit the side effects of the prior art formulations. Further, the derivatives of the present invention are almost completely devoid of gastric irritability upon oral administration, thereby enhancing significantly the therapeutic index of the derivatives tested and their efficacy.

Accordingly, in one aspect, the present invention is directed to a derivative of NSAIDs.

The preferred derivatives of the NSAIDs have the formula

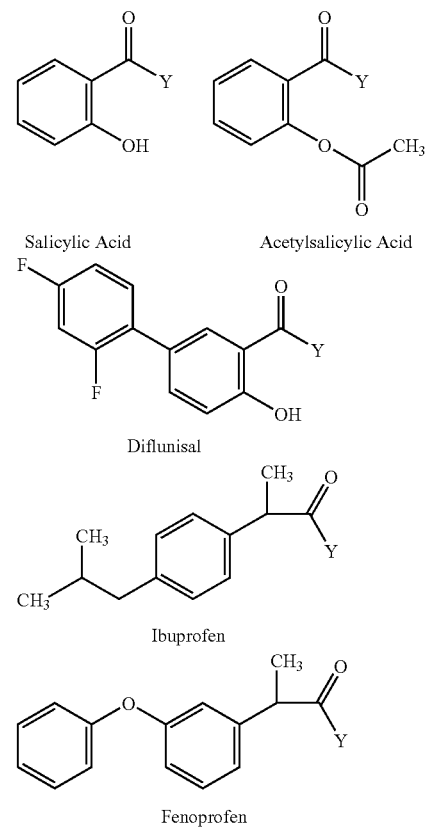

-continued

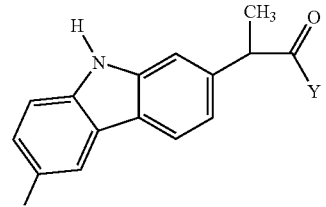
Carprofen

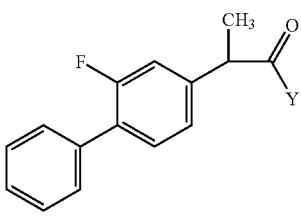
Flurbiprofen

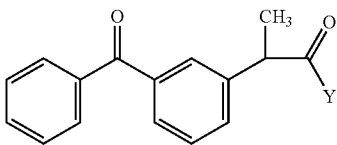
Ketoprofen

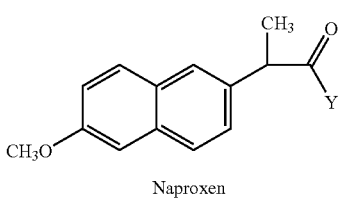
Naproxen

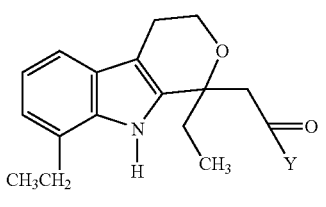
Etodolac

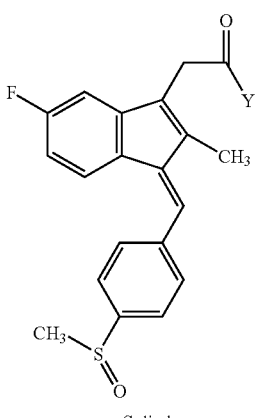
Sulindac

-continued

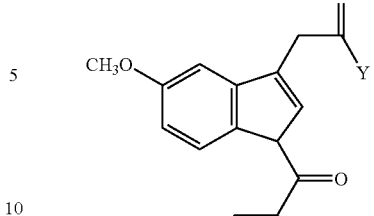
Indomethacin

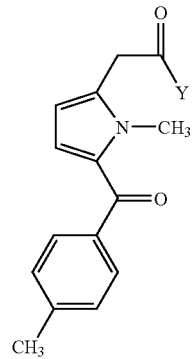
Tolmetin

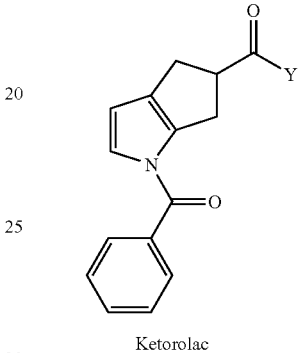
Ketorolac or pharmaceutically acceptable salts thereof; wherein Y is either NH-AA or O-AA and AA is an amino acid residue, in which either an amine group on the main chain or for those basic acids, on the side chain, if one is present (and more preferably on the main chain), or the hydroxyl group on the side chain of the AA acid residue is reacted with the carboxylic acid group of the NSAIDs.

The present invention is also directed to a pharmaceutical composition comprising a therapeutically effective amount of the various amino acid derivatives of the NSAIDs above and a pharmaceutical carrier therefor.

In another embodiment, the present invention is directed to a method of treating a patient in need of NSAID therapy, which method comprises administering to said patient an effective amount of the amino acid derivatives of the NSAIDs of the present invention.

In a further embodiment, the present invention is directed to a method of enhancing the solubility of NSAID in an aqueous solution comprising reacting the carboxyl functionality of each of the NSAID with an amino acid under effective conditions to form a covalent bond between the amino acid and the NSAID and isolating the product thereof.

In a still further embodiment, the present invention is directed to a method of substantially and in a therapeutically efficacious manner, reducing or eliminating the gastric mucosal damage of NSAIDs when administered to a patient which comprises reacting the carboxyl functionality of each of the NSAID molecule with either the amine functionality on the amino acid or hydroxyl function on the amino acids having a hydroxy group on the side chain, e.g., Threonine, hydroxy proline, tyrosine, serine and the like, or the amine of those amino acids having an amino group on the side chain, to form either an amide or ester or an amide covalent bond, respectively, and isolating the product thereof and administering said product to the patient. Preferably, the carboxyl functionality of the NSAID is reacted with the amine functionality on the main chain and/or the hydroxy group on the side chains of those amino acids having a hydroxy group on the side chain.

A. Synthesis of Ibuprofen Amino Acid Derivatives

Overview:

The procedure for the synthesis of the L-serine, L-threonine, and L-hydroxyproline esters of Ibuprofen is outlined in Synthetic Sequence section. The complete procedure and analytical data is given in the Experimental Section. Again, these synthetic schemes are exemplary. The scheme is applicable for other amino acids in the preparation of the NSAID derivatives of the present invention. In general, (±)-Ibuprofen (4-10 g, in batches) was coupled with the N-benzyloxy/benzyl ester protected amino acids (1 equivalent) with 1-(3-dimethylaminopropyl)-3-ethylcarbodiimide, hydrochloride (EDC, 1 equivalent) in the presence of a catalytic amount of 4-(N,N-dimethyamino)-pyridine (DMAP). Once the reactions were complete, any excess EDC was removed by extraction with water, DMAP was removed by extraction with dilute acid, and Ibuprofen was removed by extraction with sodium bicarbonate. After drying over sodium sulfate, filtration, and concentration the crude protected amino acid esters of (±)-Ibuprofen were either used directly or purified by flash chromatography on silica gel to generate the protected esters in good yield (85-95%). The column chromatography was generally not necessary if a slight excess of Ibuprofen and coupling agent were used, and a thorough extraction procedure was conducted. The protecting groups were removed by hydrogenation (25-35 psi $H_2$) in the presence of 10% palladium on carbon and hydrochloric acid. Yields for the deprotection step ranged from 70-90%. After filtration and drying, the hydrochloride salts of the serine and threonine esters of (±)-Ibuprofen were purified by crystallization. The hydrochloride salt of the L-hydroxyproline-Ibuprofen ester was a gel that would not solidify/crystallize. In this case the hydrogenation was repeated without the use of acid and the neutral compound was purified.

Because the Ibuprofen started as a mixture of enantiomers, the final products were delivered as a mixture of diastereomers except for the threonine ester. In the case of the threonine ester of Ibuprofen, washing with water, acetone or acetonitrile could readily separate the final diastereomeric salts. The insoluble isomer (SPI0016A) was determined to be the active isomer by comparison with an authentic standard prepared from S-(+)-Ibuprofen. The serine and hydroxyproline esters of (±)-Ibuprofen could not be readily separated in this fashion.

Synthetic Sequence:

1. SPI0015

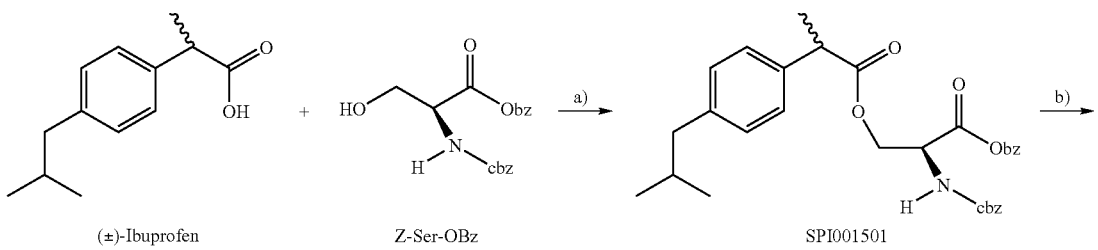

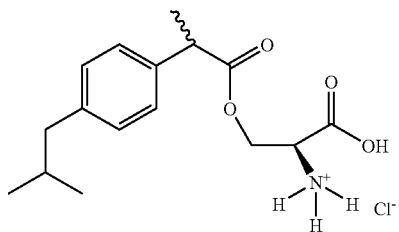

SPI0015

2. SPI0016A and SPI0016B

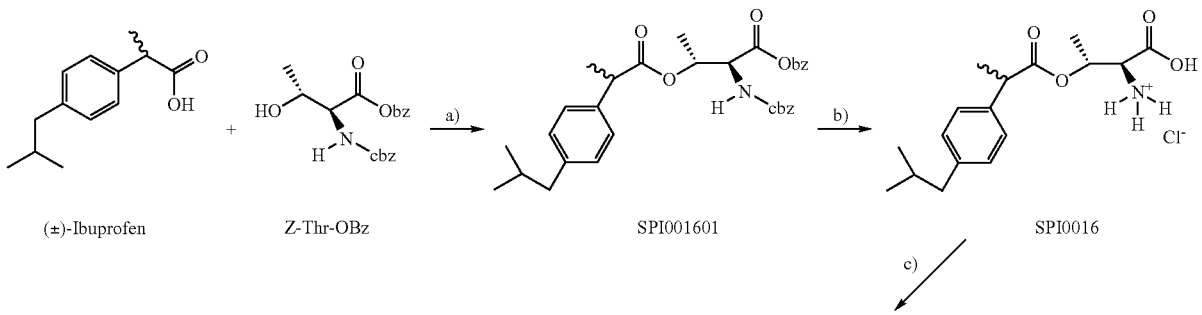

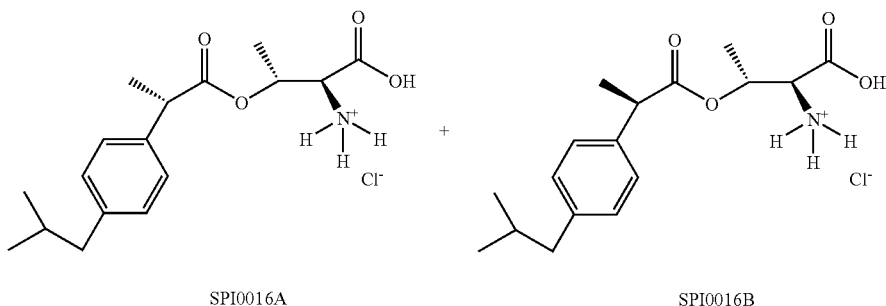

SPI0016A  +  SPI0016B

3. SPI0017

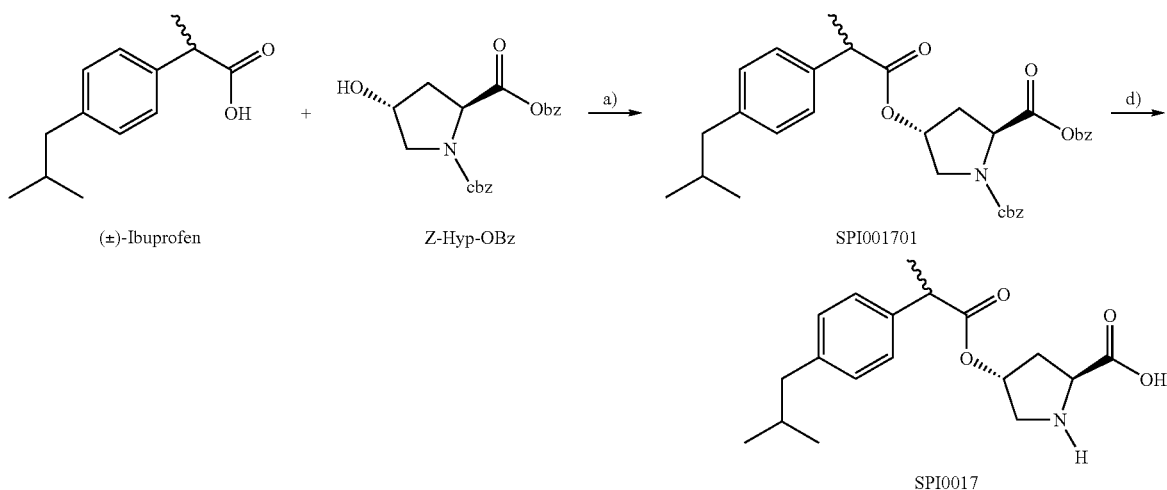

(±)-Ibuprofen     Z-Hyp-OBz              SPI001701

SPI0017

Synthesis of the L-serine, L-threonine, and L-hydroxyproline Esters of (±)-Ibuprofen: a) EDC, DMAP, CH$_2$Cl$_2$; b) HCl, 10% Pd/C, EtOH c) Acetone, d) 10% Pd/C, EtOH.

Experimental Section:

The synthesis of SPI0015, SPI0016 and SPI0017 were conducted in two or three batches. Reagents mentioned in the experimental section were purchased at the highest obtainable purity from Sigma-Aldrich, Acros, or Bachem, except for solvents, which were purchased from either Fisher Scientific or Mallinkrodt.

1) Preparation of (±)-Ibuprofen-L-Serine Ester, Hydrochloride (SPI0015).

(±)-Ibuprofen (5.04 g, 24.4 mmole), N-carbobenzyloxy-L-serine benzyl ester (8.11 g, 24.6 mmole), 1-(3-dimethylaminopropyl)-3-ethylcarbodiimide, hydrochloride (EDC, 4.87 g, 25.4 mmole), and 4-(N,N-dimethylamino)-pyridine (DMAP, 0.40 g, 3.27 mmole) were dissolved in dichloromethane (150 mL) at room temperature, under an argon atmosphere. After stirring for 22 hours under an argon atmosphere at room temperature, water (100 mL) was added and the layers were separated. The dichloromethane layer was washed again with water (100 mL) and dried for 1 hour over sodium sulfate (5 g). After filtration and concentration under reduced pressure, the remaining oil was purified by flash chromatography on silica gel (250 g), eluting with hexanes/ethyl acetate (3:1). The procedure generated the protected L-serine-(±)-Ibuprofen ester (SPI001501) as a colorless solid (11.4 g, 90% yield).

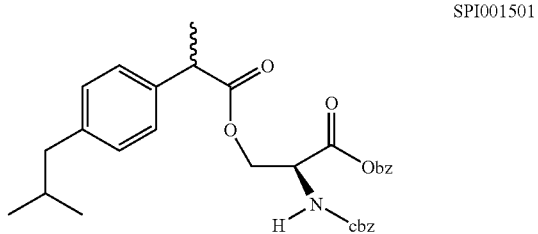

SPI001501

2(S)-Benzyloxycarbonylamino-3-[2(R,S)-(4-isobutyl-phenyl)-propionyloxy]-propionic acid benzyl ester $^1$H NMR (300 MHz, CDCl$_3$): δ=7.40-7.20 (m, 10H), 7.14-7.01 (m, 4H), 5.50 (d, ½H, J=8.4 Hz), 5.29 (d, ½H, J=8.4 Hz), 5.11-5.02 (m, 2.5H), 4.90 (d, ½H, J=12 Hz), 4.62 (m, 1H), 4.49-4.43 (m, 1H), 4.36-4.32 (m, 1H), 3.59 (m, 1H), 2.39-2.35 (m, 2H), 1.78 (m, 1H), 1.42-1.39 (m, 3H), 0.85 (d, 6H, J=6.6 Hz).

$^{13}$C NMR (75 MHz, CDCl$_3$): δ=174.05, 169.19, 169.07, 155.68, 140.73, 137.20, 136.12, 135.05, 134.91, 129.44, 128.67, 128.65, 128.60, 128.41, 128.33, 128.30, 128.19, 127.19, 127.16, 67.75, 67.32, 64.51, 64.32, 53.71, 45.16, 45.02, 30.35, 22.60, 18.27.

The protected Ibuprofen-L-serine ester (22.50 g, 43.4 mmole) was dissolved in ethanol (200 mL) at room temperature and added to a Parr bottle that contained 10% palladium on carbon (3.86 g, 50% wet) under a nitrogen atmosphere. Hydrochloric acid (10 mL 37% HCl in 30 mL water) was added and the nitrogen atmosphere was replaced with hydrogen gas (25 psi). After 4 hours of shaking, the palladium catalyst was removed by filtration through celite. The ethanol/water was removed under reduced pressure. The remaining white solids were washed with water (25 mL), acetone (20 mL) and dried under high vacuum (4 hours at 88° C.). The experiment produced (±)-Ibuprofen-L-serine ester, hydrochloride SPI0015 (11.3 g, 80% yield) as a colorless solid.

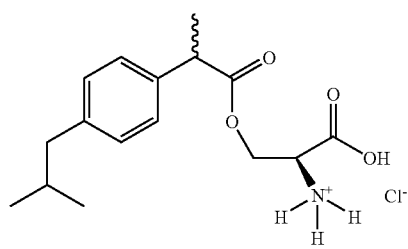

SPI0015

2(S)-Amino-3-[2(R,S)-(4-isobutylphenyl)-propionyloxy]-propionic acid, hydrochloride; ((R,S)-Ibuprofen-L-Serine ester, hydrochloride)

$^{1}$H NMR (300 MHz, DMSO): δ=8.92 (br s, 3H), 7.22 (t, 2H, J=7.5 Hz), 7.10 (d, 2H, J=7.5 Hz), 4.56 (m, 1H), 4.37-4.20 (m, 2H), 3.83 (q, 1H, J=6.9 Hz), 2.41 (d, 2H, J=6.9 Hz), 1.80 (m, 1H), 1.41 (d, 3H, J=6.9 Hz), 0.85 (d, 6H, J=6.9 Hz).

$^{13}$C NMR (75 MHz, DMSO): δ=173.36, 173.32, 168.08, 168.04, 139.70, 128.96, 129.92, 127.20, 127.05, 62.47, 51.59, 51.49, 44.28, 44.00, 43.90, 29.68, 22.28, 18.70, 18.42.

HPLC Analysis:

99.13% purity; rt=3.133 min; Luna C18 5 u column (sn 167917-13); 4.6×250 mm; 254 nm; 50% ACN/50% TFA buffer (0.1%); 35 C; 20 ul inj.; 1 ml/min; 1 mg/mL sample size; sample dissolved in mobile phase.

CHN Analysis:

calc.: C, 58.27; H, 7.33; N, 4.25. found: C, 58.44; H, 7.46; N, 4.25.

Melting point: 169.5-170.5° C.

2a) Preparation and Separation of (±)-Ibuprofen-L-Threonine Ester, Hydrochloride (SPI0016A and SPI0016B).

(±)-Ibuprofen (4.15 g, 20.11 mmole), N-carbobenzyloxy-L-threonine benzyl ester (6.90 g, 20.11 mmole), 1-(3-dimethylaminopropyl)-3-ethylcarbodiimide, hydrochloride (EDC, 3.95 g, 20.6 mmole), and 4-(N,N-dimethylamino)-pyridine (DMAP, 0.25 g, 2.0 mmole) were dissolved in dichloromethane (50 mL) at room temperature, under an argon atmosphere. After stirring for 19 hours, the dichloromethane layer was washed with water (50 mL), 5% hydrochloric acid (2×25 mL), water (25 mL), saturated sodium bicarbonate (2×25 mL), and water (50 mL). After drying for one hour over sodium sulfate (5 g), filtration, and concentration under reduced pressure, the remaining oil was used without further purification. The procedure generated the protected L-threonine-(±)-Ibuprofen ester (SPI001601) as a light yellow oil (10.2 g, 95.3% yield), which solidified on standing.

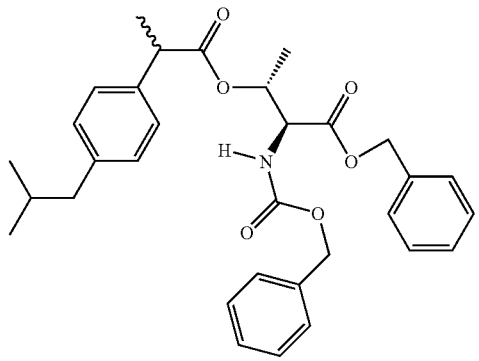

SPI001601

2(S)-Benzyloxycarbonylamino-3-[2(R,S)-(4-isobutyl-phenyl)-propionyloxy]-butyric acid benzyl ester $^{1}$H NMR (300 MHz, CDCl$_{3}$): δ=7.40-7.15 (m, 10H), 7.14-7.01 (m, 4H), 5.48-5.25 (m, 2H), 5.11-5.01 (m, 3H), 4.90 (d, ½H, J=12 Hz), 4.68 (d, ½H, J=12 Hz), 4.48 (m, 1H), 3.60-3.48 (m, 1H), 2.39 (m, 2H), 1.79 (m, 1H), 1.42-1.35 (m, 3H), 1.27 (d, 1.5H, J=6.6 Hz), 1.17 (d, 1.5H, J=6.6 Hz), 0.85 (m, 6H).

$^{13}$C NMR (75 MHz, CDCl$_{3}$): δ=173.32, 169.70, 169.30, 156.55, 140.75, 137.38, 137.22, 136.14, 135.07, 134.99, 129.45, 129.41, 128.65, 128.39, 128.22, 127.21, 127.14, 70.97, 70.70, 67.81, 67.66, 67.53, 57.83, 45.19, 30.39, 22.61, 18.57, 18.30, 17.18, 16.87.

The protected Ibuprofen-L-threonine ester (10.15 g, 19.0 mmole) was dissolved in warm ethanol (150 mL) and added to a Parr bottle that contained 10% palladium on carbon (3.4 g, 50% wet) under a nitrogen atmosphere. Hydrochloric acid (6 mL 37% HCl in 20 mL water) was added and the nitrogen atmosphere was replaced with hydrogen gas (30 psi). After 3 hours of shaking, the palladium catalyst was removed by filtration through celite (30 g). The ethanol/water was removed under reduced pressure. The experiment produced (±)-Ibuprofen-L-threonine ester, hydrochloride (SPI0016A and SPI0016B, 6.4 g, 97% crude yield) as a colorless solid. The crude mixture of diastereomers was stirred in acetone (200 mL) for 2 hours at room temperature under an argon atmosphere. After 2 hours the solids (2.84 g, SPI0016A) were filtered. The filtrate (SPI0016B, 3.0 g) was concentrated under reduced pressure.

1.) Purification of SPI0016A (Active Isomer):

After 3 batches of the S-Ibuprofen-L-threonine ester (SPI0016A) had been completed, the batches were combined (8.78 g total) and crystallized three times from DIUF ("deionized ultrafiltered") water (100 mL). Each time a small amount of zwitterion was generated. In order to regenerate the salt, the solid generated (from each crystallization) was dissolved in 1% hydrochloric acid in ethanol (3 mL 37% hydrochloric acid in 100 mL ethanol). The ethanol solution was then concentrated under reduced pressure at room temperature. After the third crystallization and regeneration procedure, the salt (5.6 g) was stirred in acetonitrile (100 mL) for 44 hours at room temperature, under an argon atmosphere. The salt was then filtered and dried under high vacuum at 50-55° until the weight was constant (5.5 g).

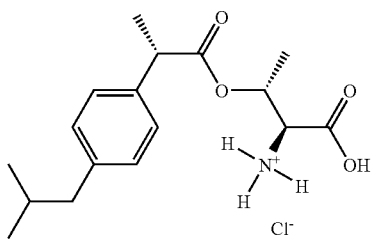

2(S)-Amino-3(R)-[2(S)-(4-isobutyl-phenyl)-propionyloxy]-butyric acid; (S-Ibuprofen-L-threonine ester, hydrochloride, active isomer)

$^1$H NMR (300 MHz, DMSO): δ=8.76 (br s, 3H), 7.19 (d, 2H, J=8.1 Hz), 7.11 (d, 2H, J=8.1 Hz), 5.28 (dq, 1H, J=6.3, 3.6 Hz), 4.14 (q, 1H, J=3.6 Hz), 3.80 (q, 1H, J=7.2 Hz), 2.41 (d, 2H, J=7.2 Hz), 1.80 (m, 1H), 1.37 (d, 3H, J=7.2 Hz), 1.21 (d, 3H, J=6.3 Hz), 0.85 (d, 6H, J=6.6 Hz).

$^{13}$C NMR (75 MHz, DMSO): δ=172.66, 168.24, 139.68, 137.24, 128.95, 126.97, 67.98, 55.35, 44.23, 43.83, 29.66, 22.24, 18.52, 16.47.

CHN Analysis:
calc.: C, 59.38; H, 7.62; N, 4.07. found: C, 59.17; H, 7.63; N, 4.04.

HPLC Analysis:
98.28% purity; r.t.=6.951 min.; 60% TFA (0.1%)/40% acetonitrile; 1 mL/min; 37.5 C; Luna C18, 3 u column (SN 167917-13), 4.6×250 mm; 22 ul injection.

Optical rotation: +24.5°
Melting Point: 189-190° C.

2) Purification of SPI0016B (Inactive Isomer):

After 3 batches of the R-Ibuprofen-L-threonine ester (SPI0016B) had been completed, the batches were combined (9.02 g total) and crystallized from DIUF (deionized ultra filtered) water (50 mL). A small amount of zwitterion was generated during the crystallization. In order to regenerate the salt, the solid generated was dissolved in 1% hydrochloric acid in ethanol (3 mL 37% hydrochloric acid in 100 mL ethanol). The ethanol solution was then concentrated under reduced pressure at room temperature. The remaining salt (5.93 g) was crystallized three times from hot toluene (100 mL) with the addition of a small amount on acetone (1 mL). The salt was then filtered and dried under high vacuum at room temperature until the weight was constant (5.1 g).

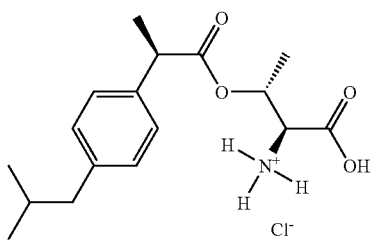

2(S)-Amino-3(R)-[2(R)-(4-isobutyl-phenyl)-propionyloxy]-butyric acid; (R-Ibuprofen-L-threonine ester, hydrochloride, inactive isomer)

$^1$H NMR (300 MHz, DMSO): δ=8.82 (br s, 3H), 7.23 (d, 2H, J=7.8 Hz), 7.10 (d, 2H, J=7.8 Hz), 5.27 (m, 1H), 4.18 (m, 1H), 3.80 (q, 1H, J=7.2 Hz), 2.41 (d, 2H, J=7.2 Hz), 1.81 (m, 1H), 1.41 (d, 3H, J=6.9 Hz), 1.34 (d, 3H, J=6.3 Hz), 0.85 (d, 6H, J=6.3 Hz).

$^{13}$C NMR (75 MHz, DMSO): δ=72.56, 168.08, 139.64, 136.98, 128.84, 127.14, 68.8, 55.29, 44.28, 29.69, 22.28, 18.24, 16.41.

CHN Analysis:
calc.: C, 59.38; H, 7.62; N, 4.07. found: C, 59.30; H, 7.60; N, 4.05.

HPLC Analysis:
98.43% purity; r.t.=6.19 min.; 60% TFA (0.1%)/40% acetonitrile; 1 mL/min; 37.5 C; Luna C18, 3 u column (SN 167917-13), 4.6×250 mm; 22 ul injection.

Optical Rotation: +10.4
Melting Point: 176-177° C.

2b) Preparation of the S-(+)-Ibuprofen-L-threonine Ester, Hydrochloride Standard (SPI0016S).

S-(+)-Ibuprofen (2.0 g, 9.69 mmole), N-carbobenzyloxy-L-threonine benzyl ester (3.25 g, 9.91 mmole), 1-(3-dimethylaminopropyl)-3-ethylcarbodiimide, hydrochloride (EDC, 1.90 g, 9.91 mmole), and 4-(N,N-dimethylamino)-pyridine (DMAP, 0.12 g, 1.0 mmole) were dissolved in dichloromethane (25 mL) at room temperature, under an argon atmosphere. After stirring for 4 hours, the dichloromethane layer was washed with water (25 mL), 5% hydrochloric acid (25 mL), saturated sodium bicarbonate (2×25 mL), and water (25 mL). After drying for one hour over sodium sulfate (5 g), filtration, and concentration under reduced pressure, the remaining oil was used without further purification. The procedure generated the protected S-(+)-Ibuprofen-L-threonine ester (SPI001601S) as a light yellow oil (5.01 g, 98% yield), which solidified on standing.

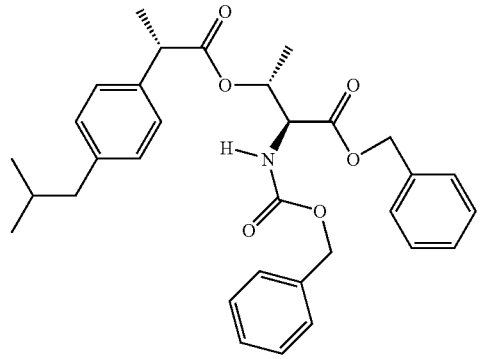

2(S)-Benzyloxycarbonylamino-3-[2(R,S)-(4-isobutyl-phenyl)-propionyloxy]-butyric acid benzyl ester $^1$H NMR (300 MHz, CDCl$_3$): δ=7.35-7.23 (m, 10H), 7.10 (d, 2H, J=7.8 Hz), 7.05 (d, 2H, J=7.8 Hz), 5.48-5.25 (m, 2H), 5.17-5.01 (m, 4H), 4.50 (dd, 1H, J=9.6, 1.8 Hz), 3.50 (q, 1H, J=7.2 Hz), 2.40 (d, 2H, J=7.2 Hz), 1.80 (m, 1H), 1.37 (d, 3H, J=7.2 Hz), 1.17 (d, 3H, J=6.3 Hz), 0.86 (d, 6H, J=6.6 Hz).

$^{13}$C NMR (75 MHz, CDCl$_3$): δ=173.29, 169.69, 156.51, 140.68, 137.21, 136.08, 135.06, 129.40, 128.70, 128.66, 128.57, 128.38, 128.24, 127.14, 70.70, 67.80, 67.53, 57.87, 45.19, 45.11, 30.39, 22.61, 18.57, 16.87.

The protected S-(+)-Ibuprofen-L-threonine ester (5.0 g, 9.40 mmole) was dissolved in warm ethanol (100 mL) and added to a Parr bottle that contained 10% palladium on carbon (1.0 g, 50% wet) under a nitrogen atmosphere. Hydrochloric acid (1 mL 37% HCl in 10 mL water) was added and the nitrogen atmosphere was replaced with hydrogen gas (32 psi). After 2 hours of shaking, the palladium catalyst was removed by filtration through celite (30 g). The ethanol/water was removed under reduced pressure. The experiment produced S-(+)-Ibuprofen-L-threonine ester, hydrochloride (SPI0016S, 2.8 g, 85% crude yield) as a colorless solid. The salt was stirred in acetone (50 mL) for 3 hours at room temperature under an argon atmosphere. After 3 hours the solids (2.24 g, 69% yield) were filtered and dried under high vacuum at room temperature, until the weight was constant.

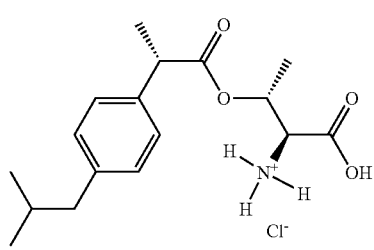

SPI0016S

2(S)-Amino-3(R)-[2(S)-(4-isobutyl-phenyl)-propionyloxy]-butyric acid; (S-Ibuprofen-L-threonine ester, hydrochloride, active isomer)

$^1$H NMR (300 MHz, DMSO): δ=8.76 (br s, 3H), 7.19 (d, 2H, J=8.1 Hz), 7.11 (d, 2H, J=8.1 Hz), 5.28 (dq, 1H, J=6.3, 3.6 Hz), 4.14 (q, 1H, J=3.6 Hz), 3.80 (q, 1H, J=7.2 Hz), 2.41 (d, 2H, J=7.2 Hz), 1.80 (m, 1H), 1.37 (d, 3H, J=7.2 Hz), 1.21 (d, 3H, J=6.3 Hz), 0.85 (d, 6H, J=6.6 Hz).

$^{13}$C NMR (75 MHz, DMSO): δ=172.66, 168.24, 139.68, 137.24, 128.95, 126.97, 67.98, 55.35, 44.23, 43.83, 29.66, 22.24, 18.52, 16.47.

HPLC Analysis:

98.28% purity; r.t.=6.951 min.; 60% TFA (0.1%)/40% acetonitrile; 1 mL/min; 37.5 C; Luna C18, 3 u column (SN 167917-13), 4.6×250 mm; 22 ul injection.

Optical rotation: +26.5°

Melting Point: 189-190° C.

3) Preparation of the (±)-Ibuprofen-L-Hydroxyproline Ester (SPI0017).

(±)-Ibuprofen (5.10 g, 24.7 mmole), N-carbobenzyloxy-L-hydroxyproline benzyl ester (8.80 g, 24.7 mmole), 1-(3-dimethylaminopropyl)-3-ethylcarbodiimide, hydrochloride (EDC, 5.10 g, 26.0 mmole), and 4-(N,N-dimethylamino)-pyridine (DMAP, 0.30 g, 2.40 mmole) were dissolved in dichloromethane (100 mL) at room temperature, under an argon atmosphere. After stirring for 24 hours under an argon atmosphere at room temperature, water (100 mL) was added and the layers were separated. The dichloromethane layer was washed again with water (100 mL), 5% sodium bicarbonate (2×50 mL) and dried for 1 hour over sodium sulfate (5 g). After filtration and concentration under reduced pressure, the remaining oil was used without further purification. The procedure generated the protected (±)-Ibuprofen-L-hydroxyproline ester (SPI001701) as a light yellow oil (11.5 g, 85% yield).

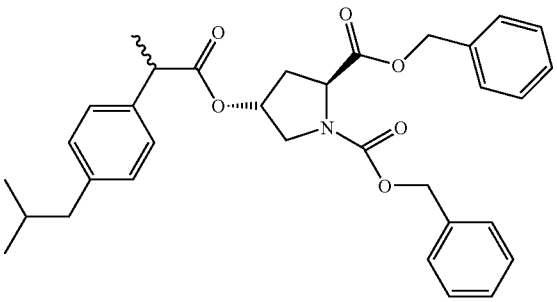

SPI001701

4(R)-[2-(4-Isobutyl-phenyl)-propionyloxy]-pyrrolidine-2(S)-carboxylic acid; ((R,S)-Ibuprofen-L-hydroxyproline ester)

$^1$H NMR (300 MHz, CDCl$_3$): δ=7.33-7.02 (m, 14H), 5.25-4.95 (m, 5H), 4.51-4.19 (m, 1H), 3.75-3.50 (m, 3H), 2.40 (d, 2H, J=6.9 Hz), 2.15 (m, 1H), 1.81 (m, 1H), 1.44 (d, 3H, J=7.0 Hz), 0.87 (d, 6H, J=6.6 Hz).

$^{13}$C NMR (75 MHz, CDCl$_3$): δ=173.99, 171.93, 171.72, 154.68, 154.15, 140.70, 137.23, 137.04, 136.23, 135.44, 135.23, 129.41, 128.59, 128.47, 128.35, 128.19, 128.08, 127.89, 127.02, 72.86, 72.16, 67.40, 67.18, 67.09, 58.12, 57.83, 52.66, 52.49, 52.13, 45.15, 36.63, 35.67, 32.07, 30.33, 29.23, 22.90, 22.58, 18.36.

The protected Ibuprofen-L-hydroxyproline ester (11.40 g, 43.4 mmole) was dissolved in ethanol (150 mL) at room temperature and added to a Parr bottle that contained 10% palladium on carbon (2.73 g, 50% wet) under a nitrogen atmosphere. The nitrogen atmosphere was replaced with hydrogen gas (34 psi). After 5 hours of shaking, the palladium catalyst was removed by filtration through celite. The ethanol was removed under reduced pressure. The remaining white solids (6.60 g) were washed with DIUF water (50 mL), diethyl ether (50 mL) and dried under high vacuum until the weight was constant. The experiment produced (±)-Ibuprofen-L-hydroxyproline ester SPI0017 (5.64 g, 84% yield) as a colorless solid.

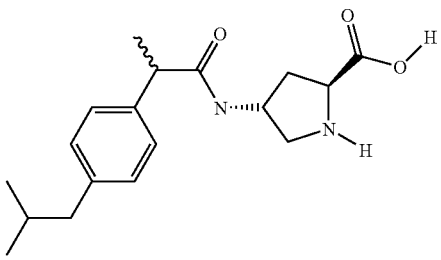

SPI0017

4(R)-[2-(4-Isobutyl-phenyl)-propionyloxy]-pyrrolidine-2(S)-carboxylic acid; ((R,S)-Ibuprofen-L-hydroxyproline ester)

$^1$H NMR (300 MHz, CDCl$_3$): δ=7.22 (d, 2H, J=7.2 Hz), 7.09 (d, 2H, J=7.2 Hz), 5.27 (m, 1H), 4.40 (t, 0.5H, J=7 Hz), 4.24 (t, 0.5H, J=9 Hz), 3.75 (m, 1H), 3.61 (m, 1H), 3.28 (d, 0.5H, J=13 Hz), 3.15 (d, 0.5H, J=13 Hz), 2.42-2.10 (m, 4H), 1.78 (m, 1H), 1.40 (br t, 3H, J=6 Hz), 0.82 (d, 6H, J=6 Hz). (mixture of diastereomers)

$^{13}$C NMR (75 MHz, CDCl$_3$): δ=173.28, 173.23, 168.98, 139.88, 137.33, 137.23, 129.12, 127.26, 127.17, 72.58, 57.60, 57.50, 50.24, 50.12, 44.34, 44.15, 34.31, 34.16, 29.77, 22.34, 18.43, 18.23. (mixture of diastereomers)

HPLC Analysis:

100% purity; r.t.=5.35, 5.22 min.; 55% TFA (0.1%), 45% ACN; 1 mL/min; 32.3 C, Luna C18, serial #188255-37; 20 ul inj.

CHN Analysis:

calc.: C, 67.69; H, 7.89; N, 4.39. found: C, 67.47; H, 7.87; N, 4.30.

Melting Point: 198-199° C.

Efficacy (Anti Nociceptive Potential) of Synthesis of the L-Serine, L-Threonine, and L-Hydroxyproline Esters of (±)-Ibuprofen by Employing Acetylcholine Induced Abdominal Constriction Method in Male Albino Mice:

The present study was conducted to evaluate the efficacy of L-serine, L-threonine, and L-hydroxyproline esters of (±)-Ibuprofen taking into account the antagonizing property on acetylcholine induced writhe as an index in albino mice. Ibuprofen (racemic mixture) and ibuprofen (S)-(+) served as reference controls.

Different new formulations of ibuprofen and reference controls viz., ibuprofen (racemic mixture) and ibuprofen (S)-(+) were administered by gavage to male albino mice (Swiss strain), using 5% (v/v) Tween 80 in milli Q water as the vehicle. The study was conducted at two dose levels viz. 50 mg and 100 mg/kg body weight along with a vehicle control group. At each dose level 10 animals were used. All the doses were expressed as ibuprofen molar equivalents. The doses used as well as the molar equivalents are presented below.

TABLE 5

Formulation: Molar Equivalent:

| Formulation | Molar equivalent |
| --- | --- |
| S-(+)-Ibuprofen-L-threonine ester | 0.833 units are equivalent to 1 unit of Ibuprofen |
| (±)-Ibuprofen-L-serine ester | 1.6 units are equivalent to 1 unit of Ibuprofen |
| (±)-Ibuprofen-L-hydroxyproline ester | 1.55 units are equivalent to 1 unit of Ibuprofen |

TABLE 6

Test Item: Group: Dose(mg/kg): Equivalent wt. Of the test item:

| Test Item | Group | Dose (mg per kg) [in terms of Ibuprofen] | Equivalent weight of the Test item [mg/kg] |
| --- | --- | --- | --- |
| Vehicle | Vehicle control Group | 0.0 | — |
| S-(+)-Ibuprofen-L-threonine ester | Test Group 1 | 50.0 | 41.65 |
|  | Test Group 2 | 100.0 | 83.30 |
| (±)-Ibuprofen-L-serine ester (Ibuprofen S) | Test Group 3 | 50.0 | 80.0 |
|  | Test Group 4 | 100.0 | 160.0 |
| (±)-Ibuprofen-L-hydroxyproline ester | Test Group 5 | 50.0 | 77.5 |
|  | Test Group 6 | 100.0 | 155.0 |
| Ibuprofen (racemic mixture) | Test Group 7 | 50.0 | 50.0 |
|  | Test Group 8 | 100.0 | 100.0 |
| Ibuprofen S+ | Test Group 9 | 50.0 | 25.0 |
|  | Test Group 10 | 100.0 | 50.0 |

The efficacy in terms of antagonizing effect on acetylcholine induced single writhe at two dose levels—50.0 and 100.0 mg/kg for the three formulations and reference controls are presented below.

TABLE 7

Test Item: Group: Dose (mg/kg): Number of animals showing absence of single writhe (out of 10)

| Test Item | Group | Dose (mg per kg) [in terms of Ibuprofen] | Number of animals showing absence of single writhe (number of animals per dose = 10) | |
| --- | --- | --- | --- | --- |
| | | | One hour after dosing | Three hours after dosing |
| Vehicle | Vehicle control | 0.0 | 0 | 0 |
| S-(+)-Ibuprofen-L-threonine ester | Low dose | 50.0 | 1 | 0 |
|  | High dose | 100.0 | 3 | 0 |
| (±)-Ibuprofen-L-serine ester | Low dose | 50.0 | 4 | 2 |
|  | High dose | 100.0 | 6 | 4 |
| (±)-Ibuprofen-L-hydroxyproline ester | Low dose | 50.0 | 5 | 4 |
|  | High dose | 100.0 | 7 | 7 |
| Ibuprofen (racemic mixture) | Low dose | 50.0 | 4 | 2 |
|  | High dose | 100.0 | 6 | 6 |
| Ibuprofen S+ | Low dose | 50.0 | 5 | 1 |
|  | High dose | 100.0 | 6 | 6 |

Statistical analysis employing Chi—square test procedure did not show any statistically significant difference among the formulations in comparison to reference control, while comparing the number of animals not showing writhe in each groups, as the respective "p" was found to be greater than 0.05, the level of significance.

From clinical observation based on the number of animals not showing writhes due to administration of acetylcholine, (±)-Ibuprofen-L-hydroxyproline ester was found to be more effective in antagonizing the acetylcholine induced writhe when compared to other formulations and Ibuprofen (racemic) and Ibuprofen (S)-(+).

TABLE 8

Summary of Efficacy of L-serine, L-threonine, and L-hydroxyproline esters of (±)-Ibuprofen, Ibuprofen (racemic mixture) and Ibuprofen (S)-(+) - Based on Antagonizing Property of Acetylcholine Induced Writhe in Albino Mice

| Dose (mg/kg) [in terms of Ibuprofen] | Test Item | Number of animals showing absence of single writhe (number of animals per dose = 10) | |
| --- | --- | --- | --- |
| | | One hour after dosing | Three hours after dosing |
| 50 mg/kg | Vehicle control | 0 | 0 |
|  | S-(+)-Ibuprofen-L-threonine ester | 1 | 0 |
|  | (±)-Ibuprofen-L-serine ester | 4 | 2 |
|  | (±)-Ibuprofen-L-hydroxyproline ester | 5 | 4 |
|  | Ibuprofen (racemic mixture) | 4 | 2 |
|  | Ibuprofen (S)-(+) | 5 | 1 |

TABLE 9

| 100 mg/kg | Vehicle control | 0 | 0 |
| | S-(+)-Ibuprofen-L-threonine ester | 3 | 0 |
| | (±)-Ibuprofen-L-serine ester | 6 | 4 |
| | (±)-Ibuprofen-L-hydroxyproline ester | 7 | 7 |
| | Ibuprofen (racemic mixture) | 6 | 6 |
| | Ibuprofen (S)-(+) | 6 | 6 |

The data were subjected to statistical analysis employing Chi—square test procedure for evaluating the efficacy of the new formulations in comparison to the reference controls. The tests did not show any statistically significant difference among the formulations in comparison to reference control, while comparing the number of animals not showing writhe in each groups, as the respective "p" was found to be greater than 0.05, the level of significance.

Figure 2:
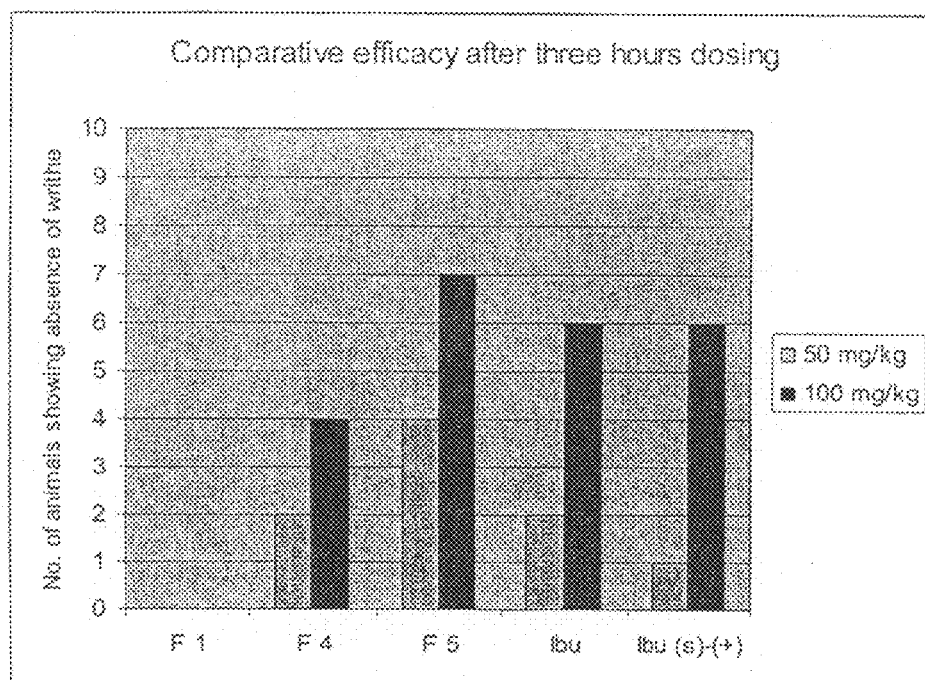
FIG. 2 graphically compares the efficacy of L-serine ester of (±) Ibuprofen, (F1), L-threonine ester of, (I) Ibuprofen (F2), L-hydroxyproline ester of (±) Ibuprofen (F3), ±Ibuprofen and S(+) Ibuprofen after 3 hour dosing, based on the antagonizing property of Acetylcholine induced writhes in albino mice.
Figure 3:
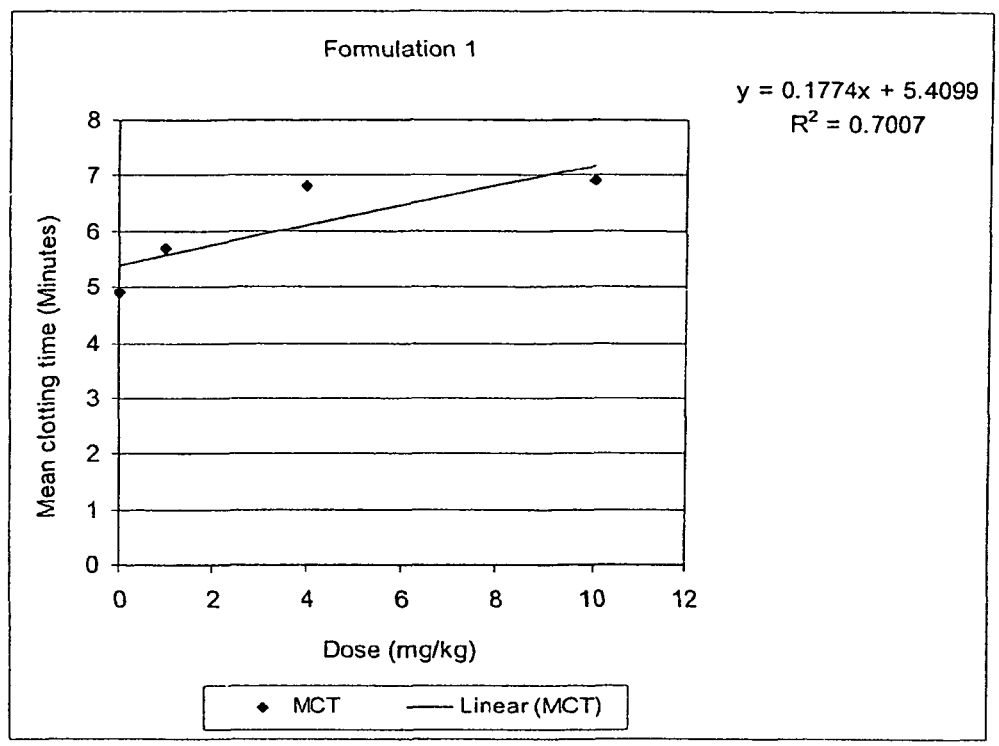
FIG. 3 depicts graphically the dose response relationship to mean clotting time (MCT) in minutes for the L-serine ester of acetylsalicylic acid (Formulation 1).

The data is also summarized in FIGS. 1 and 2. From clinical observations and bar diagram for comparative efficacy (FIGS. 1 and 2), based on the number of animals not showing writhes due to administration of acetylcholine, (±)-Ibuprofen-L-hydroxyproline ester was found to be more effective in antagonizing the acetylcholine induced writhe when compared to other formulations and Ibuprofen (racemic) and Ibuprofen (S)-(+).

Conclusion

The present study was conducted to evaluate the relative efficacy of new formulations of ibuprofen. For this the antagonizing property of new formulations on acetylcholine writhes was taken as an index to determine the relative efficacy of the formulations. Ibuprofen (racemic mixture and ibuprofen (S)-(+) served as reference controls. The study was conducted at two dose levels (50.0 and 100.0 mg/kg) along with a vehicle control group.

The efficacy in terms of antagonizing effect of acetylcholine induced single writhe at two dose levels—50.0 and 100.0 mg/kg for the three formulations and reference controls are presented below.

TABLE 10

Test Item: Group: Dose (mg/kg): No. of animals showing absence of single writhe (out of 10)

| Test Item | Group | Dose (mg per kg) [in terms of Ibuprofen] | One hour after dosing | Three hours after dosing |
| --- | --- | --- | --- | --- |
| Vehicle | Vehicle control | 0.0 | 0 | 0 |
| S-(+)-Ibuprofen-L-threonine ester | Low dose | 50.0 | 1 | 0 |
| | High dose | 100.0 | 3 | 0 |
| (±)-Ibuprofen-L-serine ester | Low dose | 50.0 | 4 | 2 |
| | High dose | 100.0 | 6 | 4 |
| (±)-Ibuprofen-L-hydroxyproline ester | Low dose | 50.0 | 5 | 4 |
| | High dose | 100.0 | 7 | 7 |
| Ibuprofen (racemic mixture) | Low dose | 50.0 | 4 | 2 |
| | High dose | 100.0 | 6 | 6 |
| Ibuprofen (S)-(+) | Low dose | 50.0 | 5 | 1 |
| | High dose | 100.0 | 6 | 6 |

Statistical analysis employing Chi—square test procedure did not show any statistically significant difference among the formulations in comparison to reference control, while comparing the number of animals not showing writhe in each groups, as the respective "p" was found to be greater than 0.05, the level of significance.

However from clinical observation based on the number of animals not showing writhes due to administration of acetylcholine (±)-Ibuprofen-L-hydroxyproline ester was found to be more effective in antagonizing the acetylcholine induced writhe when compared to other formulations and Ibuprofen (racemic) and Ibuprofen (S)-(+).

Gastric Mucosal Irritation Potential of L-Serine, L-Threonine, and L-Hydroxyproline Esters of (±)-Ibuprofen in Fasted Male Albino Rats Summary The present study was conducted to determine the relative potential of new formulations of ibuprofen (L-serine, L-threonine, and L-hydroxyproline esters of (±)-Ibuprofen) to cause gastric mucosal irritation/lesions in fasted male albino rats. Ibuprofen (racemic mixture) and Ibuprofen(S)-(±) served as reference controls.

Different new formulations of ibuprofen and ibuprofen (racemic mixture) and ibuprofen(S)-(+) were administered by gavage to fasted male albino rats (Wistar strain), using 5% solution of Tween 80 in milli Q water as the vehicle. The study was conducted at two dose levels viz. 200 mg and 300 mg/kg body weight along with a vehicle control group. At each dose level 5 animals were used. All the doses were expressed as ibuprofen (racemic mixture) molar equivalents. The doses used as well as the molar equivalents were presented below.

TABLE 11

Formulation: Molar Equivalent

| Formulation | Molar equivalent |
| --- | --- |
| S-(+)-Ibuprofen-L-threonine ester | 0.833 units are equivalent to 1 unit of Ibuprofen |
| (±)-Ibuprofen-L-serine ester | 1.60 units are equivalent to 1 unit of Ibuprofen |
| (±)-Ibuprofen-L-hydroxyproline ester | 1.55 units are equivalent to 1 unit of Ibuprofen |

The various groups used are tabulated hereinbelow:

TABLE 12

Test item: group: Dose (mg/kg) Equivalent wt.

| Test item | Group | Dose (mg per kg) [in terms of Ibuprofen] | Equivalent weight of the Test item [mg/kg] |
| --- | --- | --- | --- |
| Vehicle | Vehicle control Group | 0.0 | — |
| S-(+)-Ibuprofen-L-threonine ester | Test Group 1 | 200.0 | 0.0 |
| | Test Group 2 | 300.0 | 166.6 |
| (±)-Ibuprofen-L-serine ester | Test Group 1 | 200.0 | 249.9 |
| | Test Group 2 | 300.0 | 320.0 |
| (±)-Ibuprofen-L-hydroxyproline ester | Test Group 1 | 200.0 | 480.0 |
| | Test Group 2 | 300.0 | 310.0 |
| Ibuprofen (racemic | Test Group 1 | 200.0 | 465.0 |

TABLE 12-continued

Test item: group: Dose (mg/kg) Equivalent wt.

| Test item | Group | Dose (mg per kg) [in terms of Ibuprofen] | Equivalent weight of the Test item [mg/kg] |
|---|---|---|---|
| mixture) | Test Group 2 | 300.0 | 300.0 |
| Ibuprofen (S)-(+) | Test Group 1 | 200.0 | 100.0 |
| | Test Group 2 | 300.0 | 150.0 |

The rats were fasted for a period of 18 to 22 hours before dosing. The test item was administered as a single dose by gavage. Three hours after drug administration, the animals were killed humanely by $CO_2$ gas inhalation. The stomach was dissected out and observed for the quantity of mucous exudate, degree of hyperemia and thickening of stomach wall, hemorrhagic spots (focal or diffuse), nature of hemorrhages (petechial or ecchymotic) along with the size and perforations or any other lesions The observations on gastric mucosal irritation of animals of various groups were summarized below:

TABLE 13

Test item: Group: Dose (mg/kg): Observation

| Test Item | Group | Doe mg/kg (as per ibuprofen) | Observation |
|---|---|---|---|
| Vehicle control | Vehicle control Group | 0.0 | None of the animals showed any evidence of gastric mucosal irritation |
| S-(+)-Ibuprofen-L-threonine ester | Test Group 1 | 200.0 | None of the dosed animals showed any evidence of gastric mucosal irritation |
| | Test Group 2 | 300.0 | None of the dosed animals showed any evidence of gastric mucosal irritation. |
| (±)-Ibuprofen-L-serine ester | Test Group 1 | 200.0 | None of the dosed animals showed any evidence of gastric mucosal irritation. |
| | Test Group 2 | 300.0 | None of the dosed animals showed any evidence of gastric mucosal irritation |
| (±)-Ibuprofen-L-hydroxyproline ester | Test Group 1 | 200.0 | None of the dosed animals showed any evidence of gastric mucosal irritation |
| | Test Group 2 | 300.0 | None of the dosed animals showed any evidence of gastric mucosal irritation |
| Ibuprofen (racemic mixture) | Test Group 1 | 200.0 | Gastric mucosal irritation was observed in one animal out of 5 animals dosed. |
| | Test Group 2 | 300.0 | Gastric mucosal irritation was observed in two animals out of 5 animals dosed. |
| Ibuprofen (S)-(+) | Test Group 1 | 200.0 | Gastric mucosal irritation was observed in all the 5 animals dosed. |
| | Test Group 2 | 300.0 | Gastric mucosal irritation was observed in three animals out of 5 animals dosed. |

The results of the present study showed that none of the formulations of ibuprofen had caused any evidence of irritation of gastric mucosa in fasted male albino rats of male sex at the two dose levels tested (200 mg and 300 mg/kg body weight). In contrast, both ibuprofen (racemic mixture) and ibuprofen (S)-(+) had caused irritation of gastric mucosa at the two dose levels tested. Further ibuprofen(S)-(+) was found to be more gastric mucosal irritant than ibuprofen (racemic mixture).

28-Day Chronic Toxicity Studies with S(+) Ibuprofen L-Threonin Ester in Rats

Chronic toxicity of S(+) Ibuprofen-L-Threonine ester was compared against a vehicle, (+/−)racemic Ibuprofen and (+/−) racemic Ibuprofen-L-Hydroproline ester. Test species used was Swiss Albino Mice, both male and female with body weight range of 18-27 gms. Randomization was done by the method of stratified randomization procedure using SAS software program (Version 8.2) with stratification by body-weight.

TABLE 4

| GROUP | TEST ITEM | NUMBER OF ANIMALS | ANIMAL NUMBERS | |
|---|---|---|---|---|
| | | | Female | Male |
| Vehicle Control | Vehicle | 10 | 01 to 05 | 06 to 10 |
| Test Group 1 | Formulation 1 of Ibuprofen | 10 | 11 to 15 | 16 to 20 |
| Test Group 2 | Formulation 5 of Ibuprofen | 10 | 21 to 25 | 26 to 30 |
| Reference Test Group | Ibuprofen USP | 10 | 31 to 35 | 36 to 40 |

The test doses are expressed as Ibuprofen molar equivalents:

TABLE 5

| Test Item | Group | Dose (mg per kg) [in terms of Ibuprofen] | Equivalent weight of the Test item [mg] |
|---|---|---|---|
| Vehicle | Vehicle Control | 0.0 | 0.0 |
| L-Threonine ester of S(+) Ibuprofen | Test Group 1 | 200.0 | 334.0 |
| L-Hydroxyproline ester of Racemin Ibuprofen | Test Group 2 | 200.0 | 310.0 |
| Ibuprofen USP (Racemic mixture) | Reference Control | 200.0 | 200.0 |

The duration of dosing was 28 days. All the animals were daily tested until the end of the study for the presence/absence of clinical symptoms of toxicity. Cage side observations included changes in the skin, eyes, posture, gait, respiration and behavior pattern. The incidence of twitching, tremors, convulsions, salivation, diarrhea and death if any, were also recorded.

Animals Exposed to Different Doses of the Test Substance Did not Indicate any Symptoms of Toxicity (Table 16).

TABLE 16

Summary of Clinical Symptoms of Toxicity in Albino Mice

| GROUP (mg/kg body weight) | Symptoms of toxicity | Sex | Animal Numbers | Period of Signs in days From-to | Mortality |
|---|---|---|---|---|---|
| Vehicle Control (0.0) (No Treatment) | No symptoms of toxicity were observed | Female | 01 to 05 | 0-28 | Nil |
|  | No symptoms of toxicity were observed | Male | 6 to 10 | 0-28 | Nil |
| Test Group 1 (Ibuprofen S + T) (334.0 mg/kg) | No symptoms of toxicity were observed | Female | 11 to 15 | 0-28 | Nil |
|  | No symptoms of toxicity were observed | Male | 16 to 20 | 0-28 | Nil |
| Test Group 2 (Ibuprofen HP) (310.0 mg/kg) | No symptoms of toxicity were observed | Female | 21 to 25 | 0-28 | 1/5 |
|  | No symptoms of toxicity were observed | Male | 26 to 30 | 0-28 | Nil |
| Reference Control 3 (Ibuprofen USP) (200.0 mg/kg) | No symptoms of toxicity were observed | Female | 31 to 35 | 0-28 | 3/5 |
|  | No symptoms of toxicity were observed | Male | 36 to 40 | 0-28 | 1/5 |

In the above table, S + T Ibuprofen refers to S(+)Ibuprofen-L-Threonine Ester.

Death Record
Ibuprofen HP
Animal no. 23 (female animal) died on 21 day of dosing.
Positive Control Group
Animal no. 31 (female animal) died on 23 day of dosing.
Animal no. 32 (female animal) died on 21 day of dosing.
Animal no. 33 (female animal) died on 24 day of dosing.
Animal no. 40 (male animal) died on 10 day of dosing.

While there were no cage side specific toxicity were noted, surprisingly 40% of the animals receiving racemic ibuprofen died, only 10% of the rats receiving Hydroxyproline ester of Iburprofen did not complete the full course, and even more surprisingly, none of the animals in the S(+)Ibuprofen-L-Threonine ester group died. The average increase/decrease in body weight and the percentage change of body weight of the surviving animals in various groups are shown below:

TABLE 17

| Treatment | Average Change In body Weight (gms) | Percentage Change (No of animals survived) |
|---|---|---|
| Vehicle | 4.65 | 19.97 (10) |
| S(+)Ibuprofen Threonine Ester | −0.68 | −3.61 (10) |
| Ibuprofen Hydroxy-Proline Ester | 1.43 | 5.75 (9) |
| Racemic Ibuprofen | 2.97 | 12.54 (6) |

While there was increase in body weight in treatments with racemic Ibuprofen and Ibuprofen Hydroxyproline ester, both group have mortalities, with currently marketed Ibuprofen showing more mortality than Hydroxyproline ester. Hence all the amino acid esters are far superior to Ibuprofen racemic mixture or the active S(+)Ibuprofen. However, the best product so far seems to be S(+)Ibuprofen-L-Threonine Ester, making it one of the ideal candidates to be advanced to human trials.

Human Clinical Trials with S(+)Ibuprofen-L-Threonine Ester:

Determination of the analgesic and anti-inflammatory effects of S(+)Ibuprofen-L-Threonine Ester in three human volunteers was conducted as follows:

Two male, age 49 and 50 having severe headache took 1 capsule containing S(+)Ibuprofen-L-Threonine Ester manufacturing and formulation under GMP conditions. The capsule contents were equivalent to 200 mg of racemic Ibuprofen. Relief from headache was reported after 15 min, and complete absence of any pain from headache was reported at the end of 1 hour, which lasted for another 12 hours.

Two males age 49 and 51 took 1 capsule each containing S(+)IbuprofenL-Threonine ester for arthritic knee pain, which was perceptible. After 12 hours, both volunteers reported significant reduction is the pain associated with their right knee. Such amolearation of pain was further sustained for another 24 hours.

Pharmacokinetics of Ibuprofen in Human Volunteers:

Based upon preliminary analgesic and anti-inflammatory response from the 4 volunteers, Ibuprofen racemic drug was compared against S(+)Ibuprofen-L-Threonine ester at 200 mg equivalent dose. The plasma-concentration time profile in 6 volunteers, where S(+)Ibuprofen-L-Threonine ester concentrations were plotted against racemic ibuprofen concentrations in plasma for each volunteers.

Based upon the results of comparative bioavailablity of racemic Ibuprofen versus Ibuprofen released from S(+)Ibuprofen-L-Threonine ester it is clear that only very small amount of Ibuprofen is released intact into human blood stream. This is due to the fact that S(+)Ibuprofen-L-threonine ester does not act as a derivative of Ibuprofen, instead the Threonine ester had intact activity.

The overall bioavailability of Ibuprofen from Ibuprofen Racemic mixture of 200 mg and equivalent dose of S(+) Ibuprofen-L-Threonine ester are shown in the table below:

TABLE 18

| Volunteer | AUC1 | AUC2 | % Availability |
|---|---|---|---|
| 1 | 69197.618 | 893.226 | 1.3 |
| 2 | 41861.277 | 1978.925 | 4.7 |
| 3 | 73121.747 | 940.133 | 1.3 |
| 4 | 38993.502 | 2101.642 | 5.4 |
| 5 | 34567.246 | 1657.496 | 4.8 |
| 6 | 66710.152 | 925.000 | 1.4 |

As used herein, the term AUC refers to area under the curve. In the above table, AUC1 represents the cumulative area under the plasma concentration time curve following oral administration of 200 mg of racemic ibuprofen to human volunteers, and AUC2 represents the cumulative area under the plasma concentration time curve following oral administration of 200 mg ibuprofen equivalence of S(+)Ibuprofen-L-Threonine ester. The third column in the above table shows relative bioavailability of Ibuprofen in human plasma after oral administration of S(+)Ibuprofen-L-Threonine ester at equivalent doses. This clearly demonstrates that any activity seen in human volunteers is not due to release of any significant amounts of S(+)Ibuprofen in to the plasma after oral ingestion of the Threonine ester.

The reason that S(+)Ibuprofen advanced to human pharmacokinetic studies was due to surprising results of lack of toxicity in 28-day chronic administration in rats compared to Ibuprofen, or Hydroxyproline ester of Ibuprofen. Furthermore, earlier studies indicated that S(+)Ibuprofen is highly toxic to gastric mucosa of rats (see table X above). Similar results were also shown in various studies elsewhere, for example, other investigators compared S(+) and R(−) enantiomers of ibuprofen in male Wistar rats. At 40 mg/kg dose, microscopic evaluation of the GI tissue samples revealed significance difference in GI toxicity caused by S(+) than R(−) Ibuprofen, consistent with current inventors results (Janjikhel, R K, Bricker, J D, Borochovitz, D, Adeyeye, C M, Stereoselective Disposition of Sustained Release Microspheres of Ibuprofen Enantiomers in Rats: II, Acute Gastrointestinal Toxicity. Drug Delivery, Vol 6, No. 3, August 1999, pp 163-170). However S(+)Ibuprofen-L-Threonine ester was GI sparing, and had no toxicity.

Furthermore, other authors have claimed that R(−)Ibuprofen may be capable of inhibiting both therapeutic and toxic effects of S(+)Ibuprofen (Kaehler, S T, Phleps, W, Hesse, E. Dexibuprofen: Pharmacology, therapeutic uses and safety. Infammopharmacology, Vol 11 No. 4-6, 2003, pp 371-383). This is also consistent with current inventor's observation, since in acute GI toxicity studies racemic ibuprofen was somewhat less toxic than S(+)Ibuprofen.

Similarly, Rainsford K D, in Pharmacology and Toxicology of Ibuprofen. In: Rainsford, K D, ed. Ibuprofen, A critical bibliographic Review. London, Taylor and Francis, 2000, states that competition between the enantiomers of ibuprofen for prostaglandin production in vitro was evident, and that inhibition of binding of S(+) ibuprofen by R(−) ibuprofen in the racemic mixture contributed to the GI tolerance of the racemate.

However, what is not known in the previous art is that an amino acid derivative, e.g., an ester of S(+)Ibuprofen would also be nontoxic. For example, one trained in the art of such derivative pharmacology, would have concluded that as S(+) Ibuprofen is highly toxic to the GI mucosa, and since S(+) Ibuprofen will be released from S(+)Ibuprofen-L-Threonine ester by the esterase enzymes in GI tract, and by the action of pancreatin enzyme in the duodenum, it was expected that there will not be any reduction in toxicity. However, the current inventor surprisingly noted that S(+)Ibuprofen-L-Threonine ester is significantly and completely non-toxic to GI mucosa in the rats tested.

In spite of no ibuprofen appearing in the human plasma after oral administration of S(+)Ibuprofen-L-Threonine ester, significant analgesic and anti-inflammatory response was seen in the 2 volunteers each tested twice. This is novel since it appears, that S(+)Ibuprofen-L-threonine ester is not a derivative, and it may have intact pharmacological activity. This is also not anticipated from the prior art.

While less effectiveness was seen in rat model with S(+) Ibuprofen-L-Threonine ester, the overriding factors that demonstrate that this drug is more suitable for human treatment of various diseases such as arthritis etc., is due to the fact that on chronic toxicity trials none of the animal died in this drug group. Furthermore, no toxicity either gastric or whole animal (as determined by number of surviving rats), was observed in the rat model for S(+)-Ibuproten L-Threonine ester. Further, there is no toxicity potential in the systemic circulation in human subjects. The S(+)Ibuprofen-L-Threonine ester exhibits pharmacological actions such as analgesic, anti-inflammatory and anti-pyretic properties when administered to humans.

Synthesis of Ketoprofen Derivatives:

Overview:

The procedure for the synthesis of the L-threonine esters of Ketoprofen is outlined in Synthetic Sequence section. The complete procedure and analytical data is given in the Experimental Section. In general, (±)-Ketoprofen (5 g) was coupled with N-boc-L-threonine t-butyl ester (1 equivalent) with 1-(3-dimethylaminopropyl)-3-ethylcarbodiimide, hydrochloride (EDC, 1 equivalent) in the presence of a catalytic amount of 4-(N,N-dimethyamino)-pyridine (DMAP). Once the reaction was complete, any excess EDC was removed by extraction with water, DMAP was removed by extraction with dilute acid, and Ketoprofen was removed by extraction with sodium bicarbonate. After drying over sodium sulfate, filtration, and concentration, the crude protected L-threonine-(±)-Ketoprofen was purified by flash chromatography on silica gel to generate the protected L-threonine ester in good yield (98%). The protecting groups were removed by treatment with 2M hydrochloric acid in diethyl ether to cleave the boc group, followed by treatment with trifluoroacetic acid to remove the t-butyl ester. After drying, the mixture of L-threonine-R,S(±)-Ketoprofen esters was separated by crystallization from acetonitrile. The hydrochloride salt of the L-threonine-S(+)-Ketoprofen ester preferentially precipitated from acetonitrile. A sample of an optically pure standard was prepared starting with S(+)-ketoprofen for comparison. After drying and analysis, a sample of L-threonine-S(+)-Ketoprofen ester, hydrochloride (1.75 g) separated from the mixture was shipped to Signature Pharmaceuticals, Inc. for testing.

The L-serine and L-hydroxyproline esters of (±)-Ketoprofen were also prepared in the same manner. Attempts to separate the mixture of Ketoprofen diastereomers by crystallization, using a variety of solvents, failed to separate the mixture. Since only partial separation could be seen by HPLC analysis, the esters were purified as the mixture of diastereomers before final analysis. The preparation and final analytical data for the serine and hydroxyproline esters are also included.

Synthetic Sequence:

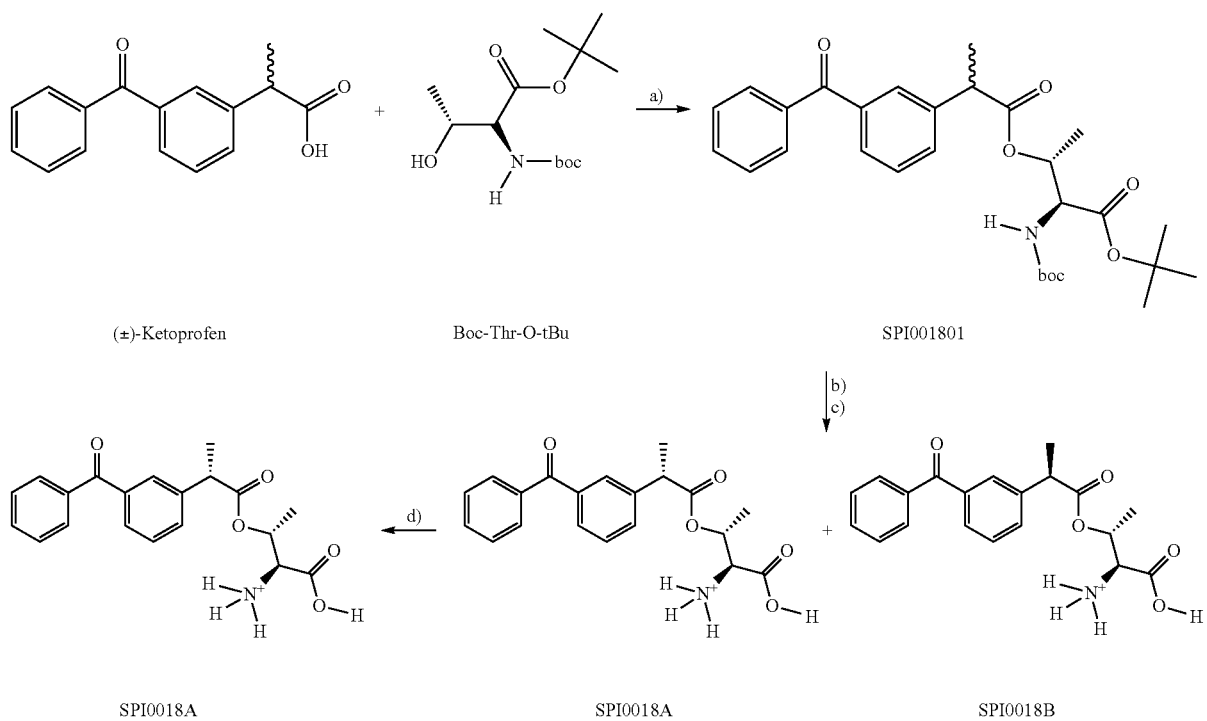

Synthesis of the L-threonine Esters of (±)-Ketoprofen: a) EDC, DMAP, CH$_2$Cl$_2$; b) HCl (2M); c) TFA; d) ACN (Crystallization).

Experimental Section:

The synthesis of SPI0018A was conducted in a single batch. Reagents mentioned in the experimental section were purchased at the highest obtainable purity from Sigma-Aldrich, Acros, or Bachem, except for solvents, which were purchased from either Fisher Scientific or Mallinkrodt.

Preparation and Separation of S(+)-Ketoprofen-L-Threonine Ester, Hydrochloride (SPI0018A).

(±)-Ketoprofen (5.32 g, 20.92 mmol), N-t-butylcarbonyl-L-threonine t-butyl ester (Boc-Thr-OtBu, 5.17 g, 18.72 mmol, prepared by the literature method), 1-(3-dimethylaminopropyl)-3-ethylcarbodiimide, hydrochloride (EDC, 4.0 g, 20.9 mmol), and 4-(N,N-dimethylamino)-pyridine (DMAP, 0.22 g) were dissolved in dichloromethane (50 mL) at room temperature, under an argon atmosphere. After stirring for 5 hours, the dichloromethane layer was washed with water (50 mL), 5% hydrochloric acid (2×25 mL), water (25 mL), saturated sodium bicarbonate (2×25 mL), and water (50 mL). After drying for one hour over sodium sulfate (5 g), filtration, and concentration under reduced pressure, the remaining oil (10.3 g) was purified by column chromatography on silica gel (150 g), eluting with hexanes/ethyl acetate (2:1). After combining the product containing fractions, concentration and drying under high vacuum, the procedure generated the protected L-threonine-(±)-Ketoprofen ester (SPI001801) as a clear oil (9.42 g, 98% yield).

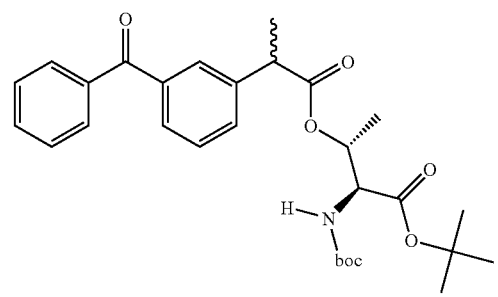

SPI001801

3-[2(R,S)-(3-Benzoyl-phenyl)-propionyloxy]-2(S)-tert-butoxycarbonylamino-butyric acid tert-butyl ester: (mix of diastereomers)

$^1$H NMR (300 MHz, CDCl$_3$): δ=7.83-7.42 (m, 9H), 5.43 (dd, 1H, J=13.2, 6.9 Hz), 5.10 (dd, 1H, J=20.7, 9.3), 4.29 (t, 1H, J=11.7 Hz), 3.75 (q, 1H, J=7.2 Hz), 1.50-1.42 (m, 19.5H), 1.30-1.18 (m, 4.5H).

$^{13}$C NMR (75 MHz, CDCl$_3$): δ=. 196.18, 172.62, 172.55, 168.85, 168.58, 155.81, 140.33, 140.23, 137.86, 137.39, 132.46, 132.42, 131.54, 131.38, 130.00, 129.31, 129.13, 129.02, 128.54, 128.27, 82.50, 82.37, 80.05, 71.38, 71.22, 57.59, 57.52, 45.46, 45.31, 28.40, 27.98, 27.84, 18.54, 18.48, 17.19, 16.84.

The protected (R,S)-Ketoprofen-L-threonine ester (9.42 g, 18.41 mmol) was dissolved in dichloromethane (25 mL) under an argon atmosphere, at room temperature. Anhydrous hydrochloric acid in diethyl ether (2M, 25 mL) was added to the solution and the mixture was allowed to stir for 17 hours at room temperature. The mixture was concentrated under reduced pressure. The remaining foam (8.2 g) was dissolved in a mixture of dichloromethane (10 mL) and trifluoroacetic acid (20 mL). After stirring at room temperature for 6.5 hours the solution was concentrated under reduced pressure. Toluene (25 mL) was added to the remaining oil and the mixture was concentrated a second time. A mixture of ethanol (20 mL) and anhydrous hydrochloric acid in diethyl ether (2M, 20 mL) was added and the solution was concentrated a third time. After drying under high vacuum for 2 hours at room temperature, the experiment produced (±)-Ketoprofen-L-threonine ester, hydrochloride (mixture of diastereomers, 7.11 g, 98% crude yield) as an off-white solid. The crude mixture of diastereomers (7.0 g) was crystallized 3 times from acetonitrile (200 mL). After the third crystallization, the remaining white solid was dried under high vacuum at 50° C. until the weight was constant (4 hours). The experiment produced L-threonine-S(+)-Ketoprofen ester, hydrochloride SPI0018A (2.2 g, 30% yield from SPI001801).

SPI0018A

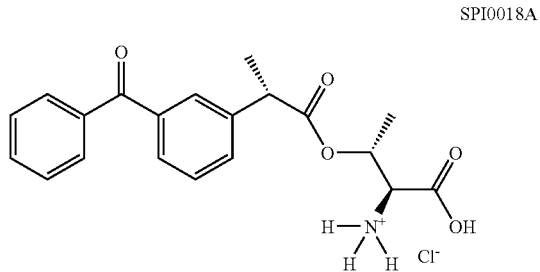

2(S)-Amino-3(R)-[2(S)-(3-benzoyl-phenyl)-propionyloxy]-butyric acid, hydrochloride (L-threonine-S (+)-Ketoprofen ester, hydrochloride)

$^1$H NMR (300 MHz, DMSO): δ=14.08 (br s, 1H), 8.72 (br s, 3H), 7.74-7.51 (m, 9H), 5.29 (t, 1H, J=4.5 Hz), 4.16 (m, 1H), 3.97 (q, 1H, J=6.3 Hz), 1.42 (d, 3H, J=6.9 Hz), 1.23 (d, 3H, J=6.3 Hz).
$^{13}$C NMR (75 MHz, DMSO): δ=195.34, 172.26, 168.21, 140.42, 137.05, 136.74, 132.66, 131.66, 129.48, 128.73, 128.49, 128.30, 68.23, 55.31, 44.00, 18.44, 16.45.
CHN Analysis:
calc.: C, 61.30; H, 5.66; N, 3.57. found: C, 61.02; H, 5.58; N, 3.58.
HPLC Analysis:
98.28% purity; r.t.=25.14 min.; 55% DIUF water (0.1% TFA)/45% methanol; 1 mL/min; 36.4 C; Luna C18, 5 u column (serial #211739-42), 4.6×250 mm; 20 ul injection.
Optical rotation: +27.0° (20 C, 174.4 mg/10 mL ethanol, 589 nm)
Melting Point: 166-167° C.
Preparation of the S-(+)-Ketoprofen-L-Threonine Ester, Hydrochloride Standard.
(+)-Ketoprofen (1.87 g, 7.74 mmol), N-t-butylcarbonyl-L-threonine t-butyl ester (Boc-Thr-OtBu, 2.25 g, 8.14 mmol, prepared by the literature method), 1-(3-dimethylaminopropyl)-3-ethylcarbodiimide, hydrochloride (EDC, 1.65 g, 8.60 mmol), and 4-(N,N-dimethylamino)-pyridine (DMAP, 0.1 g) were dissolved in dichloromethane (25 mL) at room temperature, under an argon atmosphere. After stirring for 4 hours, the dichloromethane layer was washed with water (25 mL). After drying for one hour over sodium sulfate (5 g), filtration, and concentration under reduced pressure, the remaining oil was used without purification. The procedure generated the protected L-threonine-(+)-Ketoprofen ester as a clear oil (4.01 g, ~100% yield).

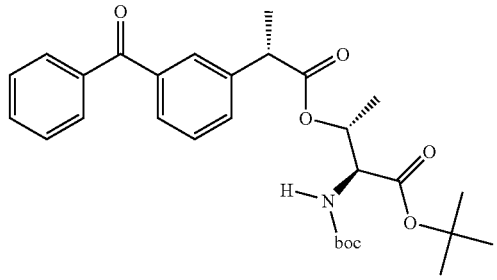

$^1$H NMR (300 MHz, CDCl$_3$): δ=7.81-7.42 (m, 9H), 5.43 (m, 1H), 5.10 (d, 1H, J=9.3), 4.29 (d, 1H, J=9.6 Hz), 3.75 (q, 1H, J=7.2 Hz), 1.50-1.42 (m, 21H), 1.18 (d, 3H, J=6.3 Hz).
$^{13}$C NMR (75 MHz, CDCl$_3$): δ=196.4, 172.79, 168.99, 155.94, 140.44, 137.99, 137.51, 132.59, 131.50, 130.13, 129.31, 129.25, 129.15, 128.66, 128.40, 82.68, 80.24, 71.37, 57.71, 45.43, 28.53, 28.10, 18.99, 16.96.
The protected (S)-Ketoprofen-L-threonine ester (3.92 g, 7.66 mmol) was dissolved in anhydrous hydrochloric acid in diethyl ether (2M, 50 mL) and stirred for 17 hours at room temperature. The mixture was concentrated under reduced pressure. The remaining foam (3.4 g) was dissolved in a mixture of dichloromethane (20 mL) and trifluoroacetic acid (20 mL). After stirring at room temperature for 6.5 hours the solution was concentrated under reduced pressure. Toluene (25 mL) was added to the remaining oil and the mixture was concentrated a second time. A mixture of ethanol (20 mL) and anhydrous hydrochloric acid in diethyl ether (2M, 20 mL) was added, and the solution was concentrated a third time. After drying under high vacuum for 2 hours at room temperature, the experiment produced S(+)-Ketoprofen-L-threonine ester, hydrochloride (3.05 g crude) as an off-white solid. The crude material was stirred with acetone (50 mL) for 2 hours at room temperature under an argon atmosphere. The remaining white solid was filtered and dried under high vacuum at 50° C. until the weight was constant (4 hours). The experiment produced L-threonine-S(+)-Ketoprofen ester, hydrochloride (2.04 g, 67% yield).
$^1$H NMR (300 MHz, DMSO): δ=14.08 (br s, 1H), 8.72 (br s, 3H), 7.74-7.51 (m, 9H), 5.29 (t, 1H, J=4.5 Hz), 4.16 (m, 1H), 3.97 (q, 1H, J=6.3 Hz), 1.42 (d, 3H, J=6.9 Hz), 1.23 (d, 3H, J=6.3 Hz).
$^{13}$C NMR (75 MHz, DMSO): δ=195.34, 172.26, 168.21, 140.42, 137.05, 136.74, 132.66, 131.66, 129.48, 128.73, 128.49, 128.30, 68.23, 55.31, 44.00, 18.44, 16.45.
HPLC Analysis:
99.43% purity; r.t.=25.14 min.; 55% DIUF water (0.1% TFA)/45% methanol; 1 mL/min; 36.4 C; Luna C18, 5 u column (serial #211739-42), 4.6×250 mm; 20 ul injection.
Optical rotation: +27.1° (20 C, 177.8 mg/10 mL ethanol, 589 nm)
Melting Point: 166-167° C.
Preparation of the (±)Ketoprofen-L-Serine Ester, Hydrochloride
(±)-Ketoprofen (7.30 g, 28.7 mmol), N-t-butylcarbonyl-L-serine t-butyl ester (Boc-Ser-OtBu, 7.50 g, 28.7 mmol, prepared by the literature method), 1-(3-dimethylaminopropyl)-3-ethylcarbodiimide, hydrochloride (EDC, 5.5 g, 28.7 mmol), and 4-(N,N-dimethylamino)-pyridine (DMAP, 0.12 g) were dissolved in dichloromethane (50 mL) at room temperature, under an argon atmosphere. After stirring for 3 hours, the dichloromethane layer was washed first with water (50 mL), then 5% hydrochloric acid (2×25 mL), then water (25 mL) again, saturated sodium bicarbonate (2×25 mL), and water (50 mL) a third time. After drying for one hour over sodium sulfate (5 g), filtration, and concentration under reduced pressure, the remaining foam was used without purification. The procedure generated the protected L-serine-(±)-Ketoprofen ester as a clear foam (13.72 g, 96% yield).

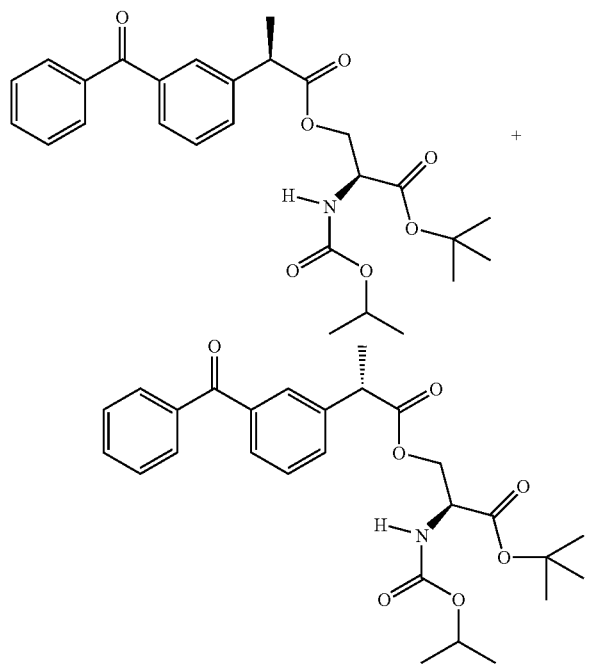

3-[2(R,S)-(3-Benzoyl-phenyl)-propionyloxy]-2(S)-tert-butoxycarbonylamino-propionic acid tert-butyl ester $^1$H NMR (300 MHz, CDCl$_3$): δ=7.77-7.38 (m, 9H), 5.29 (d, ½H, J=6.9 Hz), 5.13 (d, ½H, J=6.9 Hz), 4.44-4.30 (m, 3H), 3.78 (q, 1H, J=7 Hz), 1.50 (d, 3H, J=7 Hz), 1.39 (m, 18H).

$^{13}$C NMR (75 MHz, CDCl$_3$): δ=. 196.13, 173.37, 168.37, 154.99, 140.40, 137.89, 132.50, 131.44, 130.01, 129.25, 129.14, 128.53, 128.29, 82.72, 80.03, 65.22, 64.91, 53.62, 53.40, 45.29, 28.41, 28.02, 27.91, 18.59, 18.50.

The protected (R,S)-Ketoprofen-L-serine ester (13.6 g, 127.31 mmol) was dissolved in anhydrous hydrochloric acid in diethyl ether (2M, 100 mL) under an argon atmosphere, at room temperature. The mixture was allowed to stir for 23 hours at room temperature when dichloromethane was added (100 mL). After 48 hours, the mixture was concentrated under reduced pressure. The remaining light yellow foam (9.0 g) was dissolved in a mixture of dichloromethane (200 mL) and DIUF water (50 mL). After mixing at room temperature, the layers were separated. The dichloromethane layer was acidified with 2N hydrochloric acid in ether (5 mL), dried over sodium sulfate (10 g) filtered and concentrated under reduced pressure. The remaining foam (6.4 g) was stirred with dichloromethane (40 mL) for 30 minutes at room temperature under an argon atmosphere. Diethyl ether was added (20 mL) and the mixture was allowed to stir for 2 hours at room temperature. After 2 hours, the solids were filtered and dried under high vacuum at room temperature until a constant weight was obtained. The experiment produced L-serine-R,S(±)-Ketoprofen ester, hydrochloride (2.5 g, 22% yield).

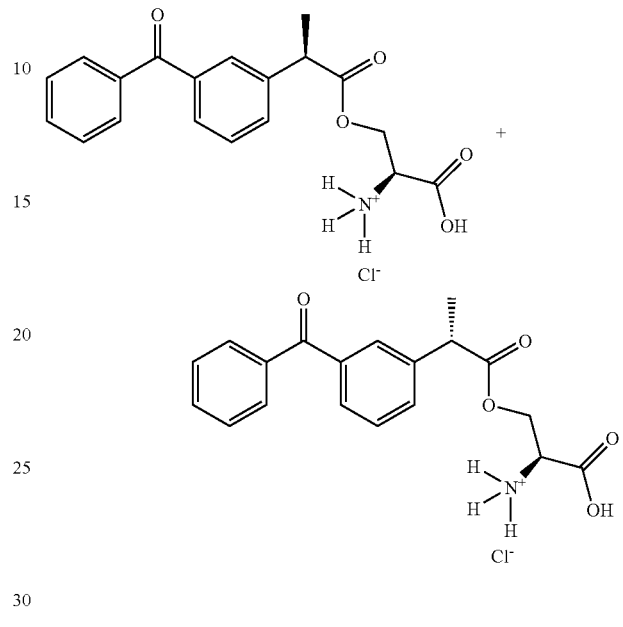

2(S)-Amino-3-[2(R,S)-(3-benzoyl-phenyl)-propionyloxy]-propionic acid, hydrochloride H NMR (300 MHz, DMSO): δ=8.79 (br s, 3H), 8.72 (br s, 3H), 7.76-7.54 (m, 9H), 4.57 (m, 1H), 4.42-4.28 (m, 2H), 4.01 (m, 1H), 1.46 (d, 3H, J=6 Hz).

$^{13}$C NMR (75 MHz, DMSO): δ=195.33, 172.92, 168.01, 167.96, 140.50, 140.39, 136.97 (d), 136.75, 132.66, 131.93 (d), 129.55, 128.65 (d), 128.49 (d), 62.18, 51.35 (d), 44.07, 18.62, 18.41.

HPLC Analysis:

98.99% purity; r.t.=9.205 min. (broad peak); 55% DIUF water (0.1% TFA)/45% methanol; 1 mL/min; 36.4 C; Luna C18, 5 u column (serial #211739-42), 4.6×250 mm; 20 ul injection.

CHN Analysis:

calc.: C, 60.40; H, 5.34; N, 3.71. found: C, 60.15; H, 5.32; N, 3.72.

Melting Point: 116-120° C. (uncorrected)

Preparation of the (±)Ketoprofen-L-Hydroxyproline Ester, Hydrochloride (±)-Ketoprofen (6.70 g, 26.3 mmol), N-t-butylcarbonyl-trans-L-hydroxyproline-t-butyl ester (Boc-Hyp-OtBu, 7.40 g, 25.7 mmol, prepared by the literature method), 1-(3-dimethylaminopropyl)-3-ethylcarbodiimide, hydrochloride (EDC, 5.25 g, 27.3 mmol), and 4-(N,N-dimethylamino)-pyridine (DMAP, 0.10 g) were dissolved in dichloromethane (50 mL) at room temperature, under an argon atmosphere. After stirring for 3.5 hours, the dichloromethane layer was washed first with water (50 mL), then, 5% hydrochloric acid (2×25 mL), then water (25 mL), then saturated sodium bicarbonate (2×25 mL), and finally water (50 mL). After drying for one hour over sodium sulfate (5 g), filtration, and concentration under reduced pressure, the remaining light green oil (13.30 g) was purified by column chromatography on silica gel (120 g), eluting with heptane/ethyl acetate (2:1). After combining the fractions containing product, concentration under reduced pressure and drying under high vacuum, the procedure generated the protected L-hydroxyproline-(±)-Ketoprofen ester as a clear oil (5.50 g, 41% yield).

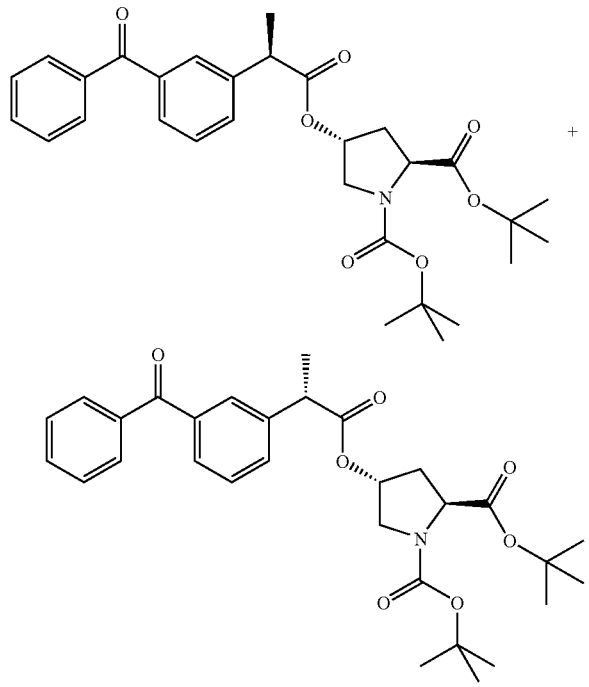

4(R)-[2(R,S)-(3-Benzoyl-phenyl)-propionyloxy]-pyrrolidine-1,2(S)-dicarboxylic acid di-tert-butyl ester $^1$H NMR (300 MHz, CDCl$_3$): δ=7.77-7.38 (m, 9H), 5.29 (d, ½H, J=6.9 Hz), 5.13 (d, ½H, J=6.9 Hz), 4.44-4.30 (m, 3H), 3.78 (q, 1H, J=7 Hz), 1.50 (d, 3H, J=7 Hz), 1.39 (m, 18H).

$^{13}$C NMR (75 MHz, CDCl$_3$): δ=196.25, 173.43 (d), 171.46 (d), 153.66 (d), 140.35, 138.00, 137.47, 132.55, 131.38, 130.05, 129.13, 128.67, 128.30, 81.55, 80.37 (d), 73.31, 72.48, 58.56, 51.86 (d), 45.43, 36.68 (d), 28.49, 28.18, 18.60.

The protected (R,S)-Ketoprofen-L-hydroxyproline ester (3.30 g, 6.31 mmol) was dissolved in anhydrous hydrochloric acid in diethyl ether (2M, 20 mL) under an argon atmosphere at room temperature. After 72 hours, the mixture was concentrated under reduced pressure. The remaining light yellow foam (2.6 g) was dissolved in a mixture of dichloromethane (50 mL) and DIUF water (10 mL). After mixing at room temperature, the layers were separated. The dichloromethane layer was acidified with 2N hydrochloric acid in ether (5 mL) dried over sodium sulfate (5 g) filtered and concentrated under reduced pressure. The remaining foam (2 g) was stirred with diethyl ether (20 mL) for 30 minutes at room temperature under an argon atmosphere. The solids were filtered and dried under high vacuum at room temperature until a constant weight was obtained. The experiment produced L-hydroxyproline-R,S(±)-Ketoprofen ester, hydrochloride (1.2 g, 48% yield).

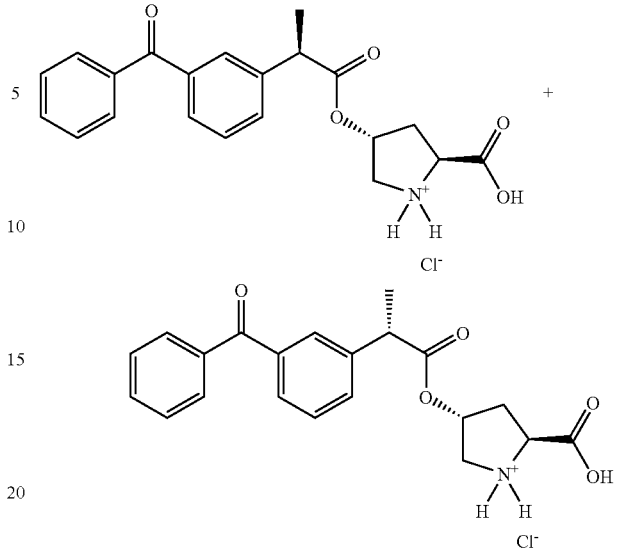

4(R)-[2(R,S)-(3-Benzoyl-phenyl)-propionyloxy]-pyrrolidine-2(S)-carboxylic acid, hydrochloride H NMR (300 MHz, DMSO): δ=10.25 (br s, 2H), 7.73-7.53 (m, 9H), 5.29 (br m, 1H), 4.38 (t, ½H, J=8.1 Hx), 4.26 (t, ½H, J=9 Hz), 3.95 (m, 1H), 3.60 (m, 1H), 3.28 (d, ½H, J=13 Hz), 3.16 (d, ½H, J=12 Hz), 2.37-2.20 (m, 2H), 1.45 (m, 3H).

$^{13}$C NMR (75 MHz, DMSO): δ=195.38, 172.78, 172.73, 169.16, 140.50, 140.41, 137.08, 136.77, 132.67, 132.01, 131.89, 129.52, 128.78, 128.50, 128.50, 72.87 (d), 57.60, 57.52, 50.16 (d), 44.30, 44.20, 34.26, 34.15, 18.43, 18.25.

HPLC Analysis:

99.99% purity; r.t.=7.842 and 7.689 min. (broad double peak); 55% DIUF water (0.1% TFA)/45% methanol; 1 mL/min; 36.4 C; Luna C18, 5 u column (serial #211739-42), 4.6×250 mm; 20 ul injection.

CHN Analysis:

calc.: C, 62.45; H, 5.49; N, 3.47. found: C, 61.78; H, 5.56; N, 3.62.

Melting Point: 170-173° C. (uncorrected).

Synthesis of Keotorlac-L-Threonine Ester and Human Trials:

Overview:

The procedure for the synthesis of the L-threonine ester of Ketorolac is outlined in Synthetic Sequence section. The complete procedure and analytical data is given in the Experimental Section. In general, (±)-Ketorolac was extracted from the tromethamine salt (10 g) and coupled with N-boc-L-threonine t-butyl ester (1 equivalent) with 1-(3-dimethylaminopropyl)-3-ethylcarbodiimide, hydrochloride (EDCI) in the presence of a catalytic amount of 4-(N,N-dimethylamino)-pyridine (DMAP). The crude protected L-threonine-(±)-Ketorolac ester was purified by flash chromatography. The protecting groups were removed by treatment with trifluoroacetic acid. The mixture of L-threonine-R,S(±)-Ketorolac ester salts was separated by crystallization from acetonitrile/acetone. A sample of S(−)-Ketorolac L-threonine ester, hydrochloride (2.1 g) separated from the mixture was shipped to Signature for testing.

Synthetic Sequence:

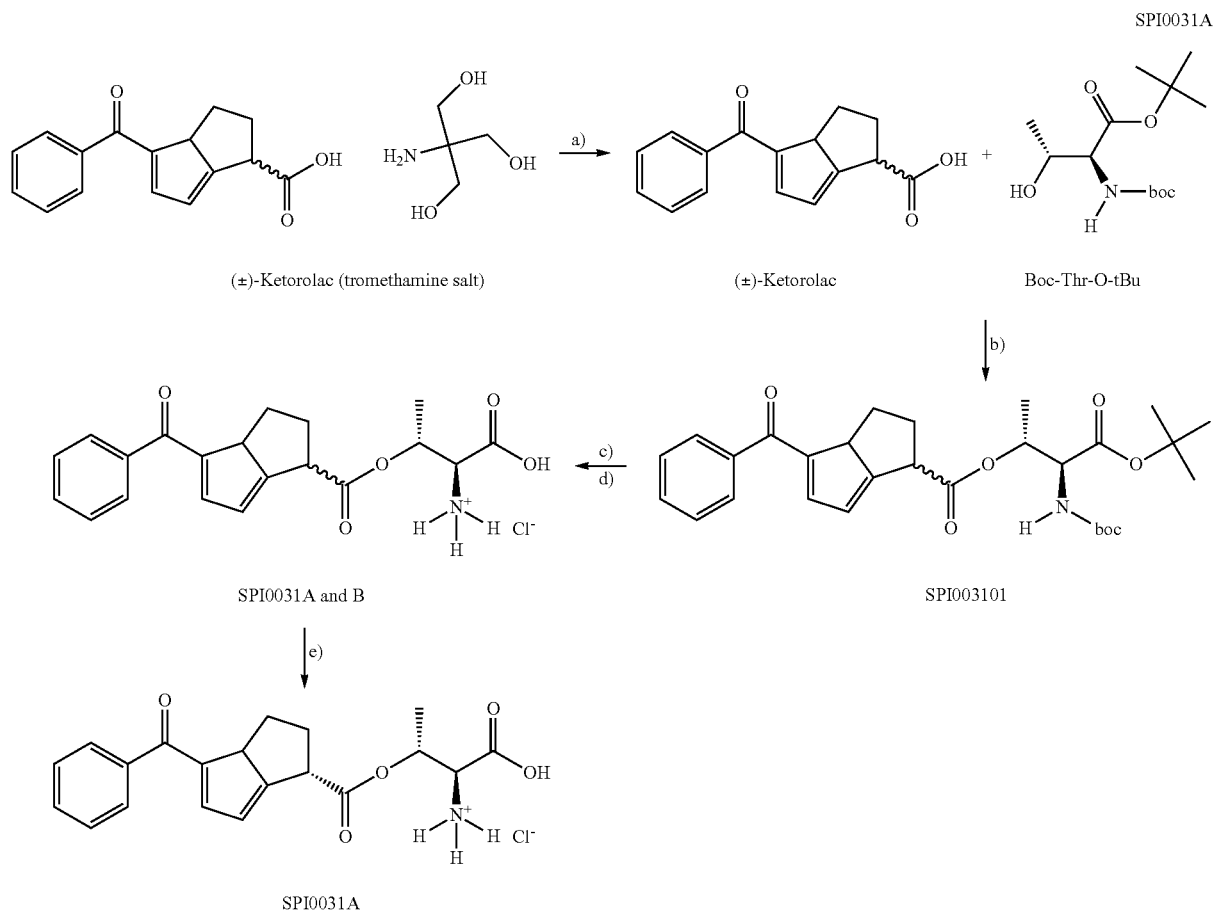

Synthesis of the L-threonine Esters of (±)-Ketorolac: a) AcOH/H₂O, CH₂Cl₂; b) EDC, DMAP, CH₂Cl₂; c) TFA; d) HCl, Ethanol; e) ACN-acetone (Crystallization).

Experimental Section:

The synthesis of SPI0031A was conducted in a single batch. The procedure was later repeated to ensure reproducibility. Reagents mentioned in the experimental section were purchased at the highest obtainable purity from Cayman Chemical, Sigma-Aldrich, Acros, or Bachem, except for solvents, which were purchased from either Fisher Scientific or Mallinkrodt.

Preparation and Separation of S(−)-Ketorolac L-Threonine Ester, Hydrochloride (SPI0031A).

(±)-Ketorolac tromethamine salt (10 g, Cayman Chemical) was dissolved in water (100 mL), acetic acid (20 mL), and dichloromethane (50 mL). After mixing for ten minutes, the layers were separated and the water fraction was extracted two additional times with dichloromethane (50 mL). The dichloromethane fractions were combined, dried over sodium sulfate, filtered, concentrated, and dried under high vacuum at room temperature until a constant weight was obtained. The procedure generated (±)-Ketrolac (6.78 g, 100% yield) as an off-white solid.

¹H NMR (300 MHz, CDCl₃): δ=9.62 (1H, br s), 7.80 (2H, d, J=6.9 Hz), 7.55-7.42 (3H, m), 6.84 (1H, d, J=4.0 Hz), 6.15 (1H, d, J=4.0 Hz), 4.62-4.41 (2H, m), 4.10 (1H, dd, J=8.4, 5.7 Hz), 2.97-2.75 (2H, m).

¹³C NMR (75 MHz, CDCl₃): δ=185.25, 176.69, 142.04, 139.05, 131.61, 129.02, 128.26, 127.31, 125.43, 103.63, 47.77, 42.64, 31.20.

(±)-Ketrolac (6.80 g, 26.6 mmol), N-tert-butylcarbonyl-L-threonine tert-butyl ester (Boc-Thr-OtBu, 7.33 g, 26.6 mmol, prepared by the literature method), 1-(3-dimethylaminopropyl)-3-ethylcarbodiimide, hydrochloride (EDCI, 5.50 g, 28.6 mmol), and 4-(N,N-dimethylamino)-pyridine (DMAP, 0.10 g) were dissolved in dichloromethane (75 mL) at room temperature, under an argon atmosphere. After stirring for 6 hours, the dichloromethane solution was washed first with water (50 mL), then with saturated sodium bicarbonate 50 mL), and finally with water (50 mL) again. After drying the dichloromethane solution for one hour over sodium sulfate (10 g), filtration, and concentration under reduced pressure, the remaining brown oil (14.55 g) was purified by column chromatography on silica gel (250 g), eluting with heptane/ethyl acetate (1:1). After combining the fractions containing product, concentration and drying under high vacuum, the procedure generated the protected L-threonine-(±)-Ketorolac ester (SPI003101) as light brown solid foam (13.53 g, 99.2% yield).

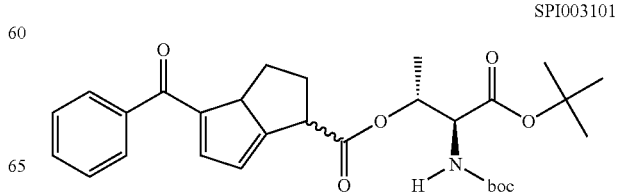

$^1$H NMR (300 MHz, CDCl$_3$): δ=7.80 (2H, m), 7.55-7.42 (3H, m), 6.81 (1H, m), 6.08 (1H, m), 5.47 (1H, m), 5.17 (1H, m), 4.60-4.34 (3H, m), 4.01 (1H, m), 2.90-2.70 (2H, m), 1.48-1.32 (21H, m).

$^{13}$C NMR (75 MHz, CDCl$_3$): δ=184.85, 169.91, 168.91, 155.84, 141.91, 139.12, 131.41, 128.86, 128.13, 127.18, 124.99, 103.56, 103.13, 82.76, 80.23, 72.15, 72.00, 57.64, 47.62, 42.71, 42.53, 32.02, 31.11, 28.44, 28.02, 17.03, 14.33.

The protected (±)-Ketorolac L-threonine ester SPI003101 (13.50 g, 26.33 mmol) was dissolved in trifluoroacetic acid (50 mL) under an argon atmosphere, at room temperature. The mixture was allowed to stir for 7 hours at room temperature under an argon atmosphere. The brown solution was concentrated under reduced pressure and dried under high vacuum at room temperature until a constant weight was achieved. The remaining brown solid (10.2 g) was stirred in acetone (250 mL) at room temperature for 3 hours. The white precipitate that formed was filtered and dried under high vacuum. The remaining solid (5.70 g) was dissolved in a minimal amount of DIUF water (5-10 mL) and a 1:1 mixture of acetonitrile-acetone (100 mL) was added drop-wise over 1 hour while stirring at room temperature. After the addition was complete, the mixture was stored for 2 hours at room temperature. The white precipitate that formed was filtered and dried under high vacuum at room temperature to a constant weight. The white solid (3.0 g) was purified a final time by dissolving in DIUF water (5 mL). Most of the water was removed under reduced pressure to generate a thin, clear oil. Acetone (100 mL) was added to the oil in a drop-wise fashion over 30 minutes while stirring under an argon atmosphere. The mixture was stored for 3 hours at −10° C. The precipitate was filtered and dried under high vacuum at room temperature until the weight was constant. The experiment produced S(−)-Ketorolac-L-threonine ester, hydrochloride SPI0031A (2.32 g, 22.4% yield based on SPI003101, 98.12% purity by HPLC) as a white solid.

$^1$H NMR (300 MHz, DMSO): δ=8.80 (3H, br s), 7.73 (2H, d, J=7.5 Hz), 7.61-7.46 (3H, m), 6.77 (1H, d, J=3.9 Hz), 6.16 (1H, d, J=3.9 Hz), 5.33 (1H, m), 4.42-4.22 (4H, m), 2.76 (2H, m), 1.35 (3H, d, J=6.6 Hz).

$^{13}$C NMR (75 MHz, DMSO): δ=183.41, 169.64, 168.19, 142.32, 138.59, 131.44, 128.35, 128.26, 126.22, 124.27, 103.18, 68.84, 55.31, 47.34, 41.83, 30.18, 16.59.

CHN Analysis:
calc.: C, 58.09; H, 5.39; N, 7.13; Cl, 9.02. (C$_{19}$H$_{21}$ClN$_2$O$_5$). found: C, 58.61; H, 5.26; N, 7.10; Cl, 8.16.

HPLC Analysis:
98.12% purity, r.t.=19.617 min, sample dissolved in DIUF water/ACN, 50% DIUF water (0.1% TFA)/50% ACN, Gemini C18 (#262049-2), 5 u, 250×4.6 mm, 1 mL/min., 37° C., 20 uL inj. vol., SPD-10 Avp, chl-210 nm.

Specific rotation: −108 deg (25° C., 52.5 mg/5 mL water, 589 nm)

Melting Point: 155-157° C. (decomposed)

Large negative specific rotation is consistent with the S(−) Ketorolac moiety.

Human Clinical Trial:

S(−)Ketorolac-L-Threonine ester capsules were filled using dextrose as the filler. The Ketorolac-L-Threonine ester dose was comparable to racemic Ketorolac Tromethamine tablets. For example, 13 mg of S(−)Ketorolac-L-Threonine ester was roughly equivalent to 13 mg of racemic Ketorolac tromethamine in tablet and/or capsule form.

A Female patient (age 72) suffering from severe ankolysing spodolytis, arthritis and other inflammatory joint problems was under treatment with Indomethacin, 25 mg twice daily dose. In order the evaluate the analgesic activity of S(−) Ketorolac-L-Threonine ester, the patient was withdrawn from Indomethacin. After 24 hours, the pain returned and she was administered with 13 mg of S(−) Ketorolac L-Threonine ester, once in the morning and once in the evening. This was repeated for 5 days. During the entire period, the patient demonstrated lack of pain, no gastric irritation symptoms, or other side effects.

About 3 months later, the same above female volunteer repeated the experiment. This time, after she went off the indomethacin, only one dose of 13 mg of S(−) Ketorolac-L-Threonine ester was administered. After the 2$^{nd}$ day, she complained of the pain resurfacing, and the dose was then increased on the morning of the 3$^{rd}$ day to twice daily of 13 mg each. Beginning the 3$^{rd}$ day she indicated of lack of any pain. This treatment was continued for another 3 days of two capsules of 13 mg each. On the morning of the 6$^{th}$ day, she was switched back to Indomethacin. This study showed that in this particular volunteer, 13 mg twice daily was the appropriate dose to alleviate her severe pain.

C. Amino Acid Derivatives of Aspirin

Overview:

The procedure for the synthesis of the L-serine, L-threonine, and L-hydroxyproline esters of acetylsalicylic acid is outlined in Synthetic Sequence section and is exemplary for other amino acids. The complete procedure and analytical data is given in the Experimental Section. In general, acetylsalicyloyl chloride (10 g-25 g, in batches) was coupled with the N-benzyloxy/benzyl ester protected amino acids in the presence of pyridine. Once the reactions were completed (24 to 48 hours at room temperature), the mixture was poured into ice-cold 2N hydrochloric acid. The dichloromethane fraction was then washed with sodium bicarbonate, water and brine. After drying over sodium sulfate, filtration, and concentration, the crude protected amino acid esters of acetylsalicylic acid were purified by flash chromatography on silica gel. The procedure generated the protected amino acid esters of acetylsalicylic acid in yields ranging from 68% to 95%. The protecting groups were removed by hydrogenation (20 psi H$_2$) in the presence of 10% palladium on carbon. The amino acid esters of acetylsalicylic acid were extracted from the palladium catalyst using water. The solution containing the product uses concentrated, and dried. The final compounds was washed with solvent (water, dioxane, acetonitrile, and/or dichloromethane) until pure and dried under high vacuum until a constant weight was achieved.

Synthetic Sequence

1. SPIB00102

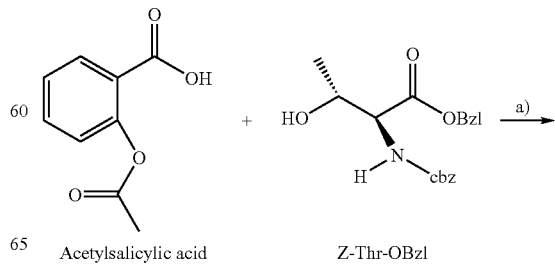

Acetylsalicylic acid     Z-Thr-OBzl

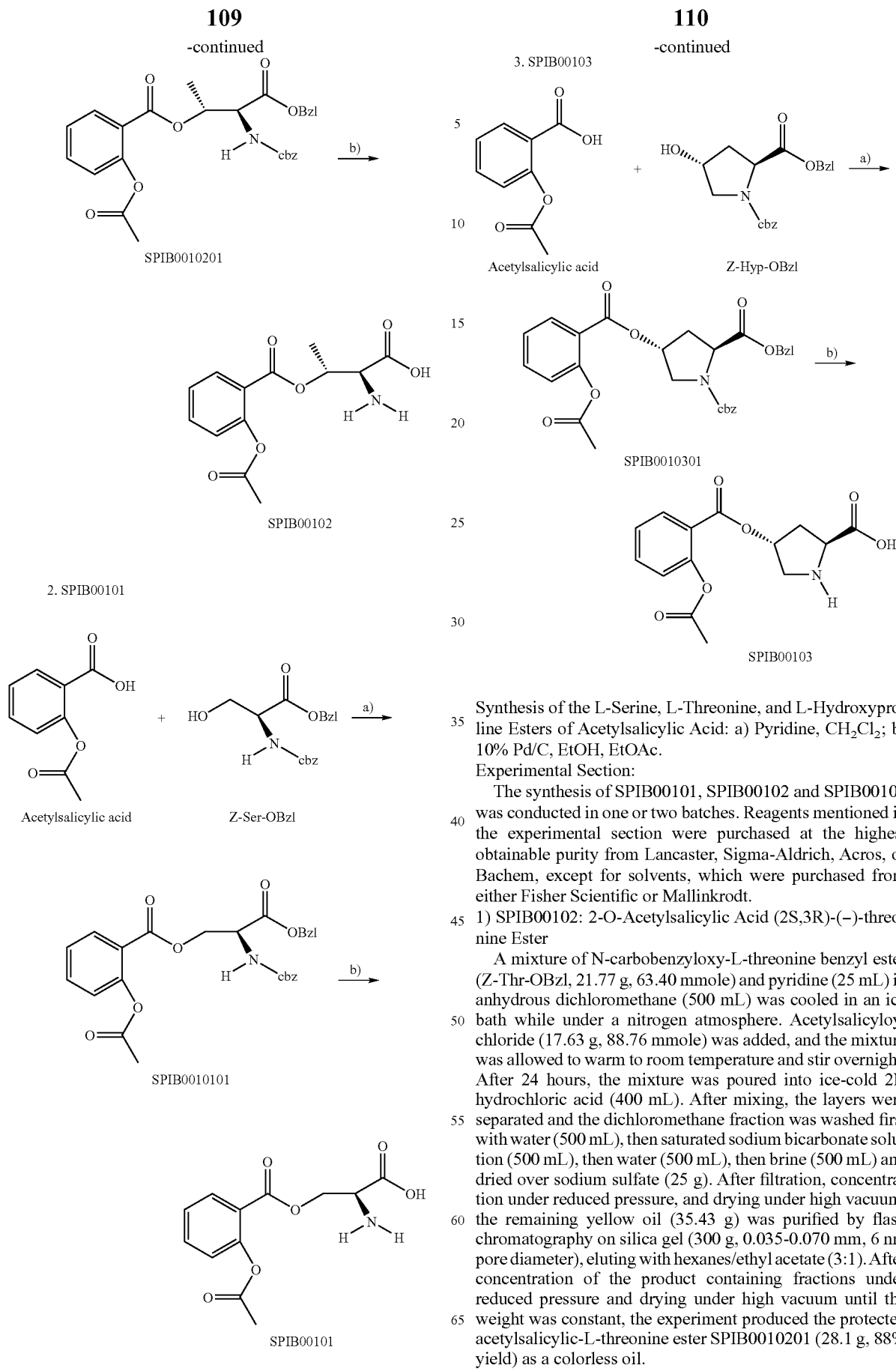

Synthesis of the L-Serine, L-Threonine, and L-Hydroxyproline Esters of Acetylsalicylic Acid: a) Pyridine, CH$_2$Cl$_2$; b) 10% Pd/C, EtOH, EtOAc.

Experimental Section:

The synthesis of SPIB00101, SPIB00102 and SPIB00103 was conducted in one or two batches. Reagents mentioned in the experimental section were purchased at the highest obtainable purity from Lancaster, Sigma-Aldrich, Acros, or Bachem, except for solvents, which were purchased from either Fisher Scientific or Mallinkrodt.

1) SPIB00102: 2-O-Acetylsalicylic Acid (2S,3R)-(−)-threonine Ester

A mixture of N-carbobenzyloxy-L-threonine benzyl ester (Z-Thr-OBzl, 21.77 g, 63.40 mmole) and pyridine (25 mL) in anhydrous dichloromethane (500 mL) was cooled in an ice bath while under a nitrogen atmosphere. Acetylsalicyloyl chloride (17.63 g, 88.76 mmole) was added, and the mixture was allowed to warm to room temperature and stir overnight. After 24 hours, the mixture was poured into ice-cold 2N hydrochloric acid (400 mL). After mixing, the layers were separated and the dichloromethane fraction was washed first with water (500 mL), then saturated sodium bicarbonate solution (500 mL), then water (500 mL), then brine (500 mL) and dried over sodium sulfate (25 g). After filtration, concentration under reduced pressure, and drying under high vacuum, the remaining yellow oil (35.43 g) was purified by flash chromatography on silica gel (300 g, 0.035-0.070 mm, 6 nm pore diameter), eluting with hexanes/ethyl acetate (3:1). After concentration of the product containing fractions under reduced pressure and drying under high vacuum until the weight was constant, the experiment produced the protected acetylsalicylic-L-threonine ester SPIB0010201 (28.1 g, 88% yield) as a colorless oil.

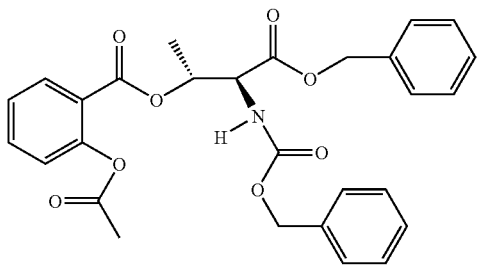

SPIB0010201

$^1$H NMR (300 MHz, CDCl$_3$): δ=7.74 (1H, d, J=7.5 Hz), 7.51 (1H, dt, J=7.5, 1.5 Hz), 7.34-7.17 (11H, m), 7.06 (1H, d, J=7.2 Hz), 5.62 (2H, m), 5.13 (4H, m), 4.65 (1H, dd, J=9.6, 2.4 Hz), 2.29 (3H, s), 1.38 (3H, d, J=6.6 Hz).

$^{13}$C NMR (75 MHz, CDCl$_3$): δ=169.35, 169.22, 162.73, 156.26, 150.41, 135.79, 134.67, 133.77, 131.24, 128.35, 128.24, 128.08, 127.95, 125.78, 123.51, 122.61, 71.22, 67.72, 67.26, 57.64, 20.98, 16.88.

The protected acetylsalicylic-L-threonine ester SPIB0010201 (14.50 g, 28.68 mmole) was dissolved in ethanol (100 mL) and ethyl acetate (100 mL) at room temperature and added to a Parr bottle that contained 10% palladium on carbon (3.0 g, 50% wet) under a nitrogen atmosphere. The nitrogen atmosphere was replaced with hydrogen gas (20 psi). After 20 hours of shaking, the palladium catalyst was removed by filtration through celite. The remaining solids (palladium/celite and product) were washed with water (600×4 mL) until the product was removed. The ethanol and water fractions were concentrated under reduced pressure at room temperature. The remaining solids were washed with water (20 mL) and dioxane (20 mL) for 48 hours. After filtration, the remaining white solid was dried at room temperature under high vacuum until the product weight was constant (16 hours). The experiment produced acetylsalicylic-L-threonine ester, SPIB00102 (4.40 g, 55% yield) as a white solid.

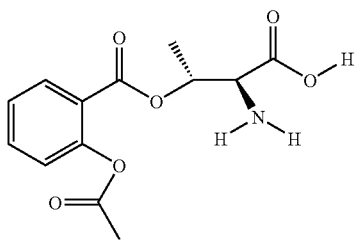

SPIB00102

$^1$H NMR (300 MHz, D$_2$O-DCl): δ=8.00 (1H, dd, J=7.8, 1.5 Hz), 7.74 (1H, dt, J=7.8, 1.5 Hz), 7.47 (1H, dt, J=7.8, 1.5 Hz), 7.27 (1H, dd, J=7.8, 1.5 Hz), 5.76 (1H, dq, J=6.9, 3.0 Hz), 4.49 (1H, d, J=3.0 Hz), 2.39 (3H, s), 1.55 (3H, d, J=6.9 Hz).

$^{13}$C NMR (75 MHz, D$_2$O-DCl): δ=173.03, 168.84, 163.97, 149.56, 135.32, 131.26, 126.85, 123.48, 121.49, 69.16, 56.36, 20.45, 15.86.

HPLC Analysis:

98.7% purity; rt=6.233 min; Luna C18 5 u column (sn 167917-13); 4.6×250 mm; 254 nm; 35% MeOH/65% TFA (0.1%) pH=1.95; 35 C; 20 ul inj.; 1 ml/min; sample dissolved in mobile phase with 1 drop phosphoric acid.

CHN Analysis:

calc.: C, 55.51; H, 5.38; N, 4.98. found: C, 55.37; H, 5.40; N, 5.03.

Melting point: 153.5° C. (dec.)

2) SPIB00101: 2-O-Acetylsalicylic Acid (2S)-(+)-serine Ester

A mixture of N-carbobenzyloxy-L-serine benzyl ester (Z-Ser-OBzl, 23.17 g, 70.34 mmole) and pyridine (30 mL) in anhydrous dichloromethane (500 mL) was cooled in an ice bath while under a nitrogen atmosphere. Acetylsalicyloyl chloride (21.07 g, 106.1 mmole) was added and the mixture was allowed to warm to room temperature and stir over two days. After 48 hours, the mixture was poured into ice-cold 2N hydrochloric acid (400 mL). After mixing, the layers were separated and the dichloromethane fraction was first washed with water (500 mL), then saturated sodium bicarbonate solution (500 mL), then water (500 mL), then brine (500 mL) and dried over sodium sulfate (25 g). After filtration, concentration under reduced pressure, and drying under high vacuum, the remaining brown solid (47.19 g) was purified by flash chromatography on silica gel (200 g, 0.035-0.070 mm, 6 nm pore diameter), eluting with hexanes/ethyl acetate (3:1). After concentration of the product containing fractions under reduced pressure and drying under high vacuum until the weight was constant, the experiment produced the protected acetylsalicylic-L-serine ester SPIB0010101 (32.97 g, 95% yield) as a white solid.

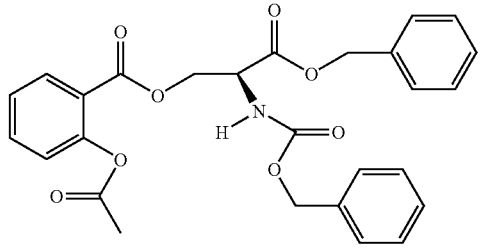

SPIB0010101

$^1$H NMR (300 MHz, CDCl$_3$): δ=7.74 (1H, d, J=7.8 Hz), 7.55 (1H, dt, J=7.8, 1.5 Hz), 7.33-7.21 (11H, m), 7.08 (1H, d, J=7.5 Hz), 5.68 (1H, d, J=8.4 Hz), 5.20 (2H, s), 5.12 (2H, s), 4.77 (1H, m), 4.66 (1H, dd, J=11.4, 3.3 Hz), 4.57 (1H, dd, J=11.4, 3.3 Hz), 2.30 (3H, s).

$^{13}$C NMR (75 MHz, CDCl$_3$): δ=169.45, 169.09, 163.68, 163.35, 155.57, 150.77, 135.87, 134.75, 134.07, 131.44, 128.50, 128.43, 128.27, 128.14, 128.04, 125.92, 123.71, 122.18, 67.83, 67.27, 64.63, 53.55, 21.03.

The protected acetylsalicylic-L-serine ester SPIB0010101 (21.0 g, 42.7 mmole) was dissolved in ethanol (100 mL) and ethyl acetate (100 mL) at room temperature and added to a Parr bottle that contained 10% palladium on carbon (4.20 g, 50% wet) under a nitrogen atmosphere. The nitrogen atmosphere was replaced with hydrogen gas (20 psi). After 5 hours additional 10% palladium catalyst (4.26 g) was added and the hydrogen atmosphere was returned (20 psi). After an additional 20 hours of shaking at room temperature, the palladium catalyst was removed by filtration through celite. The remaining solids (palladium/celite and product) were washed with water (1500×2 mL) until the product was removed. The ethanol and water fractions were concentrated under reduced pressure at room temperature. The remaining solid (7.17 g) was dissolved in DIUF water (4.3 L), filtered through celite to remove insoluble material, and concentrated under high vacuum at room temperature. The white solid was then washed with 1,4-dioxane (100 mL) and DIUF water (50 mL) overnight. After 24 hours the solid was filtered and dried under high vacuum until the weight was constant (24 hours). The experiment produced the acetylsalicylic-L-serine ester SPIB00101 (6.17 g, 54% yield) as a white solid.

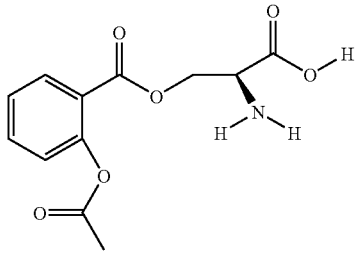

SPIB00101

$^1$H NMR (300 MHz, D$_2$O-DCl): δ=8.05 (1H, dd, J=7.8, 1.5 Hz), 7.75 (1H, dt, J=7.8, 1.5 Hz), 7.47 (1H, dt, J=7.8, 0.9 Hz), 7.27 (1H, dd, J=7.8, 0.9 Hz), 4.87 (1H, dd, J=12.6, 4.2 Hz), 4.79 (1H, dd, J=12.6, 3.0 Hz), 4.62 (1H, dd, J=4.2, 3.0 Hz), 2.39 (3H, s).

$^{13}$C NMR (75 MHz, D$_2$O-DCl): δ=173.01, 168.58, 164.54, 149.72, 135.39, 131.59, 126.87, 123.62, 121.15, 62.38, 52.05, 20.44.

HPLC Analysis:

98.1% purity; r.t.=5.839 min.; 65% TFA (0.1%)/35% methanol; 1 mL/min; 35 C; Luna C18, 3 u column (SN 184225-37), 4.6×250 mm; 22 ul injection; DAD1B, Sig=240, 4 Ref=550,100.

CHN nalysis:

calc.: C, 53.93; H, 4.90; N, 5.24. found: C, 54.02; H, 5.00; N, 5.23.

Melting point: 147.0° C. (dec.)

3) SPIB00103: 2-O-Acetylsalicylic Acid (2S,4R)-4-hydroxyproline Ester

A mixture of N-carbobenzyloxy-L-hydroxyproline benzyl ester (Z-Ser-OBzl, 21.5 g, 60.5 mmole) and pyridine (25 mL) in anhydrous dichloromethane (500 mL) was cooled in an ice bath while under a nitrogen atmosphere. Acetylsalicyloyl chloride (13.2 g, 66.6 mmole) was added and the mixture was allowed to warm to room temperature and stir overnight. After 24 hours, additional acetylsalicyloyl chloride (5.0 g, 25.2 mmole) was added and the mixture was allowed to stir overnight. After 48 hours, the mixture was poured into ice-cold 1N hydrochloric acid (500 mL). After mixing, the layers were separated and the dichloromethane fraction was washed with water (500 mL), then saturated sodium bicarbonate solution (500 mL), then water (500 mL), then brine (500 mL) and dried over sodium sulfate (25 g). After filtration, concentration under reduced pressure, and drying under high vacuum, the remaining yellow oil (40.7 g) was purified by flash chromatography on silica gel (460 g, 0.035-0.070 mm, 6 nm pore diameter), eluting with heptane/ethyl acetate (3:1). After concentration of the fractions containing product under reduced pressure and drying under high vacuum until the weight was constant, the experiment produced the protected acetylsalicylic-L-hydroxyproline ester SPIB0010301 (21.31 g, 68% yield) as a colorless oil.

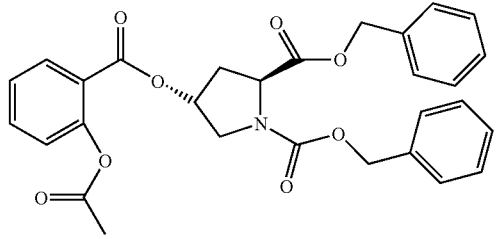

SPIB0010301

$^1$H NMR (300 MHz, CDCl$_3$): δ=7.92 (1H, d, J=7.8 Hz), 7.56 (1H, t, J=7.8 Hz), 7.34-7.21 (10H, m), 7.09 (1H, d, J=7.8 Hz), 5.48 (1H, s), 5.21 (2H, m), 5.03 (2H, d, J=15 Hz), 4.57 (1H, m), 3.85 (2H, m), 2.53 (1H, m), 2.28 (4H, m).

$^{13}$C NMR (75 MHz, CDCl$_3$): δ=171.72, 171.49, 169.25, 163.47, 163.30, 154.52, 153.93, 150.54, 136.05, 135.94, 135.21, 135.00, 134.17, 134.12, 128.43, 128.32, 128.28, 128.20, 128.05, 127.98, 127.94, 127.79, 125.89, 123.70, 122.46, 122.38, 73.24, 72.59, 67.33, 67.11, 66.97, 58.02, 57.69, 52.47, 52.15, 36.74, 35.65, 20.90.

The protected acetylsalicylic-L-hydroxyproline ester SPIB0010301 (10.6 g, 20.5 mmole) was dissolved in ethanol (75 mL) and ethyl acetate (75 mL) at room temperature and added to a Parr bottle that contained 10% palladium on carbon (3.0 g, 50% wet) under a nitrogen atmosphere. The nitrogen atmosphere was replaced with hydrogen gas (20 psi). After 17 hours of shaking at room temperature, the reaction mixture was washed with water (500 mL) for two hours. The organic layer (top) was removed via pipette and the aqueous layer was filtered through celite. The water fraction was concentrated under reduced pressure at room temperature. The remaining solid (6.71 g) was then washed with anhydrous dichloromethane (35 mL) overnight. After 24 hours the solid was filtered and dried under high vacuum until the weight was constant (24 hours). The experiment produced acetylsalicylic-L-hydroxyproline ester, SPIB00301 (2.87 g, 47.7% yield) as a white solid.

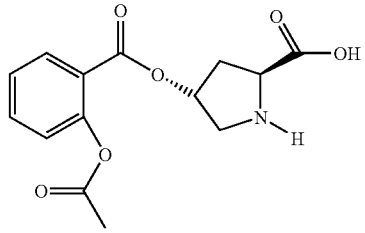

SPIB00103

$^1$H NMR (300 MHz, D$_2$O-DCl): δ=8.09 (1H, d, J=7.5 Hz), 7.75 (1H, t, J=7.5 Hz), 7.48 (1H, t, J=7.5 Hz), 7.28 (1H, d, J=7.5 Hz), 5.69 (1H, m), 4.76 (1H, t, J=7.5 Hz), 3.86 (1H, dd, J=13.5, 3.9 Hz), 3.74 (1H, d, J=13.5 Hz), 2.81 (1H, dd, J=15.0, 7.5 Hz), 2.60 (1H, m), 2.40 (3H, s).

$^{13}$C NMR (75 MHz, D$_2$O-DCl): δ=173.13, 170.25, 164.31, 149.65, 135.36, 131.54, 126.87, 123.54, 121.37, 73.86, 58.34, 50.95, 34.38, 20.48.

HPLC Analysis:

98.3% purity; r.t.=7.201 min.; 65% TFA (0.1%)/35% methanol; 1 mL/min; 35 C; Luna C18, 3 u column (SN 184225-37), 4.6×250 mm; 22 ul injection; DAD1B, Sig=240, 4 Ref=550,100.

CHN Analysis:

calc.: C, 57.34; H, 5.16; N, 4.78. found: C, 57.09; H, 5.23; N, 4.91.

Melting point: 162° C. (dec.)

Comparsion of the L-serine, L-threonine, and L-Hydroxyproline Esters of Acetylsalicylic Acid to Acetylsalicylic Acid with Respect to Gastric Mucosa Irritation The present study was conducted to determine the relative potential of the new formulations of aspirin (L-serine, L-threonine, and L-Hydroxyproline esters of acetylsalicylic acid) to cause gastric mucosal irritation/lesions in fasted male albino rats. Aspirin served as a reference control.

Different new formulations of aspirin and aspirin were administered by gavage to fasted male albino rats (Wistar strain), using 0.5% (w/v) Carboxymethylcellulose (CMC) in Phosphate Buffer (pH 2.6) solution as the vehicle. The study was conducted at two dose levels viz. 100 mg and 200 mg/kg body weight along with a vehicle control group. At each dose level 5 animals were used. All the doses were expressed as aspirin molar equivalents. The doses used as well as the molar equivalents are presented below.

TABLE 16

Formulation: Molar equivalent

| Formulation | Molar equivalent |
| --- | --- |
| L-serine ester of acetylsalicylic acid | 1.483 units are equivalent to 1 unit of aspirin |
| L-Hydroxyproline ester of acetylsalicylic acid | 1.628 units are equivalent to 1 unit of aspirin |
| L-threonine ester of acetylsalicylic acid | 1.561 units are equivalent to 1 unit of aspirin. |

TABLE 17

Test Item: Group: Dose (mg per kg) [in terms of acetylsalicylic acid]: Equivalent weight of the Test item [mg]

| Test Item | Group | Dose (mg per kg) [in terms of acetylsalicylic acid] | Equivalent weight of the Test item [mg] |
| --- | --- | --- | --- |
| Vehicle control | Vehicle control Group | 0.0 | — |
| L-serine ester of acetylsalicylic acid | Test Group 1 | 100.0 | 148.3 |
| L-serine ester of acetylsalicylic acid | Test Group 1 Test Group 2 | 100.0 200.0 | 148.3 296.6 |
| L-Hydroxyproline ester of acetylsalicylic acid | Test Group 1 Test Group 2 | 100.0 200.0 | 162.8 325.6 |
| L-threonine, ester of acetylsalicylic acid | Test Group 1 Test Group 2 | 100.0 200.0 | 156.1 312.2 |
| Reference control acetylsalicylic acid | Test Group 1 Test Group 2 | 100.0 200.0 | 100.0 200.0 |

The rats were fasted for a period of 18 to 22 hours before dosing. The test item was administered as a single dose by gavage. Three hours after drug administration, the animals were killed humanely by $CO_2$ gas inhalation. The stomach was dissected out and observed for the quantity of mucous exudate, degree of hyperemia and thickening of stomach wall, hemorrhagic spots (focal or diffuse), nature of hemorrhages (petechial or ecchymotic) along with the size and perforations The observations on gastric mucosal irritation of animals of various groups are summarized below:

TABLE 18

Test Item: Group: Dose mg/kg (as acetylsalicylic acid): Observation

| Test Item | Group | Dose mg/kg (as acetylsalicylic acid) | Observation |
| --- | --- | --- | --- |
| Vehicle control | Vehicle control Group | 0.0 | None of the animals showed any evidence of gastric mucosal irritation |
| L-serine ester of acetylsalicylic acid | Test Group 1 | 100.0 | None of the dosed animals showed any evidence of gastric mucosal irritation |
| | Test Group 2 | 200.0 | None of the dosed animals showed any evidence of gastric mucosal irritation. |
| L-Hydroxyprolin ester of acetylsalicylic acid | Test Group 1 | 100.0 | None of the dosed animals showed any evidence of gastric mucosal irritation. |
| | Test Group 2 | 200.0 | None of the dosed animals showed any evidence of gastric mucosal irritation |
| L-threonine, ester of acetylsalicylic acid | Test Group 1 | 100.0 | None of the dosed animals showed any evidence of gastric mucosal irritation |
| | Test Group 2 | 200.0 | None of the dosed animals showed any evidence of gastric mucosal irritation |
| Reference control (acetylsalicylic acid) | Test Group 1 | 100.0 | None of the dosed animals showed any evidence of gastric mucosal irritation |
| | Test Group 2 | 200.0 | All the 5 animals dosed, showed evidence of gastric mucosal irritation. |

In conclusion it was observed that none of the L-serine, L-threonine, and L-Hydroxyproline esters of acetylsalicylic acid induced any evidence of irritation of gastric mucosa at the two doses tested viz., 100 and 200 mg/kg body weight. In contrast, aspirin (acetylsalicylic acid) caused irritation of the gastric mucosal in all the fasted male albino rats at the dose level of 200 mg/kg. However at the dose level of 100 mg/kg aspirin failed to cause any evidence of gastric mucosal irritation in the male rats.

Further none of the animals of different test groups showed any clinical symptoms of toxicity during the observation period of three hours.

Efficacy of L-Serine, L-Threonine, and L-Hydroxyproline Esters of Acetylsalicylic Acid Compared to Acetylsalicylic Acid on Clotting Time in Rats Observations of Blood Clotting Time The data on the mean clotting time (MCT) of the animals of low, intermediate and high dose groups of different formulations, vehicle control and positive control groups estimated one hour after dosing were presented below (Table 19):

TABLE 19

Summary of Mean Clotting Time (±S.D.) in Minutes - L-serine, L-threonine, and L-Hydroxyproline esters of acetylsalicylic acid and Aspirin (Positive control): Low dose: Intermediate dose: High dose

| | Low Dose | Intermediate Dose | High Dose |
|---|---|---|---|
| Vehicle control | | 4.9 ± 1.10 | |
| L-serine ester of acetylsalicylic acid | 5.7 ± 1.34 | 6.8 ± 1.48 | 6.9 ± 1.37 |
| L-Hydroxyprolin ester of acetylsalicylic acid | 6.1 ± 1.10 | 5.7 ± 0.82 | 7.5 ± 1.18 |
| L-threonine, ester of acetylsalicylic acid | 5.2 ± 1.14 | 5.6 ± 0.84 | 7.4 ± 0.97 |
| Positive control (acetylsalicylic acid) | 6.2 ± 1.40 | 8.1 ± 1.97 | 9.8 ± 1.32 |

FIG. 3-6 depict the group mean data of animals regarding the dose relationship+mean clotting time in minutes for the L-series ester of aspirin and for the control.

Figure 7:
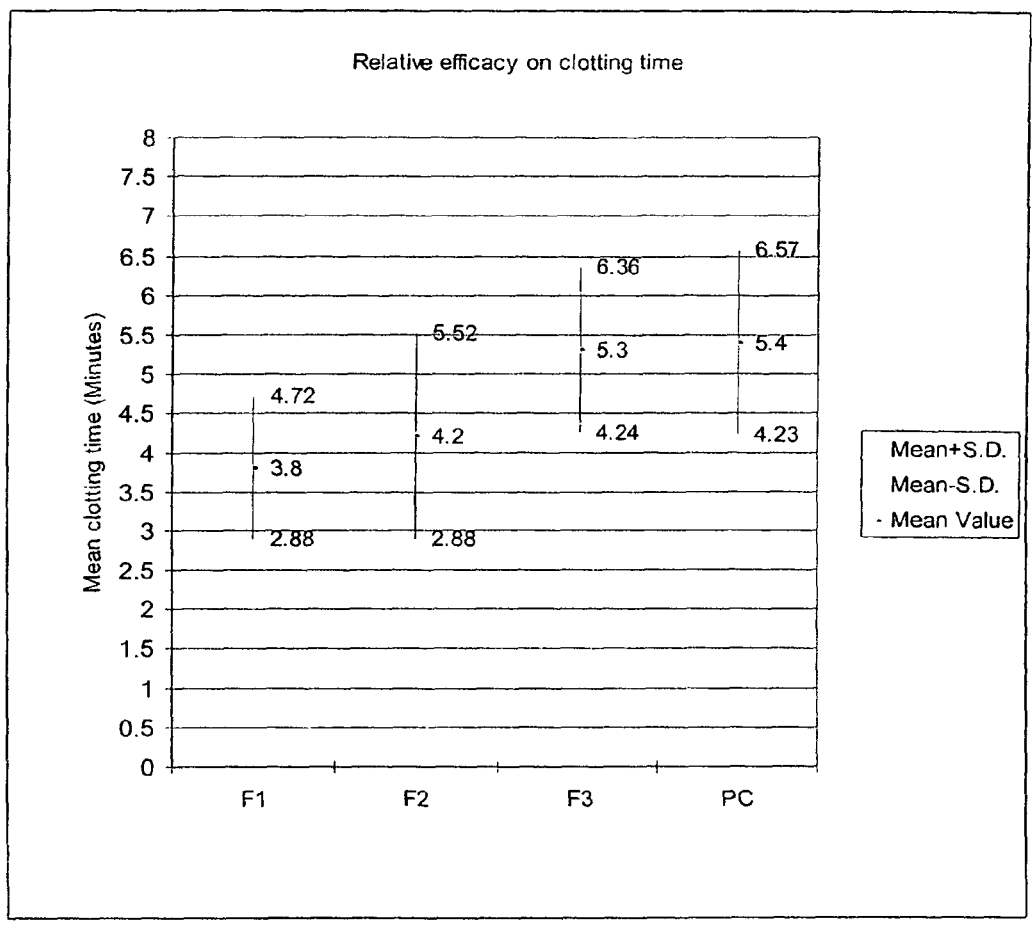
FIG. 7 graphically compares the relative efficacy of L-serine (ester of acetyl salicyclic acid (F.1), L-threonine ester of acetyl salicylic acid (F.2), L-hydroxyproline ester of acetylsalicylic acid (F.3), and acetylsalicylic acid (PC) as a function of mean clotting time in minutes.

The statistical analysis showed a significant improvement at 5% significance level in the efficacy for the high dose and mid dose when compared to the vehicle control group (FIG. 7).

Figure 4:
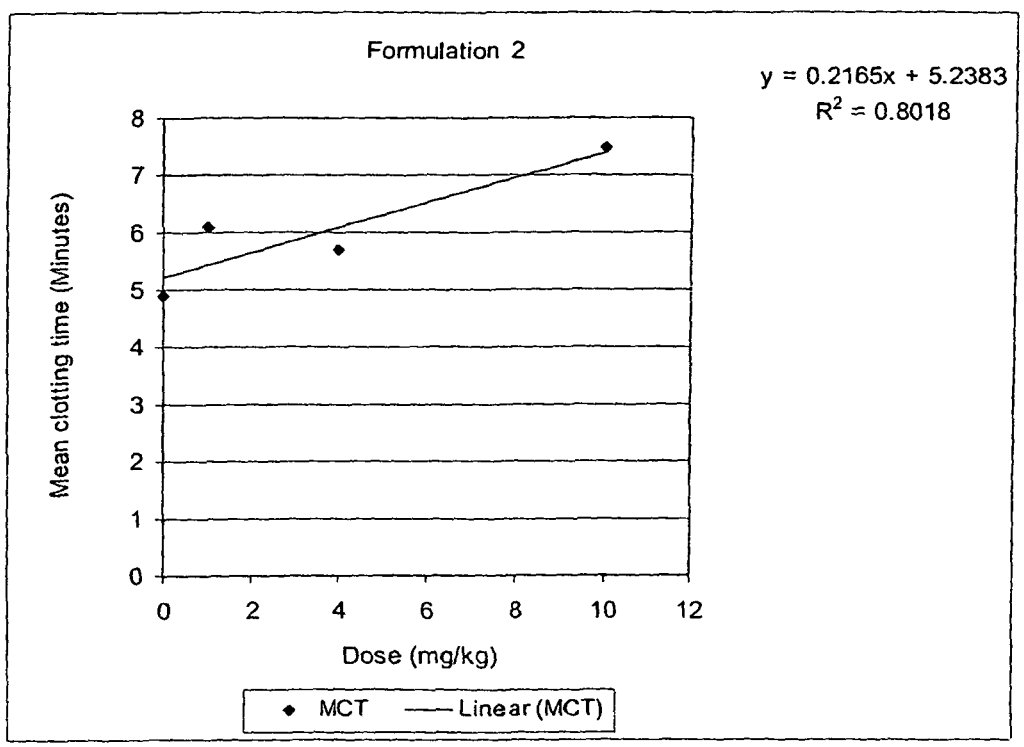
FIG. 4 depicts graphically the dose response relationship to mean clotting time (MCT) minutes for the L-hydroxyproline ester of acetylsalicylic acid (Formulation 2).

FIG. 4 shows the group mean data of animals. It provides the dose response relationship to mean clotting time (MCT) in minutes with respect to L-hydroxyproline ester of aspirin. The statistical analysis of FIG. 4 showed a significant improvement at 5% significance level in the efficacy for the high dose and low dose when compared to the vehicle control group (FIG. 6)

Figure 5:
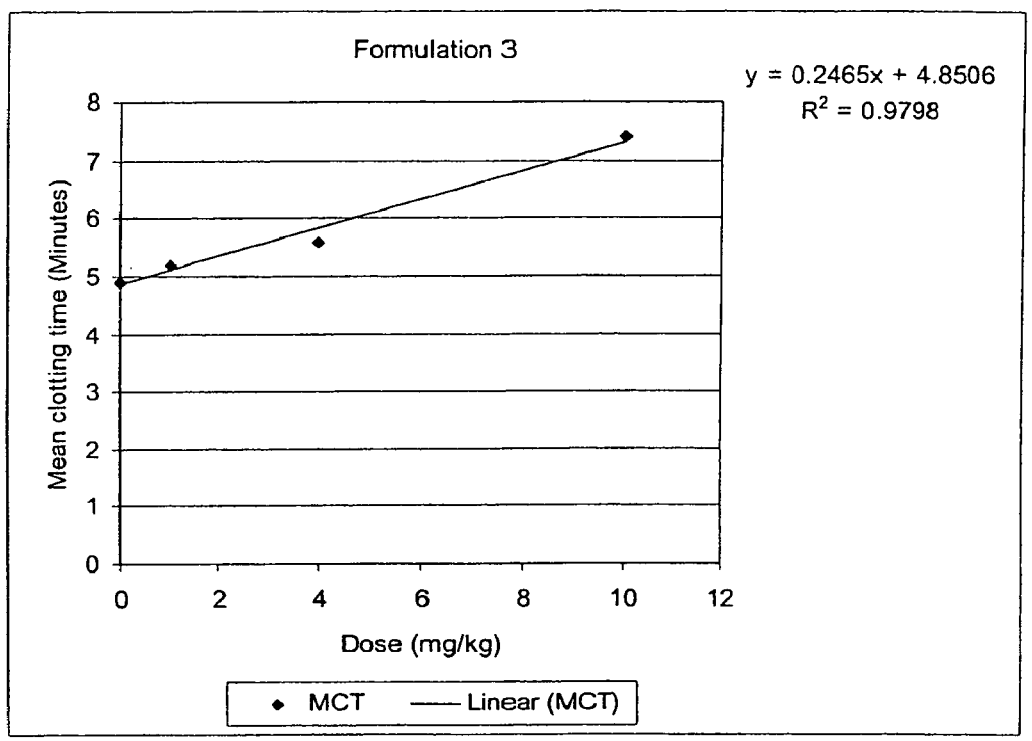
FIG. 5 depicts the dose response relationship to mean clotting time (MCT) in minutes for the L-threonine ester of acetylsalicylic acid (Formulation 3)

FIG. 5 depicts the dose response relationship to mean clotting time (MCT) in minutes of L-threonine ester of acetylsalicylic acid. The statistical analysis showed a significant improvement at 5% significance level in the efficacy for the high dose when compared to the vehicle control.

Figure 6:
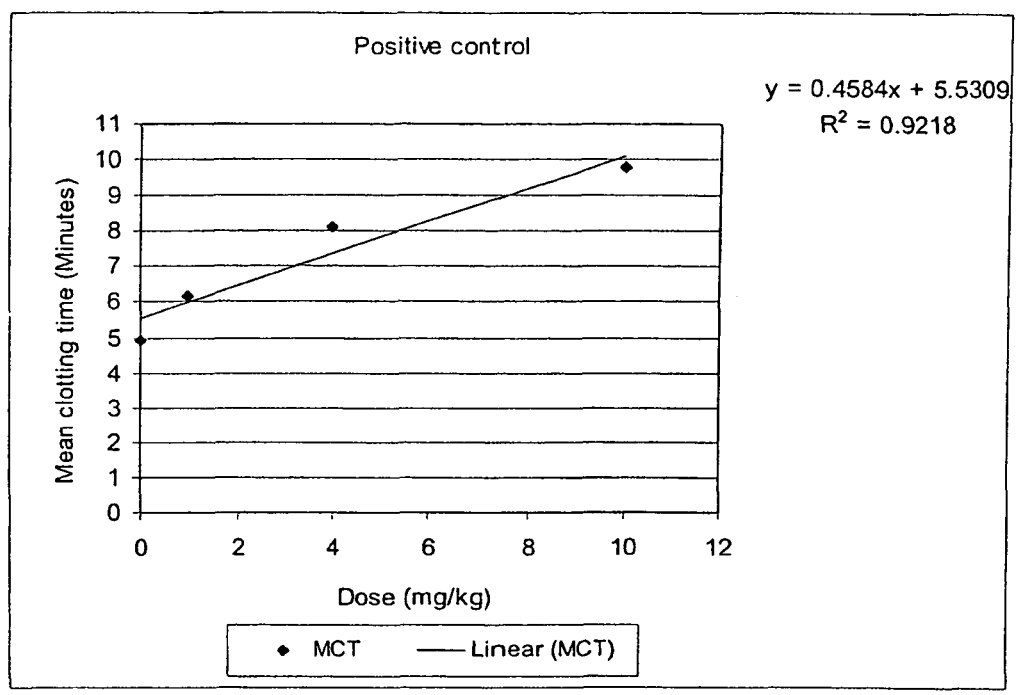
FIG. 6 depicts the dose response relationship to mean clotting time (MCT) in minutes for control (acetylsalicylic acid).

FIG. 6 depicts the dose response relationship to mean clotting time for acetylsalicylic acid. The statistical analysis showed a significant improvement at 5% significance level in the efficacy for the intermediate and high dose when compared to the vehicle control. The dose response effect were statistically significant and clearly evident (FIG. 7).

Conclusion

The present study was conducted to evaluate the efficacy of new formulations of aspirin using blood clotting time as an index in albino rats. Aspirin served as positive control. The study was conducted at three dose levels with the new formulations and positive control along with a vehicle control group.

Doses

The doses for the main study were selected based on the dose range finding experiments with acetylsalicylic acid. All the doses were expressed as aspirin molar equivalents. The doses used are presented below.

TABLE 20

Test Item: Low Dose (mg/kg): Intermediate dose 9 mg/kg): High dose (mg/kg)

| Test Item | Low Dose (mg/kg) | Intermediate Dose (mg/kg) | High Dose (mg/kg) |
|---|---|---|---|
| L-serine ester of acetylsalicylic acid | 1.0 | 4.0 | 10.0 |
| L-Hydroxyprolin ester of acetylsalicylic acid | 1.0 | 4.0 | 10.0 |
| L-threonine, ester of acetylsalicylic acid | 1.0 | 4.0 | 10.0 |
| Aspirin (Positive control) | 1.0 | 4.0 | 10.0 |

Efficacy (Blood Clotting Time)

The efficacy in terms of time required for the blood clotting time at different dose levels—low, intermediate and high dose for different formulations of various amino acid derivatives of aspirin and acetylsalicylic acid are presented below.

TABLE 21

Low dose: Intermediate dose: High dose

| | Low Dose | Intermediate Dose | High Dose |
|---|---|---|---|
| Vehicle control | | 4.9 ± 1.10 | |
| L-serine ester of acetylsalicylic acid | 5.7 ± 1.34 | 6.8 ± 1.48 | 6.9 ± 1.37 |
| L-Hydroxyprolin ester of acetylsalicylic acid | 6.1 ± 1.10 | 5.7 ± 0.82 | 7.5 ± 1.18 |
| L-threonine, ester of acetylsalicylic acid | 5.2 ± 1.14 | 5.6 ± 0.84 | 7.4 ± 0.97 |
| Positive control | 6.2 ± 1.40 | 8.1 ± 1.97 | 9.8 ± 1.32 |

L-serine, L-threonine, and L-Hydroxyproline esters of acetylsalicylic acid are as effective as acetylsalicylic acid with respect to clotting time observed after one hour after administration but are far superior in terms of the absence of gastric irritation at all levels compared to acetylsalicylic acid.

Efficacy of L-Serine, L-Threonine, and L-Hydroxyproline Esters of Acetylsalicylic Acid after Compared to Acetylsalicylic Acid on Clotting Time in Rats Estimated Two Hours after Dosing The present study was conducted to evaluate the efficacy of L-serine, L-threonine, and L-Hydroxyproline esters of acetylsalicylic acid compared to acetylsalicylic acid using blood clotting time, estimated 2 hours (±10 minutes) after dosing, as an index in albino rats. Aspirin served as positive control. Male albino rats were exposed to aspirin and to 3 new formulations of amino acid derivatives of aspirin derivatives at one dose level of 20 mg/kg body weight. No vehicle control group was used. The doses were expressed as aspirin molar equivalents. The doses used for the main experiment for different formulations and positive control was presented below.

TABLE 22

Test Item: Dose in terms of Acetylsalicylic acid 9 mg/kg

| Test Item | Dose in terms of Acetylsalicylic acid (mg/kg) |
|---|---|
| L-serine ester of acetylsalicylic acid | 20.0 |
| L-Hydroxyproline ester of acetylsalicylic acid | 20.0 |
| L-threonine ester of acetylsalicylic acid | 20.0 |
| Aspirin (Positive control) | 20.0 |

Efficacy (Blood Clotting Time)

The efficacy in terms of time required for the blood clotting time at the dose level of 20 mg/kg body weight for different formulations of amino acid derivatives of aspirin and aspirin (positive control) are presented below:

Observations of Blood Clotting Time

The data on the mean clotting time (MCT) of the animals, estimated 2 hours (±10 minutes) after dosing, at the dose level of 20 mg/kg body weight for the formulations of aspirin derivatives, vehicle control and positive control are presented below

TABLE 23

Summary of Mean Clotting Time (± S.D.) in Minutes of L-serine, L-threonine, and L-Hydroxyproline esters of acetylsalicylic acid compared to acetylsalicylic acid (Positive control)

| | Dose (20 mg/kg) |
|---|---|
| L-serine ester of acetylsalicylic acid | 3.8 ± 0.92 |
| L-Hydroxyproline ester of acetylsalicylic acid | 4.2 ± 1.32 |
| L-threonine ester of acetylsalicylic acid | 5.3 ± 1.06 |
| Positive control (acetylsalicylic acid) | 5.4 ± 1.17 |

L-serine, L-threonine, and L-Hydroxyproline esters of acetylsalicylic acid were found to be effective on clotting time.

In conclusion, it was observed that based on the time required for the blood to clot (clotting time), when estimated 2 hours after dosing, the amino acid derivatives were efficacous. However, the L-threonine ester of acetylsalicyclic acid was found to have relatively better efficacy than the other two formulations.

As shown by FIG. 7 the statistical analysis showed that L-threonine, and L-Hydroxyproline esters of acetylsalicylic acid are at least as effective as acetylsalicylic acid. There is no significant difference at 5% significance level for L-Hydroxyproline ester of acetylsalicylic acid and L-threonine ester of acetylsalicylic with respect to positive control for the mean blood clotting time observed after two hours. However, combined with the gastric irritation potential, the L-serine, L-threonine, and L-Hydroxyproline esters of acetylsalicylic acid are far superior.

The following additional data were obtained, when the same drugs were compared in rats on a different date with different time intervals and doses:

TABLE 24

| | Clotting Time (min) | | | | |
|---|---|---|---|---|---|
| Dose | ASA-Ser | ASA-Hyp | ASA-Thr | ASA | Vehicle |
| 10 mg/kg 1 hr | 6.9 | 7.5 | 7.4 | 9.8 | 4.9 |
| 10 mg/kg 24 hr | 4.4 | 3.3 | 3.6 | 4.4 | 2.7 |
| 20 mg/kg 2 hr | 3.8 | 4.2 | 5.3 | 5.4 | 2.7 |

*ASA is acetylsalicyclic acid

Two of the better esters of ASA at various conditions are as follows:
10 mg/kg 1 hr ASA-Hyp and ASA-Thr
10 mg/kg 24 hr ASA-Serine and ASA-Thr
20 mg/kg 2 hr ASA-Hyp and ASA-Thr When compared against the various amino acid esters, L-Threonine Ester of Aspirin seems to be the most preferred as it showed consistently a better response in the rat blood clotting time.

Based upon consistently improved toxicity profile, efficacy and better therapeutic index, Acetylsalicylic Acid-L-Threonine Ester was advanced to GMP synthesis.

Results of the 28-Day Chronic Dosing in Rodents, Comparative Toxicology:

The purpose of this study is to establish the toxicity of Acetylsalicylic Acid-L-Threonine Ester in relation to Aspirin (Make: Sigma, Batch number 090K0884) which served as a reference drug by conducting a 28-day repeated dose oral toxicity test in male and female albino rats.

Aspirin and Acetylsalicylic Acid-L-Threonine Ester were administered to albino rats (Wistar strain), by oral gavage daily for a period of 28 days, using 0.5% Carboxymethylcellulose (CMC) in phosphate buffer solution (pH 2.6) as vehicle. The study was conducted at one dose level only along with a vehicle control group as per the recommendation of the Sponsor. The test doses are expressed as Aspirin molar equivalents. Acetylsalicylic Acid-L-Threonine Ester was compared against Aspirin and Vehicle at 100 mg/kg dose administered to rats for 28 days.

The salient features of the study are as follows, where ASA-T represents Acetylsalicylic Acid-L-Threonine Ester:
1. All the animals of vehicle control group and the test group (Acetylsalicylic Acid-L-Threonine Ester) and reference control group (Aspirin) survived through the dosing period of 28 days.
2. None of the animals of the vehicle control group, test group (Acetylsalicylic Acid-L-Threonine Ester), and reference control group (Aspirin) exhibited any clinical symptoms of toxicity through out the dosing period.
3. The Changes in the Body weight is tabulated hereinbelow.

TABLE 25

| Body Weight | Comparison | Significance[P < 0.05] |
|---|---|---|
| Gain | ASA-T vs Aspirin vs Vehicle | Normal (Male) |
| Gain | ASA-T and Aspirin vs Vehicle | Decrease (Female) |

The percentage decrease were 29% and 21% for Acetylsalicylic Acid-L-Threonine Ester and Aspirin
4. Food intake of the animals of both the sexes of test group (Acetylsalicylic Acid-L-Threonine Ester) and reference control group (Aspirin) was found to be normal and comparable to the animals of vehicle control group.
5. Results of hematological analysis of the animals of different groups are shown in Table 26 below:

TABLE 26

| Hematological | Comparison | Significance [P < 0.05] |
|---|---|---|
| All Blood Parameters | ASA-T vs Aspirin vs Vehicle | None |
| Platelet Count | ASA-T vs Aspirin | Increase (Male) |

6. Results of clinical chemistry analysis of the animals of different groups are summarized below in Table 27:

TABLE 27

| Clinical Chemistry | Comparison | Significance [P < 0.05] |
|---|---|---|
| Alkaline Phosphatase | AST-T Ester vs Vehicle | Increase (Female) |
| Total Protein | ASA-T Ester ® vs Vehicle | Increase (Female) |
| Creatinine | ASA-T Ester ® vs Vehicle | Decrease (Male) |
| Cholesterol | ASA-T Ester ® vs Vehicle | Increase (Male) |
| Alkaline Phosphatase | Aspirin vs Vehicle | Increase (Female) |
| Sodium | Aspirin vs Vehicle | Increase (Female) |
| Blood Urea | Aspirin vs Vehicle | Decrease (Female) |
| SGPT and Cholesterol | Aspirin vs Vehicle | Increase (Male) |
| All Clinical Chemistry | ASA-T Ester ® vs Aspirin | None(but two below) |
| Blood Glucose | ASA-T Ester ® vs Aspirin | Decrease (Female) |
| Creatinine | ASA-T Ester ® vs Aspirin | Decrease (Male) |

7. Necropsy of the surviving animals at the end of the study (terminal necropsy) of vehicle control and different treatment groups did not reveal any gross pathological changes in any of the vital organs. Further there is no evidence of gastric mucosal irritation in the animals of vehicle control, test group (ASA-T Ester) and reference control group (Aspirin).

8. The data on absolute (Abs) and relative (Rel) organ weights of liver, kidney, adrenals, heart, spleen and testes showed the following changes in the organ weights are depicted in Table 28:

TABLE 28

| Rel/Abs Organ Wts | Comparison | Significance[P < 0.05] |
|---|---|---|
| Adrenals (Abs) | ASA-T Ester ® vs Vehicle | Decrease (Male) |
| Kidney (Abs) | Aspirin vs Vehicle | Decrease (Male) |
| Spleen (Abs) | Aspirin vs Vehicle | Decrease (Female) |
| Kidney (Rel) | Aspirin vs Vehicle | Increase (Male) |
| Spleen (Rel) | Aspirin vs Vehicle | Increase (Female) |
| Kidney (Abs) | ASA-T Ester vs Aspirin | Decrease (Male) |
| Spleen (Abs) | ASA-T Ester vs Aspirin | Decrease (Male) |
| Kidney (Rel) | ASA-T Ester vs Aspirin | Increase (Male) |

9. Histological sections of the following organs viz. brain, stomach, small intestines, large intestine, liver, kidney, adrenal, spleen, heart, lungs and gonads of male and female animals treated with Acetylsalicylic Acid-L-Threonine Ester or reference drug (Aspirin) groups did not show any histopathological changes and were found to be normal and comparable to that of animals of vehicle control group. However few animals treated with reference drug (Aspirin) showed mild fatty changes in the cardiac muscle fibers of heart and mild catarrhal changes of gastric mucosa.

Figure 8:
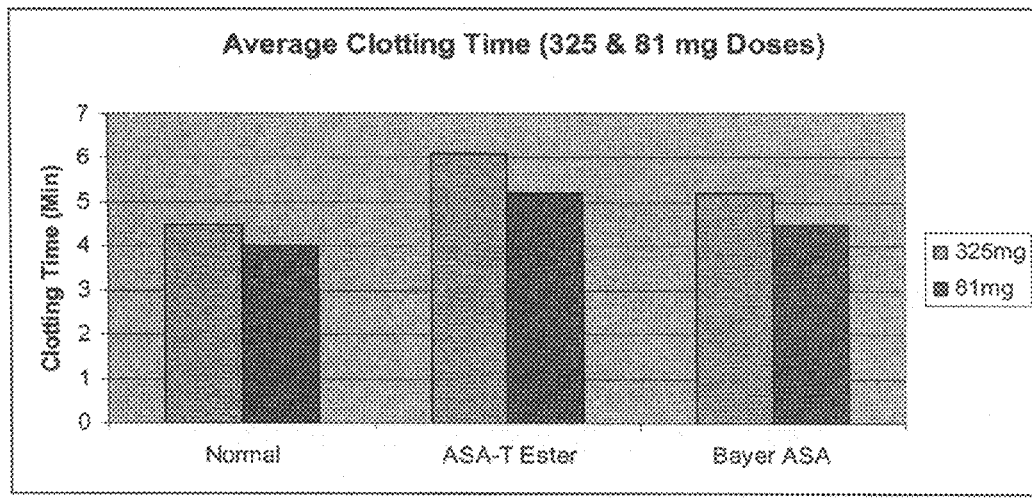
FIG. 8 compares graphically the average clotting time in minutes of Acetyl salicylic Acid L-Threonine Ester and BAYER Asiprin at 325 mg and 81 mg.
Figure 9:
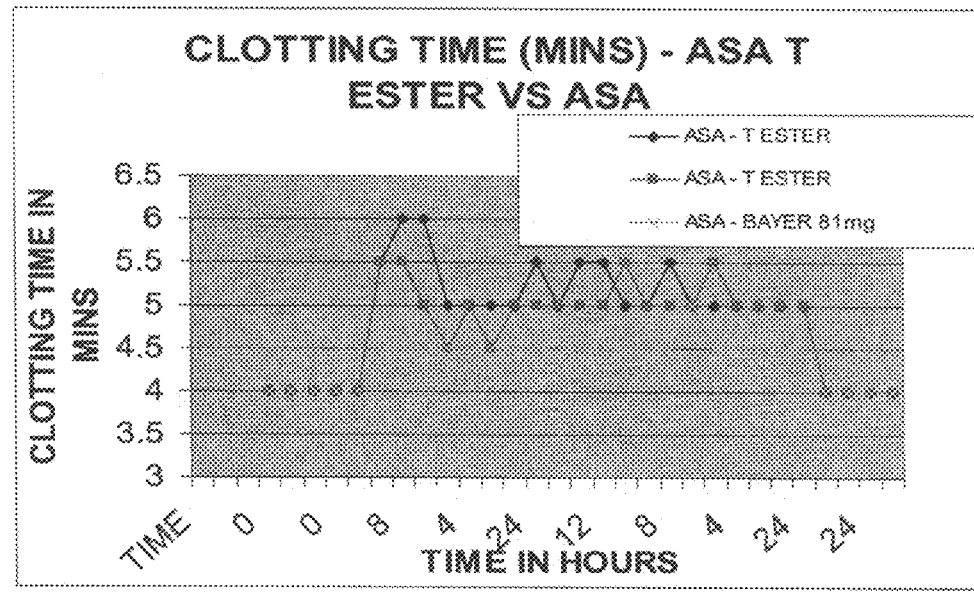
FIG. 9 compares in a bargraph the clotting time in minutes after 5 day administration of 81 mg Acetyl Salicyclic Acid L-Threonic Ester and Bayer Aspirin in 3 human volunteers, in which two volunteers took the Acetyl Salicyclic Acid L-Threonine Ester and the third took one took just the Bayer Aspirin.

Human Clinical Trials:

Several blood clotting time studies were performed on a limited number of human volunteers with Acetylsalicylic Acid-L-Threonine Ester. Results are shown in FIGS. 8-11. Attention is directed to FIG. 8 which compares the average clotting time after 325 mg and 81 mg Acetylsalicyclic Acid L-Threonine Ester and Bayer Aspirin is administered to human volunteers. The first set of columns in FIG. 8 labeled "Normal" is the average clotting time observed prior to the administration of the Aspirin or its threonine ester derivative thereof.

As clearly shown by the data in FIG. 8, Acetylsalicylic Acid-L-Threonine Ester at low dose of 80 mg was as effective as 325 mg Bayer Aspirin (with baseline correction), and obviously more effective than Bayer 81 mg Aspirin.

The data are tabulated in Table 29. The data on which the graphs of FIG. 8 are based are summarized in Table 29 below:

TABLE 29

| | AVERAGE CLOTTING TIME (MIN) | | | | |
|---|---|---|---|---|---|
| | 325 mg ASA-T ESTER Volunteer 1 | 325 mg ASA Bayer Volunteer 2 | 81 mg ASA-T ESTER Volunteer 1 | 81 mg ASA Bayer Volunteer 2 | 81 mg ASA-T ESTER Volunteer 3 |
| Normal | 4.5 | 4.5 | 4 | 4 | 4 |
| With ASA-T ESTER | 6.2 | 6.0 | 5.2 | NA | 5.1 |
| With ASA (Bayer) | 5.7 | 5.7 | NA | 4.5 | NA |

Figure 10:
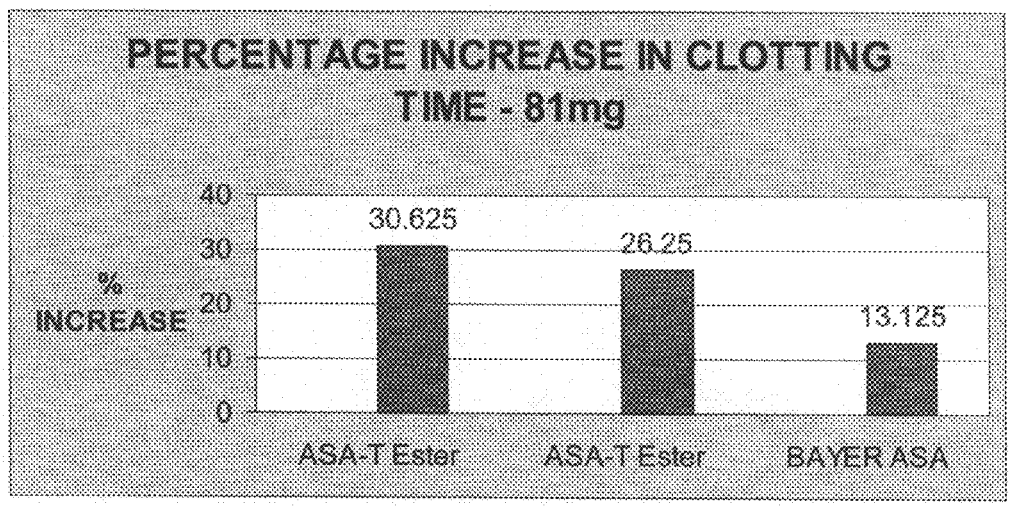
FIG. 10 compares graphically the percentage increase in clotting time after a 5 day administration to a patient of Acetylsalicylic Acid L-Threonine Ester relative to Aspirin (Bayer) at 81 mg dose. The plot was derived from the data in Table 29. Two patients took Acetylsalicyclic Acid L-Threonine Ester b over a period of five days. The third volunteer took Bayer Aspirin for 5 days.

FIG. 10.0 depicts the percentage increase in clotting time of Acetylsalicylic Acid-L-Threonine Ester relative to Aspirin (Bayer) at 81 mg dose based on 5-day average increase. This plot was derived from the data in Table 29. The two Acetylsalicylic Acid-L-Threonine Ester blocks shown above correspond to two separate volunteers who took the test drug over a period of 5 days. The third volunteer took Bayer Aspirin for 5 days. As per FIG. 2, increase in clotting time occurred on the very first day of drug intake, and remained higher than Bayer ASA during the subsequent administrations.

Figure 11:
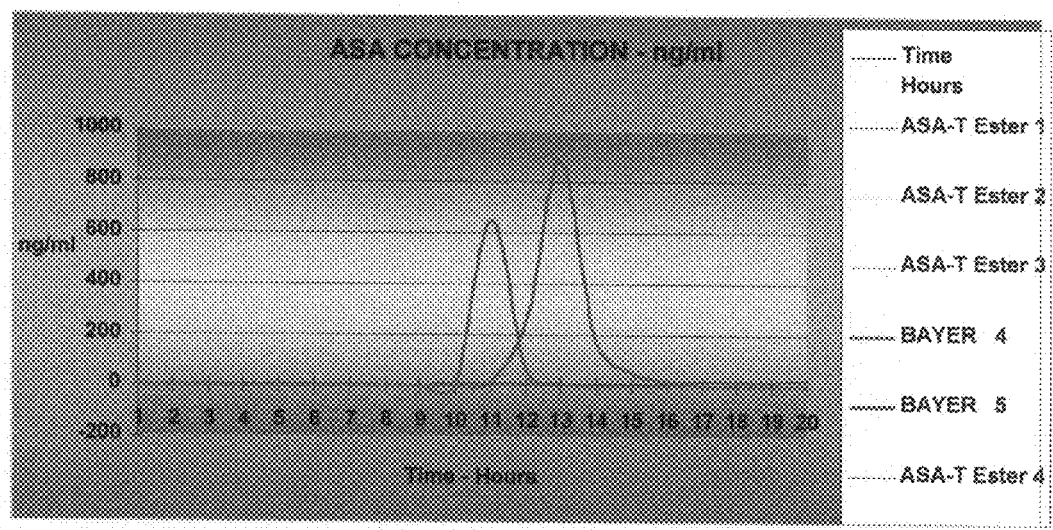
FIG. 11 plots the concentration of Aspirin versus time in four volunteers who took acetyl salicylic Acid L-Threonine Ester and two volunteers who took Bayer Aspirin.

Pharmacokinetic Results in 4 volunteers who took Acetylsalicylic Acid-L-Threonine Ester versus two volunteers who took Bayer Aspirin at 325 mg dose are shown in FIG. 11.

FIG. 11 is a plot of the concentration of Aspirin versus time in 4 volunteers who took Acetylsalicylic Acid-L-Threonine Ester and 2 volunteers who took Bayer Aspirin. No Aspirin was found in blood for volunteers who took Acetylsalicylic Acid-L-Threonine Ester. The two volunteers who took Bayer Aspirin showed Plasma levels of Aspirin.

Figure 12:
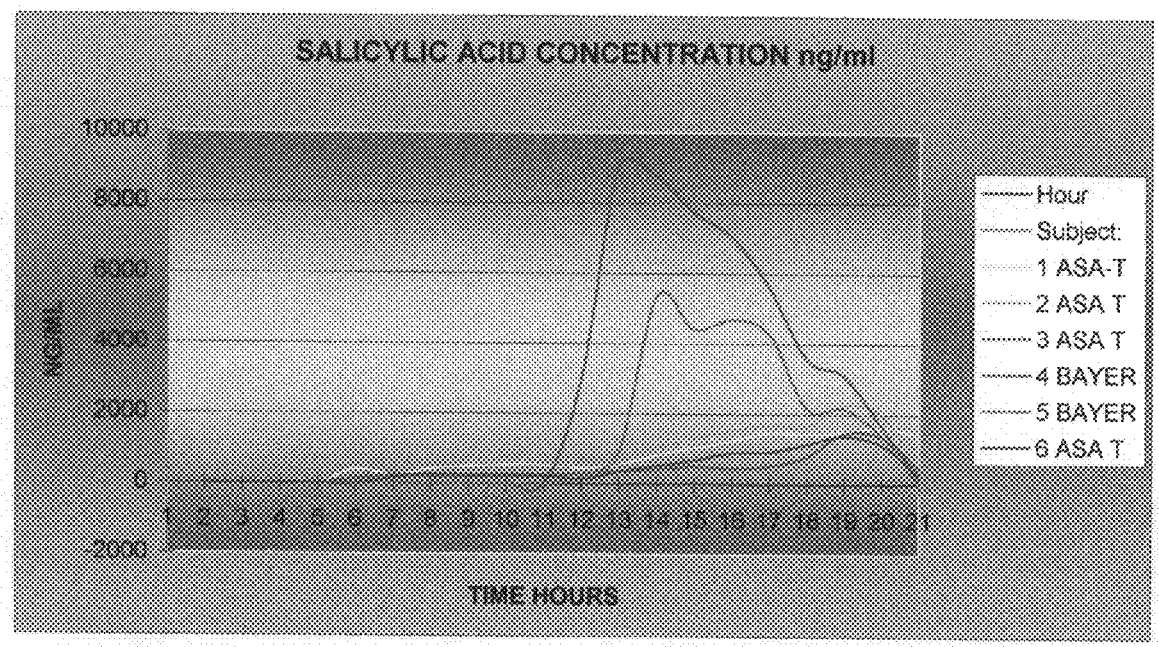
FIG. 12 is a plot of the plasma concentration of salicyclic acid in humans plasma with respect to 4 of volunteers who were administered Acetyl-salicuclic Acid L-Threonie Ester and two volunteer who were administered Aspirin.

This is shown in FIG. 12 which depicts the concentration of salicyclic Acid in human plasma with respect to four volunteers who took Acetylsalicyclic Acid-L-Threonine Ester and two volunteers who took Aspirin.

Rapid influx and efflux of Salicylic Acid from Aspirin administration was seen in the two volunteers who took Aspirin (FIG. 12). There was prolonged and sustained formation and disappearance of Salicylic acid in volunteers who took Acetylsalicylic Acid-L-Threonine Ester (FIG. 7). Without wishing to be bound, this phenomenon is believed to be attributed to the high likelihood of Acetylsalicylic Acid-L-Threonine Ester exhibiting sustained, specific and irreversible acetylation of the platelets in the portal circulation. Since there was no aspirin found in the systemic circulation after oral dosing of Acetylsalicylic Acid-L-Threonine Ester, it is likely that site specific action of acetylation of the platelets has been achieved, and the unwanted effect of aspirin in the endothelial system has been avoided. Thus it is evident from the human pharmacokinetic studies, clinical trials, and rat gastric mucosa irritation results, Acetylsalicylic Acid-L-Threonine Ester is a superior anti-platelet drug that does not have the toxicity of Aspirin and which exhibits a much better Therapeutic Index.

Therefore, Acetylsalicylic Acid-L-Threonine Ester is a Superior Anti platelet drug than acetylsalicyclic acid, for several reasons:

1. It does not produce any gastric irritation;
2. It does not inhibit prostaglandin synthesis;
3. It does not have any COX-1 or COX-2 activity on the endothelial or vascular tissues, as no ASA from Acetylsalicylic Acid-L-Threonine Ester reaches systemic circulation.
4. Thus, none of the side effects of Aspirin is observed with Acetylsalicylic Acid-L-Threonine Ester.

There are a number of screening tests to determine the utility of the derivatives created according to the disclosed methods. These include both in vitro and in vivo screening methods.

The in vitro methods include acid/base hydrolysis of the derivatives, hydrolysis in pig pancreas hydrolysis in rat intestinal fluid, hydrolysis in human gastric fluid, hydrolysis in human intestinal fluid, and hydrolysis in human blood plasma. These assays are described in Simmons, D M, Chandran, V R and Portmann, G A, Danazol Amino Acid Derivatives: In Vitro and In Situ Biopharmaceutical Evaluation, Drug Development and Industrial Pharmacy, Vol 21, Issue 6, Page 687, 1995, the contents of all of which are incorporated by reference.

The NSAID amino acid derivatives of the present invention are effective in treating diseases or conditions in which NSAIDs normally are used. These amino acid derivatives disclosed herein enhance the therapeutic benefits of the NSAIDs by reducing or eliminating biopharmaceutical and pharmacokenetic barriers associated with each of them. However it should be noted that these amino acid derivatives themselves will have sufficient activity without releasing any active drug in the mammals. Since the amino derivatives are more soluble in water than Ibuprofen or other NSAIDs, they do not need to be associated with a carrier vehicle, such as alcohol or castor oil which may be toxic or produce unwanted side reactions. Moreover, oral formulations containing the NSAID derivatives are absorbed into the blood and are quite effective.

Thus, the amino acid derivatives of the present invention, discussed hereinabove enhance the therapeutic benefits by removing biopharmaceutical and pharmacokenetic barriers of existing drugs.

Furthermore, these amino acid derivatives are easily synthesized in high yields using reagents which are readily and commercially available.

IV. Proline Derivative of Acetaminophen
Overview:

The procedure for the synthesis of the L-proline ester of acetaminophen is outlined in Synthetic Sequence section. The synthesis is exemplary. The complete procedure and analytical data is given in the Experimental Section. Acetaminophen (10 g) was coupled with Boc-L-proline with EDC in the presence of a catalytic amount of DMAP. Once the reaction was complete (3 hours at room temperature), the solution was washed with water. After drying over sodium sulfate, filtration, and concentration the crude protected amino acid ester of acetaminophen was purified by flash chromatography on silica gel. The procedure generated the protected L-proline ester of acetaminophen in 72%. The protecting group was removed by dissolving the ester in dichloromethane and passing hydrogen chloride through the solution at room temperature. After filtration, the final salt was stirred in tetrahydrofuran until pure. The yield for the deprotection step was 91.4% after filtration and drying under high vacuum at 90° C. for 4 hours.

Synthetic Sequence:

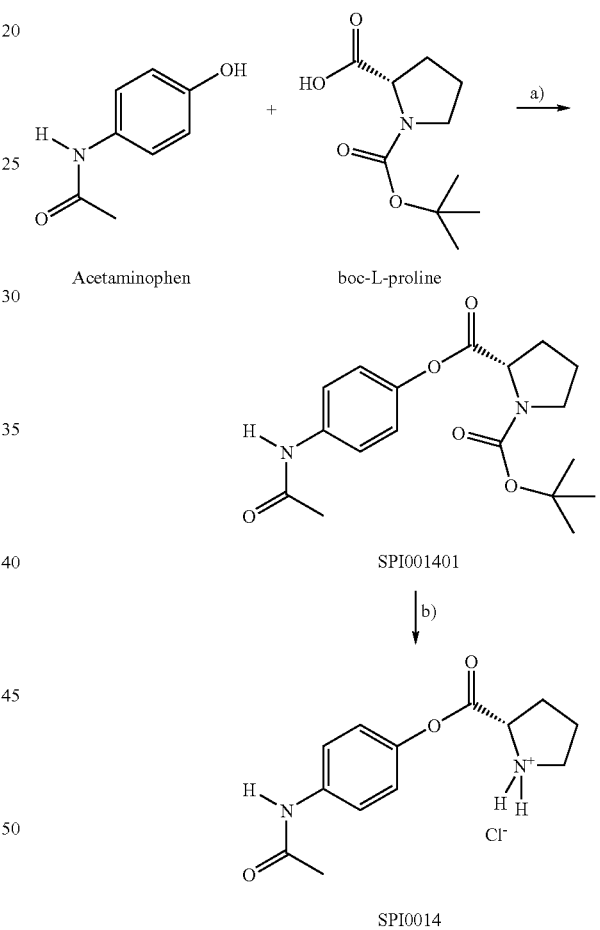

Synthesis of the L-proline Ester of Acetaminophen: a) EDC, DMAP, $CH_2Cl_2$; b) HCl (g), $CH_2Cl_2$.

Experiment Section:

The synthesis of SPI0014 was conducted in one batch. Reagents mentioned in the experimental section were purchased at the highest obtainable purity from Lancaster, Sigma-Aldrich, or Acros, except for solvents, which were purchased from either Fisher Scientific or Mallinkrodt.

SPI0014: Pyrrolidine-2(S)-carboxylic Acid 4-acetylaminophenyl ester, Hydrochloride A mixture of Boc-L-proline (14.39 g, 68.80 mmole), acetaminophen (10.02 g, 66.28 mmole), EDC (12.9 g, 67.29 mmole) and DMAP (1.10 g, 9.0 mmole) in anhydrous dichloromethane (100 mL) was stirred for 3 hours at room temperature under an argon atmosphere. After 3 hours, water (120 mL) was added. After mixing for 5 minutes, the layers were separated and the dichloromethane fraction was washed with water (120 mL) and dried over sodium sulfate (5 g). After filtration, concentration under reduced pressure, and drying under high vacuum, the remaining oil (24.10 g) was purified by flash chromatography on silica gel (100 g, 0.035-0.070 mm, 6 nm pore diameter), eluting with hexanes/ethyl acetate (1:2). After concentration of the product containing fractions under reduced pressure and drying at high vacuum until the weight was constant, the experiment produced the protected acetaminophen-L-proline ester SPI001401 (16.71 g, 72.3% yield) as a white solid (foam).

SPI001401

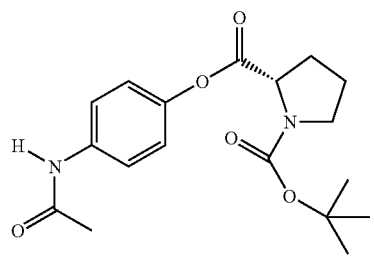

$^1$H NMR (300 MHz, CDCl$_3$): δ=8.83 (½H, s), 8.70 (½H, s), 7.58 (½H, d, J=7.5 Hz), 7.46 (½H, d, J=7.5 Hz), 6.96 (2H, m), 4.47 (1H, m), 3.59-3.45 (2H, m), 2.36 (1H, m), 2.17-1.90 (6H, m), 1.46 (9H, m).

$^{13}$C NMR (75 MHz, CDCl$_3$): δ=171.91, 171.75, 169.02, 154.44, 153.78, 146.36, 146.21, 121.44, 121.23, 120.82, 80.41, 80.17, 59.16, 46.78, 46.55, 31.06, 30.11, 28.50, 24.57, 24.28, 23.78.

The protected acetaminophen-L-proline ester SPI001401 (16.60 g, 47.64 mmole) was dissolved in dichloromethane (400 mL) and hydrogen chloride gas was passed through the solution for 2 hours at room temperature. The remaining solids were allowed to settle (for 1 hour). The dichloromethane was carefully decanted away from the white precipitate. Tetrahydrofuran (200 mL) was added to the precipitate and the mixture stirred for 2 hours under an argon atmosphere. After filtration, the remaining white solid was dried under high vacuum at 90° C. until the product weight was constant (4 hours). The experiment produced acetaminophen-L-proline ester, hydrochloride SPI0014 (12.4 g, 91.4% yield) as a white solid.

$^1$H NMR (300 MHz, CDCL$_3$-DMSO): δ=10.41 (1H, br s), 10.26 (1H, s), 9.55 (1H, br s), 7.70 (2H, d, J=9 Hz), 7.12 (2H, d, J=9 Hz), 4.66 (t, 1H, J=8.4 Hz), 3.33 (2H, m), 2.43 (1H, m), 2.28 (1H, m), 2.08 (s, 3H), 2.04 (2H, m).

$^{13}$C NMR (75 MHz, CDCL$_3$-DMSO): δ=168.08, 167.25, 144.55, 137.40, 121.12, 119.64, 58.53, 45.33, 27.74, 23.86, 23.08.

HPLC Analysis:
99.45% purity; rt=5.733 min; Luna C18 5 u column (sn 167917-13); 4.6×250 mm; 254 nm; 15% MeOH/85% hexane sulfonate buffer (110 mMol, pH=6); 35 C; 20 ul inj.; 1 ml/min; 5 mg/mL sample size.

CHN Analysis:
calc.: C, 54.84; H, 6.02; N, 9.84. found: C, 54.66; H, 5.98; N, 9.65.

Melting point: 221-222° C.

V. Amino Acid Derivative of Cyclosporine A

The macrocyclic immunosuppresants comprise a class of structurally distinctive, cyclic, poly, N-methylated undecaptides, and similar semi-synthetic macrolide structures commonly possessing pharmacological, in particular immunosuppressive, anti-inflammatory and/or anti-parasitic activity. The first of the cyclosporine to be isolated was the naturally occurring fungal metabolite Ciclosporin or Cyclosporine also known as cyclosporine A, which has the formula:

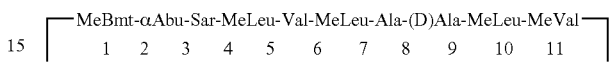

wherein MeBmt represents N-methyl-(4R)-4-but-2E-en-1-yl-4-methyl-(L) threonyl residue of the formula

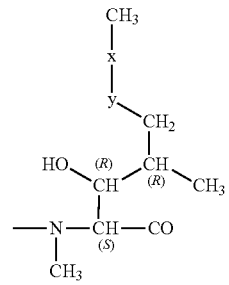

in which -x-y- is CH=CH— (trans). Other similar products include, sirolimus (b), tacrolimus (c), and pimecrolimus (d), having the following structures:

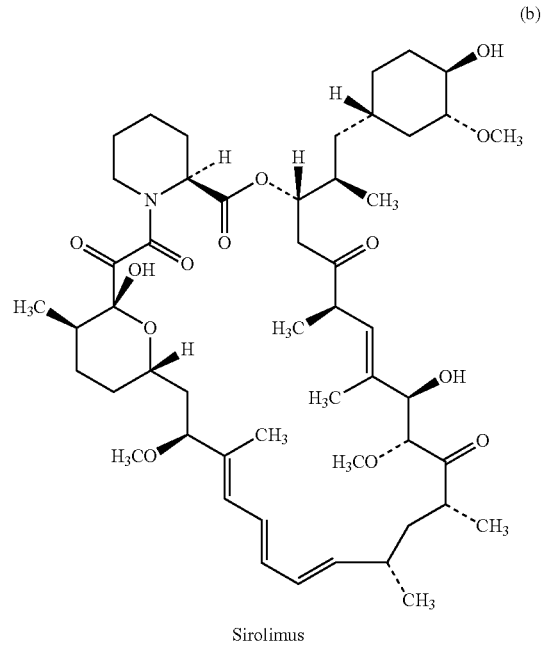

Sirolimus

-continued (c)

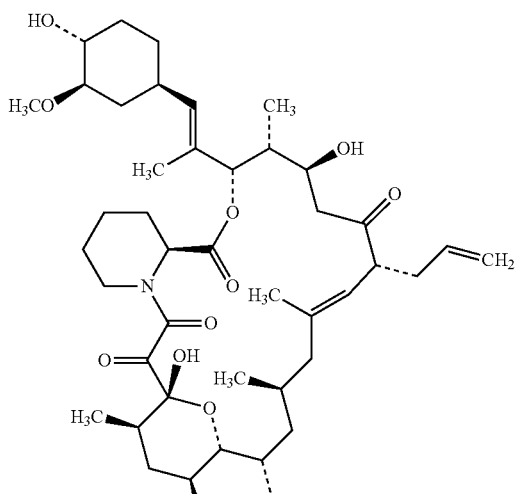

Tacrolimus (d)

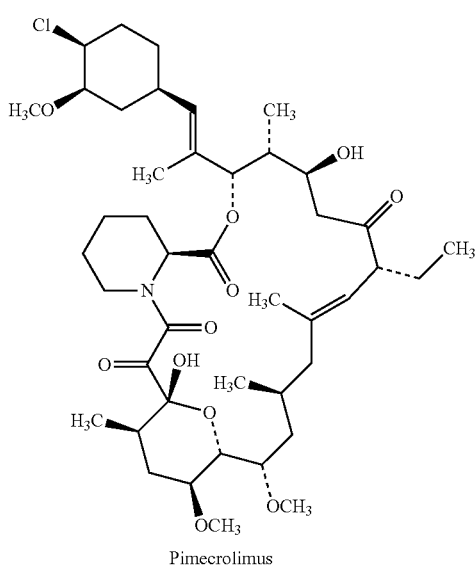

Pimecrolimus

The class comprised by the cyclosporines is thus now very large indeed and includes, for example, [Thr]$^2$-, [Val]$^2$-, [Nva]$_2$- and [Nva]$^2$-[Nva]$^5$-Ciclosporin (also known as cyclosporines C, D, G and M respectively), [Dihydrop-MeBmt]$^1$-[Val]$^2$-ciclosporin (also known as dihydro-cyclosporine D), [(D)Ser]$^8$-Ciclosporin, [MeIle]$^{11}$-Ciclosporin, [(D)MeVal]$^{11}$-Ciclosporin (also known as cyclosporine H), [MeAla]$^6$-Ciclosporin, [(D)Pro]$^3$-Ciclosporin and so on.

In accordance with conventional nomenclature for cyclosporines, these are defined throughout the present specification and claims by reference to the structure of cyclosporine (i.e., Cyclosporine A). This is done by first indicating the amino acid residues present which differ from those present in cyclosporine (e.g., "[(D)Pro]$^3$" to indicate that the cyclosporine in question has a -(D)Pro- rather than -Sar-residue at the 3-position) and then applying the term Cyclosporine to characterize remaining residues which are identical to those present in Cyclosporines A.

As used herein, the term "cyclosporines" refers to the various types of cyclosporines, in which x-y in the MeBmt residue has a cis or trans CH=CH or in which x-y therein is also included in those derivatives in which one or more of those amino acids in positions 2-11 of Cyclosporine A is replaced by a different amino acid. It is preferred, however, that no more than two of the amino acids are replaced in the formula of cyclosporine A and more preferentially not more than one of the amino acids is replaced by an amino acid.

In addition, amino acid residues referred to by abbreviation, e.g., -Ala-, -MeVal- and -αAbu-, are, in accordance with conventional practice, to be understood as having the (L)-configuration unless otherwise indicated, e.g. as in the case of "-(D)Ala-". Residue abbreviations preceded by "Me" as in the case of "-MeLeu-", represent α-N-methylated residues. Individual residues of the cyclosporine molecule are numbered, as in the art, clockwise and starting with the residue -MeBmt-, dihydro-MeBmt- etc. . . . in position 1. The same numerical sequence is employed throughout the present specification and claims.

Because of their unique pharmaceutical potential, the macrocyclic immunosuppressants have attracted considerable attention in the press. The term "macrocyclic immuno-suppressants" includes various natural and semi-synthetic derivatives of cyclosporine, and other macrolides such as sirolimus, tacrolimus and pimecrolimus. The primary area of clinical investigation for the above drugs has been as immunosuppressive agents, in particular in relation to its application to recipients of organ transplants, e.g., heart, lung, combined heart-lung, liver, kidney, pancreatic, bone-marrow, skin and corneal transplants, and in particular allogenic organ transplants. These drugs are also used in the treatment of psoriasis, atompic dermatitis, rheumatoid arthritis and nephritic syndrome.

Macrocyclic immunosuppressants are also useful for treating various autoimmune diseases and inflammatory conditions and especially inflammatory conditions with an aetiology, including an autoimmune component, such as arthritis (for example, rheumatoid arthritis, arthritis chronica progredient and arthritis deformons) and rheumatic diseases. Specific autoimmune diseases for which cyclosporine therapy has been proposed or applied include, autoimmune hematological disorder (including, e.g., hemolytic anemia, aplastic anemia, pure red cell anemia, and idiopathic thrombocytopaenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease, including, e.g., ulcerative colitis and Crohn's disease), endocrine opthalmopathy Graves disease, sarcoidosis, multiple sclerosis, primary billiary cirrhosis, juvenile diabetes (diabetes mellitus type I), uvetis (anterior and posterior), keratoconjunctivitis sicca and vernal keratoconjunctivitis, interstial lung fibrosis, psoriatic arthritis, atopic dermatitis and glomerulonephritis (with and without nephrotic syndrome, e.g., including idiopathic nephritic syndrome or minimal change nephropathy).

Furthermore, macrocyclic immunosuppressants also have applicability as an anti-parasitic, in particular anti-protozoal agent, and are suggested to be useful for treating malaria, coccidiomycosis and schistomsomiasis. More recently, they have been taught to be useful as agents for reversing or abrogating anti-neoplastic agent resistance contumors, and the like.

Despite the very major contribution which macrocyclic immunosuppressants have made, difficulties have been encountered in providing more effective and convenient means of administration (e.g., galenic formulations, for example, oral dosage form, which are both convenient and for the patient as well as providing appropriate bioavailability and allowing dosaging at an appropriate and controlled dosage rate) as well as the reported occurrence of undesirable side reactions; in particular nephrotoxic reactions have been obvious serious impediments to its wider use or application.

Moreover, the above mentioned macrocyclic immunosuppressants are characteristically highly hydrophobic and readily precipitate in the presence of even very minor amounts of water, e.g., on contact with the body (e.g., stomach fluids). It is accordingly extremely difficult to provide e.g., oral formulations, which are acceptable to the patient in terms of form and taste, which are stable on storage and which can be administered on a regular basis to provide suitable and controlling patient dosaging.

Proposed liquid formulations, e.g., for oral administration of macrocyclic immunosuppressants, have heretofore been based primarily on the use of ethanol and oils or similar excipients as carrier media. Thus, the commercially available macrocyclic immunosupressant drink-solution employs ethanol and olive oil or corn-oil as carrier medium in conjunction with solvent systems comprising e.g., ethanol and LABRIFIL and equivalent excipients as carrier media. Thus, the commercially available macrocyclic immunosupressant drink solution employs ethanol and olive oil or corn-oil as carrier medium in conjunctions with a Labrifil as a surfactant. See e.g., U.S. Pat. No. 4,388,307. Use of the drink solution and similar composition as proposed in the art is, however, accompanied by a variety of difficulties.

Further, the palatability of the known oil based system has proved problematic. The taste of the known drink-solution is, in particular, unpleasant. Admixture with an appropriate flavored drink, for example, chocolate drink preparation, at high dilution immediately prior to ingestion has generally been practiced in order to make regular therapy at all acceptable. Adoption of oil based systems has also required the use of high ethanol concentrations to itself inherently undesirable, in particular where administration to children is forseen. In addition, evaporation of the ethanol, e.g., from capsules (adopted in large part, to meet problems of palatability, as discussed or other forms (e.g., when opened)) results in the development of a macrocyclic immunosupressant precipitate. When such compositions are presented in, for example, soft gelatin encapsulated form an additional problem arises. This particular difficulty necessitates packaging of the encapsulated product in an air-tight component, for example, an air-tight blister or aluminum-foil blister package. This in turn renders the product both bulky and more expensive to produce. The storage characteristics of the aforesaid formulations are, in addition, far from ideal.

Bioavailability levels achieved using existing oral macrocyclic immunosupressant dosage system are also low and exhibit wide variation between individuals, individual patient types and even for single individuals at different times during the course of therapy. Reports in the literature indicate that currently available therapy employing the commercially available macrocyclic immunosupressant drink solution provides an average absolute bioavailability of approximately 30% only, with the marked variation between individual groups, e.g., between liver (relatively low bioavailability) and bone-marrow (relatively high bioavailability) transplant recipients. Reported variation in bioavailability between subjects has varied from one or a few percent for some patients, to as much as 90% or more for others. And as already noted, marked change in bioavailability for individuals with time is frequently observed. Thus, there is a need for a more uniform and high bioavailability of macrocyclic immunosupressant in patients.

Use of such dosage forms is also characterized by extreme variation in required patient dosaging. To achieve effective immunosuppressive therapy, blood or blood serum levels compounds of the cyclosporin have to be maintained within a specified range. This required range can in turn, vary, depending on the particular condition being treated, e.g., whether therapy is to prevent transplant rejection or for the control of an autoimmune disease, or condition and on whether or not alternative immunosuppressive therapy is employed concomitantly with any of the immunosuppressants of the formula described herein. Because of the wide variations in bioavailability levels achieved with conventional dosage forms, daily dosages needed to achieve required blood serum levels will also vary considerably from individual to individual and even for a single individual. For this reason it is necessary to monitor blood/blood-serum levels of patients receiving macrocyclic immunosuppressant therapy at regular and frequent intervals. Monitoring of blood/blood-serum levels, which is generally performed by RIA or equivalent immunoassay technique, e.g. employing monoclonal antibody based technology, has to be carried out on a regular basis. This is inevitably time consuming and inconvenient and adds substantially to the overall cost of therapy.

It is also the case that blood/blood serum macrocyclic immunosuppressant levels achieved using available dosage systems exhibit extreme variation between peak and trough levels. That is, for each patient, effective macrocyclic immunosuppressant levels in the blood vary widely between administrations of individual dosages.

There is also a need for providing macrocyclic immunosuppressant in a water soluble form for injection. It is well known that Cremephore L used in a current formulations of macrocyclic immunosuppressants is a polyoxyethylated derivative of castor oil and is a toxic vehicle. There have been a number of incidences of anaphylaxis due to the castor oil component. At present there is no formulation that would allow the macrocyclic immunosuppressants to be in aqueous solution at the concentrations needed due to poor water solubility of the drug.

Beyond all these very evident practical difficulties lies the occurrence of undesirable side reactions already alluded to, observed employing available oral dosage forms.

Several proposals to meet these various problems have been suggested in the art, including both solid and liquid oral dosage forms. An overriding difficulty which has, however, remained is the inherent insolubility of the macrocyclic immunosuppressants in aqueous media, hence preventing the use of a dosage form which can contain macrocyclic immunosuppressants in sufficiently high concentration to permit convenient use and yet meet the required criteria in terms of bioavailability, e.g. enabling effective resorption from the stomach or gut lumen and achievement of consistent and appropriately high blood/blood-serum levels.

The particular difficulties encountered in relation to oral dosaging with macrocyclic immunosuppressants have inevitably led to restrictions in the use of macrocyclic immunosuppressant therapy for the treatment of both relatively less severe or endangering disease conditions. A particular area of difficulty in this respect has been the adoption of macrocyclic immunosuppressant therapy in the treatment of autoimmune diseases and other conditions affecting the skin, for example, for the treatment of atopic dermatitis and psoriasis and, as also widely proposed in the art, for hair growth stimulation, e.g. in the treatment of alopecia due to ageing or disease.

Thus while oral macrocyclic immunosuppressant therapy has shown that the drug is of considerable potential benefit to patients suffering e.g. from psoriasis, the risk of side-reaction following oral therapy has prevented common use. Various proposals have been made in the art for application of macrocyclic immunosuppressants, e.g. cyclosporine, in topical form and a number of topical delivery systems have been described. Attempts at topical application have however failed to provide any demonstrably effective therapy.

However, the present invention overcomes the problems described hereinabove. More specifically, an embodiment of the present invention is an amino acid derivative of macrocyclic immunosuppressant which significantly enhances its solubility in aqueous solutions, thereby avoiding the need to utilize a carrier, such as ethanol or castor oil when administered as a solution. Moreover, the amino acid derivatives of macrocyclic immunosuppressants, in accordance with the present invention, do not exhibit the side effects of the prior art formulations. Further, the inventor has found that the macrocyclic immunosuppressant amino acid derivatives of the present invention enhance their absorption when administered in the form of the amino acid derivative to a patient, thereby enhancing significantly their bioavailability and efficacy.

Accordingly, in one aspect, the present invention is directed to an amino acid derivative of macrocyclic immunosuppressants. The amino acid derivative consists of an amino acid esterified to the free hydroxy group present on the macrocyclic immunosuppressents; e.g., on the side chain of cyclosporine, sirolimus, tacrolimus and either one of the hydroxyl groups of the pimecrolimus molecule.

For example, an aspect of the present invention is directed to, the compounds of the formulas

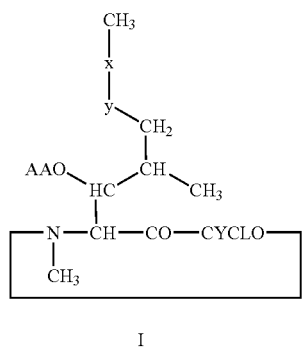

(a)

I

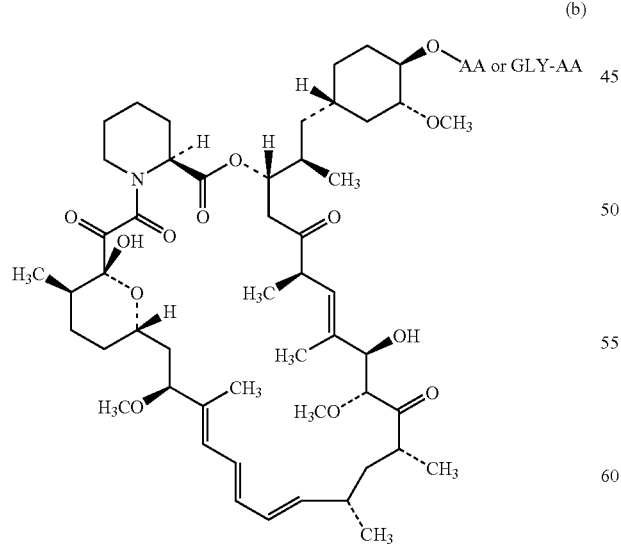

(b)

SIROLIMUS

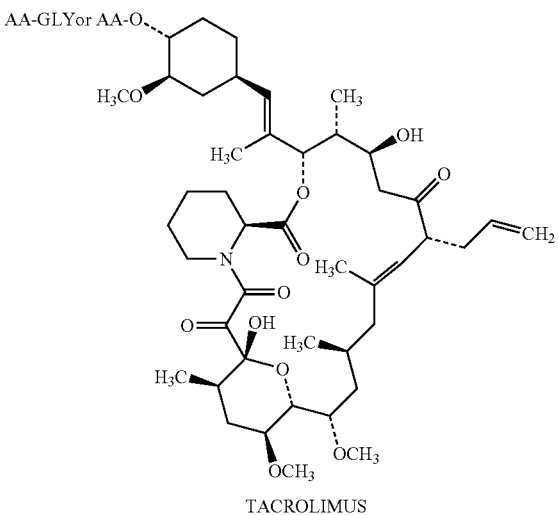

(c)

TACROLIMUS

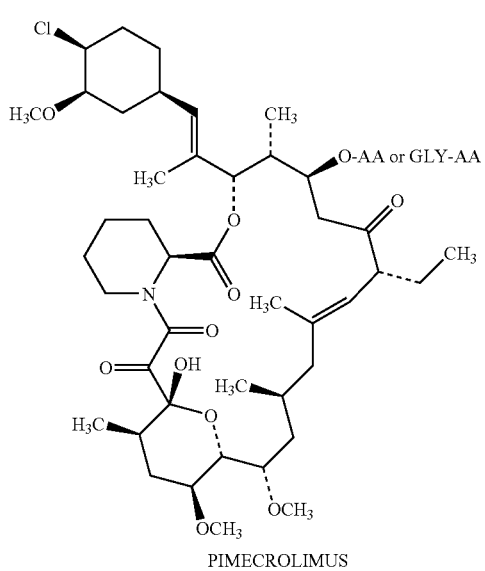

(d)

PIMECROLIMUS or pharmaceutically acceptable salts thereof;
wherein CYCLO represents the residues at positions 2-11 of the cyclosporine molecule; x-y is CH=CH or $CH_2CH_2$ and AA is an amino acid or a dipeptide of the formula GLY-AA. In the latter case, GLY is glycine and AA is any α-amino acid but preferably the L-α-amino acid and more preferably the naturally occurring amino acids, especially in the L-form. In the dipeptide structure, an AA is attached to the drug via OH group using glycine as the spacer. Glycine is esterified to cyclosporine and then glycine is bonded to any AA via amide linkage using amino group of glycine and carboxylic acid group of AA.

The present invention is also directed to a pharmaceutical composition comprising a therapeutically effective amount of the compounds of the Formulae a-d above and a pharmaceutical carrier therefor.

In another embodiment, the present invention is directed to a method of treating a patient in need of macrocyclic immunosuppressant therapy, which method comprises administering to said patient an effective amount of the compounds of Formulae a-d.

In a further embodiment, the present invention is directed to a method of enhancing the solubility of a macrocyclic immunosuppressant in an aqueous solution comprising reacting said immunosuspressant having a hydroxy group thereof, e.g., hydroxy functionality in the MeBmt moiety at position 1 of the cyclosporine molecule as well as the specified hydroxyl functions in formulas b-d, with an amino acid or acylating derivative thereof under ester forming conditions, and isolating the product or by using a simple amino acid or a dipeptide structure or acylating derivative wherein the AA is attached to drug using glycine as the spacer and isolating and isolating the product thereof.

In a still further embodiment, the present invention is directed to a method of enhancing the bioavailability of a macrocyclic immunosuppressant when administered to a patient which comprises reacting the immunosuspressant having a hydroxy group thereon, e.g., the hydroxy functionality in the MeBmt moiety in position 1 of the cyclosporine molecule, with an amino acid or acylating derivative under ester forming conditions and as well as the specified hydroxyl functions in formulas b-d with an amino acid or acylating derivative thereof under ester forming conditions or by using a simple amino acid or a dipeptide structure wherein the AA is attached to the drug using glycine as the spacer and isolating the product thereof and administering said product to the patient.

Overview:

The procedure for the synthesis of the N-(L-proline)-glycine and N-(L-lysine)-glycine esters of Cyclosporine A is outlined in Synthetic Sequence section. These examples are exemplary of the synthetic scheme using amino acids. The complete procedure and analytical data is given in the Experimental Section. Cyclosporine A (15 g) was coupled with chloroacetic anhydride (4 equivalent) in anhydrous pyridine. The experiment produced the chloroacetate ester of Cyclosporine A (SPI001201, 14 g, 88% yield) in good yield. The chloroacetate ester (10.1 g) was then treated with sodium azide in DMF to generate the azidoacetate ester of Cyclosporine A (SPI001202, 9.9 g, 97% yield). The azidoacetate (9.8 g) was then reduced with tin chloride (9 g) to prepare the glycine ester of Cyclosporine A (8.54 g, 89% yield). The glycine ester of Cyclosporine A (SPI001203) was then coupled with a two-fold excess of either boc-L-proline or Boc-L-lysine using EDC as the coupling agent. After purification by column chromatography, the boc protecting groups were removed from the dipeptide esters of Cyclosporine A at low temperature (5° C.) by treatment with 2M hydrochloric acid in diethyl ether. The L-lysine-glycine ester salt of Cyclosporine A did not require additional purification and was dried. The L-proline-glycine ester salt of Cyclosporine A required purification. The salt was converted to the free-base with sodium bicarbonate and purified by filtration through silica gel (eluting with acetone). The salt was then formed at low temperature with dilute anhydrous hydrochloric acid and dried.

Synthetic Sequence:

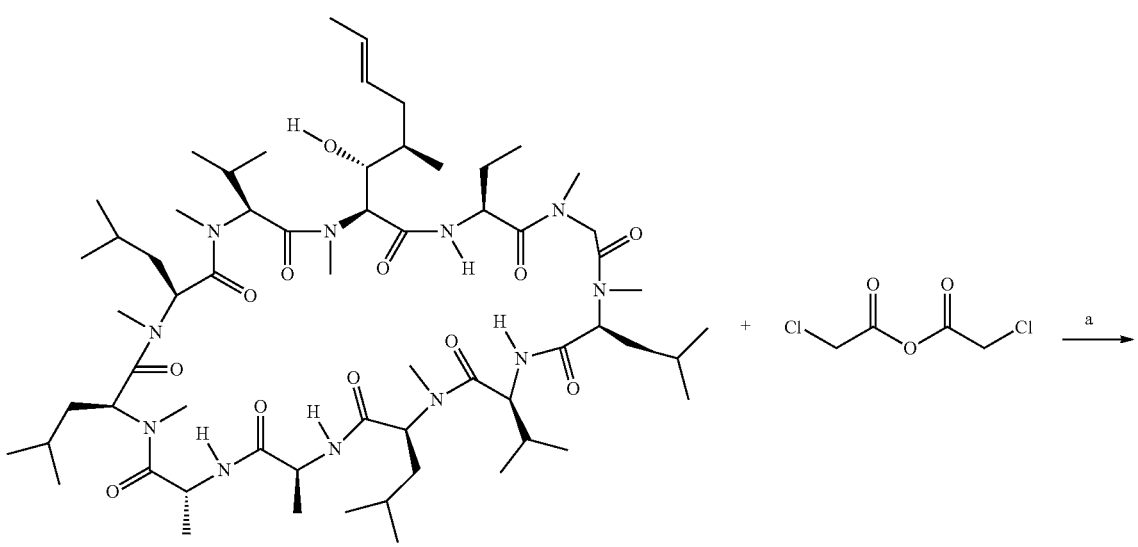

Cyclosporin A

-continued
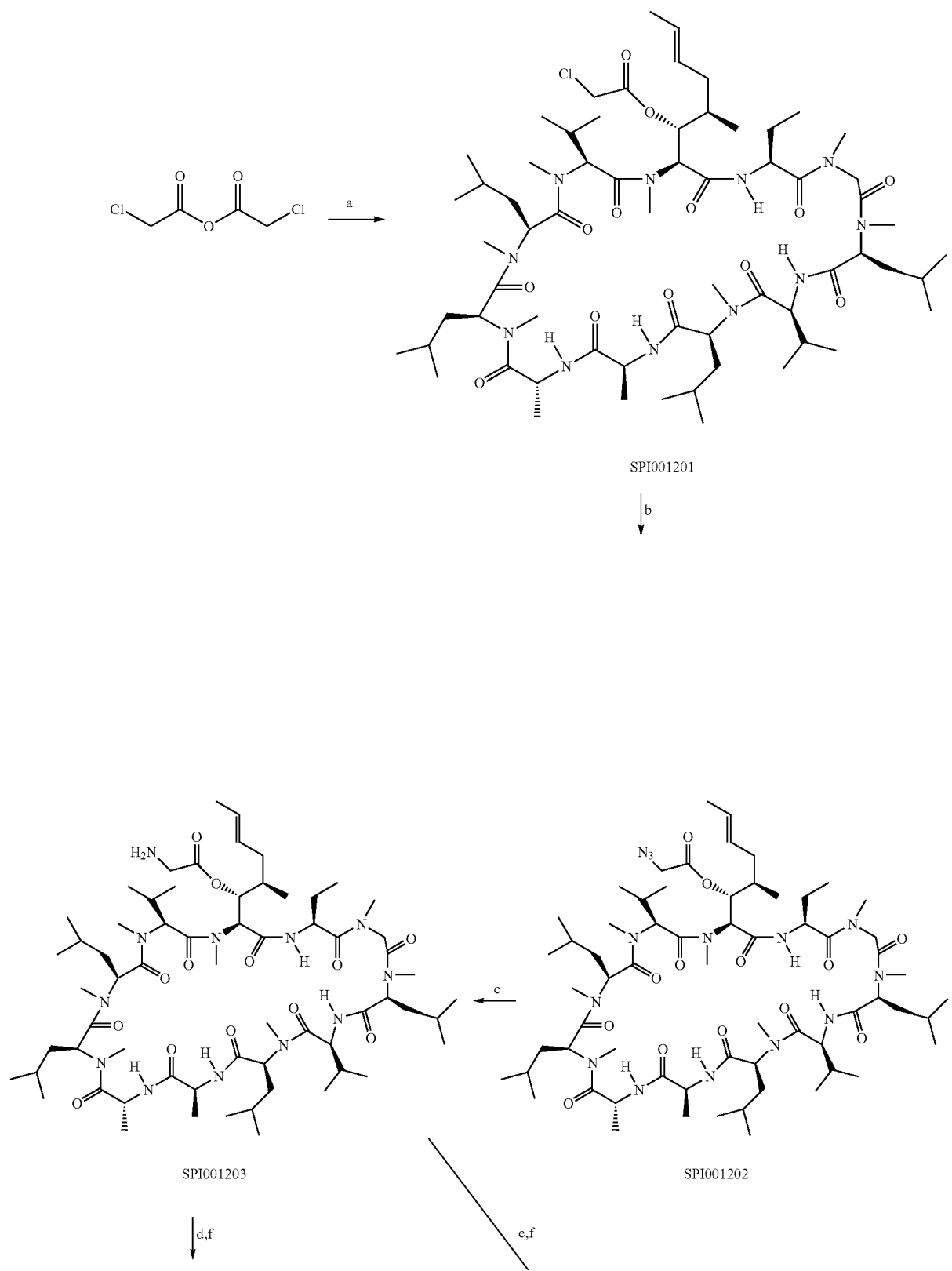

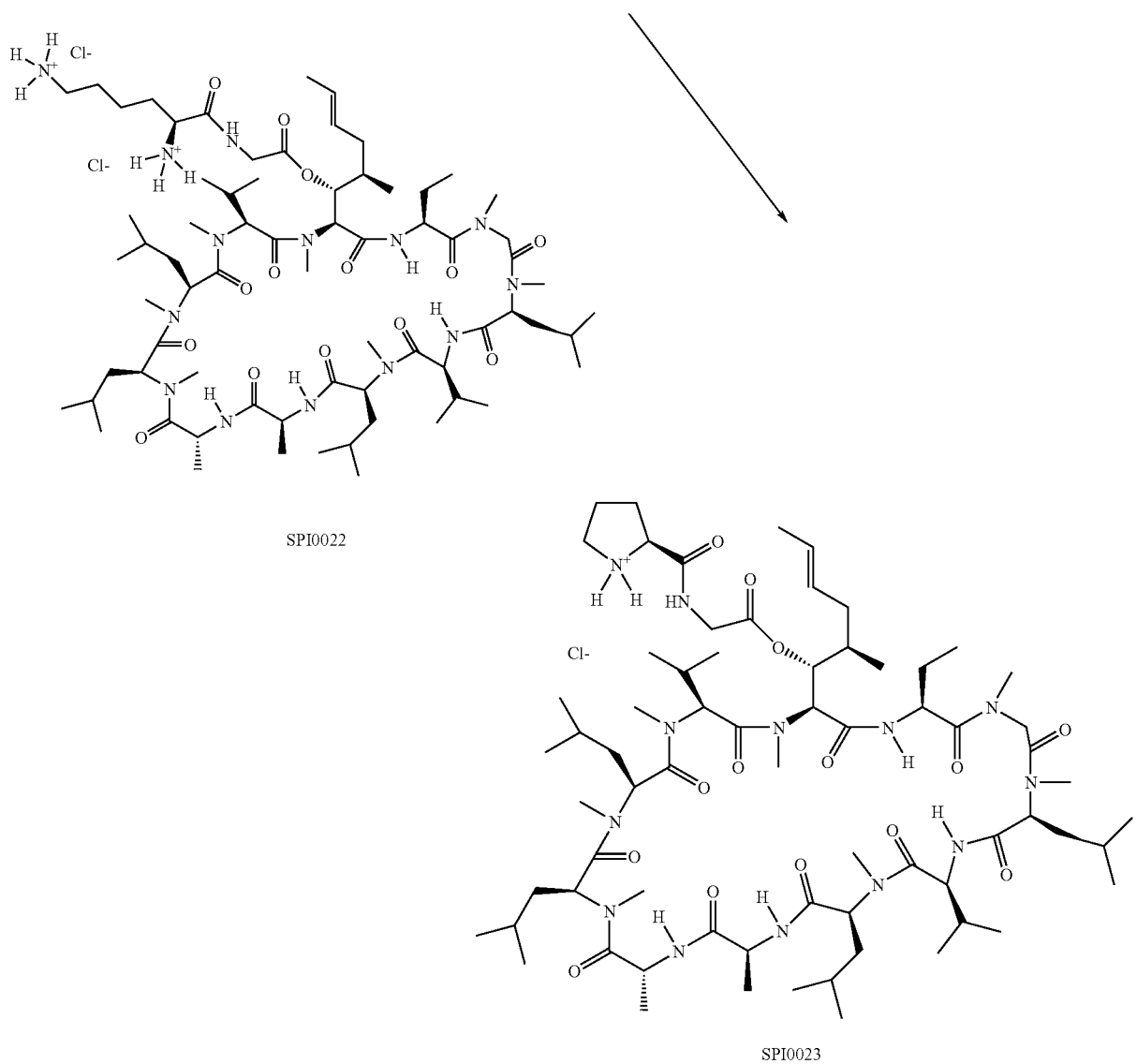

SPI0022

SPI0023

Synthesis of the N-(L-proline)-glycine and N-(L-Lysine)-glycine Esters of Cyclosporine A: a) Pyridine; b) NaN$_3$, DMF; c) SnCl$_2$, Methanol; d) boc-L-lysine, EDC; e) boc-L-proline, EDC; f) HCl, Et$_2$O.

Experimental Section:

The synthesis of SPI0022 and SPI0023 was conducted in batches. Generally a small-scale experiment was performed first followed by a larger batch. Reagents mentioned in the experimental section were purchased at the highest obtainable purity from Aldrich, Acros, or Bachem, except for solvents, which were purchased from either Fisher Scientific or Mallinckrodt. The Cyclosporine A (USP grade) used in these procedures was provided by Signature Pharmaceuticals, Inc.

1) SPI001201

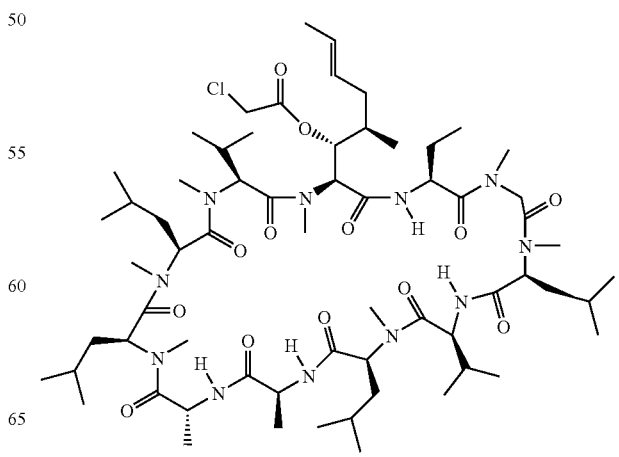

Cyclosporine A (15.01 g, 0.0124 moles) was dissolved in anhydrous pyridine (35 mL) at room temperature, under an argon atmosphere. The solution was cooled to 5° C. in an ice/water batch and chloroacetic anhydride (9.10 g, 0.053 moles) was added. After stirring for 10 minutes, the ice bath was removed and the solution was allowed to stir under an argon atmosphere at room temperature for 17 hours. After 17 hours, diethyl ether (200 mL) was added. The ether was washed with water (2×100 mL) and dried for 1 hour over sodium sulfate (10 g). After filtration and concentration under reduced pressure, the remaining yellow foam was dried under high vacuum (1 hour at room temperature) and purified by flash chromatography on silica gel (200 g), eluting with heptane/acetone (2:1). After combining and concentrating the product containing fractions, the remaining light yellow foam (14.8 g) was purified a final time by crystallization from hot diethyl ether (140 mL). After cooling (−10° C., 2 hours), filtration, and drying under high vacuum, the procedure generated the chloroacetate ester of Cyclosporine A SPI001201 as a white solid (14.0 g, 88.3% yield).

Cyclosporine A Chloroacetate Ester:
$^1$H NMR (300 MHz, CDCl$_3$):
δ=8.50 (d, 1H, J=9.6 Hz), 7.95 (d, 1H, J=6.6 Hz), 7.46 (d, 1H, J=9.0 Hz), 7.40 (d, 1H, J=7.8 Hz), 5.35-4.52 (m, 15H), 4.37 (t, 1H, J=7.2 Hz), 4.12 (d, 1H, J=14.7 Hz), 3.89 (d, 1H, J=14.7 Hz), 3.45-3.0 (m, 15H), 2.8-2.5 (m, 6H), 2.5-1.5 (m, 16H), 1.5-0.7 (m, 53H).
$^{13}$C NMR (75 MHz, CDCl$_3$):
δ=173.78, 173.37, 172.86, 172.61, 171.28, 171.18, 170.91, 170.79, 168.78, 167.64, 167.18, 128.77, 126.68, 75.46, 65.95, 58.89, 57.47, 55.80, 55.31, 54.86, 54.34, 50.19, 48.91, 48.35, 48.02, 44.80, 40.96, 39.44, 37.07, 35.93, 33.85, 33.25, 32.40, 31.74, 31.50, 30.38, 30.12, 29.82, 29.53, 25.13, 24.92, 24.78, 24.40, 23.99, 23.75, 22.85, 21.94, 21.41, 21.25, 20.84, 19.85, 18.79, 18.32, 17.89, 17.82, 15.46, 15.24, 10.08.

2) SPI001202

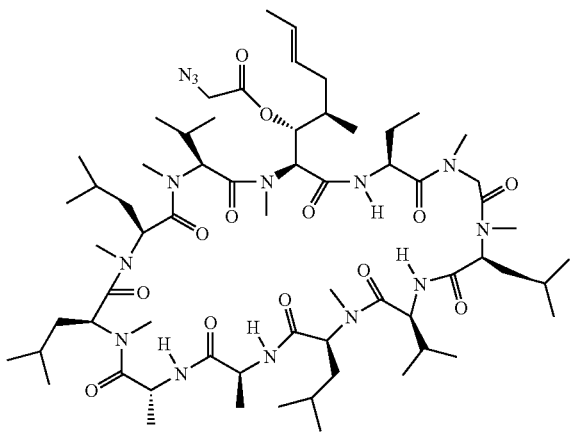

The chloroacetate ester of Cyclosporine A SPI001201 (10.10 g, 7.89 mmole) was dissolved in anhydrous N,N-dimethlformamide (30 mL) at room temperature. Sodium azide (2.15 g, 33.0 mmole) was added. The mixture was allowed to stir at room temperature for 24 hours in the dark, under an argon atmosphere. After 24 hours, diethyl ether (150 mL) was added and the precipitate was filtered. The ether was washed with water (2×00 mL), dried over sodium sulfate (15 g) for 30 minutes, filtered, and concentrated under reduced pressure. The remaining white solid was dried under high vacuum for 1 hour at room temperature. The experiment produced the azidoacetate ester of Cyclosporine A SPI001202 (9.90 g, 97% yield) as a white solid, which was used without further purification.

Cyclosporine A Azidoacetate Ester:
$^1$H NMR (300 MHz, CDCl$_3$):
δ=8.48 (d, 1H, J=9.3 Hz), 7.95 (d, 1H, J=6.9 Hz), 7.45 (d, 1H, J=9.0 Hz), 7.39 (d, 1H, J=7.8 Hz), 5.5-4.5 (m, 15H), 4.31 (t, 1H, J=6.6 Hz), 4.04 (d, 1H, J=17.3 Hz), 3.53 (d, 1H, J=17.3 Hz), 3.45-3.0 (m, 15H), 2.8-2.5 (m, 6H), 2.5-1.5 (m, 16H), 1.5-0.7 (m, 53H).
$^{13}$C NMR (75 MHz, CDCl$_3$):
δ=173.76, 173.32, 172.82, 172.53, 171.13, 170.89, 170.76, 170.69, 169.70, 168.20, 167.49, 128.63, 126.61, 74.96, 58.91, 57.39, 55.56, 55.21, 54.80, 54.23, 50.14, 48.99, 48.23, 48.24, 47.93, 44.71, 40.89, 39.33, 39.22, 37.02, 35.83, 33.81, 32.96, 32.31, 31.67, 31.42, 30.31, 30.09, 29.76, 29.47, 25.08, 24.92, 24.84, 24.67, 24.51, 24.40, 23.94, 23.82, 23.71, 21.85, 21.33, 21.25, 20.82, 19.79, 18.71, 18.25, 17.92, 17.81, 15.17, 10.03.

3) SPI001203

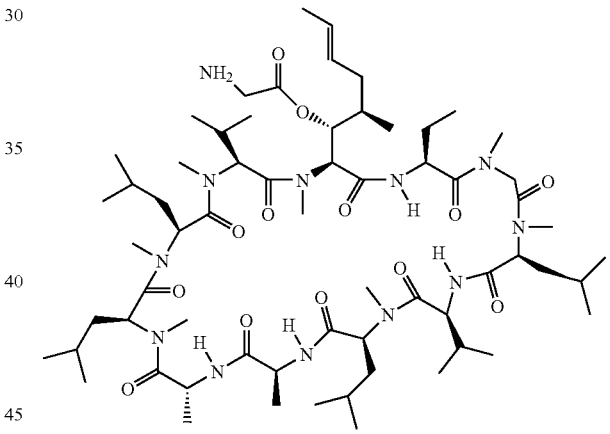

The azidoacetate ester of Cyclosporine A SPI001202 (9.80 g, 7.62 mmole) was dissolved in methanol (250 mL) at room temperature. Water (40 mL) was added followed by tin (II) chloride (5 g, 26.3 mmole). The solution was allowed to stir for 1 hour at room temperature when an additional quantity of tin (II) chloride (4 g, 21.0 mmole) was added. The solution was allowed to stir for an additional 2 hours at room temperature. Water (200 mL) containing ammonium hydroxide (40 mL, 29%) was added. After filtration, the solution was concentrated (to 200 mL) under reduced pressure. The remaining aqueous solution was extracted with ethyl acetate (2×200 mL). The ethyl acetate fractions were combined, dried over sodium sulfate (20 g), filtered and concentrated under reduced pressure. The remaining clear foam was purified by filtration through silica gel (150 g), eluting with dichloromethane/methanol (20:1). The procedure generated the glycine ester of Cyclosporine A as a clear, solid foam (8.54 g, 89% yield).

Glycine Ester of Cyclosporine A:

$^1$H NMR (300 MHz, CDCl$_3$):

δ=8.60 (d, 1H, J=9.6 Hz), 8.06 (d, 1H, J=6.9 Hz), 7.53 (d, 1H, J=8.4 Hz), 7.51 (d, 1H, J=6.6 Hz), 5.7-4.52 (m, 15H), 4.41 (t, 1H, J=6.9 Hz), 3.5-3.0 (m, 17H), 2.82-2.5 (m, 8H), 2.5-1.5 (m, 16H), 1.5-0.7 (m, 53H).

$^{13}$C NMR (75 MHz, CDCl$_3$):

δ=174.10, 173.67, 173.23, 172.72, 172.55, 171.18, 171.10, 170.73, 170.61, 169.68, 167.77, 128.82, 126.42, 73.83, 58.57, 57.32, 55.99, 55.20, 54.74, 54.31, 50.08, 48.82, 48.28, 47.90, 44.70, 43.81, 40.74, 39.33, 39.24, 37.02, 35.84, 33.72, 33.07, 32.39, 31.72, 31.41, 30.25, 29.98, 29.74, 29.51, 25.05, 24.81, 24.73, 24.54, 24.31, 23.91, 23.78, 23.68, 21.86, 21.33, 21.25, 20.68, 19.76, 18.74, 18.24, 17.94, 17.79, 15.18, 10.03.

4) SPI0022

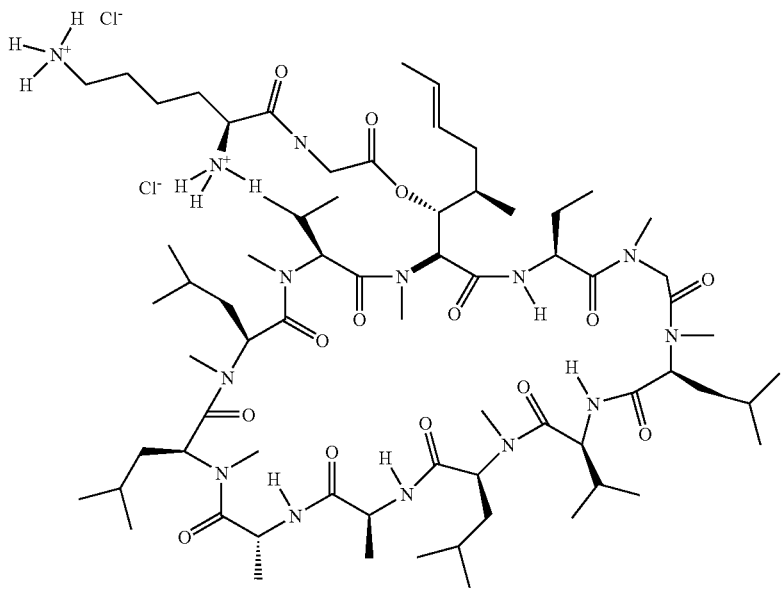

The glycine ester of Cyclosporine A (SPI001203, 2.0 g, 1.59 mmole) was dissolved in anhydrous dichloromethane (25 mL) with boc-L-lysine (1.31 g, 3.78 mmole) and EDC (0.75 g, 3.9 mmole), under an argon atmosphere at room temperature. The boc-L-lysine was prepared from the dicyclohexylamine salt (2.0 g in 50 mL ether) by extraction with cold potassium hydrogen sulfate solution (1 g in 50 mL water) followed by cold water (2×50 mL). The ether containing the boc-L-lysine was dried over sodium sulfate (5 g), filtered, concentrated and dried under high vacuum for one hour at room temperature. A few crystals of DMAP were added to the mixture of EDC, boc-L-lysine, and the glycine ester of Cyclosporine A and the solution was allowed to stir for 4 hours at room temperature. The dichloromethane solution was extracted with DIUF water (50 mL), 5% sodium bicarbonate solution (50 mL), and with DIUF water (50 mL). After drying over sodium sulfate (10 g), the dichloromethane solution was filtered and concentrated under reduced pressure. The remaining white foam (3.01 g) was purified by flash column chromatography on silica gel (50 g), eluting with heptane/acetone (2:1). The product containing fractions were combined, concentrated under reduced pressure, and dried under high vacuum. The purified protected intermediate (2.34 g white solid, 92.8% yield) was placed in a flask under an argon atmosphere, which was cooled in an ice-water bath. Cold anhydrous 2 M hydrochloric acid in diethyl ether (20 mL) was added and the solution stirred for 8 hours (at 5° C.). The mixture was slowly allowed to warm to room temperature overnight. After stirring for a total of 20 hours, the flask was cooled again in an ice-water bath for 30 minutes. The product was filtered and dried under high vacuum for 1 hour at room temperature and then at 50° C. for 4 hours. The experiment produced Cyclosporine A N-(L-lysine)-glycine ester, dihydrochloride trihydrate (SPI0022, 1.59 g, 73.9% yield) as a white solid.

$^1$H NMR (300 MHz, CDCl$_3$, NMR data is for the free base): δ=8.58 (d, 1H, J=9.3 Hz), 8.04 (d, 1H, J=6 Hz), 7.80 (d, 1H, J=6 Hz), 7.49 (d, 2H, J=8.4 Hz), 5.70-4.6 (m, 17H), 4.41 (m, 1H), 4.28 (dd, 1H, J=17, 7.2 Hz), 3.67 (d, 1H, J=17 Hz), 3.46 (s 3H), 3.4-2.8 (m, 16H), 2.8-2.5 (m, 8H), 2.5-1.35 (m, 24H), 1.5-0.7 (m, 50H).

$^{13}$C NMR (75 MHz, CDCl$_3$, NMR data is for the free base):

δ=175.23, 173.77, 173.34, 172.75, 172.63, 171.34, 171.22, 170.94, 170.84, 170.91, 169.89, 169.70, 128.74, 126.67, 74.41, 58.82, 57.43, 55.91, 55.21, 54.81, 54.42, 50.17, 48.89, 48.31, 47.98, 44.78, 41.92, 40.82, 40.69, 39.44, 39.32, 27.19, 35.91, 34.88, 33.71, 33.25, 33.12, 32.44, 31.83, 31.50, 30.38, 30.06, 29.81, 29.55, 25.14, 24.90, 24.52, 24.43, 24.00, 23.76, 21.93, 21.42, 21.29, 20.81, 19.84, 18.82, 18.32, 17.96, 17.86, 15.21, 10.10.

CHN Analysis:

Calculated for $C_{70}H_{128}Cl_2N_{14}O_{15} \cdot 3H_2O$: C, 55.50; H, 8.92; and N, 12.74. found: C, 58.28; H, 8.98; and N, 13.16.

HPLC Analysis:

99.60% purity; r.t.=14.763 min.; 80% acetonitrile/20% Tris base in DIUF water; 1 mL/min; 60 C; Synergi Hydro RP, 4 u column (serial #163383-7), 4.6×250 mm; 20 ul; UV=210 nm.

Melting point: 196.0-198° C. (uncorrected)

5) SPI0023

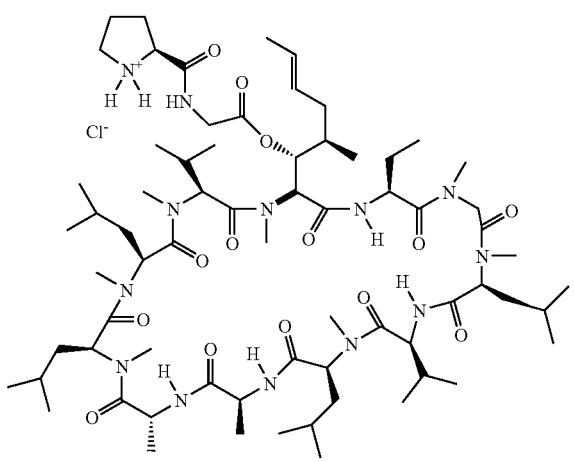

The glycine ester of Cyclosporine A (SPI001203, 7.50 g, 5.95 mmole) was dissolved in anhydrous dichloromethane (50 mL) with boc-L-proline (2.56 g, 11.90 mmole) and EDC (2.28 g, 11.9 mmole), under an argon atmosphere at room temperature. A few crystals of DMAP were added to the mixture of EDC, boc-L-proline, and the glycine ester of Cyclosporine A and the solution was allowed to stir for 3 hours at room temperature. The dichloromethane solution was extracted with DIUF water (50 mL), 5% sodium bicarbonate solution (2×50 mL), and with DIUF water (50 mL). After drying over sodium sulfate (10 g), the dichloromethane was filtered and concentrated under reduced pressure. The remaining white foam (9.50 g) was purified by flash column chromatography on silica gel (150 g), eluting with heptane/acetone (2:1 followed by 1:1). The product containing fractions were combined, concentrated under reduced pressure, and dried under high vacuum (7.94 g white solid, 91.7% yield) for 10 minutes at room temperature.

The purified protected intermediate (6.46 g) was placed in a flask under an argon atmosphere, which was cooled in an ice-water bath. Cold anhydrous 2 M hydrochloric acid in diethyl ether (150 mL) was added and the solution stirred for 8 hours (at 5° C.). The mixture was slowly allowed to warm to room temperature overnight. After stirring for a total of 20 hours, the flask was cooled again in an ice-water bath for 30 minutes. The product was filtered and dried under high vacuum for 30 minutes at room temperature. The Cyclosporine A N-(L-proline)-glycine ester, hydrochloride (5.17 g, 84.6% yield, and 90% purity by HPLC) was converted to the free base by dissolving the salt in DIUF water (25 mL) that contained sodium bicarbonate (1 g). The free base was extracted with dichloromethane (3×25 mL), which was dried over sodium sulfate (5 g), filtered and concentrated. The remaining off-white solid (5 g) was purified by filtration through silica gel (100 g), eluting with acetone. The product containing fractions were combined, concentrated under reduced pressure, and dried under high vacuum for 30 minutes at room temperature. The hydrochloride salt was regenerated by dissolving the free base (3.8 g) in diethyl ether (25 mL) and adding it to anhydrous 2M hydrochloric acid (5 mL) in heptane (50 mL), while cooling in an ice-water bath. After 20 minutes at 5° C., the white solid was filtered and dried under high vacuum for 6 hours at room temperature. The experiment produced Cyclosporine A N-(L-proline)-glycine ester, hydrochloride (SPI0023, 3.8 g) as a white solid.

$^1$H NMR (300 MHz, CDCl$_3$):

δ=14.20 (br s, 2H), 8.62 (d, 1H, J=10 Hz), 8.06 (d, 1H, J=6.9 Hz), 7.61 (d, 1H, J=8.1 Hz), 7.48 (d, 1H, J=9 Hz), 5.70-5.50 (m, 3H), 5.40-4.60 (m, 12H), 4.37 (m, 1H), 4.20 (d, 1H, J=18 Hz), 3.97 (d, 1H, J=18 Hz), 3.70 (m, 1H), 3.45 (s, 3H), 3.23-3.08 (m, 12H), 2.66 (s, 3H), 2.60 (s, 3H), 2.50-1.80 (m, 15H), 1.78-1.20 (m, 15H), 1.15-0.66 (m, 46H).

$^{13}$C NMR (75 MHz, CDCl$_3$):

δ=174.15, 173.49, 172.67, 172.59, 171.86, 171.20, 171.13, 171.02, 170.83, 169.68, 168.77, 167.55, 128.30, 127.10, 80.09, 75.58, 62.65, 59.35, 57.36, 55.53, 55.30, 54.78, 54.35, 53.60, 50.25, 50.09, 48.92, 48.18, 48.12, 44.62, 40.59, 40.02, 39.43, 39.30, 37.13, 35.88, 33.74, 33.07, 32.19, 32.01, 31.86, 31.50, 31.43, 30.43, 29.93, 29.72, 29.30, 29.16, 27.56, 26.04, 25.00, 24.86, 24.74, 24.39, 20.96, 19.81, 18.71, 18.26, 18.09, 17.85, 17.79, 15.09, 14.30, 10.00.

CHN Analysis:

Calculated for $C_{69}H_{122}ClN_{13}O_{14}$: C, 59.48; H, 8.83; and N, 13.07. found: C, 59.84; H, 9.02; and N, 12.65.

HPLC Analysis:

99.59% purity; r.t.=10.613 min.; 85% acetonitrile/15% Tris base in DIUF water; 1.2 mL/min; 60 C; Synergi Hydro RP, 4 u column (serial #163383-7), 4.6×250 mm; 20 ul; UV=210 nm.

Melting point: 197.0-199° C. (uncorrected)

The amino acid derivatives of cyclosporin of the present invention are effective in treating diseases or conditions in which macrocyclic immunosuppressants normally are used. These derivatives are transformed within the body to release the active compound and enhances the therapeutic benefits of the macrocyclic immunosuppressants by reducing or eliminating biopharmaceutical and pharmacokenetic barriers associated with each of them. However it should be noted that these derivatives themselves will have sufficient activity without releasing any active drug in the mammals. Since the derivatives are more soluble in water then cyclosporine or other macrocyclic immunosuppressants, it does not need to be associated with a carrier vehicle, such as alcohol or castor oil which may be toxic or produce unwanted side reactions. Moreover, oral formulations containing the derivatives of the derivatives are absorbed into the blood and are quite effective.

Thus, the derivative of cyclosporin of the present invention enhances the therapeutic benefits by removing biopharmaceutical and pharmacokenetic barriers of existing drugs.

Furthermore, the derivatives are easily synthesized in high yields using reagents which are readily and commercially available.

Animal Effiacy Study Results for Cyclosporine Derivatives:

A simple method to test the efficacy of cyclosporine A and its analogs, Cyclosporine-glycine-proline (Cyclosporine GP) ester, Cyclosporine-glycine-lysine (Cyclosporine GL) ester and Cyclosporine-glycine (Cyclosporine G) ester is to treat ulcerative colitis induced by administering 5% Dextran Sodium Sulfate (DSS) ad libitum to laboratory mice. This model has been used consistently with most immunosuppressants to demonstrate both actual treatment after induction of colitis, and also prophylactic treatments. Results from both types of studies are shown below.

Calculation of Disease Activity Index (DAI)

Percent animal body weight loss, stool consistency and occult blood at the end of the study will be taken into consideration to calculate Disease Activity Index ("DAI") of each animal. The following scoring system outlined in Table 30 was for the percent body weight loss, stool consistency and occult blood:

TABLE 30

| Score | Weight loss (%) | Stool consistency | Blood in feces |
|---|---|---|---|
| 0 | 0 or gain | Normal | Negative |
| 1 | 1-4.9 | Soft | +/− |
| 2 | 5.0-9.9 | Mixed (soft & Diarrhea) | + |
| 3 | 10-15 | Diarrhea | ++ |
| 4 | >15 | Bloody Diarrhea | +++ (Gross blood) |

The scores for each parameter for each mouse at the end of study are added together and divided by three (number of observations) to determine DAI. The mean group DAI is the determined. A score of 3 was assigned for any animal that died during the testing.

Results from the Study are Indicated in Table 31:

In this study, DSS administration is coupled with administration of either test or reference drug from day 1. No of mice used were 10 in each group:

TABLE 31

| Drug | Mean DAI |
|---|---|
| Vehicle | 1.500 |
| Cyclosporine A (Ref) | 1.400 |
| Cyclosporine-G | 1.531 |
| Cyclosporine-GL | 1.100 |
| Cyclosporine-GP | 1.062 |

While Cyclosporine G didn't perform as expected in this model, Cyclosporine GP had statistically significant performance compared to Cyclosporine A.

Results from Disease Treatment Study:

Much more dramatic results were obtained when the mice were initially treated with DSS to induce colitis. Once clear symptoms of colitis were seen, DSS was replaced by drinking water, and treatment started with test and reference drugs, including vehicle control. All results are mean of 10 mice. The mean DAI os tabulated hereinbelow in Table 32:

TABLE 32

| Drug | Mean DAI |
|---|---|
| Vehicle | 1.832 |
| Cyclosporine A (Ref) | 0.300 |
| Cyclosporine-G | 0.100 |
| Cyclosporine-GL | 0.532 |
| Cyclosporine-GP | 0.066 |

Clearly Cyclosporine G and Cyclosporine-GP showed statistically significant results, significant improvement over Cyclosporine reference drug. Notice in the treatment study, 5 out of 10 mice died in the vehicle control, 1 died with cyclosporine-GL treatment, and none died in the cyclosporine-A, Cyclosporine-G and Cyclosporine-GP treated groups.

Development of Cyclosporine GP Ophthalmic Preparation:

Clear, aqueous solutions of the Cyclosporine GP was prepared by dissolving sufficient quantities of Cyclosporine GP in distilled water, and pH adjusted to around 5 to produce 0.2% w/v concentrations. Allowable quantities of HCl, and alcohol as per US FDA ophthalmic additive content regulations were added to keep the mixture stable and solubilized in the ophthalmic preparation. The resulting clear solution was stable for 3 months at room temperature. This solution appeared pharmaceutically elegant than currently available formulations such as Restasis® and other cloudy preparations using cremaphor or castor oil to make emulsion of cyclosporine in water.

As indicated hereinabove the solubility of the amino acid derivatives of the macrocyclic immunosuppressent with an OH group functionality group thereon with which the amino acid can form an ester linkage is significantly enhanced in aqueous solution relative to the corresponding macroscopic immunosuppressents which are not linked to the amino acids. For example, the solubility of cyclosporine in water is approximately 30 microgram/ml (US patent publication 20040138108). The solubility of Cyclosporine-glycine-proline ester in aqueous solution at room temperature was 60 times that of Cyclosporine A in water, and equaled approximately 2000 micrograms/ml.

VI. Valproic Acid Esters

Valproic acid (2-Propylpentanoic acid) is low molecular weight carboxylic acid derivative which is widely used as an anti-convulsive agent, useful in the treatment of epilepsy and also possess vasodilatation activity in the brain to relieve migraine headaches. It is administered orally to control epileptic episodes in humans and also alleviate severe pain associated with migraine headaches.

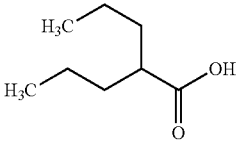

VALPROIC ACID

Valproic acid has been shown to have a large number of therapeutic applications, which are quite varying and somewhat surprising. For example, in addition to its efficacy in the treatment of epilepsy and migraine headaches, it has been shown to be effective in the treatment of certain psychiatric illnesses, such as bipolar disorder, mood stabilization, control of aggression, impulsivity in personality disorder, agitation in dementia, and has also been of use as adjunct therapy in the treatment of post traumatic stress disorder (PTSD).

Mechanism of Action:

In spite of being used in the treatment of epilepsy for a number of years, the exact mechanism of action of Valproic acid is still unknown. It has been postulated that it exerts its action by increasing concentration of gamma-amino butyric acid (GABA) in the brain. Gamma-amino butyric acid is a neurotransmitter, a chemical that nerves use to communicate with one another.

Valproate is the drug of choice in myoclonic epilepsy, with or without generalized tonic-clonic seizures, including juvenile myoclonic epilepsy of Janz that begins in adolescence or early adulthood. Photosensitive myoclonus is usually easily controlled. Valproate also is effective in the treatment of benign myoclonic epilepsy, postanoxic myoclonus, and, with clonazepam, in severe progressive myoclonic epilepsy that is characterized by tonic-clonic seizures as well. It also may be preferred in certain stimulus-sensitive (reflex, startle) epilepsies.

Although Valproate may be effective for infantile spasms, it is relatively contraindicated in children whose spasms are due to hyperglycinemia or other underlying metabolic (mitochondrial) abnormalities. In general, atonic and akinetic seizures in patients with Lennox-Gastaut syndrome are difficult to control, but Valproate is the drug of choice for treatment of mixed seizure types. Since this drug has been useful in some patients who are refractory to all other antiepileptic drugs, it may warrant a trial in nearly all nonresponsive patients regardless of seizure type.

In spite of it usefulness, hepatotoxicity may be fatal, but is idiosyncratic and not preventable by routinely monitoring liver enzymes. Hepatotoxicity occurs in very young children, most often those on multiple anticonvulsants. Valproate-induced cytopenias may be dose-related and warrant monitoring of complete blood counts during therapy. Encephalopathy with hyperammonemia without liver function test abnormalities may occur. Pregnant women in their first month are at risk for neural tube defects.

Valproic acid is a low molecular weight liquid with characteristic odor. Taken orally, it has unpleasant taste and can severely irritate mouth and throat. In order to convert Valproic acid into a solid dosage form convenient for oral administration, a number of derivatives with covalent and ionic bond with the carboxylic acid have been made. A simple sodium salt of Valproic acid, resulting in Valproate sodium is available as a solid. However a stable coordination complex, know as Divalproex sodium was formed by partial neutralization of two molecules of Valproic acid with one atom of sodium. This product is the most widely available commercial Valproic acid hemisalt. It is marketed by Abbott Laboratories in the USA under the brand name Depakote®. Depakote® is also available in extended release formulation for oral administration.

A significant disadvantage of Valproic acid is that in liquid form, it is difficult to administer. Furthermore, administration of Valproic acid in different forms does not uniformly produce desired bioavailability. For example, the overall bioavailability of Valproate from Valproic acid, its sodium salt, Divalproex®, and their extended release formulations are not quite interchangeable. Since continuous monitoring of the plasma profile of a patient to whom Valproic acid is administered is essential, any change in plasma concentration due to changes in the formulation can adversely affect the overall therapeutic outcome.

The amino acid derivatives of Valproic acid improve the therapeutic effectiveness, uniform blood profile, develop pharmaceutically elegant formulation and reduce first pass metabolism, exhibited by valproic acid alone.

Until now there has been no pharmaceutical preparation available in the market that can deliver Valproic acid without harmful side effects. The present invention, however, has produced a number of water soluble, non-toxic derivatives of Valproic acid which are suitable for delivering Valproic acid consistently in the body without any harmful side effects and without the needs for expensive additives and excipients.

Accordingly, in one aspect, the present invention is directed to a class of amino acid derivatives of Valproic acid or acylating derivative thereof. The derivative consists of the hydroxyl group of an amino acid esterified to the free carboxyl group present on the Valproic acid molecules. In another embodiment, the amine group of the amino acid is reacted with COOH of the valproic acid or acylating derivative thereof to form an amide linkage.

More specifically, an embodiment of the present invention is directed to, the compounds of the formula

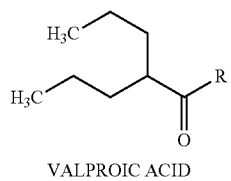

VALPROIC ACID or pharmaceutically acceptable salts thereof wherein R is either NH-AA or O-AA and AA is an amino acid less an amino group in NHAA or less an hydroxy group in O-AA, in which either an amine group or the hydroxyl group is reacted with the carboxylic acid group of Valproic Acid.

Recently A small proof of concept study (Depletion of latent HIV-1 infection in vivo: a proof-of-concept study Lehrman G, Hogue I B, Palmer S, Jennings C, Spina C A, Wiegand A, Landay A L, Coombs R W, Richman D D, Mellors J W, Coffin J M, Bosch R J, Margolis D M. The Lancet—Vol. 366, Issue 9485, 13 Aug. 2005, Pages 549-555) demonstrated that Valproic Acid might reduce the pool of dormant HIV infected cells in the body.

As part of its life cycle, HIV needs to insert its genetic material into the DNA of the human CD4 T-cells which it infects. These incorporated genes of the virus are then used as template for the production of new virus particles in active cells. This process leads to the cells being over-activated, eventually causing most of them to commit suicide or 'apoptosis' and the CD4 cell counts to fall.

However, a small proportion of the HIV-infected cells do not die, but become dormant within the lymph node or other areas of the body. Since they are not actively producing new HIV particles, the genes of the virus remain hidden within the nuclei of these cells. These cells, which are distributed throughout the body, are highly stable and long-lasting, but remain ready to start pumping out new HIV particles if they become activated by stimulation of the immune system.

Currently available anti-retroviral drug combinations (known as AIDS cocktail) can reduce HIV to undetectable levels in the blood, but they can only do so by preventing HIV from making copies of itself, or 'replicating' in the body. Anti-retroviral drugs typically can not remove HIV's genes that are integrated into the human cells' DNA, leaving the reservoir of the HIV in latent infected cells untouched.

Valproic Acid (VPA) which is currently used worldwide for the treatment of bipolar disorders and epilepsy is an inhibitor of a cellular enzyme called histone deacetylase 1 (HDAC1). This enzyme has been shown to be crucial in keeping HIV's gene hidden within the host cells' DNA.

In the test tube, studies have shown that VPA can stimulate the release of the HIV from resting infected T-Cells. Consequently, scientists are trying to find out whether giving the drug to HIV-positive patients could stimulate the release of resting cells to start producing and expressing HIV particles and thus eliminate the hidden stores of HIV from the body. Once the viral particles are exposed to anti-retroviral drugs, the disease is cured since there are no hidden reservoirs in the body in the short run.

Problems with VPA Therapy:

1. A small proof of concept study explained above was done in a limited number of patients (4 patients), and it was not a proof of efficacy study. When these 4 patients were treated for 18 weeks with Valproic acid ("VPA"), the investigators saw a decline in resting cells containing HIV genes between 68 to 84%, and in the 4$^{th}$ patient, had smaller reduction to 29%.

2. VPA is not without its severe side effects and adverse reactions. FDA has mandated boxed bold letter warnings for this drug to be included in all product inserts. Serious box warning include hepatotoxicity, teratogenicity, pancreatitis.

3. Other serious side effects include urea cycle disorders (UCD), somnolence in the elderly, thrombocytopenia, hyperammonemia, birth defects, mania, and various GI, Nervous system, respiratory system, skin disorders and weight gain.

4. While VPA has shown to be carcinogenic and mutagenic in animal models, such effects in humans are unknown.

5. Dr. Robert Siliciano from the Johns Hopkins University is of the opinion that "its extremely unlikely that this approach would work", who is one of the scientists who discovered dormant infection of the HIV in the mid-1990s.

6. According to Dr. Siliciano, 99.9999% of the hidden HIV infection has to be "kicked" out of the dormant human CD4 T-cells. In the proof of concept study, it was shown that reduction levels varied between 29 to 84%, far short of the 99.9999% demanded by Dr. Siliciano.

Solution to the Problem:

The amino acid derivatives of valproic acid represent the solution to the problem. They are effective in expelling the virus, e.g., HIV virus from the human immune cell reservoirs. Table 33 lists as examples, 6 amino acid derivatives of valproic acid effective in expelling the virus:

TABLE 33

| No | Drug | Mol. Wt |
|---|---|---|
| 1 | Valproic Acid L-Threonine Ester | 281.78 |
| 2 | Valproic Acid Serine Ester | 267.76 |
| 3 | Valproic Acid Serine Amide Nitrate | 276.29 |
| 4 | Valproic Acid Tyrosine Ester | 343.85 |
| 5 | Valproic Acid Hydroxyproline Amide | 257.33 |
| 6 | Valproic Acid Hydroxyproline Ester | 257.33 |

The present invention is also directed to a pharmaceutical composition comprising a therapeutically effective amount of the an amino acid derivative of Valproic acid and a pharmaceutical carrier therefor.

In another embodiment, the present invention is directed to a method of treating a patient in need of Valproic acid therapy, which method comprises administering to said patient an effective amount of the amino acid derivative of the Valproic acid.

In a further embodiment, the present invention is directed to a method of converting liquid Valproic acid into a solid powder by reacting the carboxyl functionality of the Valproic acid with either the amine or hydroxyl functionality of an amino acid or acylating derivative thereof and isolating the product(s) thereof.

In a still further embodiment, the present invention is directed to a method of substantially and in a therapeutically efficacious manner, reducing or eliminating the potential first pass metabolism thereby improving the consistent therapeutic effect by administering to a patient an amino acid derivative which comprises reacting the COOH functionality of the Valproic acid molecule with either the $NH_2$ or OH functionality of the amino acids to form an ester or amide covalent bond, respectively, and isolating the product thereof and administering said product to the patient.

The present inventor has found that when naturally occurring amino acids are esterified to Valproic acid, the resulting derivatives are pharmaceutically elegant free flowing powders, and are rapidly absorbed into the body and release non-toxic amino acids upon cleavage in the body and require none of the emulsifiers, additives and other excipients associated with volproic acid.

Furthermore, the amino acid derivatives of Valiproic acid are effective anti-epileptics and exhibit such effect intact. Thus the current amino acid derivatives are effective anti-epileptics and useful in the treatment of a number of psychiatric illnesses and exhibit such potential with or without releasing the active parent drug.

The amino acid derivative of Valproic acid exhibits a bulk density which is much higher than the corresponding sodium salts, and they are suitable for compacting large weight tablets and capsules. Furthermore, the amino acid derivatives of Valproic acid do not exhibit bitter taste and unusual odor of the Valproic acid.

As indicated hereinabove, the amino acid derivatives are effective anti-epileptics with or without releasing Valproic acid. However, when administered in vivo, the amino acid derivative release in vivo the active drug with all its pharmacological and psychoactive properties.

In conclusion, the amino acid derivative of Valproic acid clearly provides a number of advantages over Valproic acid. For example, they are less toxic than the corresponding valproic acid when administered in vivo, the valproic acid amino acid derivatives may be metabolized to cleave the amino acid moiety from the valproic acid, which are non-toxic. This results in a high therapeutic index. Secondly, the amino acid derivatives may or may not cleaved in the body to release Valproic acid. The amino acid derivative of valproic acid exhibits the same utility as valproic acid itself. Furthermore, due to their high water solubility, they can be easily administered by either forming an in-situ solution just before IV administration using lyophilized sterile powder or providing the drug in solution in prefilled syringe or bottles for infusion. The amino acid esters are more stable than Valproic acid since the COOH group in Valproic acid is blocked so as to minimize any reaction with bases. Thus the amino acid derivatives of Valproic acid are more effective than Valproic acid itself without the toxicity and other pharmaceutical problems associated with current marketed formulations of valproic acid.

The procedures for the synthesis of the L-serine, L-threonine, and L-hydroxyproline esters of valproic acid (2-propylpentanoic acid) are outlined in Synthetic Sequence section and is exemplary for the preparation of the various derivatives of the present invention. The complete procedure and analytical data is given in the Experimental Section. In general, valproic acid (2-8 g, in batches) was coupled with the N-benzyloxy/benzyl ester protected amino acids using EDC in the presence of a catalytic amount of DMAP. Once the reactions were complete (20 hours at room temperature), the mixture was extracted with DIUF water, dried over sodium sulfate, and concentrated under reduced pressure. The crude material was either used directly for the deprotection step or purified by column chromatography. The procedure generated the protected amino acid esters of valproic acid in yields ranging from 72% to 92%. The protecting groups were removed by hydrogenation (30 psi $H_2$) in the presence of 10% palladium on carbon. The amino acid esters of valproic acid were extracted away from the palladium catalyst with ethanol, concentrated, and dried. The final salts were formed by acidification with hydrochloric acid. The crude salts (yields ranging from 57% to 92%) were then purified by the methods described in the Experimental Section.

Synthetic Sequence:

1. SPIC001

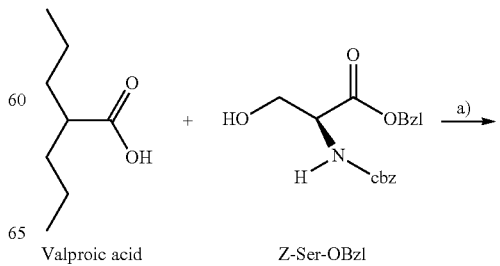

Valproic acid      Z-Ser-OBzl

-continued

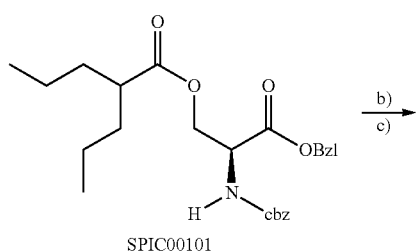

SPIC00101

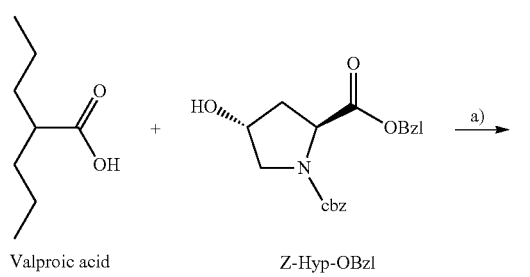

SPIC001

2. SPIC002

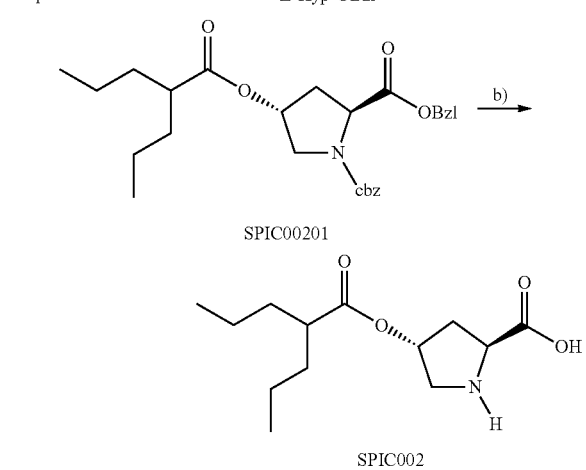

3. SPIC003

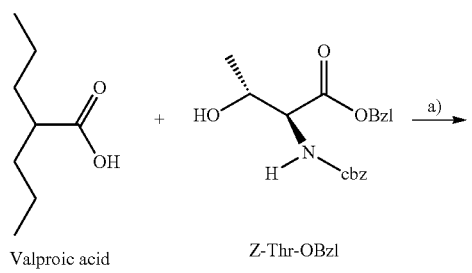

-continued

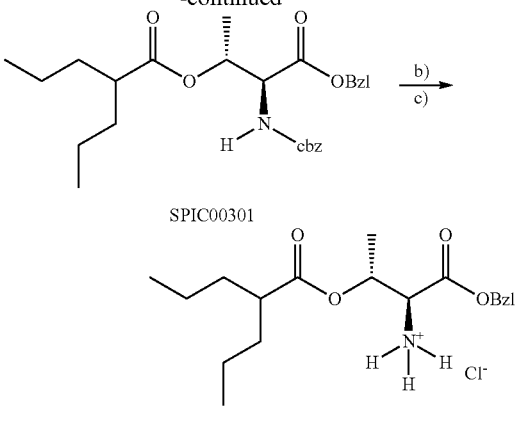

Synthesis of the L-serine, L-threonine, and L-hydroxyproline Esters of Valproic Acid: a) EDC, DMAP, $CH_2Cl_2$; b) $H_2$, 10% Pd/C, EtOAc; c) HCl.

Experimental Section:

The synthesis of SPIC001, SPIC002 and SPIC003 were conducted in one or two batches. Reagents mentioned in the experimental section were purchased at the highest obtainable purity from Lancaster, Sigma-Aldrich, Acros, or Bachem, except for solvents, which were purchased from either Fisher Scientific or Mallinkrodt.

1) SPIC001: 2-Propylpentanoic Acid 2(S)-amino-2-carboxyethyl ester, Hydrochloride L-Serine-valproic Acid Ester Hydrochloride A mixture of 2-propylpentanoic acid (valproic acid, 6.48 g, 44.93 mmole), N-carbobenzyloxy-L-serine benzyl ester (Z-Ser-OBzl, 14.80 g, 44.93 mmole), EDC (8.61 g, 44.91 mmole), and DMAP (549 mg, 4.49 mmole) in anhydrous dichloromethane (50 mL) was stirred under an argon atmosphere at room temperature for 20 hours. After 20 hours, the dichloromethane was washed with water (3×50 mL), dried over magnesium sulfate (5 g), filtered and concentrated under reduced pressure. The remaining colorless oil (20.87 g) was purified by column chromatography on silica gel (150 g, 0.035-0.070 mm, 6 nm pore diameter), eluting with hexanes/ethyl acetate (3:1). After concentration of the product containing fractions under reduced pressure and drying under high vacuum until the weight was constant, the experiment produced the protected L-serine-valproate ester SPIC00101 (18.9 g, 92% yield) as a colorless oil.

SPIC00101

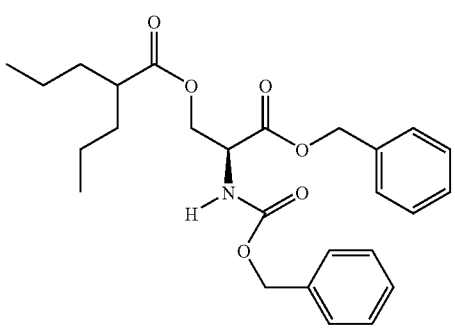

¹H NMR (300 MHz, DMSO): δ=7.96 (1H, d, J=8.1 Hz), 7.35 (10H, m), 5.14 (2H, s), 5.05 (2H, s), 4.51 (1H, m), 4.29 (2H, m), 2.29 (1H, m), 1.50-1.25 (4H, m), 1.25-1.10 (4H, m), 0.80 (6H, t, J=6.6 Hz).

¹³C NMR (75 MHz, DMSO): δ=174.88, 169.15, 155.85, 136.58, 135.45, 128.26, 128.18, 127.47, 127.71, 127.57, 66.32, 65.66, 62.47, 53.09, 44.20, 33.86, 33.79, 19.95, 13.85.

The protected L-serine-valproate ester SPIC00101 (18.9 g, 41.48 mmole) was dissolved in ethanol (60 mL) and ethyl acetate (60 mL) at room temperature and added to a Parr bottle (500 mL) that contained 10% palladium on carbon (3.0 g, 50% wet) under a nitrogen atmosphere. The nitrogen atmosphere was replaced with hydrogen gas (30 psi). After 4 hours of shaking, additional palladium catalyst (1.0 g) in ethanol\ethyl acetate (1:1, 100 mL) was added and the reaction mixture shook overnight under hydrogen gas (30 psi) at room temperature. After 24 hours the catalyst was removed by filtration through a thin layer of activated carbon. The ethanol and ethyl acetate were concentrated under reduced pressure at room temperature. After drying under high vacuum, the remaining solids were acidified with hydrochloric acid in diethyl ether (2M, 24.6 mL). The mixture was stored in a refrigerator for two hours before filtration and washing with additional cold diethyl ether (10 mL). After filtration, the remaining white solid was dried at room temperature under high vacuum until the product weight was constant (24 hours). The experiment produced L-serine-valproic acid ester, hydrochloride SPIC001 (6.34 g, 57% yield) as a white solid.

SPIC001

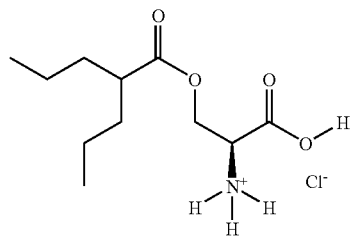

¹H NMR (300 MHz, DMSO): δ=8.73 (br s, 3H), 4.47 (dd, 1H, J=12.9, 4.5 Hz), 4.31 (dd, 2H, J=12.9, 3.6 Hz), 2.36 (m, 1H), 1.50 (m, 2H), 1.39 (m, 2H), 1.20 (m, 4H), 0.84 (t, 6H, J=7 Hz).

¹³C NMR (75 MHz, DMSO): δ=174.67, 168.19, 61.84, 51.16, 44.12, 33.76, 33.58, 20.07, 19.92, 13.97, 13.89.

HPLC Analysis:
98.49% purity; rt=4.767 min; Luna C18 5 u column (sn 167917-13); 4.6×250 mm; 254 nm; 33% ACN/66% DIUF water; 35 C; 20 ul inj.; 1 ml/min; 20 mg/mL sample size; sample dissolved in mobile phase.

CHN Analysis:
calc.: C, 49.34; H, 8.28; N, 5.23. found: C, 49.22; H, 8.35; N, 5.24.

Melting point: 159-160° C.

2) SPIC002: 4(R)-(2-Propyl-pentanoyloxy)-pyrrolidine-2 (S)-carboxylic Acid
(L-Hydroxyproline-valproic Acid Ester)

A mixture of 2-propylpentanoic acid (valproic acid, 4.32 g, 30 mmole), N-carbobenzyloxy-L-hydroxyproline benzyl ester (Z-Hyp-OBzl, 10.66 g, 30 mmole), EDC (5.74 g, 30 mmole), and DMAP (366 mg, 3 mmole) in anhydrous dichloromethane (30 mL) was stirred under an argon atmosphere at room temperature for 20 hours. After 20 hours, the dichloromethane was washed with water (3×30 mL), dried over magnesium sulfate (5 g), filtered and concentrated under reduced pressure. The remaining colorless oil SPIC00201 (11.95 g, 24.7 mmole, 82.4% yield) was used without purification.

SPIC00201

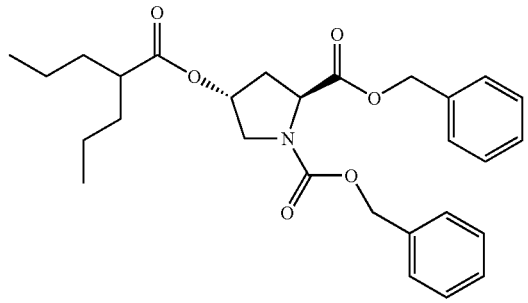

¹H NMR (300 MHz, CDCl₃): δ=7.29 (10H, m), 5.28-5.00 (5H, m), 4.55 (½H, t, J=8 Hz), 4.46 (½H, t, J=8 Hz), 3.80-3.60 (2H, m), 2.43-2.16 (3H, m), 1.60-1.45 (2H, m), 1.40-1.32 (2H, m), 1.28-1.20 (4H, m), 0.86 (6H, m).

¹³C NMR (75 MHz, DMSO): δ=174.74, 171.40, 171.05, 153.79, 153.31, 136.34, 136.20, 135.57, 135.38, 128.24, 128.13, 127.95, 127.87, 127.67, 127.52, 127.28, 127.10, 72.29, 71.53, 66.34, 66.10, 57.66, 57.19, 52.27, 51.89, 44.13, 40.33, 35.78, 34.79, 34.04, 33.92, 33.35, 20.00, 19.91, 13.79, 13.73.

The protected L-hydroxyproline-valproate ester SPIC00201 (17.24 g, 35.79 mmole) was dissolved in ethanol (50 mL) and ethyl acetate (100 mL) at room temperature and added to a Parr bottle (500 mL) that contained 10% palladium on carbon (3.5 g, 50% wet) under a nitrogen atmosphere. The nitrogen atmosphere was replaced with hydrogen gas (30 psi). After 15 hours of shaking, the catalyst was removed by filtration through a thin layer of celite and activated carbon. The ethanol and ethyl acetate mixture was concentrated under reduced pressure at room temperature. After drying overnight under high vacuum at room temperature, the experiment produced L-hydroxyproline-valproic acid ester SPIC002 (9.2 g, 99.8% yield) as a white solid. In order to remove trace impurities, the zwitterion was purified by reverse-phase column chromatography (50 g ODS silica gel) in two batches. The zwitterion was placed on the column in DIUF water and eluted with mixture of DIUF water/methanol (2:1, 1:1, 1:2, 100% methanol).

The product containing fractions were combined, concentrated under reduced pressure at 20° C. (or less), and dried under high vacuum at room temperature until the weight was constant (24 hours, 6.4 g white solid recovered).

SPIC002

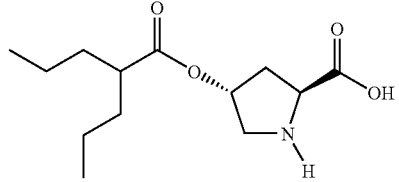

¹H NMR (300 MHz, CDCl₃): δ=12.40 (br s, 1H), 8.32 (br s, 1H), 5.28 (m, 1H), 4.11 (t, 1H, J=7.2 Hz), 3.59 (m, 1H), 3.34 (br d, 1H, J=10.5 Hz), 2.50-2.22 (m, 3H), 1.62-1.50 (m, 2H), 1.50-1.32 (m, 2H), 1.32-1.19 (m, 4H), 0.88 (t, 6H, J=7.2 Hz).

$^{13}$C NMR (75 MHz, CDCl$_3$): δ=175.99, 173.35, 71.83, 59.56, 49.77, 45.08, 36.19, 34.51, 20.87, 14.31.

HPLC Analysis:

99.20% purity; r.t.=7.228 min.; 70% DIUF water/30% acetonitrile; 1 mL/min; 36.8 C; Luna C18, 5 u column (serial #167917-13), 4.6×250 mm; 22 ul injection; sample dissolved in mobile phase.

CHN Analysis:

calc.: C, 60.68; H, 9.01; N, 5.44. found: C, 60.58; H, 9.12; N, 5.48.

Melting point: 179.0-180.0° C.

3) SPIC003: 2-Propyl-pentanoic Acid 2(S)-amino-2-carboxy-1(R)-methyl-ethyl Ester, Hydrochloride L-Threonine-valproic Acid Ester, Hydrochloride A mixture of 2-propylpentanoic acid (valproic acid, 4.32 g, 30 mmole), N-carbobenzyloxy-L-threonine benzyl ester (Z-Thr-OBzl, 10.30 g, 30 mmole), EDC (5.74 g, 30 mmole), and DMAP (366 mg, 3.0 mmole) in anhydrous dichloromethane (30 mL) was stirred under an argon atmosphere at room temperature for 20 hours. After 20 hours, the dichloromethane was washed with water (3×30 mL), dried over magnesium sulfate (5 g), filtered and concentrated under reduced pressure. The remaining colorless oil (13.44 g) was purified by column chromatography on silica gel (100 g, 0.035-0.070 mm, 6 nm pore diameter), eluting with hexanes/ethyl acetate (4:1).

After concentration of the product containing fractions under reduced pressure and drying under high vacuum until the weight was constant, the experiment produced the protected L-threonine-valproate ester SPIC00301 (12.65 g, 89.8% yield) as a colorless oil.

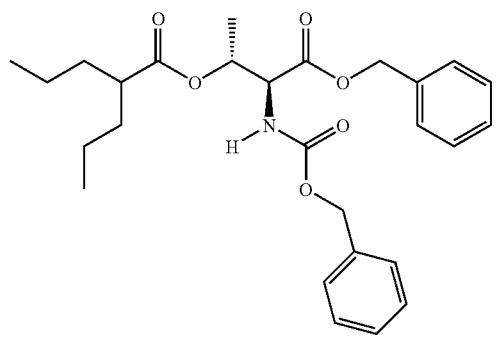

SPIC00301

$^1$H NMR (300 MHz, CDCl$_3$): δ=7.40-7.05 (11H, m), 5.45 (1H, m), 5.17-5.02 (4H, m), 4.53 (1H, d, J=9.6 Hz), 2.24 (1H, m), 1.58-1.40 (2H, m), 1.40-1.15 (9H, m), 0.86 (6H, m).

$^{13}$C NMR (75 MHz, DMSO): δ=174.24, 169.29, 156.48, 136.61, 135.34, 128.26, 128.20, 127.74, 127.67, 127.58, 69.04, 66.33, 65.78, 57.62, 44.50, 33.89, 33.80, 20.03, 19.91, 16.40, 13.87.

The protected L-threonine-valproate ester SPIC00301 (12.65 g, 26.9 mmole) was dissolved in ethanol (50 mL) and ethyl acetate (50 mL) at room temperature and added to a Parr bottle (500 mL) that contained 10% palladium on carbon (2.53 g, 50% wet) under a nitrogen atmosphere. The nitrogen atmosphere was replaced with hydrogen gas (30 psi). After 20 hours the catalyst was removed by filtration through a thin layer of activated carbon, washing with ethanol (25 mL). The ethanol and ethyl acetate were concentrated under reduced pressure at room temperature. After drying under high vacuum, the remaining solids (6.13 g) were acidified with hydrochloric acid (3.1 mL conc.) in DIUF water (50 mL). The solution was filtered a second time through activated carbon and dried overnight in a freeze-dryer. The experiment produced L-threonine-valproic acid ester, hydrochloride SPIC003 (6.52 g, 86.0% yield) as a white solid.

The combined batches of the L-threonine-valproic acid ester, hydrochloride SPIC003 (8.8 g) were purified by crystallization form acetonitrile. After the salt was dissolved in hot acetonitrile (225 mL), the material was treated activated acrbon, filtered, and placed in a 5° C. refrigerator overnight. The white solids were filtered after 18 hours, washed with cold acetonitrile (10 mL), and dried under high vacuum at room temperature until the product weight was constant (24 hours). The process recovered L-threonine-valproic acid ester, hydrochloride SPIC003 (6.82 g, 77.5% recovery) as a white solid.

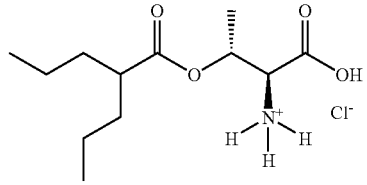

SPIC003

$^1$H NMR (300 MHz, DMSO): δ=8.71 (br s, 3H), 5.28 (m, 1H), 4.16 (d, 1H, J=2.7 Hz), 2.33 (m, 1H), 1.56-1.40 (m, 2H), 1.37-1.27 (m, 5H), 1.21-1.13 (m, 4H), 0.84 (t, 6H, J=6.6 Hz).

$^{13}$C NMR (75 MHz, DMSO): δ=173.97, 168.19, 67.69, 55.42, 44.43, 33.95, 33.78, 20.07, 19.95, 16.54, 13.94.

HPLC Analysis:

98.88% purity; r.t.=4.864 min.; 70% DIUF water/30% acetonitrile; 1 mL/min; 40 C; Luna C18, 5 u column (serial #211739-42), 4.6×250 mm; 20 ul injection; sample dissolved in mobile phase.

CHN Analysis:

calc.: C, 51.15; H, 8.59; N, 4.97. found: C, 51.29; H, 8.59; N, 4.98.

Melting point: 144° C.

The procedure for the synthesis of the L-serine, L-serine(O-nitroxy ester), L-hydroxyproline, and L-tyrosine conjugates of valproic acid (2-propylpentanoic acid) is outlined in Synthetic Sequence section. The complete procedure and analytical data is given in the Experimental Section. In general, valproic acid (2-8 g, in batches) was coupled with the corresponding protected amino acids. The protected intermediates were purified by column chromatography and the protective groups were removed. The final amides were purified by crystallization from ether. A portion of the L-serine amide was nitrated at low temperature with slight excess of a standard nitrating solution to form the nitroxy ester, which could be separated from starting material by crystallization from toluene. The final products were dried to a constant weight before analysis by NMR, HPLC, melting point, and CHN analysis.

Synthetic Sequence:

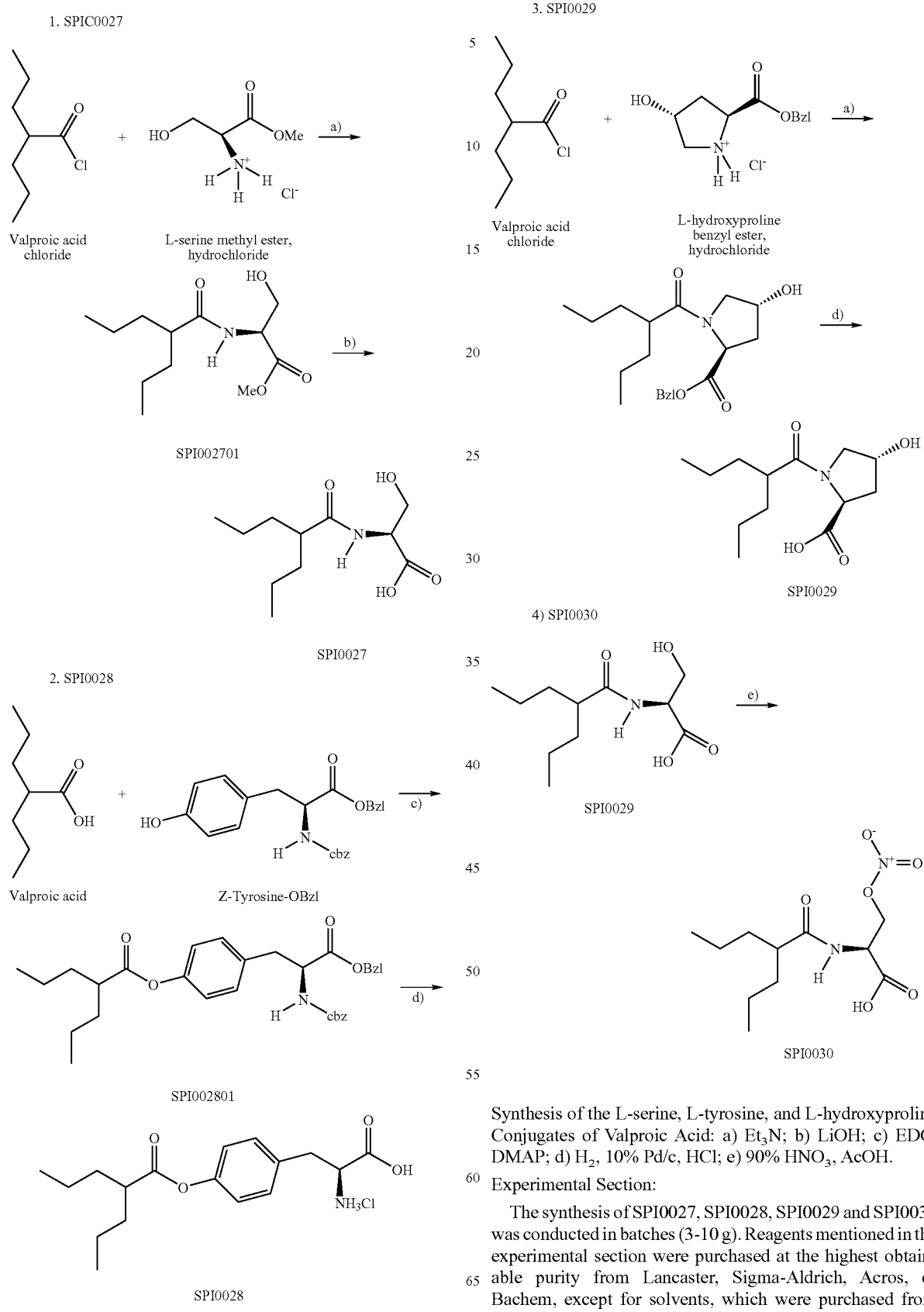

Synthesis of the L-serine, L-tyrosine, and L-hydroxyproline Conjugates of Valproic Acid: a) Et$_3$N; b) LiOH; c) EDC, DMAP; d) H$_2$, 10% Pd/c, HCl; e) 90% HNO$_3$, AcOH.

Experimental Section:

The synthesis of SPI0027, SPI0028, SPI0029 and SPI0030 was conducted in batches (3-10 g). Reagents mentioned in the experimental section were purchased at the highest obtainable purity from Lancaster, Sigma-Aldrich, Acros, or Bachem, except for solvents, which were purchased from either Fisher Scientific or Mallinkrodt.

1) SPI0027: Hydroxy-(2(S)-propyl-pentanoylamino)-acetic acid (L-serine-valproic acid amide)

A) Preparation of SPI002701 (Protected Intermediate):

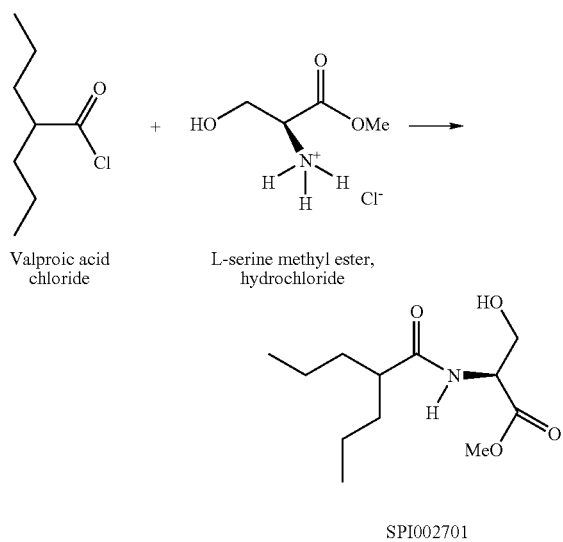

A mixture of 2-propylpentanoic acid (valproic acid 16.0 g, 0.11 mole) and thionyl chloride (30 mL) were stirred at room temperature for 4 hours. After 4 hours, the solution was concentrated under reduced pressure to prepare the acid chloride of valproic acid (17.8 g, 98.8% yield). A portion of the remaining colorless oil (11.0 g) was added drop-wise to an ice-cold mixture of L-serine methyl ester, hydrochloride (10.60 g, 0.068 mole) and triethylamine (30 mL) in anhydrous dichloromethane (100 mL). After the addition, the mixture stirred for 2 hours under an argon atmosphere, while cooling with an ice/water batch. The ice bath was removed and the mixture stirred for 2 hours at room temperature. The solvent and excess triethylamine were removed under reduced pressure and a fresh aliquot of dichloromethane (100 mL) was added. The mixture was then extracted with water (50 mL), 5% hydrochloric acid (2×50 mL), saturated sodium bicarbonate solution (2×50 mL), and DIUF water (50 mL). The remaining dichloromethane solution was dried over sodium sulfate (10 g), filtered, and concentrated under reduced pressure. The remaining light yellow solid (17.22 g) was purified by column chromatography on silica gel (350 g, 0.035-0.070 mm, 6 nm pore diameter), eluting with hexanes/ethyl acetate (1:2). After concentration of the product containing fractions under reduced pressure and drying under high vacuum until the weight was constant, the experiment produced the methyl ester protected L-serine-valproate amide SPI002701 (9.45 g, 57% yield) as a white solid.

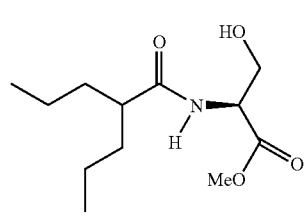

SPI002701

$^1$H NMR (300 MHz, CDCl$_3$): δ=6.55 (1H, d, J=7.2 Hz), 4.70 (1H, m), 4.0-3.89 (2H, m), 3.78 (3H, s), 3.16 (1H, m), 2.17 (1H, m), 1.61 (2H, m), 1.46-1.23 (6H, m), 0.90 (6H, t, J=7.2 Hz).
$^{13}$C NMR (75 MHz, CDCl$_3$): δ=176.81, 171.08, 63.78, 54.67, 52.90, 47.61, 35.37, 21.01, 20.91, 14.38.

B) Deprotection of SPI002701:

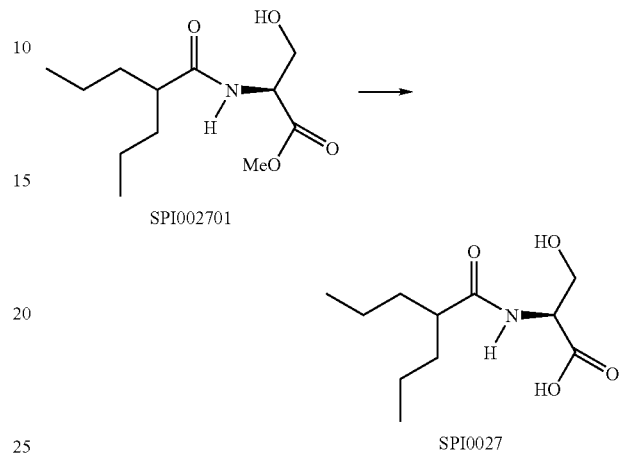

The protected methyl ester protected L-serine-valproate amide SPI002701 (9.40 g, 38.3 mmol) was dissolved in THF (100 mL) and water (50 mL) containing lithium hydroxide (1.40 g, 58.4 mmol) that was cooled in an ice-water batch. After stirring for 3 hours while cooling in ice, 10% hydrochloric acid (50 mL) and the product was extracted with dichloromethane (2×100 mL). The dichloromethane fractions were combined, dried over sodium sulfate (10 g), filtered and concentrated under reduced pressure. The crude product (9.6 g, light yellow solid) was dissolved in diethyl ether (40 mL) and stored overnight at −10° C. After filtration, the remaining white solid was dried at room temperature under high vacuum until the product weight was constant (24 hours). The experiment produced L-serine-valproic amide SPI0027 (5.62 g, 63% yield) as a white solid.

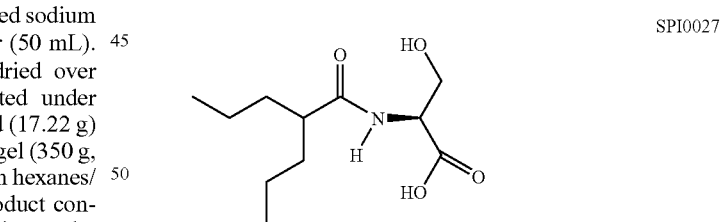

SPI0027

$^1$H NMR (300 MHz, DMSO): δ=12.3 (br s, 1H), 7.91 (d, 1H, J=7.5 Hz), 4.90 (br s, 1H), 4.28 (m, 1H), 3.63 (m, 2H), 2.82 (m, 1H), 1.42 (m, 2H), 1.21 (m, 6H), 0.82 (t, 6H, J=7 Hz).
$^{13}$C NMR (75 MHz, DMSO): δ=174.92, 171.95, 61.51, 54.42, 44.85, 35.03, 34.88, 20.18, 20.03, 14.18, 14.13.

HPLC Analysis:
100% purity; r.t.=4.867 min.; 35% DIUF water (0.1% TFA)/65% methanol; 1 mL/min; 39.8 C; Synergi Polar-RP 5 u column (serial #234257), 4.6×250 mm; 20 ul injection; DAD1 A, Sig=210.4, Ref=550,100.

CHN Analysis:
calc. (C10H19NO4): C, 57.12; H, 9.15; N, 6.06. found: C, 57.34; H, 9.22; N, 5.89.

Melting point: 65-67° C.

2) SPI0028: 2-Propyl-pentanoic acid 4-(2(S)-amino-2-carboxy-ethyl)-phenyl ester, hydrochloride, (L-Tyrosine-valproic acid ester, hydrochloride)

A) Preparation of SPI002801 (Protected Intermediate):

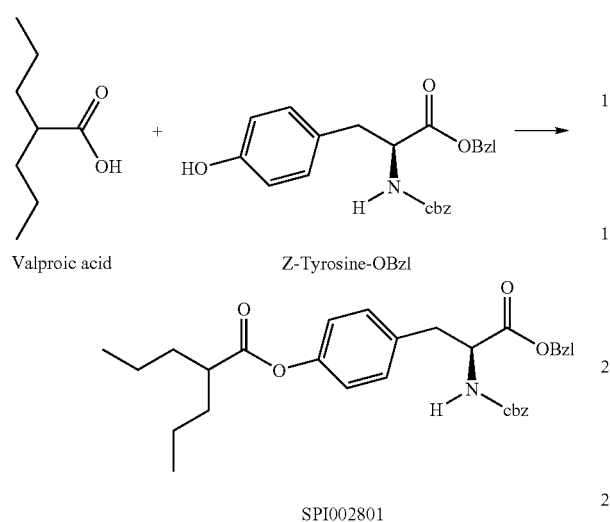

A mixture of 2-propylpentanoic acid (valproic acid, 2.66 g, 18.4 mmole), N-carbobenzyloxy-L-tyrosine benzyl ester (5.0 g, 12.3 mmole), EDC (3.54 g, 18.4 mmole), and DMAP (150 mg, 1.23 mmole) in anhydrous dichloromethane (25 mL) was stirred under an argon atmosphere at room temperature for 2 hours. After 2 hours, the dichloromethane solution was washed with water (2×25 mL), 5% hydrochloric acid (2×25 mL), 5% sodium bicarbonate (2×25 mL), and DIUF water (25 mL). The dichloromethane was dried over magnesium sulfate (5 g), filtered and concentrated under reduced pressure. The remaining white solid (8.14 g) was purified by column chromatography on silica gel (120 g), eluting with 3:1 heptane/ethyl acetate. The product containing fractions were combined, washed with additional saturated sodium bicarbonate (100 mL, to remove valproic acid), and dried over sodium sulfate (10 g). After concentration and drying to a constant weight, the experiment generated the protected intermediate SPI002801 (6.5 g, 99% yield) as a white solid.

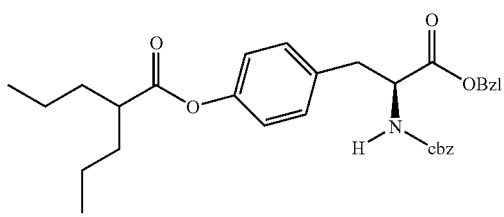

SPI002801

$^1$H NMR (300 MHz, CDCl$_3$): δ=7.33 (10H, m), 6.98 (2H, d, J=8.4 Hz), 6.89 (2H, d, J=8.4 Hz), 5.26-5.09 (4H, m), 4.68 (1H, dd, J=13.5, 6.6 Hz), 3.09 (2H, m), 2.59 (1H, m), 1.80-1.36 (8H, m), 0.96 (6H, t, J=7.2 Hz).

$^{13}$C NMR (75 MHz, CDCl$_3$): δ=174.86, 171.24, 155.64, 149.90, 135.06, 133.01, 130.34, 128.71, 128.59, 128.24, 128.18, 121.76, 67.50, 67.18, 54.99, 45.58, 45.22, 37.76, 34.92, 34.63, 20.97, 20.83, 14.33.

B) Deprotection of SPI002801:

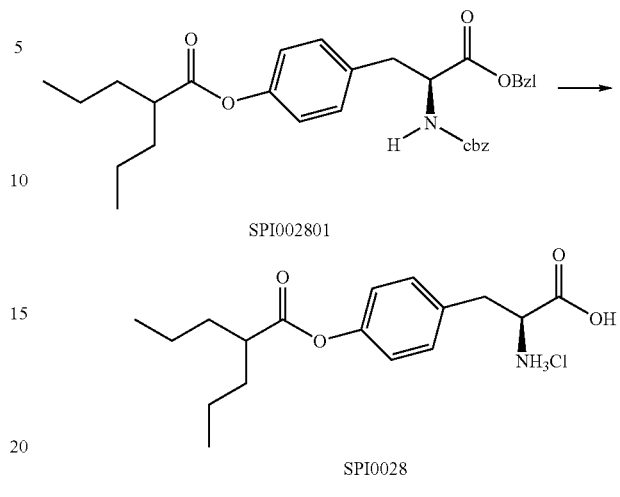

The protected L-tyrosine-valproate ester SPI002801 (6.5 g) was dissolved in ethyl acetate (100 mL) at room temperature and added to a Parr bottle (500 mL) that contained 10% palladium on carbon (2.25 g, 50% wet) under a nitrogen atmosphere. The nitrogen atmosphere was replaced with hydrogen gas (32 psi). After 5 hours of shaking, the ethyl acetate was acidified with 2N hydrogen chloride in diethyl ether (20 mL) and the catalyst was removed by filtration through a thin layer of celite 521 (20 g). The ethyl acetate mixture was concentrated under reduced pressure at room temperature. After drying for 2 hours under high vacuum at room temperature, The remaining solid (5.4 g) was stirred in diethyl ether (100 mL) overnight under an argon atmosphere. After filtration and drying to a constant weight under high vacuum, the experiment produced L-tyrosine-valproic acid ester SPI0028 (3.50 g, 72% yield) as a white solid.

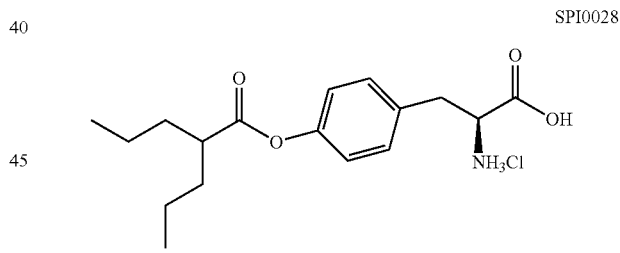

SPI0028

$^1$H NMR (300 MHz, DMSO): δ=8.63 (br s, 3H), 7.34 (d, 2H, J=8.4 Hz), 7.02 (d, 2H, J=8.4 Hz), 4.11 (br t, 1H), 3.18 (d, 2H, J=4.8 Hz), 2.57 (m, 1H), 1.66-1.45 (m, 4H), 1.45-1.29 (m, 4H), 0.91 (t, 6H, J=7.5 Hz).

$^{13}$C NMR (75 MHz, DMSO): δ=174.02, 169.99, 149.36, 132.52, 130.62, 121.55, 53.16, 44.47, 34.95, 34.15, 20.19, 13.97.

HPLC Analysis:
99.75% purity; r.t.=7.433 min.; 60% DIUF water (0.1% TFA)/40% acetonitrile; 1 mL/min; 39 C; Luna C18, 5 u column (serial #191070-3), 4.6×250 mm; 20 ul injection; DAD1 A, Sig=210, Ref=550,100.

CHN Analysis:
calc. (C17H26ClNO4): C, 59.38; H, 7.62; N, 4.07. found: C, 59.46; H, 7.58; N, 4.14.

Melting point: 192.0-194.0° C.

3) SPI0029: 4(R)-Hydroxy-1-(2-propyl-pentanoyl)-pyrrolidine-2(S)-carboxylic acid (Valproic-L-hydroxyproline amide)

A) Preparation of SPI002901 (Protected Intermediate):

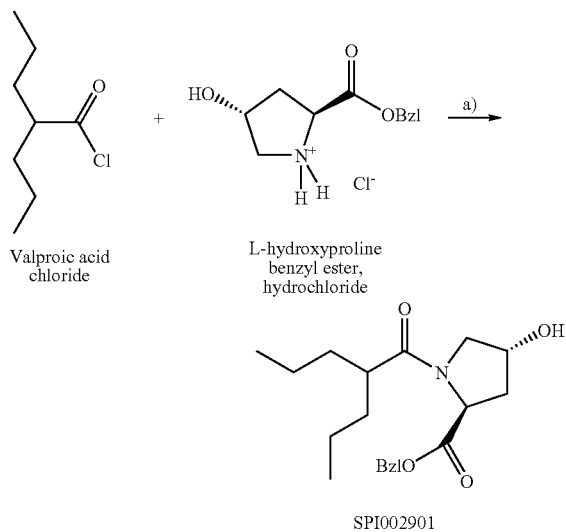

A mixture of 2-propylpentanoic acid (valproic acid 2.95 g, 0.02 mole) and thionyl chloride (8 mL) were stirred at room temperature for 4 hours. After 4 hours, the solution was concentrated under reduced pressure. The remaining colorless oil was added drop-wise to an ice-cold mixture of L-hydroxyproline benzyl ester, hydrochloride (Bachem, 6.2 g) and triethylamine (10 mL) in anhydrous dichloromethane (50 mL). After the addition, the mixture stirred for 2 hours under an argon atmosphere, while cooling with an ice/water batch. The ice bath was removed and the mixture stirred for 4 hours at room temperature. The solvent and excess triethylamine were removed under reduced pressure and a fresh aliquot of dichloromethane (100 mL) was added. The mixture was then extracted with water (50 mL), 5% hydrochloric acid (2×50 mL), saturated sodium bicarbonate solution (2×50 mL), and DIUF water (50 mL). The remaining dichloromethane solution was dried over sodium sulfate (10 g), filtered, and concentrated under reduced pressure. The remaining crude product (6.2 g) was purified by column chromatography on silica gel (110 g, 0.035-0.070 mm, 6 nm pore diameter), eluting with hexanes/ethyl acetate (1:1). After concentration of the product containing fractions under reduced pressure and drying under high vacuum until the weight was constant, the experiment produced the protected L-hydroxyproline-valproate amide SPI002901 (5.70 g, 80% yield) as a colorless oil.

SPI002901

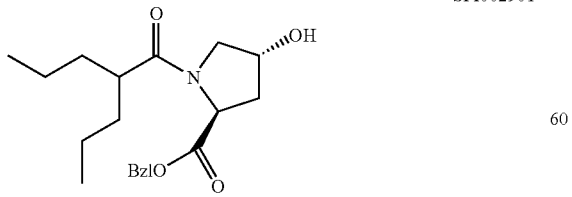

$^1$H NMR (300 MHz, CDCl$_3$): δ=7.37-7.27 (5H, m), 5.14 (2H, d, J=12.6 Hz), 4.63 (1H, t, J=7.8 Hz), 4.52 (1H, m), 3.76 (1H, dd, J=10.4, 4.2 Hz), 3.58 (1H, dd, J=10.4, 1.5 Hz), 2.47 (1H, m), 2.25 (1H, m), 2.04 (1H, m), 1.64-1.55 (2H, m), 1.43-1.19 (6H, m), 0.8 (6H, m).

$^{13}$C NMR (75 MHz, CDCl$_3$): δ=175.96, 172.21, 135.67, 128.56, 128.23, 70.15, 67.00, 58.02, 55.33, 43.56, 37.76, 35.44, 35.08, 21.02, 20.71, 14.51.

The protected L-hydroxyproline-valproate ester SPI002901 (9.3 g, 26.7 mmole) was dissolved in ethyl acetate (25 mL) at room temperature and added to a Parr bottle (500 mL) that contained 10% palladium on carbon (1.53 g, 50% wet) under a nitrogen atmosphere. The nitrogen atmosphere was replaced with hydrogen gas (35 psi). After 20 hours the catalyst was removed by filtration through a thin layer of activated carbon, washing with ethanol (25 mL). The ethanol and ethyl acetate were concentrated under reduced pressure at room temperature. After drying under high vacuum, the remaining solid (6.54 g) was crystallized from t-butyl methyl ether (100 mL, 48 hours at −10° C.). After filtration and drying to a constant weight, the experiment produced L-hydroxyproline-valproic amide SPI0029 (5.17 g, 83% yield) as a white solid.

$^1$H NMR (300 MHz, DMSO): δ=12.6 (br s, 1H), 5.39 (br s, 1H), 4.69-4.48 (m, 2H), 3.90-3.58 (m, 4H), 2.78 (m, 1H), 2.51-2.32 (m, 2H), 2.22-2.12 (m, 1H), 1.80-1.42 (m, 8H), 1.11 (m, 6H).

$^{13}$C NMR (75 MHz, DMSO): δ=173.80, 173.43, 68.78, 75.42, 55.04, 42.10, 37.29, 35.13, 34.74, 20.17, 19.74, 14.28, 14.24.

HPLC Analysis:

99.89% purity; r.t.=7.20 min.; 70% DIUF water (0.1% TFA)/30% ACN; 1 mL/min; 39.8 C; Synergi Polar-RP 5 u column (serial #161309), 4.6×250 mm; 20 ul injection; DAD1 A, Sig=210.4, Ref=550,100.

Specific Rotation: −56.8 (5 mg/mL in ethanol at 25 C)

CHN Analysis:

calc. (C13H23NO4): C, 60.68; H, 9.01; N, 5.44. found: C, 60.71; H, 9.03; N, 5.45.

Melting point: 113-114° C.

4) SPI0030: 3-Nitroxy-2(S)-(2-propyl-pentanoylamino)-propionic acid (L-serine(O-nitroxy ester)-valproic acid amide)

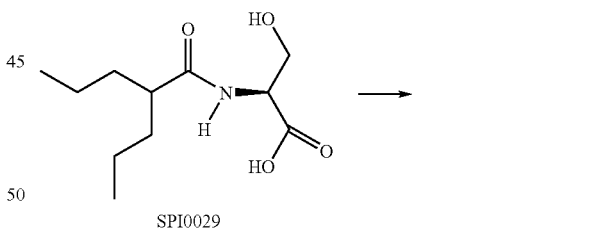

SPI0029

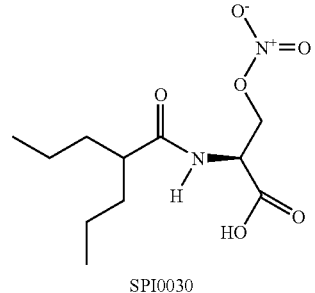

SPI0030

The L-serine valproic amide (SPI0029, 8.4 g, 0.036 mole) was dissolved in glacial acetic acid (60 mL). The flask was cooled in an ice/water bath under an argon atmosphere and cold 90% nitric acid (6.0 mL) was added. After 4 hours at 5° C., the solution was poured into ice (400 g) and extracted with dichloromethane (2×150 mL). The dichloromethane fractions were combined, dried over sodium sulfate (15 g), filtered and concentrated. Toluene (150 mL) was added to the remaining oil and the solution was concentrated a second time to remove acetic acid. After drying under high vacuum to a constant weight, the remaining oil (12.4 g) was dissolved in toluene (50 mL) and stored at −10° C. overnight. After 72 hours at −10° C., the solids were filtered and dried to a constant weight. The experiment produced the nitroxy ester of the L-serine-valproic amide SPI0030 (4.37 g, 43% yield) as a white solid.

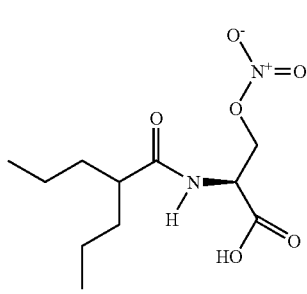

SPI0030

$^1$H NMR (300 MHz, CDCl$_3$): δ=8.88 (br s, 1H), 6.60 (d, 1H, J=7.2 Hz), 5.00 (m, 1H), 4.87 (m, 2H), 2.23 (m, 1H), 1.56 (m, 2H), 1.43 (m, 2H), 1.29 (m, 6H), 0.89 (t, 6H, J=7.2 Hz).
$^{13}$C NMR (75 MHz, CDCl): δ=177.83, 170.88, 71.42, 50.60, 47.47, 35.15, 20.88, 14.28.
HPLC Analysis:
99.25% purity; r.t.=5.400 min.; 65% methanol/35% phosphate buffer (pH=3); 1 mL/min; 36.0 C; Synergi Polar-RP 5 u column (serial #161309-2), 4.6×250 mm; 20 ul injection; Sig=210.4.
Specific Rotation: −19.7 (10.1 mg/mL in ethanol at 25 C)
CHN Analysis:
calc. (C11H20N2O6): C, 47.82; H, 7.30; N, 10.14. found: C, 48.12; H, 7.19; N, 9.84.
Melting point: 49.0-51.0° C.
Solubility of the above esters were determined in water at room temperature by dissolving excess of each of the drug and allowing them to settle for a few hours. The resulting solutions were centrifuged at 1500 rpm for 3 min and the supernatant liquid was analyzed. It was shown that these esters possess solubility in water in excess of 50 mg/mL.
There are a number of screening tests to determine the utility of the derivatives created according to the disclosed methods. These include both in vitro and in vivo screening methods.

The in vitro methods include acid/base hydrolysis of the derivatives, hydrolysis in pig pancreas, hydrolysis in rat intestinal fluid, hydrolysis in human gastric fluid, hydrolysis in human intestinal fluid, and hydrolysis in human blood plasma. These assays are described in Simmons, D M, Chandran, V R and Portmann, G A, Danazol, Amino Acid Derivatives: In Vitro and In Situ Biopharmaceutical Evaluation, Drug Development and Industrial Pharmacy, Vol. 21, Issue 6, Page 687, 1995, the contents of all of which are incorporated by reference.

The amino acid derivatives of Valproic acid of the present invention are effective in treating diseases or conditions in which Valproic acid normally is used. Without wishing to be bound, it is believed that the amino acid derivatives disclosed herein are transformed within the body to release the active compound. Alternatively, the amino acid derivative may not be transformed to release the active component in the body. This latter form enhances the therapeutic benefits of the Valproic acid by reducing or eliminating biopharmaceutical and pharmacokinetic barriers associated with each of them. However it should be noted that these derivatives themselves will have sufficient activity without releasing any active drug in the mammals.

Thus, the amino acid derivative of the present invention enhances the therapeutic benefits by removing biopharmaceutical and pharmacokinetic barriers of existing drugs. Furthermore, the derivatives are easily synthesized in high yields using reagents which are readily and commercially available.
Synthesis of Clopidogrel Derivatives:
Overview:

The procedure for the synthesis of the L-serine and L-threonine esters of clopidogrel is outlined in Synthetic Sequence section. The complete procedure and analytical data are given in the Experimental Section. In general, the hydrosulfate salt of clopidogrel (Xiangding Chemical International Company) was treated with sodium bicarbonate to generate the free amine. The methyl ester was then removed by displacement with lithium iodide in pyridine. The unwanted isomer generated in the reaction was partially removed by crystallization from water. The acid intermediate was then coupled with the tert-butyl ester of boc-L-serine or boc-L-threonine using EDC. The protected intermediate esters were purified twice by column chromatography and treated with dilute hydrochloric acid in acetic acid at low temperature to remove the protective groups. Washing the final salts with ethyl acetate purified the amino acid ester salts of clopidogrel. The final salts were dried under high vacuum and shipped to Signature Pharmaceuticals Inc., after analysis by NMR, HPLC, CHN, specific rotation, and melting point.
Synthetic Sequence:

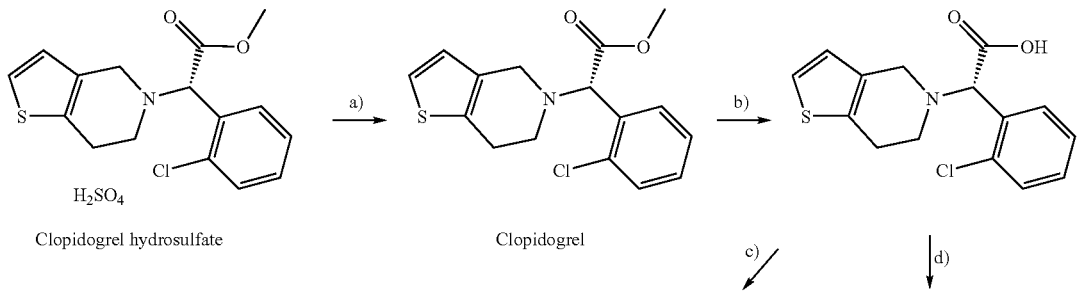

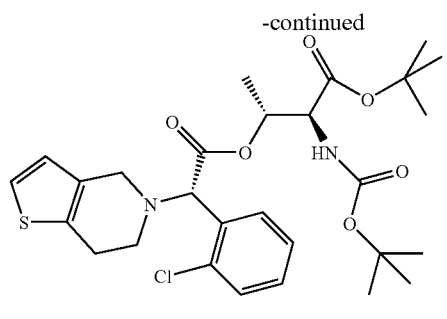

SPIB00301-01

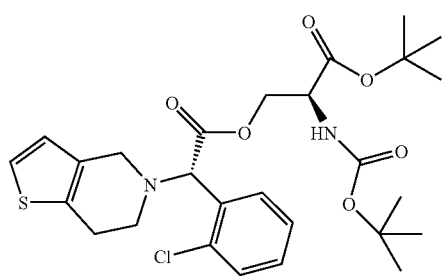

SPIB00302-01 e) ↓ e) ↓

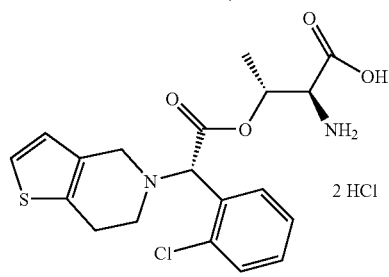

2 HCl

SPIB00301

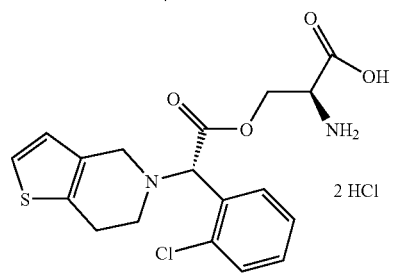

2 HCl

SPIB00302

Synthesis of the L-serine and L-threonine Esters of Clopidogrel: a) NaHCO$_3$; b) LiI, pyridine; c) boc-THR-(OtBu), EDC, DMAP; d) boc-SER-(OtBu), EDC, DMAP; e) 1 M HCl, AcOH.

Experimental Section:

The syntheses of SPIB00301 and SPIB00302 were conducted in batches. Reagents mentioned in the experimental section were purchased at the highest obtainable purity from Lancaster, Sigma-Aldrich, Acros, Bachem, or Xiangding Chemical International, except for solvents, which were purchased from either Fisher Scientific or Mallinkrodt.

1) Preparation of Clopidogrel Acid:

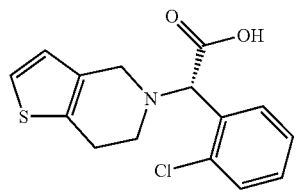

To a solution of clopidogrel hydrosulfate (97.7 g, 233 mmol) in DIUF water (1 L) was added sodium bicarbonate (39.1 g, 466 mmol) in small portions. After mixing, t-butyl methyl ether (1 L) was added and the solution stirred for 30 minutes. The layers were separated and the aqueous layer was extracted a second time with t-butyl methyl ether (300 mL). The organic layers were combined, washed with brine (500 mL), and dried over sodium sulfate. After filtration, the t-butyl methyl ether was removed under reduced pressure. The remaining clopidogrel (yellow oil, 77.82 g, 104% yield) was dried under high vacuum at room temperature for 18 hours until most of the t-butyl methyl ether was removed. The clopidogrel (77.8 g, 242 mmol) was dissolved in pyridine (200 mL) and added to a refluxing solution of anhydrous lithium iodide (120 g, 897 mmol) in pyridine (800 mL). After 8 hours at reflux, the flask was cooled to room temperature and the pyridine was removed under reduced pressure (at 40° C.). The remaining wet solid (470 g) was dissolved in DIUF water (300 mL) and acidified to pH=5.5 with acetic acid (50 mL). The product was then extracted with dichloromethane (3×300 mL). The dichloromethane fractions were combined, dried over sodium sulfate, filtered, concentrated under reduced pressure, and dried under high vacuum. The remaining yellow mixture (161.3 g) was mixed with anhydrous THF (500 mL) for 60 minutes. After 60 minutes, the salts were removed by filtration. The filtrate was concentrated under reduced pressure to leave a brown oil (128.3 g), which was dissolved in DIUF water (3×200 mL) and freeze-dried under high vacuum to remove traces of solvent. The remaining yellow solid (108.5 g) was again added to water (600 mL) and sonicated. The solids were removed by filtration and the filtrate was freeze-dried under high vacuum. The remaining solid (68.7 g) was partitioned between water (400 mL) and t-butyl methyl ether (400 mL), stirred for 24 hours, stored over the weekend at 5° C., and filtered. The layers were separated and the aqueous layer was extracted a second time with t-butyl methyl ether (300 mL). The purified product was then extracted from the aqueous layer with dichloromethane (2×200 mL). The dichloromethane fractions were combined, dried over sodium sulfate, filtered, concentrated and freeze-dried (from 100 mL DIUF water). The procedure generated the acid of clopidogrel (28.5 g) as a yellow solid.

$^1$H NMR (300 MHz, CDCl$_3$): δ 8.02 (1H, s br), 7.88 (1H, d, J=7.5 Hz), 7.37 (1H, d, J=8.1 Hz), 7.22 (1H, t, J=7.5 Hz), 7.13 (2H, m), 6.65 (1H, d, J=4.8 Hz), 5.14 (1H, s), 4.14 (2H, m), 3.37 (1H, m), 3.28 (1H, m), 3.00 (2H, m).

$^{13}$C NMR (75 MHz, CDCl$_3$): δ 169.75, 135.08, 131.71, 131.49, 130.07, 129.98, 129.82, 129.08, 127.44, 125.06, 124.14, 67.23, 50.22, 48.30, 22.62.

Specific rotation: +43.5 deg (23° C., 0.0216 g/2 mL methanol, 589 nm)

2) Preparation of the L-Threonine Ester of Clopidogrel:
Coupling Procedure:

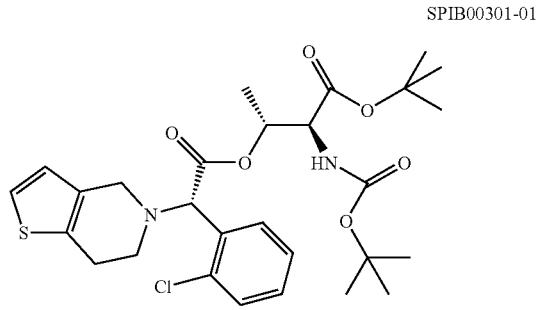
SPIB00301-01

A mixture of the acid of clopidogrel (14.1 g, 45.8 mmol), boc-L-threonine tert-butyl ester (11.4 g, 41.6 mmol, prepared by the literature method), 1-[3-dimethylamino)propyl]-3-ethylcarbodiimide hydrochloride (EDCI, 7.38 g, 38.5 mmol), and DMAP (0.783 g, 6.4 mmol) in anhydrous dichloromethane (300 mL) was stirred at room temperature under an argon atmosphere for 22 hours. Additional dichloromethane (1.2 L) was added and the dichloromethane solution was washed with water (1200 mL) and 5% sodium bicarbonate solution (1200 mL). After drying the dichloromethane solution over sodium sulfate, filtration, and concentration under reduced pressure, the residue (24 g) was purified by column chromatography on silica gel (500 g), eluting with heptane-ethyl acetate (8:1). The product containing fractions were combined and concentrated to provide the protected L-threonine ester of clopidogrel SPIB0030101 (13.5 g, 52% yield), as clear liquid.

$^1$H NMR (300 MHz, CDCl$_3$): δ 7.69 (1H, m), 7.42 (1H, dd, J=7.2, 2.1 Hz), 7.29 (2H, m), 7.06 (1H, d, J=5.1 Hz), 6.65 (1H, d, J=5.1 Hz), 5.47 (1H, m), 5.16 (1H, m), 4.84 (1H, s), 4.30 (1H, d, J=3.6 Hz), 3.65 (2H, m), 2.85 (4H, m), 1.46 (18H, m), 1.15 (3H, d, J=6 Hz).

$^{13}$C NMR (75 MHz, CDCl$_3$): δ 169.46, 168.91, 155.89, 134.63, 133.68, 133.23, 129.96, 129.85, 129.52, 127.27, 125.22, 122.80, 82.61, 80.14, 71.62, 68.16, 57.65, 50.72, 48.51, 28.50, 27.89, 25.65, 16.84.

Deprotection and Purification:

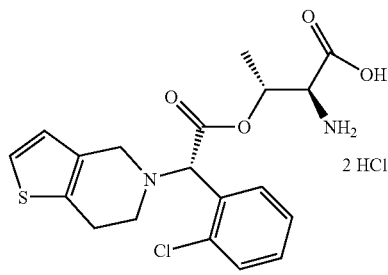
SPIB00301

A solution of hydrogen chloride (1.0 M in acetic acid, 210.6 mL) was added drop-wise to a solution of the protected L-threonine ester of clopidogrel SPIB0030101 (11.9 g, 21.06 mmol) in anhydrous dichloromethane (115 mL) that was cooled in an ice batch, under an argon atmosphere. The mixture was stored for 6.5 days at 5° C. The mixture was concentrated under reduced pressure and dried under high vacuum to generate a light, yellow solid (13.22 g). Ethyl acetate (150 mL) was added to the solid and the mixture was sonicated for 5 minutes. The ethyl acetate was removed by filtration and the remaining solid was added to an additional volume of ethyl acetate (150 mL) and the mixture was sonicated a second time for 5 minutes. After filtration the sonication process was repeated a third time. The white, solid product (10.5 g) was filtered and dissolved in dichloromethane (320 mL). Ethyl acetate (150 mL) was added and the solution was stored at −20° C. overnight. The solids were filtered and the crystallization process was repeated with methanol (1.5 mL)/dichloromethane (180 mL) and ethyl acetate. The solids were filtered and freeze-dried under high vacuum. The procedure generated the clopidogrel-L-threonine ester, dihydrochloride SPIB00301 (6.1 g, 60% yield, 99.51% purity by HPLC) in monohydrate form (as white solid).

$^1$H NMR (300 MHz, DMSO): δ 7.78-7.58 (m, 4H), 7.42 (m, 1H), 6.80 (m, 1H), 5.95 (m, 1H), 5.85 (m, 1H), 4.43 (m, 1H), 4.31-4.17 (m, 3H), 3.84 (m, 2H), 3.33 (m, 2H), 1.33 (d, 3H, J=6 Hz).

$^{13}$C NMR (75 MHz, DMSO): δ 170.56, 167.11, 136.33, 134.39, 132.46, 129.93, 127.46, 126.66, 126.51, 126.01, 73.09, 66.88, 62.91, 57.94, 51.81, 22.93, 16.75.

HPLC Analysis:

99.51% purity, r.t.=10.042 min, sample dissolved in DIUF water/ACN, 75% DIUF water (0.1% TFA)/25% ACN, Hydro-RP (#162383-7), 4 u, 250×4.6 mm, 1 mL/min., 40° C., 20 uL inj. vol., SPD-10 Avp, chl-210 nm.

Melting point: 110-112° C. (Thomas Hoover CMPA, uncorrected)

Specific rotation: +22.5 deg (25° C., 27.7 mg/5 mL ethanol 589 nm)

CHN Analysis:

calc.: C, 45.66; H, 5.04; N, 5.60; Cl, 21.28. (C$_{19}$H$_{25}$Cl$_3$N$_2$O$_5$S). found: C, 44.89; H, 4.96; N, 5.61; Cl, 21.32.

3) Preparation of the L-Serine Ester of Clopidogrel:
Coupling Procedure:

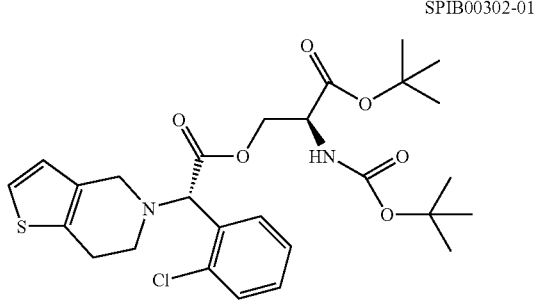

SPIB00302-01

A mixture of the acid of clopidogrel (10.24 g, 33.2 mmol), boc-L-serine tert-butyl ester (7.80 g, 29.8 mmol), 1-[3-dimethylamino)propyl]-3-ethylcarbodiimide hydrochloride (EDCI, 8.94 g, 46.6 mmol), and DMAP (0.25 g) in anhydrous dichloromethane (200 mL) was stirred at room temperature under an argon atmosphere for 4 hours. The dichloromethane solution was washed with water (2×200 mL) and saturated sodium bicarbonate (250 mL). After drying over sodium sulfate, filtration, and concentration under reduced pressure, the remaining yellow oil (18.62 g) was purified twice by column chromatography on silica gel (300 g), on it eluting with heptane-ethyl acetate (9:1). The product containing fractions were combined in two fractions and concentrated. The procedure generated the protected L-serine ester of clopidogrel SPIB0030201 (6.32 g, 34% yield).

$^1$H NMR (300 MHz, CDCl$_3$): δ 7.67 (1H, m), 7.42 (1H, m), 7.29 (2H, m), 7.06 (1H, d, J=5.1 Hz), 6.66 (1H, d, J=5.1 Hz), 4.95 (1H, d, J=7.8 Hz), 4.89 (1H, s), 4.44 (3H, d), 3.72 (1H, d, J=14.4 Hz), 3.60 (1H, d, J=14.4 Hz), 2.87 (4H, m), 1.42 (18H, m).

$^{13}$C NMR (75 MHz, CDCl$_3$): δ 170.16, 168.19, 154.79, 134.48, 133.61, 133.11, 129.81, 129.75, 129.42, 127.13, 125.10, 122.64, 82.72, 79.94, 71.62, 67.77, 64.71, 53.46, 50.66, 48.39, 28.36, 27.97, 25.55.

Deprotection and Purification:

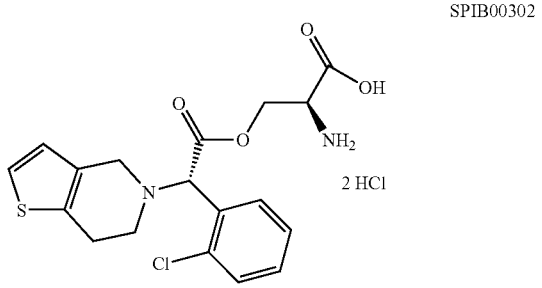

SPIB00302

A solution of hydrogen chloride (1.0 M in acetic acid, 100 mL) was added drop-wise to a solution of the protected L-serine ester of clopidogrel SPIB0030201 (6.30 g, 11.43 mmol) in anhydrous dichloromethane (100 mL) that was cooled in an ice batch, under an argon atmosphere. The mixture was stored for 4 days at 5° C. The mixture was concentrated under reduced pressure and dried under high vacuum to generate a colorless gel. Ethyl acetate (250 mL) was added to the gel and the mixture was sonicated for 5 minutes. The white, solid product was filtered and dried under high vacuum. The white, solid product (6.4 g) was filtered and dissolved in dichloromethane (250 mL). Ethyl acetate (150 mL) was added and the solution was stored at −20° C. overnight. After filtration and freeze-drying, the procedure generated the clopidogrel-L-serine ester, dihydrochloride SPIB00302 (4.8 g, 97% yield, 96.64% purity by HPLC) in monohydrate form (as off-white solid).

$^1$H NMR (300 MHz, DMSO): δ 9.18 (br s, 3H), 8.16 (d, 1H, J=6.6 Hz), 7.66-7.40 (m, 4H), 6.87 (m, 1H), 5.76 (br s, 1H), 4.75 (m, 2H), 4.49 (m, 1H), 4.40-4.0 (m, 1H). 3.40-3.80 (m, 1H), 3.17 (m, 2H).

$^{13}$C NMR (75 MHz, DMSO): δ 167.50, 164.29, 134.23, 132.29, 131.35, 130.93, 130.41, 128.26, 127.81, 126.98, 125.33, 124.73, 66.12, 63.95, 50.82, 50.15, 49.12, 22.13.

HPLC Analysis:

96.64% purity, r.t.=10.56 min, sample dissolved in DIUF water/ACN, 83% DIUF water (0.1% TFA), 17% ACN, Gemini-C18 (#262049-2), 5 u, 250×4.6 mm, 1 mL/min., 40° C., 20 uL inj. vol., SPD-10 Avp, chl-210 nm.

Specific rotation: +42.0 deg (25° C., 34.0 mg/5 mL ethanol 589 nm)

Melting point: 100-102° C. (Thomas Hoover CMPA, uncorrected)

CHN Analysis:

calc.: C, 44.50; H, 4.77; N, 5.77; Cl, 21.89. (C$_{18}$H$_{23}$Cl$_3$N$_2$O$_5$S). found: C, 44.63; H, 4.69; N, 5.76; Cl, 22.20.

Synthesis of Danazol Proline Ester

Overview:

The procedure for the synthesis of the L-proline esters of Danazol is outlined in Synthetic Sequence section. The complete procedure and analytical data is given in the Experimental Section. In general, Danazol (4-7 g, in batches) was coupled with N-tert-butoxycarbonyl-L-proline(1.2-1.6 equivalents) with 1-(3-dimethylaminopropyl)-3-ethylcarbodiimide, hydrochloride (EDC, 1.2-1.4 equivalents) in the presence of catalytic amount of 4-(N,N-dimethylamino)-pyridine (DMAP). Once the reaction was complete, the excess EDC and N-tert-butoxycarbonyl-L-proline were removed by extraction. The crude protected ester of Danazol was purified by column chromatography on silica gel. Unreacted Danazol was collected and reprocessed. The yield for the coupling step was 80-96%. The protective group was removed with 2M hydrogen chloride solution in diethyl ether at low temperature. The hydrochloride salt of the Danazol-L-proline ester was purified as the free base by column chromatography. Once pure, the free base of Danazol-L-proline ester was converted to the hydrochloride salt with diluted hydrogen chloride solution in diethyl ether, at low temperature.

Synthetic Sequence:

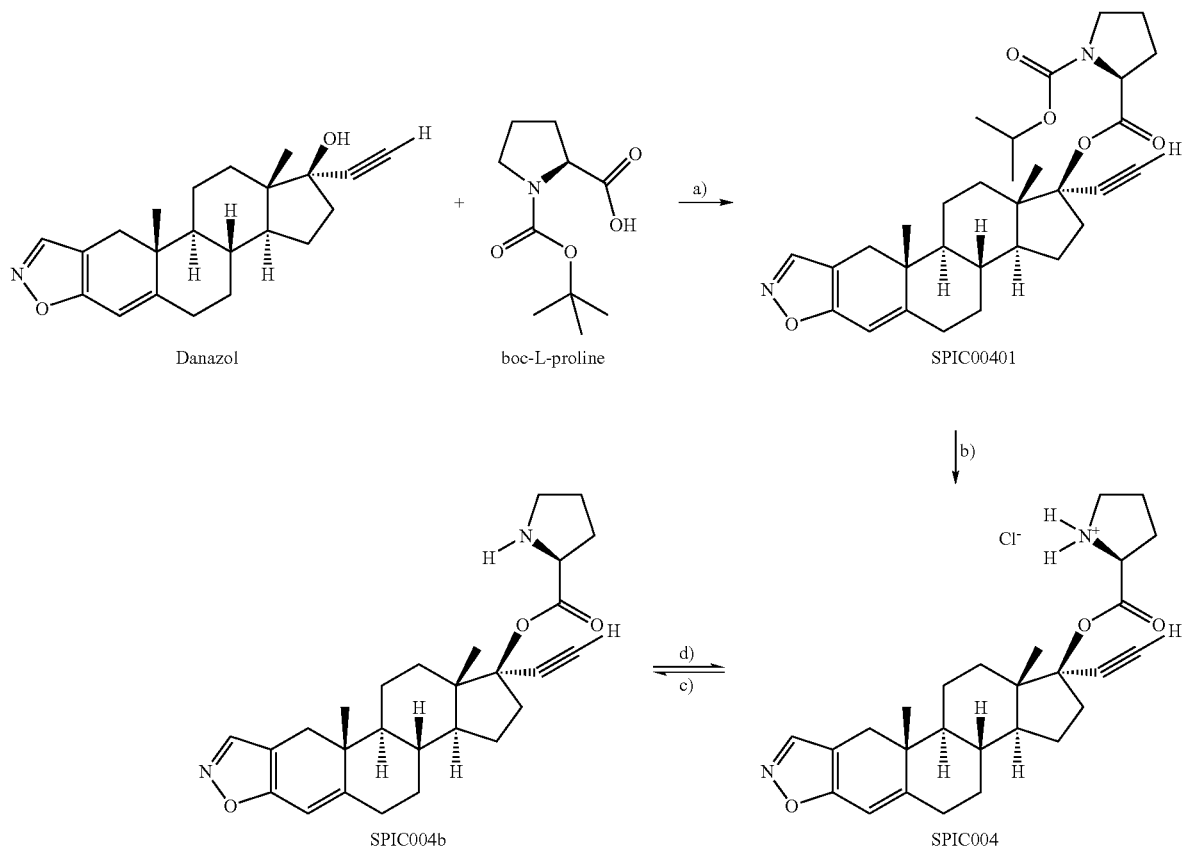

Synthesis of the L-proline Ester of Danazol: a) EDC, DMAP, $CH_2Cl_2$; b) HCl, Diethyl Ether; c) NaHCO3, $CH_2Cl_2$; d) HCl, $CH_2Cl_2$, Diethyl Ether.

Experimental Section:

The synthesis of SPIC004 was conducted in several small batches. A representative batch for each step is described below. Reagents mentioned in the experimental section were purchased at the highest obtainable purity from Spectrum, Fluka, Acros and Sigma-Aldrich.

1) Synthesis of SPC00401: Danazol-N-tert-butoxycarbonyl-L-proline ester

Danazol (7.0 g, 20.74 mmole), N-tert-butoxycarbonyl-L-proline (4.55 g, 21.14 mmole), 1-(3-dimethylaminopropyl)-3-ethylcarbodiimide, hydrochloride (EDC, 4.0 g, 20.86 mmole) and 4-(N,N-dimethylamino)-pyridine (DMAP, 0.27 g, 2.2 mmole) were dissolved in anhydrous dichloromethane (28 ml) while stirring and cooling in an ice-water bath. The ice bath was removed and the mixture was allowed to stir at room temperature for 24 hours. After stirring under an argon atmosphere at room temperature for 24 hours, additional N-tert-butoxycarbonyl-L-proline (0.9 g, 4.18 mmole), EDC (0.8 g, 4.17 mmole) and DMAP (0.06 g, 0.5 mmole) were added to the reaction mixture. After 6 days of stirring under an argon atmosphere at room temperature, additional reagents were added: N-tert-butoxycarbonyl-L-proline (0.9 g, 4.18 mmole), EDC (0.8 g, 4.17 mmole) and DMAP (0.06 g, 0.5 mmole). After 8 days, the reaction mixture was diluted with dichloromethane (40 mL), and extracted with saturated sodium bicarbonate solution (2×100 mL) and DIUF water (3×100 mL). After drying over anhydrous sodium sulfate, the solution was filtered and concentrated under reduced pressure. The light yellow solid foam (12.6 g) that remained was purified by column chromatography on silica gel (450 g, 0.035-0.070 mm, 6 nm pore diameter), eluting with toluene: acetone (9:1). The product containing fractions were combined, concentrated under reduced pressure, and dried under high vacuum until a constant weight was obtained. The experiment produced the protected Danazol-L-proline ester (SPIC00401) as a white, solid foam (7.8 g, 70.3% yield). A second fraction containing a mixture of Danazol and the protected Danazol-L-proline ester (3.7 g) was also recovered. The recovered mixture was reprocessed (as above) to produce an additional amount of SPIC00401 (2.88 g, 26.0%).

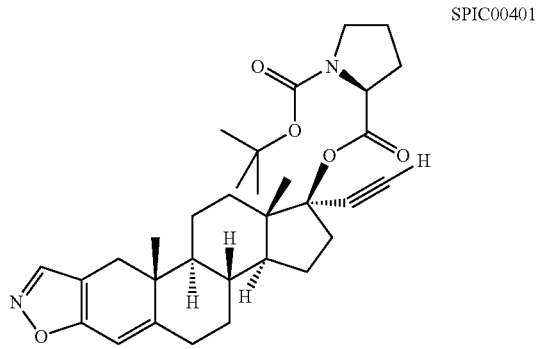

SPIC00401

Pyrrolidine-1,(2S)-dicarboxylic acid 1-tert-butyl ester 2-(1-ethynyl-10a,12a-dimethyl-2,3,3a,3b,4,5, 10,10a,10b,11,12,12a-dodecahydro-1H-7-oxa-8-aza-dicyclopenta[a,h]phenanthren-1-yl)ester $^1$H NMR (300 MHz, CDCl$_3$): δ=8.00 (1H, s), 6.17 (1H, s), 4.32-4.20 (1H, m), 3.58-3.35 (2H, m), 2.84-1.0 (37H, m). (Mixture of conformational isomers)

$^{13}$C NMR (75 MHz, CDCl$_3$): δ=171.52, 171.21, 164.82, 154.27, 154.09, 153.77, 148.68, 108.94, 107.68, 85.06, 84.85, 82.94, 80.07, 79.71, 75.57, 75.15, 59.40, 58.92, 53.87, 48.47, 48.36, 47.69, 46.66, 46.45, 41.18, 37.51, 36.84, 33.54, 33.08, 32.38, 31.07, 30.89, 29.77, 28.69, 28.57, 24.39, 23.95, 23.72, 21.72, 18.97, 13.77. (Mixture of conformational isomers)

2) Synthesis of SPIC004: Danazol-L-proline Ester, Hydrochloride

To a stirred solution of protected Danazol-L-proline ester SPIC00401 (7.8 g, 14.58 mmole) in anhydrous diethyl ether (32 mL) cooled in an ice-water bath, a solution of hydrogen chloride in diethyl ether (73 mL, 2M, 146 mmole) was added drop-wise under an argon atmosphere. After 4 days stirring at room temperature, the mixture was concentrated under reduced pressure and dried under high vacuum. To the remaining yellow solid (6.68 g) was added anhydrous diethyl ether (70 mL). The mixture was stirred at room temperature for 20 hours under an argon atmosphere. Crude Danazol-L-proline ester, hydrochloride SPIC004 (4.6 g, 67.0% yield, HPLC purity 94%) was isolated as a light, yellow solid.

3) Conversion and Purification of SPIC004b: Danazol-L-proline Ester

To a cold solution of Danazol-L-proline ester, hydrochloride SPIC004 (10.45 g, 22.18 mmole) in DIUF water (100 mL) was added dichloromethane (100 mL). Solid sodium bicarbonate (3.72 g, 44.36 mmole) was added in portions. The layers were separated and the aqueous layer was extracted with dichloromethane (2×50 mL). The organic layer was dried over anhydrous sodium sulfate, filtered, and concentrated under reduced pressure. The remaining oil (12.1 g) was purified by column chromatography on silica gel, eluting with 2-propanol. The product containing fractions were combined and concentrated under reduced pressure. The remaining yellow solid foam (8.44 g) was dissolved at room temperature in anhydrous diethyl ether (85 mL) and kept at −10° C. for 24 hours. After filtration of the solid product and drying under high vacuum, Danazol-L-proline ester SPIC004b (5.89 g, 61.0% yield) as a light yellow solid (powder) was isolated.

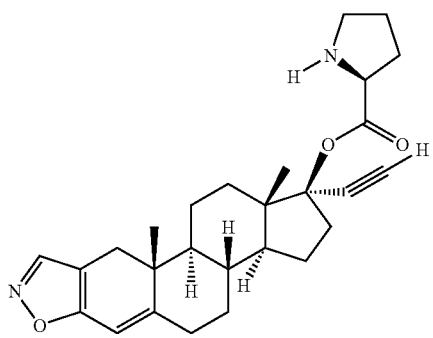

Pyrrolidine-(2S)-carboxylic acid 1-ethynyl-10a, 12a-dimethyl-2,3,3a,3b,4,5,10,10a,10b,11,12,12a-dodecahydro-1H-7-oxa-8-aza-dicyclopenta[a,h] phenanthren-1-yl ester $^1$H NMR (300 MHz, CDCl$_3$): δ=8.00 (1H, s), 6.18 (1H, s), 3.73 (1H, m), 3.10 (1H, m), 2.89 (1H, m), 2.76-2.70 (2H, m), 2.62-2.35 (3H, m), 2.25-1.07 (18H, m), 1.02 (3H, s), 0.91 (3H, s).

$^{13}$C NMR (75 MHz, CDCl$_3$): δ=173.93, 164.83, 154.16, 148.64, 108.91, 107.66, 85.09, 82.97, 75.30, 59.94, 53.85, 48.49, 47.73, 47.17, 41.17, 37.53, 36.85, 33.54, 33.26, 32.37, 30.88, 30.31, 25.63, 23.91, 21.38, 18.98, 13.67.

4) Regeneration of SPIC004: Danazol-L-proline Ester, Hydrochloride

Hydrogen chloride solution (26.8 mL, 1M, 26.8 mmole) was added drop-wise, under an argon atmosphere, to a stirred solution of Danazol-L-proline ester SPIC004b (5.8 g, 13.35 mmole) in anhydrous dichloromethane (30 mL), cooled at −15° C. After stirring for 4 hours in an ice-water bath, the suspension was filtered, the solid dried under high vacuum at room temperature until the weight was constant. The procedure generated the purified Danazol-L-proline ester, hydrochloride SPIC004 as a very light yellow solid (5.62 g, 89.3%, HPLC purity 98.2%).

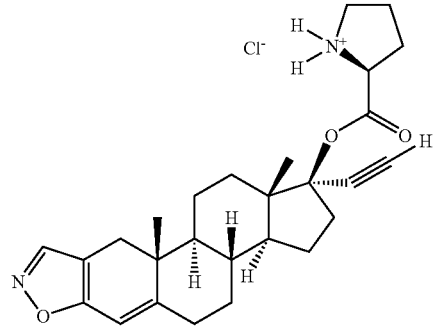

Pyrrolidine-(2S)-carboxylic acid 1-ethynyl-10a,12a-dimethyl-2,3,3a,3b,4,5,10,10a,10b,11,12,12a-dodecahydro-1H-7-oxa-8-aza-dicyclopenta[a,h] phenanthren-1-yl ester, hydrochloride $^1$H NMR (300 MHz, DMSO-d$_6$): δ=10.40 (1H, br s), 9.17 (1H, br s), 8.34 (1H, s), 6.28 (1H, s), 4.36 (1H, dd, J=7.2, 6.9 Hz), 3.76 (1H, s), 3.22 (2H, m), 2.73 (1H, d, J=15.9 Hz), 2.60-2.32 (7H, m), 2.0-1.35 (12H, m), 1.13 (1H, m), 0.97 (3H, s), 0.93 (3H, s).

$^{13}$C NMR (75 MHz, DMSO-d$_6$): δ=166.79, 163.73, 154.27, 148.86, 108.06, 107.49, 85.95, 82.09, 78.68, 58.55, 53.15, 47.97, 47.26, 45.11, 40.44, 36.41, 35.86, 32.69, 32.52, 31.35, 30.33, 27.73, 23.23, 22.89, 20.63, 18.49, 13.26.

HPLC Analysis: 98.27% purity, r.t.=14.48 min, sample dissolved in DIUF water/ACN, 50% DIUF water (0.1% TFA)/50% ACN, Gemini C18 (#262049-2), 5 u, 250×4.6 mm, 1 mL/min., 40° C., 20 uL inj. vol., SPD-10 Avp, chl-210 nm.

CHN Analysis: calculated: C, 68.85; H, 7.49; N, 5.95; Cl, 7.53. found: C, 68.66; H, 7.49; N, 5.89; Cl, 7.76.

Specific rotation: −6.67 deg (20° C., 19.5 mg/l mL ethanol, 589 nm)

Melting point: 195.0-198.0° C. (dec.)

Preparation of Benazepril Esters

Overview:

The procedure for the synthesis of the L-serine, L-threonine, and L-hydroxyproline esters of benazepril is outlined in Synthetic Sequence section. The complete procedure and analytical data are given in the Experimental Section. In general, benazepril (Xiangding Chemical International Company) was butylated to protect the free acid group. The ethyl ester was then hydrolyzed to the acid with sodium hydroxide. The amine present in the molecule was protected with a tert-butyloxycarbonyl group to prevent dimerization during the subsequent coupling reaction. The protected intermediate was then coupled with the tert-butyl ester of boc-L-serine, boc-L-threonine, or boc-L-hydroxyproline using EDC. The protected intermediate esters were treated with dilute hydrochloric acid in acetic acid at low temperature to remove all of the protecting groups. The final amino acid ester salts of benazepril were purified by washing with ethyl acetate and dichloromethane, dried under high vacuum, and analyzed by NMR, HPLC, CHN, specific rotation, and melting point.

Synthetic Sequence:

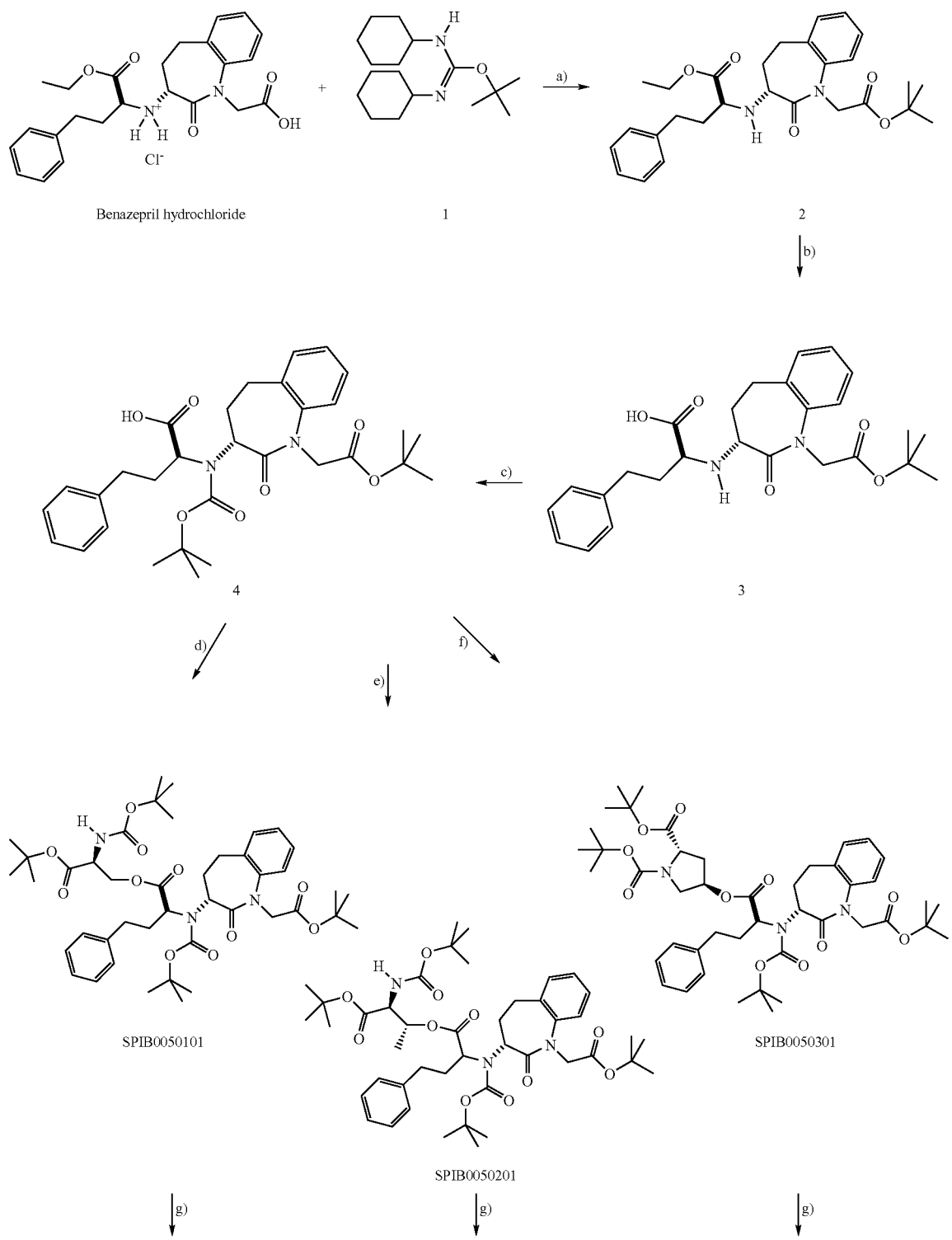

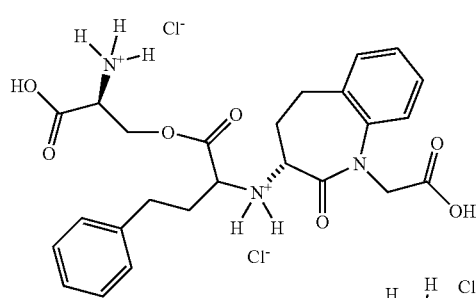

SPIB00501

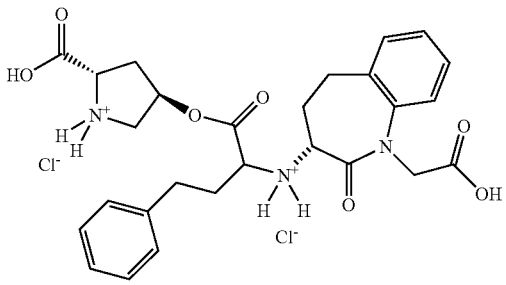

SPIB00503

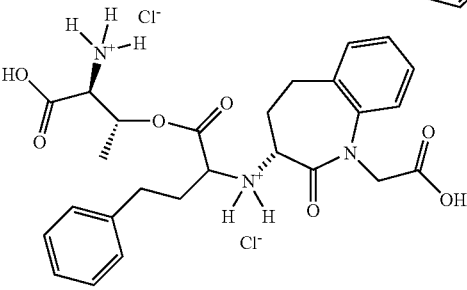

SPIB00502

Synthesis of the L-serine, L-threonine, and L-hydroxyproline Esters of Benazepril: a) THF; b) NaOH, MeOH, $H_2O$; c) $(Boc)_2O$, $Et_3N$, $CH_2Cl_2$; d) Boc-Ser-OtBu, EDC, DMAP, $CH_2Cl_2$; e) Boc-Thr-OtBu, EDC, DMAP, $CH_2Cl_2$; f) Boc-Hyp-OtBu, EDC, DMAP, $CH_2Cl_2$; g) HCl, AcOH, $CH_2Cl_2$.

Experimental Section:

The synthesis of SPIB00501, SPIB00502 and SPIB00503 was conducted in batches. Reagents mentioned in the experimental section were purchased at the highest obtainable purity from Lancaster, Sigma-Aldrich, Acros, Bachem, or Xiangding Chemical International, except for solvents, which were purchased from either Fisher Scientific or Mallinkrodt.

1) Butylation of Benazepril:

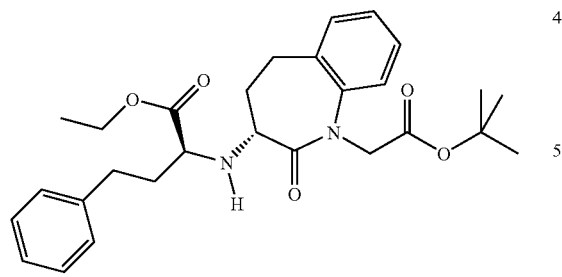

2

A solution of 2-tert-butyl-1,3-dicyclohexyl isourea 1 (569 g, 2.03 mol, prepared by the literature procedure) in THF (500 mL) was added drop-wise to a mixture of benazepril hydrochloride (117 g, 0.254 mol) in anhydrous THF (500 mL) and cooled in an ice-water bath. After 2 hours, the ice bath was removed and the mixture was allowed to stir for 4 days at room temperature under an argon atmosphere. The reaction mixture was filtered and the precipitate (DCU) was washed with methyl t-butyl ether (3×500 mL). The filtrates were combined and washed with 5% sodium bicarbonate solution (1 L) and brine (1 L). The ether-THF solution was dried over sodium sulfate, filtered, and concentrated under reduced pressure. The remaining mixture (202 g) was purified by column chromatography on silica gel (1 Kg), eluting with heptane-ethyl acetate (4:1). The product containing fractions were combined and concentrated under reduced pressure and dried at high vacuum till a constant weight was achieved and a butylated benazepril 2 (88.17 g, 72% yield) was isolated as a yellow oil.

$^1$H NMR (300 MHz, $CDCl_3$): δ 7.18 (9H, m), 4.61 (1H, d, J=16.8 Hz), 4.31 (1H, d, J=16.8 Hz), 4.04 (2H, m), 3.25 (3H, m), 2.69 (2H, m), 2.57 (1H, m), 2.39 (1H, m), 2.19 (1H, s, br), 1.99 (3H, m), 1.43 (9H, s), 1.11 (3H, t, J=7.2 Hz).

$^{13}$C NMR (75 MHz, $CDCl_3$): δ 173.89, 173.58, 167.59, 141.21, 140.83, 135.91, 129.27, 128.21, 128.16, 127.50, 126.53, 125.71, 122.04, 81.88, 60.48, 60.18, 56.90, 51.16, 37.81, 35.13, 32.10, 28.52, 28.01, 14.14.

2) Saponification of the Butylated Benazepril:

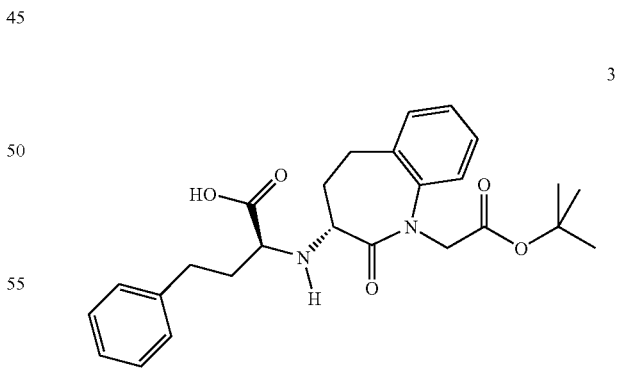

3

A sodium hydroxide solution (8.08 g, 0.202 mol) in DIUF water (540 mL) was added in a drop-wise fashion to the butylated benazepril 2 (88.17 g, 0.184 mol) dissolved in methanol (1.6 L), while cooling the methanol solution in ice bath. The solution was allowed to stir for 18 hours under an argon atmosphere while cooling in an ice bath. The reaction mixture was allowed to warm to room temperature and stir at room temperature for an additional 24 hours. The reaction mixture was concentrated under reduced pressure and dried under high vacuum to produce a mixture of solid and liquid (130 g). The residue was cooled in an ice bath and a solution of acetic acid in water (1:10 v/v acetic acid/water) was added drop-wise to adjust the solution to pH=7. A white precipitate formed which was filtered overnight in two crops (141.3 g and 7.05 g). The combined precipitates fractions were stirred with dichloromethane (500 mL) for one hour. After filtration and drying under high vacuum, 3 (48.6 g, 59% yield) was isolated as a white solid.

$^1$H NMR (300 MHz, CD$_3$OD): δ 7.34-7.16 (9H, m), 4.65 (1H, d, J=17.4 Hz), 4.44 (1H, d, J=17.4 Hz), 3.87 (1H, dd, J=11.4, 7.8 Hz), 3.45 (1H, t, J=5.7 Hz), 3.37 (1H, dd, J=12.9, 5.4 Hz), 2.74 (3H, m), 2.60 (1H, m), 2.34 (1H, m), 2.11 (2H, m), 1.43 (9H, s).

$^{13}$C NMR (75 MHz, CD$_3$OD): δ 172.67, 168.85, 168.71, 142.04, 140.99, 135.75, 130.65, 129.51, 129.38, 129.24, 128.69, 127.05, 123.88, 83.38, 63.51, 59.07, 52.20, 34.95, 34.29, 32.47, 28.40, 28.27.

3) Amine Protection:

4

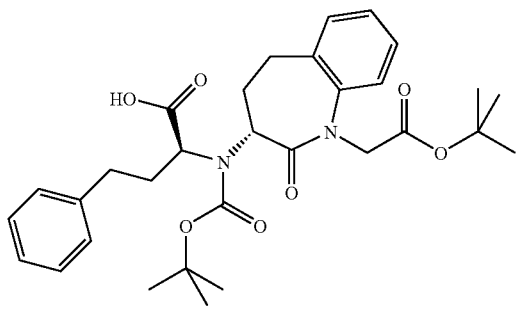

A solution of di-tert-butyl dicarbonate (38.2 g, 175 mmol) in anhydrous dichloromethane (200 mL) was added in a drop-wise fashion to a solution of acid 3 (72.0 g, 159 mmol) and triethylamine (64.4 g, 636 mmol) in anhydrous dichloromethane (600 mL) cooled in an ice bath, under an argon atmosphere. The mixture was allowed to stir at room temperature for 3 days under an argon atmosphere. The reaction mixture was extracted with ice-cold 0.5N hydrochloric acid (1.3 L) and brine (600 mL). The dichloromethane solution was dried over sodium sulfate, filtered, and concentrated under reduced pressure. The remaining yellow foam (87.1 g) was purified by column chromatography on silica gel (1 Kg), eluting with heptane-ethyl acetate (4:1). The product containing fractions were combined, concentrated under reduced pressure, and dried under high vacuum. The amine 4 (40.0 g, 45% yield) was isolated as a white solid.

$^1$H NMR (300 MHz, CDCl$_3$): δ 13.22 (1H, s, br), 7.32-7.19 (9H, m), 4.80 (1H, dd, J=12.3, 7.8 Hz), 4.75 (1H, d, J=16.8 Hz), 4.17 (1H, d, J=16.8 Hz), 3.75 (1H, dd, J=9.0, 3.3 Hz), 3.18 (1H, m), 2.86 (2H, m), 2.66 (1H, m), 2.53 (1H, m), 2.00 (1H, m), 1.78 (1H, m), 1.60 (1H, m), 1.41 (9H, s), 1.40 (9H, s).

$^{13}$C NMR (75 MHz, CDCl$_3$): δ 175.15, 171.44, 166.64, 154.36, 141.25, 139.77, 134.87, 129.28, 128.69, 128.41, 128.26, 127.55, 126.03, 122.54, 82.94, 82.59, 57.07, 55.39, 51.76, 34.73, 33.42, 32.95, 28.07, 28.00, 27.85.

4) Preparation of the L-Serine Ester of Benazepril:

Coupling Procedure:

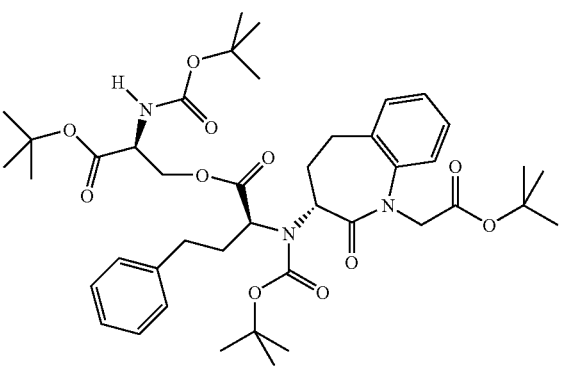

SPIB0050101

A mixture of acid 4 (15.5 g, 28.0 mmol), boc-L-serine tert-butyl ester (6.66 g, 25.5 mmol, prepared by the literature method), 1-[3-dimethylamino)propyl]-3-ethylcarbodiimide hydrochloride (EDCI, 6.84 g, 35.7 mmol), and DMAP (0.436 g, 3.57 mmol) in anhydrous dichloromethane (180 mL) was stirred at room temperature under an argon atmosphere for 2 days. The solution was diluted with dichloromethane and washed with water (300 mL), 5% sodium bicarbonate solution (300 mL), and brine (300 mL). After drying over sodium sulfate, filtration, and concentration under reduced pressure, the remaining mixture (22.37 g) was purified by column chromatography on silica gel (600 g), eluting with heptane and ethyl acetate (4:1). The product containing fractions (16.38 g) were combined and concentrated and purified a second time by column chromatography on silica gel (1 Kg), eluting with heptane and ethyl acetate (6:1). The product containing fractions were combined, concentrated, and dried under high vacuum. The protected L-serine ester of benazepril SPIB0050101 (15.4 g, 76% yield) was isolated as a white foam.

$^1$H NMR (300 MHz, CDCl$_3$): δ 7.30-7.10 (9H, m), 6.22 (1H, d, J=6.9 Hz), 5.36 (1H, d, J=17.4 Hz), 4.98 (1H, m), 4.70 (1H, d, J=9.6 Hz), 4.58 (1H, m), 4.45 (1H, d, J=8.7 Hz), 4.28 (1H, m), 4.04 (1H, d, J=17.4 Hz), 3.32 (1H, m), 2.90 (1H, m), 2.73-2.52 (3H, m), 2.06 (2H, m), 1.77 (1H, m), 1.49 (9H, s), 1.41 (9H, s), 1.34 (18H, s).

$^{13}$C NMR (75 MHz, CDCl$_3$): δ 171.59, 170.95, 168.83, 167.50, 155.86, 154.14, 141.52, 140.07, 135.70, 129.35, 128.45, 128.31, 127.71, 126.89, 125.86, 122.03, 82.03, 81.89, 81.02, 79.56, 64.89, 57.28, 53.64, 53.28, 49.54, 36.19, 34.80, 34.31, 28.49, 28.32, 27.95.

HPLC Analysis:

98.41% purity; r.t.=11.595 min.; 25% DIUF water/75% acetonitrile; 1 mL/min; 40° C.; Synergi Polar-RP (serial #161309-2), 4.6×250 mm; 20 ul injection.

Deprotection and Purification:

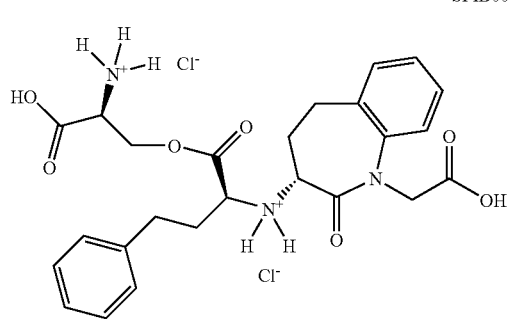

SPIB00501

A solution of hydrogen chloride (1.0 M in acetic acid, 384 mL) was added drop-wise to a solution of the protected L-serine ester of benazepril SPIB0050101 (15.3 g, 19.2 mmol) in anhydrous dichloromethane (240 mL) that was cooled in an ice batch, under an argon atmosphere. The mixture was stored for 7 days at 5° C. The mixture was concentrated under reduced pressure and dried under high vacuum to generate a colorless gel. Ethyl acetate (150 mL) was added to the gel and the mixture was sonicated for 5 minutes. The white, solid product was concentrated under reduced pressure. An additional amount of ethyl acetate (150 mL) was added to the solid and the mixture was heated to reflux for 10 minutes. The solution was cooled to room temperature. The solids were filtered and dried under high vacuum. The benazepril-serine ester salt (12.3 g) was purified by stirring the material in anhydrous dichloromethane (60 mL) overnight, at room temperature. After filtration and drying, the recovered material (9.3 g) was purified a final time by stirring the material in ethyl acetate (60 mL) overnight, at room temperature. The final salt was filtered and dried under high vacuum (at 45° C.) overnight. In order to remove traces of solvent the final salt (8.70 g) was dissolved in DIUF water (150 mL) and freeze-dried. Benazeprilat L-serine ester, dihydrochloride SPIB00501 (8.61 g, 80% yield, 99.69% purity by HPLC) was isolated in monohydrate form (as white solid).

$^1$H NMR (300 MHz, DMSO): δ 10.89 (4H, s, br), 8.88 (3H, s, br), 7.33-7.17 (9H, m), 4.67 (1H, d, J=17.4 Hz), 4.47 (3H, m), 4.28 (1H, m), 3.83 (1H, m), 3.73 (1H, t, J=9.0 Hz), 3.23 (1H, m), 2.66 (3H, m), 2.52 (1H, m), 2.26 (1H, m), 2.09 (2H, m).

$^{13}$C NMR (75 MHz, DMSO): δ 169.76, 168.27, 168.11, 167.68, 140.51, 139.72, 134.67, 129.29, 128.35, 128.24, 127.94, 126.88, 125.96, 123.14, 62.85, 58.33, 56.34, 51.05, 50.29, 33.88, 31.78, 30.54, 26.87.

HPLC Analysis:

99.69% purity, r.t.=12.408 min, sample dissolved in DIUF water/ACN, 82% DIUF water (0.1% TFA)/18% ACN, Synergi Polar-RP (#258258-4), 4 u, 250×4.6 mm, 1 mL/min., 30° C., 20 uL inj. vol., SPD-10 Avp, chl-210 nm.

Specific rotation: −123.3 deg (20° C., 21.3 mg/2 mL ethanol, 589 nm).

Melting point: 148.0° C. decomposed (Thomas Hoover CMPA, uncorrected)

CHN Analysis:

calc.: C, 53.29; H, 5.85; N, 7.46; Cl, 10.70. ($C_{25}H_{29}N_3O_7$-1.7 HCl—$H_2O$). found: C, 53.30; H, 5.86; N, 7.35; Cl, 10.78.

5) Preparation of the L-Threonine Ester of Benazepril:
Coupling Procedure:

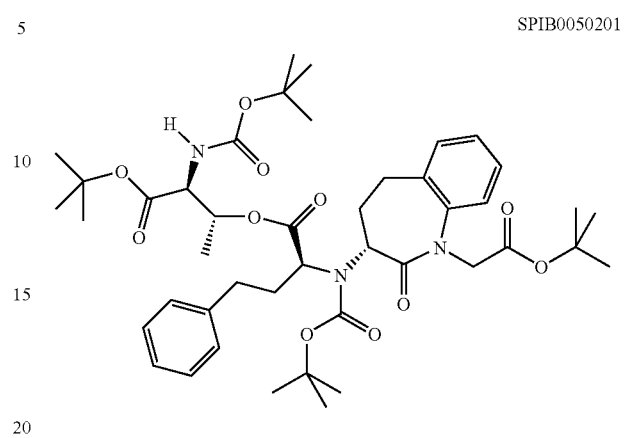

SPIB0050201

A mixture of acid 4 (20.7 g, 37.5 mmol), boc-L-threonine tert-butyl ester (9.36 g, 34.0 mmol, prepared by the literature method)[1], 1-[3-dimethylamino)propyl]-3-ethylcarbodiimide hydrochloride (EDCI, 9.12 g, 47.6 mmol), and DMAP (0.582 g, 4.76 mmol) in anhydrous dichloromethane (250 mL) was stirred at room temperature under an argon atmosphere for 3 days. The reaction solution was washed with water (2×250 mL), 5% sodium bicarbonate solution (250 mL), and brine (250 mL). After drying over sodium sulfate, filtration, and concentration under reduced pressure, the remaining yellow oil (38.7 g) was purified by column chromatography on silica gel (1 Kg), eluting with heptane-ethyl acetate (4:1). The product containing fractions were combined and concentrated. The L-threonine ester of benazepril SPIB0050201 (18.51 g, 67% yield) was isolated.

$^1$H NMR (300 MHz, CDCl$_3$): δ 7.26-7.16 (9H, m), 5.63 (1H, s, br), 5.40 (1H, s, br), 4.99 (2H, m), 4.11 (1H, d, J=15.6 Hz), 3.27 (1H, s, br), 2.68 (2H, s, br), 2.56 (1H, dd, J=13.2, 6.0 Hz), 2.35 (2H, s, br), 2.05 (2H, m), 1.47-1.26 (39H, m).

$^{13}$C NMR (75 MHz, CDCl$_3$): δ 170.34, 169.72, 168.86, 167.71, 156.18, 154.83, 141.23, 140.60, 135.58, 129.08, 128.41, 127.61, 126.53, 125.91, 122.09, 82.26, 81.68, 80.85, 79.66, 71.64, 58.04, 55.76, 54.23, 50.01, 35.20, 34.54, 33.87, 28.41, 28.28, 27.96, 17.28.

HPLC Analysis:

98.30% purity; r.t.=11.924 min.; 25% DIUF water/75% acetonitrile; 1 mL/min; 40° C.; Synergi Polar-RP (serial #161309-2), 4.6×250 mm; 20 ul injection, 210 nm.

Melting point: 74.8° C.

Deprotection and Purification:

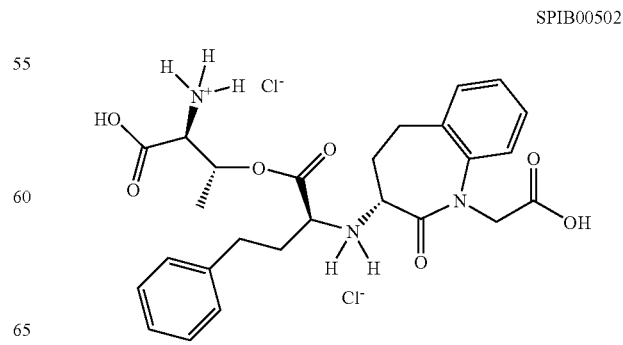

SPIB00502

A solution of hydrogen chloride (1.0 M in acetic acid, 452 mL) was added drop-wise to a solution of the protected L-threonine ester of benazepril SPIB0050201 (18.3 g, 22.6 mmol) in anhydrous dichloromethane (250 mL) that was cooled in an ice batch, under an argon atmosphere. The reaction mixture was stored for 8 days at 5° C., then concentrated under reduced pressure and dried under high vacuum to generate white foam. Ethyl acetate (200 mL) was added to the foam and the mixture was sonicated for 5 minutes. The white, solid product was concentrated under reduced pressure. An additional amount of ethyl acetate (200 mL) was added to the solid and the mixture was heated to reflux for 15 minutes. After cooling the solution to room temperature, the solids were filtered and dried under high vacuum (at 40° C.) until a constant weight was achieved. The remaining salt (11.9 g) was purified by stirring in anhydrous dichloromethane (90 mL) for three days at room temperature. The salt was filtered and dried under high vacuum (at 45° C.) until a constant weight was achieved. In order to remove traces of solvent the final salt (11.02 g) was suspended in DIUF water (200 mL) and freeze-dried. The benazeprilat L-threonine ester, dihydrochloride SPIB00502 (10.87 g, 81% yield, 97.55% purity by HPLC) was isolated in dihydrate form (as a white solid).

$^1$H NMR (300 MHz, DMSO): 810.62 (3H, s, br), 8.85 (4H, s, br), 7.33-7.18 (9H, m), 5.29 (1H, m), 4.65 (1H, d, J=17.1 Hz), 4.42 (1H, d, J=17.1 Hz), 4.12 (1H, d, J=2.4 Hz), 3.84 (1H, m), 3.58 (1H, dd, J=8.7, 8.1 Hz), 3.23 (1H, m), 2.67 (3H, m), 2.54 (1H, m), 2.26 (1H, m), 2.09 (2H, m), 0.97 (3H, d, J=6.3 Hz).

$^{13}$C NMR (75 MHz, DMSO): δ 169.73, 167.81, 167.35, 166.45, 140.28, 139.67, 134.59, 129.33, 128.36, 127.97, 127.04, 126.11, 123.14, 69.75, 58.70, 56.21, 55.40, 50.07, 33.58, 31.97, 30.64, 26.73, 16.09.

HPLC Analysis:

97.55% purity, r.t.=15.517 min, sample dissolved in DIUF water/ACN, 82% DIUF water (0.1% TFA)/18% ACN, Synergi Polar-RP (#258258-4), 4 u, 250×4.6 mm, 1 mL/min., 35° C., 20 uL inj. vol., SPD-10 Avp, chl-210 nm.

Specific rotation: −134 deg (21° C., 21.6 mg/2 mL ethanol, 589 nm)

Melting point: 152.0-153.0° C. (Thomas Hoover CMPA, uncorrected)

CHN Analysis:

calc.: C, 52.59; H, 6.15; N, 7.08; Cl, 10.75. ($C_{26}H_{31}N_3O_7 \cdot 1.8HCl \cdot 1.7H_2O$). found: C, 52.81; H, 6.15; N, 7.37; Cl, 10.79.

6) Preparation of the L-hydroxyproline Ester of Benazepril:
Coupling Procedure:

SPIB0050301

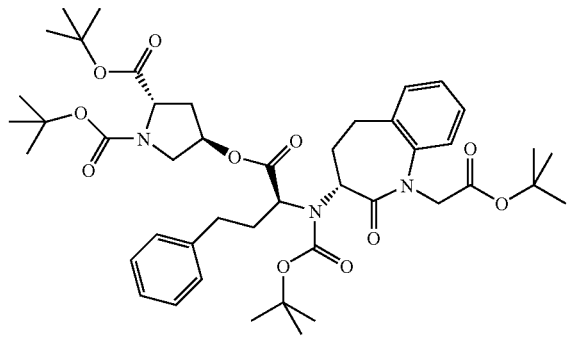

A mixture of acid 4 (35.8 g, 64.8 mmol), boc-L-hydroxyproline tert-butyl ester (16.9 g, 58.9 mmol, prepared by the literature method), 1-[3-dimethylamino)propyl]-3-ethylcarbodiimide hydrochloride (EDCI, 15.8 g, 82.5 mmol), and DMAP (1.01 g, 8.25 mmol) in anhydrous dichloromethane (600 mL) was stirred at room temperature under an argon atmosphere for 6 days. The dichloromethane solution was washed with water (400 mL), 5% sodium bicarbonate solution (400 mL), and brine (400 mL). After drying over sodium sulfate, filtration, and concentration under reduced pressure, the remaining brown oil (51.5 g) was purified by column chromatography on silica gel (1 Kg), eluting with heptane-ethyl acetate (4:1). The product containing fractions were combined and concentrated. The protected L-hydroxyproline ester of benazepril SPIB0050301 (19.69 g, 41% yield) was isolated as white foam.

$^1$H NMR (300 MHz, CDCl$_3$): δ 7.27-7.12 (9H, m), 5.33 (1H, m), 4.85 (2H, dd, J=17.1, 5.4 Hz), 4.36 (1H, m), 4.23 (1H, t, J=7.50 Hz), 4.10 (1H, dd, J=17.1, 3.6 Hz), 3.73 (1H, m), 3.65 (1H, m), 3.24 (1H, m), 2.71 (2H, m), 2.57-2.40 (3H, m), 2.21-1.97 (4H, m), 1.44 (36H, m), 1.47-1.37 (36H, m).

$^{13}$C NMR (75 MHz, CDCl$_3$): δ 171.53, 171.42, 170.90, 170.84, 170.59, 167.62, 154.61, 153.90, 153.48, 141.29, 141.25, 140.69, 135.46, 129.13, 128.43, 128.34, 127.71, 126.58, 125.92, 122.20, 81.72, 81.24, 80.78, 80.03, 79.88, 73.04, 72.25, 58.52, 58.04, 54.58, 52.03, 51.67, 50.41, 36.72, 35.58, 34.52, 33.93, 28.40, 28.34, 28.04, 27.99.

Deprotection and Purification:

SPIB00503

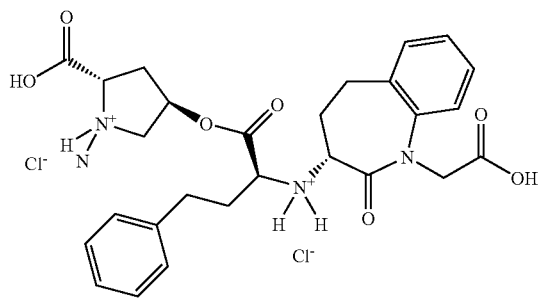

A solution of hydrogen chloride (1.0 M in acetic acid, 400 mL) was added drop-wise to a solution of the protected L-hydroxyproline ester of benazepril SPIB0050301 (19.69 g, 24.0 mmol) in anhydrous dichloromethane (265 mL) that was cooled in an ice batch, under an argon atmosphere. The reaction mixture was stored for 4 days at 5° C. and then was concentrated under reduced pressure and dried under high vacuum to generate a light, yellow foam. Ethyl acetate (200 mL) was added to the yellow foam and the mixture was sonicated for 5 minutes. The white, solid product was concentrated under reduced pressure. An additional amount of ethyl acetate (200 mL) was added to the solid and the mixture was heated to reflux for 15 minutes. The solution was cooled to room temperature. The solids were filtered and dried under high vacuum at 35° C. The remaining solid (14.50 g) was purified by stirring in anhydrous dichloromethane (60 mL) overnight at room temperature. The remaining salt (13.19 g) was filtered and dried under high vacuum at 45° C. for 20 hours. In order to remove trace of solvent, the salt was dispersed in DIUF water (500 mL) and freeze-dried. Benazeprilat trans-4-hydroxy-L-proline ester, dihydrochloride SPIB00503 (12.5 g, 87% yield, 99.95% purity by HPLC) was isolated in monohydrate form (as a white solid).

$^1$H NMR (300 MHz, DMSO): δ 10.34 (6H, s, br), 7.34-7.17 (9H, m), 5.25 (1H, m), 4.66 (1H, d, J=17.4 Hz), 4.43 (1H, d, J=17.4 Hz), 4.24 (1H, t, J=9.0 Hz), 3.88 (1H, m), 3.77 (1H, t, J=9.0 Hz), 3.51 (1H, dd, J=12.6, 3.9 Hz), 3.23 (2H, m), 2.66 (4H, m), 2.22 (3H, m), 2.11 (2H, m).

$^{13}$C NMR (75 MHz, DMSO): δ 169.80, 169.01, 167.93, 167.88, 140.40, 139.76, 134.59, 129.17, 128.33, 128.27, 127.87, 126.87, 126.01, 123.13, 74.10, 57.88, 57.39, 56.31, 50.23, 49.95, 33.98, 33.69, 31.68, 30.60, 26.79.

HPLC Analysis:
99.95% purity, r.t.=16.725 min, sample dissolved in DIUF/ACN, 82% DIUF water (0.1% TFA)/18% ACN, Synergi Polar-RP (#258258-4), 4 u, 250×4.6 mm, 1 mL/min., 30° C., 20 uL inj. vol., SPD-10 Avp, chl-210 nm.

Specific rotation: −116.0 deg (20° C., 23.7 mg/2 mL ethanol, 589 nm)

Melting point: 168.0° C. decomposed (Thomas Hoover CMPA, uncorrected)

CHN Analysis:
calc.: C, 55.52; H, 5.96; N, 7.19; Cl, 9.41. ($C_{27}H_{31}N_3O_7 \cdot 1.55HCl-H_2O$). found: C, 55.55; H, 5.99; N, 7.16; Cl, 9.67.

Literature Cited: Moore, J. W.; Szelke, M. *Tetrahedron Lett.* 1970, 4423-4426.

Synthesis and Efficacy Studies of Enalapril Derivatives:
Overview:

The procedure for the synthesis of the L-serine, L-threonine, and L-hydroxyproline esters of enalapril is outlined in Synthetic Sequence section. The complete procedure and analytical data are given in the Experimental Section. In general, the maleate salt of enalapril (Xiangding Chemical International Company) was butylated to protect the free acid group. The ethyl ester was then hydrolyzed to the acid with sodium hydroxide, followed by acidification. The amine present in the molecule was protected with a tert-butyloxycarbonyl group to prevent dimerization during the subsequent coupling reaction. The protected intermediate was then coupled with the tert-butyl ester of boc-L-serine, boc-L-threonine, or boc-L-hydroxyproline using EDC. The protected intermediate esters were treated with dilute hydrochloric acid in acetic acid at low temperature to remove all of the protecting groups. Washing with ethyl acetate and dichloromethane (or ACN) purified the amino acid ester salts of Enalapril. The final salts were dried under high vacuum and analyzed for NMR, HPLC, CHN, specific rotation, and melting point.

Synthetic Sequence:

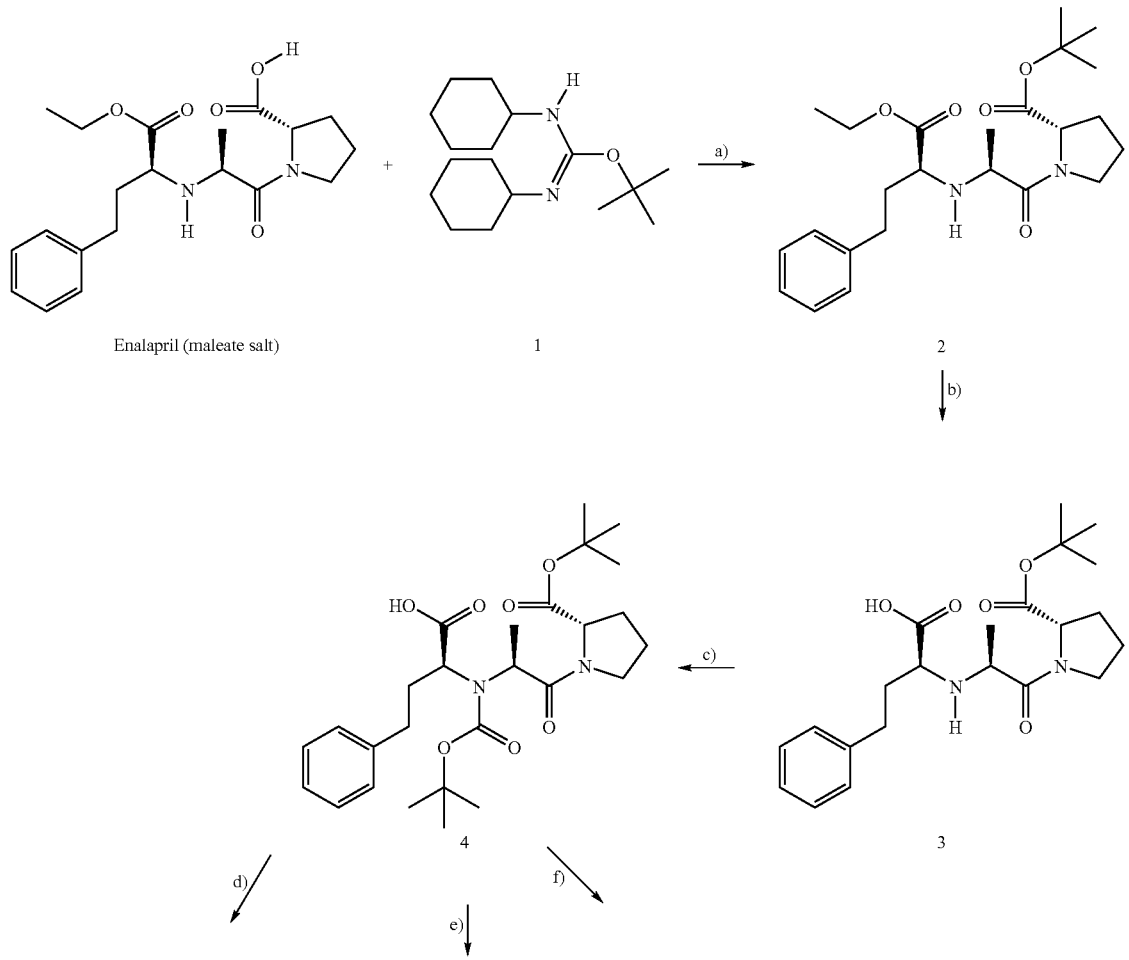

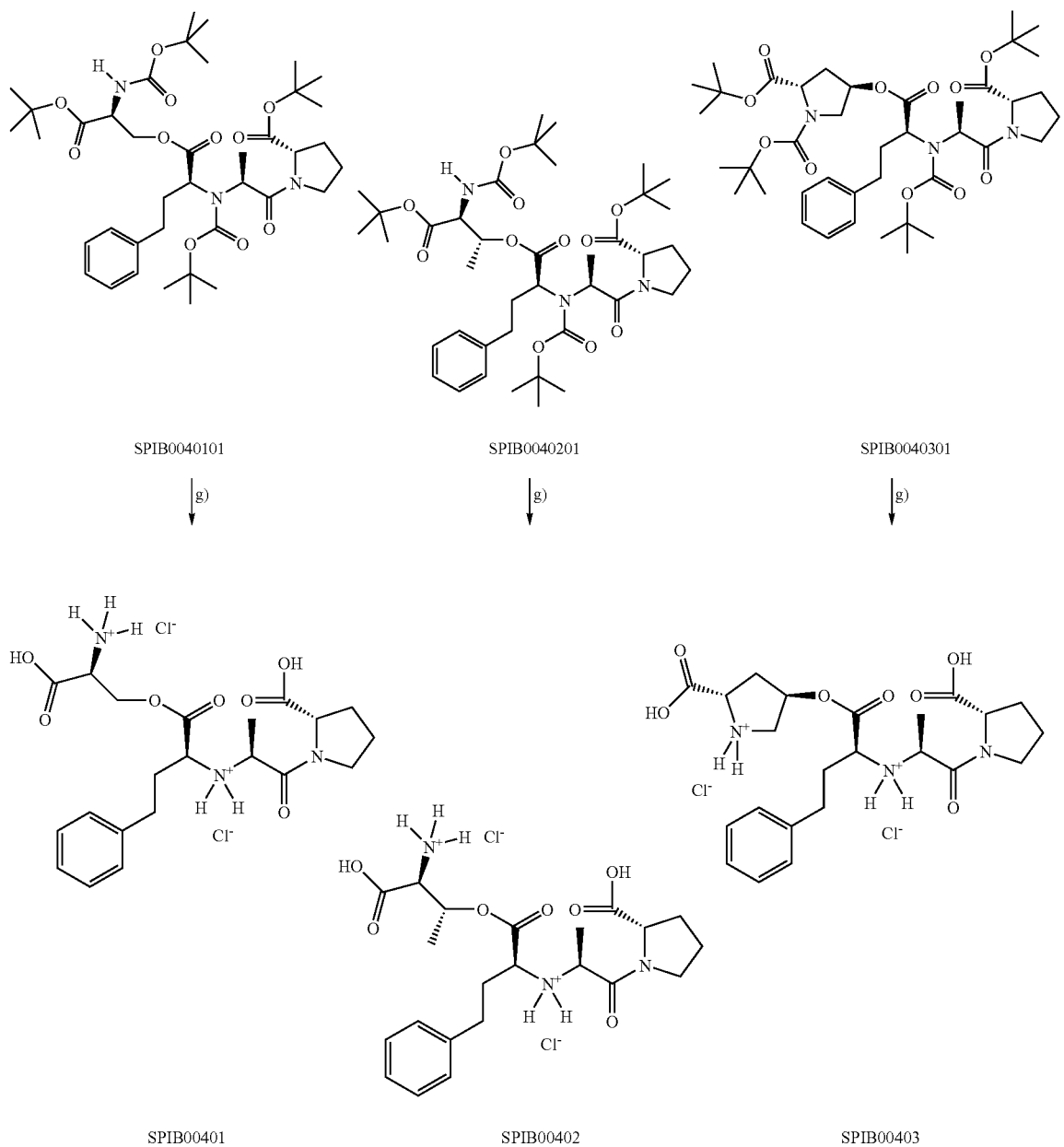

SPIB0040101   SPIB0040201   SPIB0040301

SPIB00401   SPIB00402   SPIB00403

Synthesis of the L-serine, L-threonine, and L-hydroxyproline Esters of Enalapril: a) THF; b) NaOH, MeOH, H₂O; c) (Boc)₂O, Et₃N, CH₂Cl₂; d) Boc-Ser-OtBu, EDC, DMAP, CH₂Cl₂; e) Boc-Thr-OtBu, EDC, DMAP, CH₂Cl₂; f) Boc-Hyp-OtBu, EDC, DMAP, CH₂Cl₂; g) HCl, AcOH, CH₂Cl₂.

Experimental Section:

The synthesis of SPIB00401, SPIB00402 and SPIB00403 was conducted in batches. Reagents mentioned in the experimental section were purchased at the highest obtainable purity from Lancaster, Sigma-Aldrich, Acros, Bachem, or Xiangding Chemical International, except for solvents, which were purchased from either Fisher Scientific or Mallinkrodt.

1) Butylation of Enalapril:

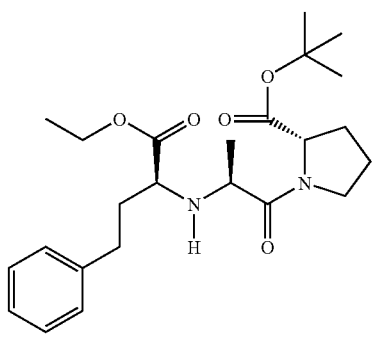

2

A solution of 2-tert-butyl-1,3-dicyclohexyl isourea 1 (592 g, 2.11 mol, prepared by the literature procedure) in THF (500 mL) was added drop-wise to a mixture of enalapril maleate (130 g, 0.264 mol) in anhydrous THF (600 mL) cooled in an ice-water bath. The mixture was allowed to stir for 24 hours at room temperature under an argon atmosphere. The reaction mixture was filtered, and the precipitate (DCU) was washed with dichloromethane (3×500 mL). The filtrates were combined and concentrated to produce a green oil. The residue was diluted with dichloromethane (1 L), washed with 5% sodium bicarbonate solution (1 L), and washed with brine (500 mL). The dichloromethane solution was dried over sodium sulfate, filtered, and concentrated under reduced pressure. The remaining mixture (189 g) was purified by column chromatography on silica gel (1 Kg), eluting with heptane-ethyl acetate (2:1). The product containing fractions were combined and concentrated under reduced pressure and dried at high vacuum. Butylated enalapril 2 (87.3 g, 76% yield) was obtained as a light yellow oil.

$^1$H NMR (300 MHz, CDCl$_3$): δ 7.31-7.15 (5H, m), 4.43 (1H, dd, J=8.4, 3.3 Hz), 4.18 (2H, q, J=7.2 Hz), 3.52 (3H, m), 3.25 (1H, t, J=6.6 Hz), 2.67 (2H, m), 2.24 (1H, s, br), 2.18 (1H, m), 1.98 (5H, m), 1.45 (9H, s), 1.29 (3H, d, J=7.2 Hz), 1.25 (3H, t, J=7.2 Hz).

$^{13}$C NMR (75 MHz, CDCl$_3$): δ 173.99, 173.03, 170.81, 141.07, 128.15, 128.09, 125.68, 81.03, 60.59, 59.93, 59.44, 53.36, 46.41, 35.06, 31.95, 28.86, 27.88, 24.72, 18.80, 14.28.

2) Saponification of the Butylated Enalapril:

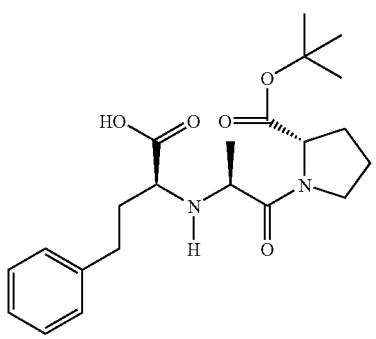

3

A sodium hydroxide solution (80.8 g, 2.02 mol) in DIUF water (1 L) was added in a drop-wise fashion to the butylated enalapril 2 (87.2 g, 0.202 mol) dissolved in methanol (1 L), while cooling the methanol solution in an ice bath. The solution was allowed to stir for 18 hours under an argon atmosphere while cooling in an ice bath. The reaction mixture was concentrated under reduced pressure and dried under high vacuum to produce a cloudy solution (847 g). The residue was cooled in an ice bath and a solution of acetic acid in water (1.2 L, 1:10 v/v acetic acid/water) was added drop-wise to adjust the solution to pH=7. A white precipitate formed which was extracted with dichloromethane (4×500 mL). The combined dichloromethane fractions were dried over sodium sulfate, filtered, and concentrated under reduced pressure to generate a brown foam-like solid (73.4 g). After additional drying under high vacuum, 3 (61.5 g, 75% yield) was obtained as a light brown solid, which was used without additional purification.

$^1$H NMR (300 MHz, CDCl$_3$): δ 7.12 (5H, m), 5.31 (2H, s, br), 4.41 (1H, dd, J=9.0, 3.6 Hz), 3.97 (1H, q, J=6.6 Hz), 3.53 (1H, m), 3.42 (1H, m), 3.31 (1H, t, J=6.3 Hz), 2.72 (2H, m), 2.21-1.91 (6H, m), 1.52 (3H, d, J=6.6 Hz), 1.43 (9H, s).

$^{13}$C NMR (75 MHz, CDCl$_3$): δ 172.66, 170.29, 168.74, 140.46, 128.30, 128.18, 125.80, 81.63, 61.74, 59.75, 54.57, 46.64, 35.53, 31.89, 28.90, 27.97, 24.61, 16.47.

3) Amine Protection:

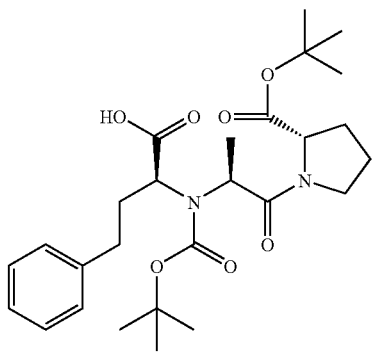

4

A solution of di-tert-butyl dicarbonate (36.5 g, 167 mmol) in anhydrous dichloromethane (200 mL) was added in a drop-wise fashion to a solution of 3 (61.5 g, 152 mmol) and triethylamine (61.5 g, 608 mmol) in anhydrous dichloromethane (600 mL) cooled in an ice bath, under an argon atmosphere. The mixture was allowed to stir at room temperature for 3 days at room temperature under an argon atmosphere. The reaction mixture was washed with ice-cold 0.5N hydrochloric acid (1.2 L) and brine (600 mL). The dichloromethane solution was dried over sodium sulfate, filtered, and concentrated under reduced pressure. The remaining yellow oil (87 g) was purified by column chromatography on silica gel (1 Kg), eluting with heptane-ethyl acetate (3:1). The product containing fractions were combined, concentrated under reduced pressure, and dried under high vacuum until the weight was constant. A protected amine 4 (28.7 g, 37% yield) was obtained as a white solid.

$^1$H NMR (300 MHz, CDCl$_3$): δ 13.61 (1H, br s), 7.30-7.16 (5H, m), 4.79 (1H, q, J=7.5 Hz), 4.47 (1H, dd, J=8.7, 4.5 Hz), 3.75 (2H, m), 3.54 (1H, m), 2.84 (2H, m), 2.68 (1H, m), 2.22 (1H, m), 1.98 (4H, m), 1.43 (9H, s), 1.10 (3H, d, J=7.5 Hz).

$^{13}$C NMR (75 MHz, CDCl$_3$): δ 174.62, 172.12, 170.10, 154.70, 141.23, 128.57, 128.41, 126.00, 82.74, 81.81, 60.00, 55.63, 53.00, 46.89, 34.27, 33.40, 28.80, 28.16, 27.99, 24.86, 14.08.

4) Preparation of the L-serine Ester of Enalapril:
Coupling Procedure:

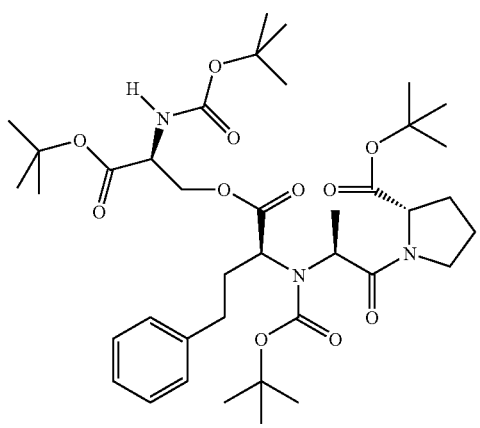

A mixture of 4 (15.3 g, 30.3 mmol), boc-L-serine tert-butyl ester (7.19 g, 27.5 mmol, prepared by the literature method), 1-[3-dimethylamino)propyl]-3-ethylcarbodiimide hydrochloride (EDCI, 7.38 g, 38.5 mmol), and DMAP (0.47 g, 3.85 mmol) in anhydrous dichloromethane (200 mL) was stirred at room temperature under an argon atmosphere for 4 days. The dichloromethane solution was washed with water (2×200 mL) and brine (200 mL). After drying the dichloromethane solution over sodium sulfate, filtration, and concentration under reduced pressure, the residue (24.6 g) was purified by column chromatography on silica gel (700 g), eluting with heptane-ethyl acetate (4:1). The product containing fractions were combined and concentrated. The remaining white solid (14.1 g) was crystallized from heptane (100 mL) and methyl tert-butyl ether (50 mL). After filtration and drying, the protected L-serine ester of enalapril SPIB0040101 (13.5 g, 66% yield) was obtained as a white solid.

$^1$H NMR (300 MHz, CDCl$_3$): δ 7.29 (2H, m), 7.20 (3H, m), 5.55 (1H, d, J=7.8 Hz), 5.26 (1H, m), 4.50-4.23 (5H, m), 3.79 (1H, m), 3.66 (1H, m), 2.76 (1H, m), 2.58 (2H, m), 2.25 (1H, m), 1.97 (4H, m), 1.44 (36H, m), 1.27 (3H, d, J=6.6 Hz).

$^{13}$C NMR (75 MHz, CDCl$_3$): δ 171.11, 169.36, 168.33, 155.18, 154.32, 141.43, 128.21, 128.19, 125.78, 82.48, 80.98, 80.86, 79.75, 65.05, 59.58, 55.70, 53.34, 50.12, 47.00, 35.20, 34.19, 29.14, 28.35, 28.27, 27.96, 27.90, 24.50, 16.55.

HPLC Analysis:
98.81% purity; r.t.=9.433 min.; 25% DIUF water/75% acetonitrile; 1 mL/min; 39° C.; Synergi Polar-RP (serial #234257-1), 4.6×250 mm; 20 ul injection; RI 210 nm.

Melting point: 134-135° C. (Thomas Hoover CMPA, uncorrected)

Deprotection and Purification:

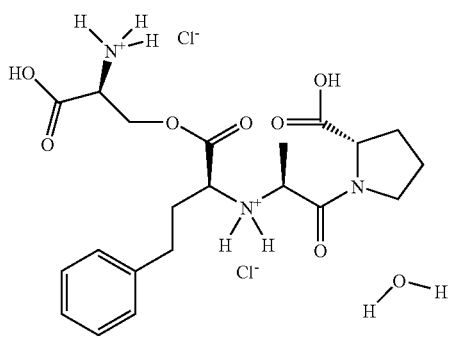

SPIB00401

A solution of hydrogen chloride (1.0 M in acetic acid, 360 mL) was added drop-wise to a solution of the protected L-serine ester of enalapril SPIB0040101 (13.4 g, 17.9 mmol) in anhydrous dichloromethane (190 mL) that was cooled in an ice batch, under an argon atmosphere. The mixture was stored for 8 days at 5° C. The mixture was concentrated under reduced pressure and dried under high vacuum to generate a light, yellow oil (19.56 g). Ethyl acetate (100 mL) was added to the oil and the mixture was sonicated for 5 minutes. The white, solid product (14.8 g) was filtered and dried under high vacuum. An additional amount of ethyl acetate (200 mL) was added to the solid and the mixture was heated to reflux for 10 minutes. While the solution was cooling, the solid was sonicated for 30 minutes and stirred for 2 hours at room temperature. The solids were filtered and dried under high vacuum. The remaining salt (10.5 g) was purified twice by stirring the material in anhydrous dichloromethane (60 mL) overnight, at room temperature. The final salt was filtered and dried under high vacuum at room temperature until a constant weight was obtained. Enalaprilic acid L-serine ester, dihydrochloride SPIB00401 (8.01 g, 88% yield, 97.09% purity by HPLC) was obtained in monohydrate form (as white solid).

$^1$H NMR (300 MHz, DMSO): δ 10.76 (4H, s, br), 9.02 (3H, s, br), 7.25 (5H, m), 4.67 (2H, m), 4.35 (3H, m), 3.93 (1H, m), 3.70 (1H, m), 3.42 (1H, m), 2.62 (2H, m), 2.17 (3H, m), 1.89 (3H, m), 1.44 (3H, d, J=6.0 Hz).

$^{13}$C NMR (75 MHz, DMSO): δ 172.53, 167.89, 167.03, 166.94, 140.26, 128.33, 126.11, 63.21, 58.90, 58.44, 53.97, 51.13, 46.83, 31.44, 30.45, 28.65, 24.71, 15.35.

HPLC Analysis:
97.09% purity; r.t.=8.367 min.; 85% DIUF water (0.1% TFA)/15% ACN; 1 mL/min; 36.0 C; Synergi Polar-RP 5 u column (serial #161309-2), 4.6×250 mm; 20 ul injection; Sig=210.4.

HRMS [M-2HCl—H$_2$O+H]: calc. 436.2084 (C$_{21}$H$_{31}$Cl$_2$N$_3$O$_7$). found 436.2079.

Melting point: 129.5° C. decomposed (Thomas Hoover CMPA, uncorrected)

CHN Analysis:
calc.: C, 47.91; H, 6.32; N, 7.98. (C$_{21}$H$_{31}$Cl$_2$N$_3$O$_7$—H$_2$O). found: C, 47.95; H, 6.32; N, 7.83.

5) Preparation of the L-threonine Ester of Enalapril:
Coupling Procedure:

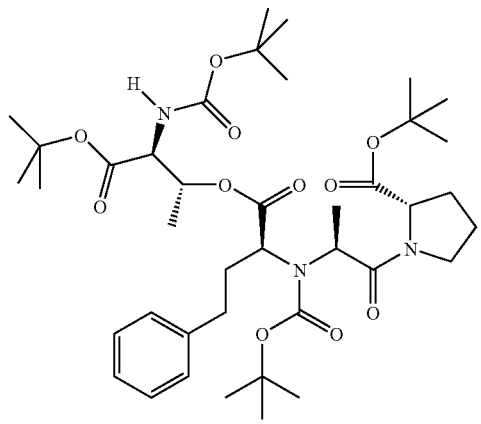

SPIB0040201

A mixture of 4 (28.4 g, 56.3 mmol), boc-L-threonine tert-butyl ester (14.1 g, 51.2 mmol, prepared by the literature method), 1-[3-dimethylamino)propyl]-3-ethylcarbodiimide hydrochloride (EDCI, 13.7 g, 71.7 mmol), and DMAP (0.876 g, 7.17 mmol) in anhydrous dichloromethane (450 mL) was stirred at room temperature under an argon atmosphere for 13 days. The dichloromethane solution was washed with water (2×500 mL) and brine (500 mL). After drying over sodium sulfate, filtration, and concentration under reduced pressure, the remaining yellow oil (46.49 g) was purified by column chromatography on silica gel (1 Kg), eluting with heptane-ethyl acetate (5:1). The product containing fractions were combined in two fractions and concentrated. Protected L-threonine ester of enalapril SPIB0040201 (7.35 g and 6.83 g, 36.3% yield) was present in both fractions. Both fractions were deprotected as described below and recombined in the final purification.

$^1$H NMR (300 MHz, CDCl$_3$): δ 7.30 (2H, m), 7.21 (3H, m), 5.28 (2H, m), 5.14 (1H, d, J=8.4 Hz), 4.30-4.22 (3H, m), 3.85 (1H, m), 3.65 (1H, m), 2.65 (2H, m), 2.39 (1H, m), 2.20 (1H, m), 1.99 (4H, m), 1.46 (36H, m), 1.25 (6H, m).

$^{13}$C NMR (75 MHz, CDCl$_3$): δ 171.23, 170.89, 170.03, 168.57, 155.82, 154.64, 141.43, 128.37, 128.24, 125.92, 82.83, 81.06, 80.01, 79.73, 72.23, 68.34, 59.80, 59.20, 57.69, 55.65, 50.78, 47.08, 34.40, 29.14, 28.41, 28.30, 28.03, 24.67, 20.01, 17.15.

Deprotection and Purification:

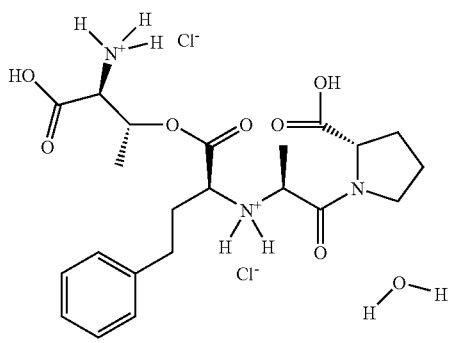

SPIB00402

A solution of hydrogen chloride (1.0 M in acetic acid, 185 mL) was added drop-wise to a solution of one of the batches of the protected L-threonine ester of enalapril SPIB0040261 (7.05 g, 9.25 mmol batch 1, 6.63 g, 8.70 mmol, batch 2) in anhydrous dichloromethane (100 mL) that was cooled in an ice batch, under an argon atmosphere. The mixture was stored for 7 days at 5° C. The mixture was concentrated under reduced pressure and dried under high vacuum to generate a colorless gel. Ethyl acetate (250 mL) was added to the gel and the mixture was sonicated for 5 minutes. The white, solid product was filtered and dried under high vacuum. An additional amount of ethyl acetate (100 mL) was added to the solid and the mixture was heated to reflux for 10 minutes. After cooling the solution to room temperature, the solids were filtered and dried under high vacuum until a constant weight was achieved. The deprotection step was then repeated with the second batch of material.

Both batches of the final salt (4.84 g from batch 1 and 4.30 from batch 2) were combined and purified by stirring in anhydrous dichloromethane (60 mL) overnight at room temperature. The final salt was filtered and dried under high vacuum. The washing procedure was then repeated for two days with ethyl acetate (40 mL) and for 18 hours with acetonitrile (50 mL). After filtration and drying, enalaprilic acid L-threonine ester, dihydrochloride SPIB00402 (7.75 g, 82% yield, 97.61% purity by HPLC) was isolated in monohydrate form (as white solid).

$^1$H NMR (300 MHz, DMSO): δ 10.50 (3H, s, br), 8.96 (4H, s, br), 7.24 (5H, m), 5.44 (1H, m), 4.58 (0.3H, m), 4.34-3.90 (3.4H, m), 3.78 (0.3H, m), 3.64 (0.7H, m), 3.47 (1H, m), 3.29 (0.3H, m), 2.72 (1H, m), 2.52 (1H, m), 2.16 (3H, m), 1.87 (2.7H, m), 1.60 (0.3H, m), 1.44 (6H, m).

$^{13}$C NMR (75 MHz, DMSO): δ 173.21, 172.55, 168.02, 167.88, 166.99, 166.71, 140.36, 128.37, 126.14, 70.43, 70.22, 58.96, 58.25, 58.13, 55.56, 54.85, 53.63, 46.65, 46.48, 32.13, 31.55, 30.47, 28.67, 24.70, 21.88, 16.99, 16.56, 16.50, 15.12.

HPLC Analysis:

97.61% purity, r.t.=9.258 min, sample dissolved in DIUF water/ACN, 85% DIUF water (0.1% TFA)/15% ACN, Synergi Polar-RP (#161309-2), 4 u, 250×4.6 mm, 1 mL/min., 40° C., 20 uL inj. vol., SPD-10 Avp, chl-210 nm.

Specific rotation: −33.8 deg (21° C., 17.3 mg/2 mL ethanol, 589 nm)

Melting point: 147.0-148.0° C. decomposed (Thomas Hoover CMPA, uncorrected)

CHN Analysis:
calc.: C, 49.90; H, 6.61; N, 7.94; Cl, 11.38. ($C_{22}H_{31}N_3O_7 \cdot 1.7HCl—H_2O$). found: C, 50.12; H, 6.61; N, 7.90; Cl, 11.33.

6) Preparation of the L-hydroxyproline Ester of Enalapril: Coupling Procedure:

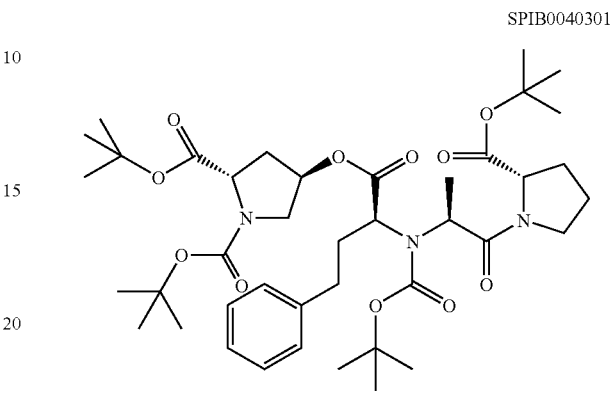

SPIB0040301

A mixture of 4 (24.6 g, 48.7 mmol), boc-L-hydroxyproline tert-butyl ester (12.7 g, 44.3 mmol, prepared by the literature method), 1-[3-dimethylamino)propyl]-3-ethylcarbodiimide hydrochloride (EDCI, 11.9 g, 62.0 mmol), and DMAP (0.757 g, 6.20 mmol) in anhydrous dichloromethane (400 mL) was stirred at room temperature under an argon atmosphere for 9 days. The dichloromethane solution was washed with water (400 mL), 5% sodium bicarbonate solution (400 mL), water (400 mL), and brine (400 mL). After drying the dichloromethane solution over sodium sulfate, filtration, and concentration under reduced pressure, the residual green oil (42.0 g) was purified by column chromatography on silica gel (1 Kg), eluting with heptane-ethyl acetate (5:1). The product containing fractions were combined, concentrated, and dried under high vacuum till a constant weight was obtained, yielding protected L-hydroxyproline ester of enalapril SPIB0040301 (11.41 g, 33% yield).

$^1$H NMR (300 MHz, CDCl$_3$): δ 7.29 (2H, m), 7.19 (3H, m), 5.24 (2H, m), 4.21 (3H, m), 3.74 (3H, m), 3.50 (1H, m), 2.77 (1H, m), 2.67-2.50 (2H, m), 2.23 (3H, m), 1.98 (4H, m), 1.44 (36H, m), 1.30 (3H, m).

$^{13}$C NMR (75 MHz, CDCl$_3$): δ 171.09, 170.91, 169.08, 154.37, 153.80, 153.44, 141.49, 128.37, 128.27, 125.91, 81.48, 81.30, 81.10, 80.32, 73.15, 72.46, 59.78, 58.49, 55.48, 51.95, 51.65, 50.36, 47.27, 36.74, 35.60, 35.17, 34.32, 29.29, 28.40, 28.31, 28.03, 24.70, 16.45.

Deprotection and Purification:

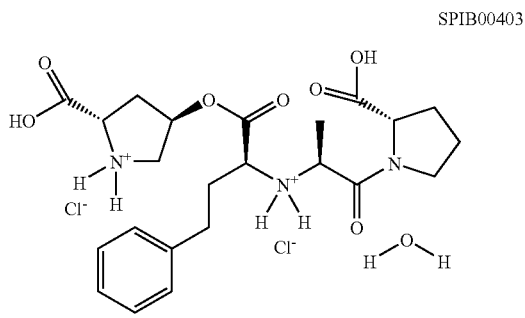

SPIB00403

A solution of hydrogen chloride (1.0 M in acetic acid, 290 mL) was added drop-wise to a solution of the protected L-hydroxyproline ester of enalapril SPIB0040301 (11.23 g, 14.5 mmol) in anhydrous dichloromethane (160 mL) that was cooled in an ice batch, under an argon atmosphere. The mixture was stored for 8 days at 5° C. The mixture was concentrated under reduced pressure and dried under high vacuum to generate yellow foam. Ethyl acetate (100 mL) was added to the yellow foam, and the mixture was sonicated for 5 minutes. The white, solid product was filtered and dried under high vacuum. An additional amount of ethyl acetate (100 mL) was added to the solid, and the mixture was heated to reflux for 10 minutes. After cooling the solution to room temperature, the solids were filtered and dried under high vacuum until a constant weight was achieved. The remaining solid (6.89 g) was purified by stirring in anhydrous dichloromethane (60 mL) overnight at room temperature. The remaining salt (5.80 g) was filtered and dried under high vacuum. In order to remove trace of solvent, the salt was dissolved in water (100 mL) and freeze-dried. Enalaprilic acid trans-4-hydroxy-L-proline ester, dihydrochloride SPIB00403 (5.40 g, 67% yield, 99.68% purity by HPLC) was obtained in monohydrate form (as white solid).

$^1$H NMR (300 MHz, DMSO): δ 10.65 (6H, s, br), 7.32-7.19 (5H, m), 5.44 (0.3H, m), 5.36 (0.7H, m), 4.67 (0.3H, m), 4.44 (1H, t, J=8.7 Hz), 4.28 (1.7H, m), 3.96 (1H, m), 3.73-3.31 (4H, m), 2.78 (1H, m), 2.61 (1H, m), 2.33 (1H, m), 2.18 (3.3H, m), 1.93-1.59 (3.7H, m), 1.46 (3H, m).

$^{13}$C NMR (75 MHz, DMSO): δ 173.31, 172.50, 169.24, 167.85, 167.66, 167.21, 140.30, 140.22, 128.27, 128.22, 126.01, 74.64, 58.89, 58.70, 57.92, 57.74, 57.58, 57.39, 54.68, 53.96, 50.31, 50.09, 46.59, 46.41, 34.16, 34.06, 31.93, 31.34, 30.34, 28.55, 24.62, 21.84, 16.53, 15.20.

HPLC Analysis:

99.68% purity, r.t.=6.700 min, sample dissolved in DIUF water/ACN, 82% DIUF water (0.1% TFA)/18% ACN, Synergi Polar-RP (#258258-4), 4 u, 250×4.6 mm, 1 mL/min., 35° C., 20 uL inj. vol., SPD-10 Avp, chl-210 nm.

Specific rotation: −36.2 deg (21° C., 16.8 mg/2 mL ethanol, 589 nm)

Melting point: 159.0-160.0° C. (Thomas Hoover CMPA, uncorrected)

CHN Analysis:

calc.: C, 50.01; H, 6.47; N, 7.61; Cl, 11.87. ($C_{23}H_{31}N_3O_7 \cdot 1.85HCl \cdot 1.3H_2O$). found: C, 50.11; H, 6.57; N, 7.47; Cl, 11.84.

Effect of Various ACE Inhibitor Enalapril Derivatives on Hemodynamics in Spontaneously Hypertensive Rats (SHRs).

ACE inhibitors have been known to be useful in antihypertensive therapy for many years. Some ACE inhibitors are delivered orally as the parent drug (captopril) while others are delivered as pro-drugs in order to obtain clinically useful plasma concentrations. This study provides data on the effect of these various enalapril derivatives on hemodynamics in SHRs when given orally and compared to enalapril.

Methods

Briefly, SHRs fitted with right carotid catheters were orally gavaged with 100 mg/kg enalapril or equivalent does of the enalapril derivatives, and the blood pressures were followed continuously up to 3 hours and then a measurement at 24 hours. The animals were conscious throughout the procedure and were placed in a restrainer and hooked up to a pressure transducer and a signal processor. After 3 hours, the animals were placed back into their cage, and blood pressure was finally measured again at 24 hours.

Results

Enalapril reduced blood pressure at 3 hours and 24 hours by approximately 20% depending on if data from systolic, diastolic or mean blood pressure were analyzed. The pressures generally stayed at baseline levels up to the 3 hour time point, and the pressure at 3 hours was remarkably similar to that seen at 24 hours. Vehicle treated animals showed no change in blood pressure throughout the study.

The reduction in blood pressures caused by the various agents was associated with a slightly greater drop in diastolic pressure than in systolic pressure. For the purpose of comparison, mean arterial blood pressures are utilized for this project summary. For the enalapril series, enalalpril and the amino acid derivatives of enalapril reduced arterial blood pressure.

No reflex tachycardia was noted and this is not unusual for ACE inhibitors. Heart rates tended to come down with time in all groups as the animals became more accustomed to the restrainers.

VII Water Soluble Derivatives of Fibric Acid Derivatives

Fibric acid compounds are useful anti-hyperlipidemic drugs useful in the treatment of hyperlipidemia in mammals where the symptoms are elevated triglycerides, low HDL (High density lipoproteins or "good" cholesterol, and elevated cholesterol. Fibric Acid compounds are also useful in reducing LDL (Low density lipoproteins, or "bad" cholesterol). The general structure of the fibric acid analogs is represented below, where X is various mixed aliphatic and aromatic functionalities. Specific compounds included in this formula are clofibric acid, fenofibric acid, ciprfibrate and gemfibrozil and the like.

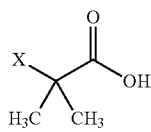

FIBRIC ACID ANALOGS

Typical examples of the chemical moiety X in the above structure are shown below.

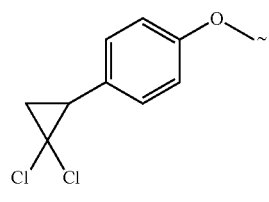

Ciprofibric Acid

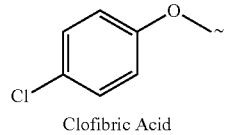

Clofibric Acid

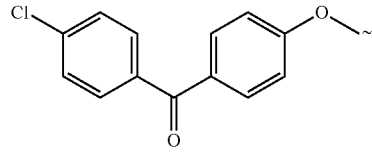

Fenofibric Acid

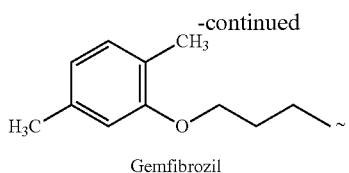

Gemfibrozil

As used herein, the term "fibric acid compounds" refers to the fabric acid analogs depicted here which are not bonded to an amino acid. When the fibric acid compounds are bonded to an amino acid, they will be referred to as fibric acid "amino acid derivatives" or like term.

Fibric acid analogs shown in the structure above have been shown to have a large number of therapeutic applications, which are quite diverse and somewhat surprising. Broadly, these compounds are useful in the treatment dyslipidemia and dyslipoproteinemia. Dyslipidemia and dyslipoproteinemia are herein defined to include the group selected from hypercholesterolemia, abnormal and elevated levels of cholesterol, abnormal and elevated levels of LDL cholesterol, abnormal and elevated levels of total cholesterol, abnormal and elevated levels of plasma cholesterol, abnormal and elevated levels of triglycerides, hypertrigylceridaemia, abnormal levels of lipoproteins, abnormal and elevated levels of low density lipoproteins (LDLs), abnormal and elevated levels of very low density lipoproteins, abnormal and elevated levels of very low intermediate density lipoproteins, abnormal levels of high density lipoproteins, hyperlipidemia, hyperchylomicronemia, abnormal levels of chylomicrons, related disorders, and combinations thereof such as those described in The ILIB Lipid Handbook for Clinical Practice, Blood Lipids and Coronary Heart Disease, Second Edition, A. M. Gotto et al, International Lipid Information Bureau, New York, N.Y., 2000, the contents of which is hereby incorporated by reference.

Mechanism of Action:

The mechanism of action of Fibric acid compounds seen in clinical practice have been explained in-vivo in transgenic mice and in vitro in human hepatocytes cultures by the activation of peroxisome proliferator activated receptor alpha (PPAR-alpha). Through this mechanism, Fibric acid compounds increase lipolysis and elimination of triglyceride-rich particles from plasma by activating lipoprotein lipase and reducing production of apoprotein C-III (an inhibitor of lipoprotein lipase activity).

The resulting fall in triglycerides produces an alteration in the size and composition of LDL from small, dense particles (which are thought to be atherogenic due their susceptibility to oxidation), to large buoyant particles. These larger particles have greater affinity for cholesterol receptors and are catabolized rapidly. Activation of PPAR-alpha also induces an increase in the synthesis of apoproteins A-I, A-II, and HDL cholesterol. The Fibric Acid compounds depicted hereinabove are also useful in the treatment of gout, as they reduce serum uric acid levels in hyperurecemic patients.

Hyperlipidemia types include type I, type IIa, type IIb, type III, type IV, and type V. These types can be characterized according to the levels relative to normal levels of lipids (cholesterol and triglycerides) and lipoproteins in patients. Different classifications are derived from Drug Facts and Comparisons, 52nd Edition (1998) page 1066 which is hereby incorporated by reference.

Many of the fibric acid compounds when administered orally do not have sufficient bioavilability, and furthermore absorption is variable and erratic and is dependent upon the intake of food. In fact absolute bioavialability of many of the fibric acid compounds is not possible since the ones currently marketed are insoluble in water, hence a parenteral formulation is difficult to prepare or not available. Furthermore, since these drugs usually are administered as esters, they have to be metabolized in the body to release active drug, which are the fibric acids. However, due to the ester formation of these drugs, they are quite insoluble in water, hence are difficult to formulate, and are not easily broken down in the body to release active drugs.

Many of the Fibric acid compounds are low to medium molecular weight solids with characteristic odor. Taken orally they have unpleasant taste and can severely irritate mouth and throat. Taken with food provides more blood concentration compared to fasting. Overall bioavailability has been reported anywhere between 40-60 and quite variable among patients. As shown hereinbelow, this fed fast difference in bioavailability is more pronounced when the Fibric acid compounds are compared with that of the amino acid derivatives of Fibric acids.

One of the significant problems associated with currently marketed fibric acid compounds is that they are administered as prodrugs to patients which are metabolized to cleave off the prodrug moiety, e.g., esters or alcohol and the cleaved products may themselves be highly toxic. For example, in the case of fenofibrate and gemfibrozil, isopropyl alcohol is released as the esterase enzyme cleave the pro-moiety from the fenofibric acid. It is well known that isopropanol is highly toxic when released into any of the mammalian tissues.

In order to improve the therapeutic effectiveness, uniform blood profile, develop pharmaceutically elegant formulation and improve the solubility of the drug in water, the present invention provides alternative derivatives of Fibric acid compounds which overcome many of the difficulties stated above.

Accordingly, in one aspect, the present invention is directed to alternate class of derivatives of Fibric acid compounds, namely amino acid derivatives. The amino acid derivative consists of the hydroxyl group of an amino acid esterified to the free carboxyl group present on the Fibric acid compounds. In another embodiment, the amine group of the amino acid is reacted with COOH of the fibric acids to form an amide linkage.

More specifically, in one aspect of the present invention is directed to, the compounds of the formulas

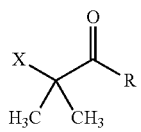

FIBRIC ACID ANALOGS where x is as defined hereinabove
or pharmaceutically acceptable salts thereof; wherein R is either NH-AA or O-AA and AA is an amino acid, without the amino group or hydroxy group, in which either an amine group or the hydroxyl group, respectively, is reacted with the carboxylic acid group of Fibric acid compounds.

The present invention is also directed to a pharmaceutical composition comprising a therapeutically effective amount of the various Fibric acid amino acid derivatives and a pharmaceutical carrier therefor.

In another embodiment, the present invention is directed to a method of treating a patient in need of Fibric acid therapy, which method comprises administering to said patient an effective amount of the Fibric acid amino acid derivatives.

In a further embodiment, the present invention is directed to a method of converting liquid Fibric acid compounds into a solid powder by reacting the carboxyl functionality of the Fibric acid compounds with either amine or hydroxyl functionality of an amino acid undo conditions sufficient to form a covalent bond between the amino acid and the fibric acid compound and isolating the product thereof.

In a still further embodiment, the present invention is directed to a method of substantially and in a therapeutically efficacious manner, administer the fibric acid amino acid derivatives which in this form facilities the absorption of the fibric acid moiety, thereby improving the consistent therapeutic effect which method comprises administering to a patient the amino acid derivative of fibric acid, prepared by a process which comprises reacting the COOH functionality of the Fibric acid compound with an amino acid, especially either $NH_2$ of the amino acid or OH functionality of the hydroxy containing amino acids to form an amide or ester covalent bond respectively and isolating the product thereof.

The present inventor has found that amino acid esterified to Fibric acid compounds, especially the naturally occurring amino acids, are pharmaceutically elegant free flowing powders, and are rapidly absorbed into the body. If cleaved in the body, they release non-toxic amino acids upon cleavage in the body. However, the amino acid derivatives of fibric acid have the same utility as the fibric acid compounds from which they are prepared and which are not bound to an amino acid. They require none of the emulsifiers, additives and other excipients.

Furthermore, the present inventor has found that the amino acid derivatives of Fibric acid derivatives are highly effective anti-hyperlipidemics and exhibit such effect intact. The amino acid derivatives are effective anti-hyperlipidemics and are useful in the treatment of a number of high cholesterol related illnesses and exhibit such potential with or without releasing the active parent drug.

While the amino acid derivatives of fibric acid of the present invention are not expected to possess any acidic activity due to blockage of the carboxylic acid group responsible for such, the present inventor has found that the amino derivatives of fibric acid are effective anti-hyperlipidemics with or without releasing Fibric acid derivatives. However, without wishing to be bound, it is believed that Fibric acid amino acid derivatives described herein may or may not release in vivo the active drug with all its pharmacological and cholesterol lowering properties.

The present invention clearly provides a number of advantages over Fibric acid compounds, for example, all of the side chains cleaved in vivo, if at all, from these derivatives are naturally occurring essential amino acids and hence are non-toxic. This results in high therapeutic index. Secondly the amino acid derivatives may be readily cleaved in the body to release Fibric acid or its active component. On the other hand, the fibric acid amino acid derivatives of the present invention exhibit the same therapeutic properties as the fibric acid compounds from which they are found thereon. Furthermore, due to their high water solubility, the amino acid derivatives can be easily administered by either forming an in-situ solution just before IV administration using lyophilized sterile powder or providing the drug in solution in prefilled syringe or bottles for infusion. The amino acid esters are more stable than Fibric acid compounds since the COOH group in Fibric acid is blocked to reaction with bases. Thus the Fibric acid amino acid derivatives described here are more effective then Fibric acid derivatives itself without the toxicity and other pharmaceutical problems associated with current marketed formulations.

The amino acid derivatives of this invention are anti-hyperlipidemic drugs useful in the treatment of hyperlipidemia in mammals where the symptoms are elevated triglycerides, low HDL (High density lipoproteins or "good" cholesterol, and elevated cholesterol. The Fibric Acid amino acid derivatives are also useful in reducing LDL (Low density lipoproteins, or "bad" cholesterol).

Typical examples of synthesis of L-threonine, L-hydroxyproline and L-serine esters of Fibric acid derivatives are shown in the synthetic processes outlined below. These procedures are applicable to all other compounds of the Fibric acid derivatives class as well.

Synthesis of Fibric Acid Derivatives

The procedure for the synthesis of the L-serine, L-threonine, and L-hydroxyproline esters of fenofibric acid is outlined in Synthetic Sequence section and is exemplary. The complete procedure and analytical data is given in the Experimental Section. In general, fenofibric acid (100 g batches) was prepared from 4-chloro-4'-hydroxybezophenone in accordance with the procedures in the literature. Fenofibric acid was coupled with the t-butyl esters of N-Boc protected amino acid (L-serine, L-threonine, and L-hydroxyproline) using EDC as the coupling agents and a catalytic amount of DMAP. The protecting groups were removed at low temperature (5° C., 3-6 days) with a mixture of hydrochloric acid in acetic acid (1M) with dichloromethane. The amino acid ester salts of fenofibric acid were purified by crystallization from ethyl acetate, and dried under high vacuum.

Synthetic Sequence:

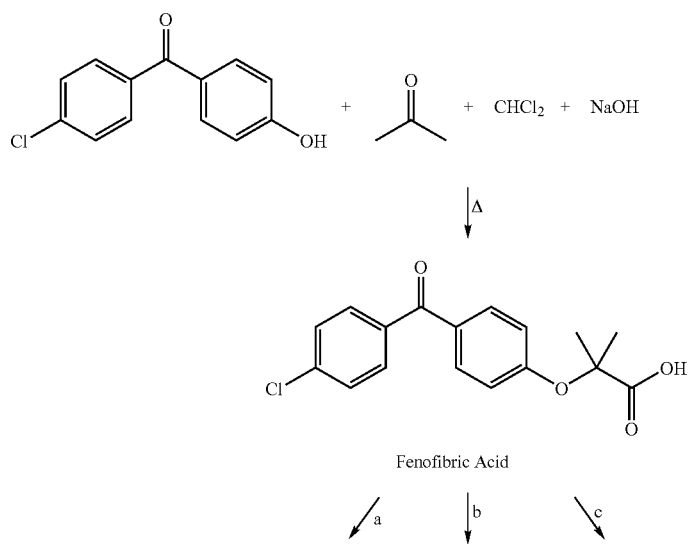

Fenofibric Acid

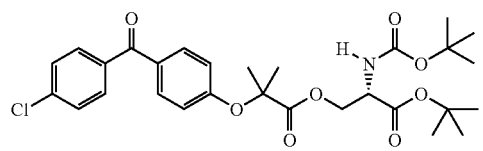
SPIB0020101

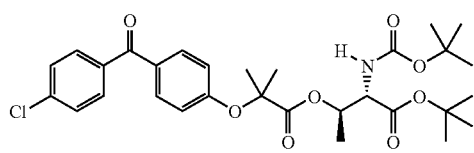
SPIB0020201

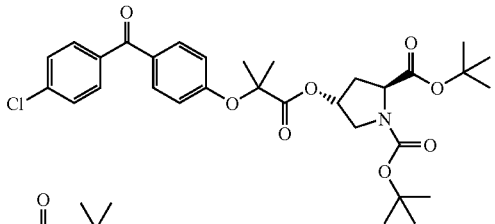
SPIB0020301

↓d  ↓d  ↓d

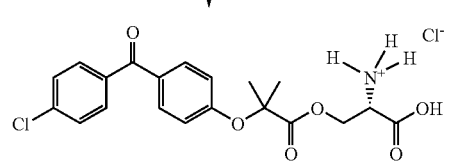
SPIB00201

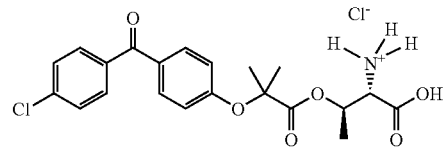
SPIB00202

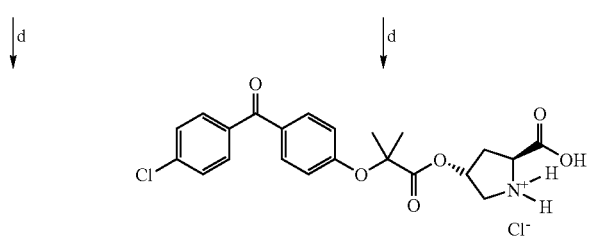
SPIB00203

Synthesis of the L-serine, L-threonine, and L-hydroxyproline Esters of Fenofibric Acid: a) Boc-Ser-OtBu, EDC, DMAP, $CH_2Cl_2$; b) Boc-Thr-OtBu, EDC, DMAP, $CH_2Cl_2$; c) Boc-Hyp-OtBu, EDC, DMAP, $CH_2Cl_2$; d) HCl, AcOH, $CH_2Cl_2$.

Experimental Section:

The synthesis of SPIB00201, SPIB00202 and SPIB00203 was conducted in one or two batches. Reagents mentioned in the experimental section were purchased at the highest obtainable purity from Lancaster, Sigma-Aldrich, Acros, or Bachem, except for solvents, which were purchased from either Fisher Scientific or Mallinkrodt.

1) Synthesis of Fenofibric Acid:

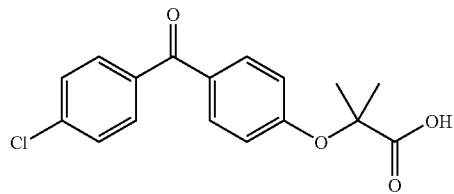

A mixture of 4-chloro-4'-hydroxybezophenone (116 g, 0.500 mole) and sodium hydroxide (120 g, 3.00 mole) in acetone (1 L) was heated to reflux for 2 hours. The heating was stopped and the heating source was removed. A mixture of chloroform (179 g, 1.50 mole) in acetone (300 mL) was added drop-wise. The reaction mixture was stirred overnight without heating. The mixture was heated to reflux for 8 hours and then allowed to cool to room temperature. The precipitate was removed by filtration and washed with acetone (100 mL). The filtrate was concentrated under reduced pressure to give a brown oil. Water (200 mL) was added to the brown oil and was acidified (to pH=1) with 1N hydrochloric acid. The precipitate, which formed was filtered and dried under high vacuum. The remaining yellow solid (268 g) was recrystallized from toluene in 4 batches (400 mL toluene each). After filtration and drying under high vacuum, the fenofibric acid (116 g, 73% yield) was obtained as a light yellow solid.

$^1$H NMR (300 MHz, DMSO-$d_6$): δ=13.22 (1H, s, br), 7.72 (4H, d, J=8.4 Hz), 7.61 (2H, d, J=7.8 Hz), 6.93 (2H, d, J=7.8 Hz), 1.60 (6H, s).

$^{13}$C NMR (75 MHz, DMSO-$d_6$): δ=192.96, 174.18, 159.35, 136.84, 136.12, 131.67, 131.02, 129.12, 128.43, 116.91, 78.87, 25.13.

2) SPIB00201: L-serine-fenofibric Acid Ester

To a mixture of fenofibric acid (11.6 g, 36.3 mmol), N-carbobenzyloxy-L-serine t-butyl ester (Boc-Ser-OtBu, 8.62 g, 33.0 mmol), EDC (7.59 g, 39.6 mmol), and DMAP (484 mg, 3.96 mmol) cooled in an ice-water bath was added anhydrous dichloromethane (150 mL) dropwise. After the addition was complete, the ice bath was removed and the reaction mixture was stirred under an argon atmosphere at room temperature for 20 hours. After 20 hours, the additional dichloromethane (200 mL) was added, and the solution was washed with water (2×200 mL) and brine (200 mL). After drying over sodium sulfate and filtration, the solution was concentrated under reduced pressure. The remaining yellow oil (21.2 g) was purified by column chromatography on silica gel (400 g, 0.035-0.070 mm, 6 nm pore diameter), eluting with heptane/ ethyl acetate (3:1). After concentration of the product-containing fractions under reduced pressure and drying under high vacuum until the weight was constant, the experiment produced the protected L-serine-fenofibric acid ester SPIB0020101 (16.2 g, 87% yield) was obtained as a light yellow oil.

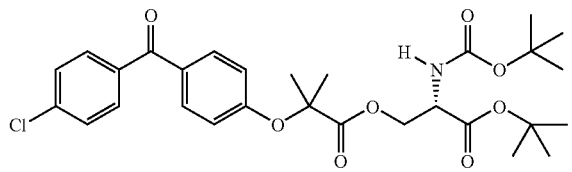

$^1$H NMR (300 MHz, CDCl$_3$): δ=7.75 (2H, d, J=9.0 Hz), 7.72 (2H, d, J=9.0 Hz), 7.45 (2H, d, J=8.7 Hz), 6.86 (2H, d, J=8.7 Hz), 5.04 (1H, d, J=6.9 Hz), 4.55-4.42 (3H, m), 1.66 (3H, s), 1.65 (3H, s), 1.43 (9H, s), 1.39 (9H, s).

$^{13}$C NMR (75 MHz, CDCl$_3$): δ=193.92, 172.99, 168.07, 159.24, 154.87, 138.24, 136.19, 131.94, 131.06, 130.40, 128.41, 117.26, 82.88, 80.13, 79.24, 65.44, 53.44, 28.27, 27.92, 25.70, 25.30.

To a stirred solution of the protected L-serine-fenofibric acid ester SPIB0020101 (16.2 g, 28.8 mmol) in anhydrous dichloromethane (100 mL) cooled to 5° C., under an argon atmosphere was added a solution of hydrogen chloride in acetic acid (400 mL, 1M, 400 mmol) drop-wise. The reaction mixture was stirred for 3 days at 5° C. After three days, the mixture was concentrated under reduced pressure and dried under high vacuum to remove acetic acid. To the remaining light yellow oil (24.7 g) was added ethyl acetate (100 mL). The solution was concentrated and dried a second time. To the remaining light yellow oil (17.0 g) was added ethyl acetate (65 mL). The mixture was heated to reflux for 5 minutes and cooled to room temperature. The precipitate was removed by filtration and dried under high vacuum overnight at room temperature, then at 43° C. for one hour. The experiment produced the L-serine-fenofibric acid ester, hydrochloride SPIB00201 (7.66 g, 60% yield) was obtained as a white solid.

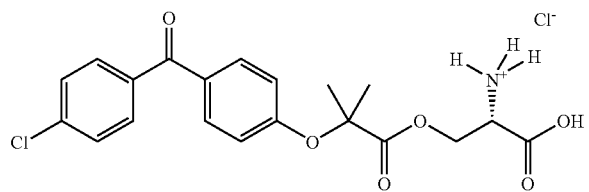

$^1$H NMR (300 MHz, DMSO-d$_6$): δ=14.12 (1H, s, br), 8.77 (3H, s, br), 7.72 (4H, m), 7.62 (2H, d, J=8.4 Hz), 6.92 (2H, d, J=9.0 Hz), 4.62 (1H, dd, J=12.0, 4.2 Hz), 4.50 (1H, dd, J=12.0, 2.4 Hz), 4.41 (1H, m), 1.64 (3H, s), 1.63 (3H, s).

$^{13}$C NMR (75 MHz, DMSO-d$_6$): δ=193.06, 171.70, 168.06, 158.72, 136.93, 136.06, 131.73, 131.09, 129.62, 128.49, 117.64, 79.02, 62.99, 51.11, 25.04, 24.94.

HPLC Analysis:

100% purity; r.t.=4.361 min.; 55% TFA (0.1%), 45% ACN; 1 mL/min; 32.3 C, Luna C18, serial #167917-13; 20 ul inj., NB275-49.

CHN Analysis:

calc.: C, 54.31; H, 4.79; N, 3.17. found: C, 54.37; H, 4.78; N, 3.12.

Melting point: 151° C. (dec.)

3) SPIB00202: L-threonine-fenofibric Acid Ester

To a mixture of fenofibric acid (25.5 g, 79.9 mmol), N-carbobenzyloxy-L-threonine t-butyl ester (Boc-Thr-OtBu, 20.0 g, 72.6 mmol, prepared by the literature method), EDC (16.7 g, 87.1 mmol), and DMAP (1.06 g, 8.71 mmol) cooled in an ice-water bath was added anhydrous dichloromethane (200 mL), dropwise. After the addition was complete, the ice bath was removed and the reaction mixture was stirred under an argon atmosphere at room temperature for 20 hours. After 20 hours, additional EDC (1.39 g, 7.26 mmol) was added, and the reaction mixture was allowed to stir over the weekend at room temperature under an argon atmosphere. After 4 days, additional dichloromethane (300 mL) was added, and the solution was washed with water (300 mL) and brine (300 mL). After drying over sodium sulfate and filtration, the solution was concentrated under reduced pressure. The remaining yellow oil (53.5 g) was purified by column chromatography on silica gel (500 g, 0.035-0.070 mm, 6 nm pore diameter), eluting with heptane/ethyl acetate (3:1). After concentration of the product-containing fractions under reduced pressure and drying under high vacuum until the weight was constant, the protected L-threonine-fenofibric acid ester SPIB0020201 (34.1 g, 82% yield) was obtained as a white foam.

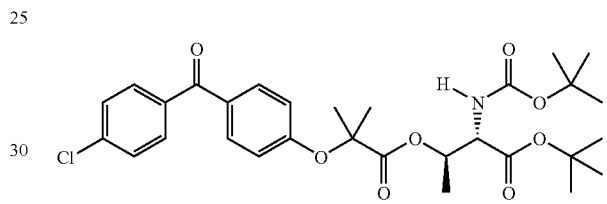

$^1$H NMR (300 MHz, CDCl$_3$): δ=7.74 (2H, d, J=8.4 Hz), 7.72 (2H, d, J=8.4 Hz), 7.45 (2H, d, J=8.4 Hz), 6.87 (2H, d, J=8.4 Hz), 5.47 (1H, m), 4.98 (1H, d, J=9.9 Hz), 4.31 (1H, d, J=9.9 Hz), 1.65 (3H, s), 1.64 (3H, s), 1.45 (9H, s), 1.42 (9H, s), 1.22 (3H, d, J=6.3 Hz).

$^{13}$C NMR (75 MHz, CDCl$_3$): δ=193.94, 172.14, 168.70, 159.26, 155.62, 138.28, 136.18, 131.90, 131.08, 130.37, 128.43, 117.40, 82.70, 80.17, 79.38, 72.02, 57.46, 28.30, 27.99, 26.44, 24.79, 16.90.

To a stirred solution of the protected L-threonine-fenofibric acid ester SPIB0020201 (34.1 g, 59.2 mmol) in anhydrous dichloromethane (100 mL) cooled to 5° C., under an argon atmosphere was added a solution of hydrogen chloride in acetic acid (600 mL, 1M, 600 mmol) drop-wise. The reaction mixture was kept for 6 days at 5° C. The mixture was concentrated under reduced pressure and dried under high vacuum to remove acetic acid. To the remaining white solid (45.8 g) was added ethyl acetate (500 mL). The mixture was heated to reflux for 10 minutes and cooled to room temperature. The precipitate was removed by filtration and dried under high vacuum overnight at room temperature, yielding the L-threonine-fenofibric acid ester, hydrochloride SPIB00202 (26.3 g, 97% yield) as a white solid.

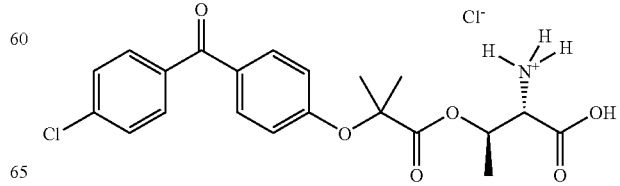

$^1$H NMR (300 MHz, DMSO-d$_6$): δ=14.10 (1H, s, br), 8.84 (3H, s, br), 7.73 (4H, m), 7.63 (2H, d, J=8.1 Hz), 6.89 (2H, d, J=8.7 Hz), 5.44 (1H, m), 4.31 (1H, s), 1.64 (3H, s), 1.62 (3H, s), 1.38 (3H, d, J=6.3 Hz).

$^{13}$C NMR (75 MHz, DMSO-d$_6$): δ=193.04, 171.00, 168.13, 158.76, 136.90, 136.08, 131.70, 131.06, 129.49, 128.48, 117.41, 78.99, 69.40, 55.21, 25.59, 24.22, 16.06.

HPLC Analysis:

98.59% purity; r.t.=4.687 min.; 55% TFA (0.1%), 45% ACN; 1 mL/min; 32.3 C, Luna C18, serial #167917-13; 20 ul inj., NB275-49, DAD1 B, Sig=210.4, Ref=550,100.

CHN Analysis:

calc.: C, 55.27; H, 5.08; N, 3.07. found: C, 54.98; H, 5.13; N, 3.03.

Melting point: 160.5° C. (dec.)

4) SPIB00203: L-hydroxyproline-fenofibric Acid Ester

To a mixture of fenofibric acid (24.9 g, 78.1 mmol), N-carbobenzyloxy-L-hydroxyproline t-butyl ester (Boc-Hyp-OtBu, 20.4 g, 71.0 mmole, prepared in accordance with the procedure in the literature), EDC (16.3 g, 85.2 mmol), and DMAP (1.04 g, 8.52 mmol) cooled in an ice-water bath was added anhydrous dichloromethane (200 mL) dropwise. After the addition was complete, the ice bath was removed and the reaction mixture was stirred under an argon atmosphere at room temperature for 20 hours. After 20 hours, additional EDC (1.63 g, 8.52 mmol) was added and the experiment was allowed to stir over the weekend at room temperature under an argon atmosphere. After 4 days, the resulting solution was washed with water (200 mL) and brine (200 mL). After drying over sodium sulfate followed by filtration, the solution was concentrated under reduced pressure. The remaining yellow oil (49.4 g) was purified by column chromatography on silica gel (500 g, 0.035-0.070 mm, 6 nm pore diameter), eluting with heptane/ethyl acetate (2:1). After concentration of the product containing fractions under reduced pressure and drying under high vacuum until the weight was constant, the protected L-hydroxyproline-fenofibric acid ester SPIB0020301 (26.4 g, 63% yield) was obtained as a colorless oil.

SPIB0020301

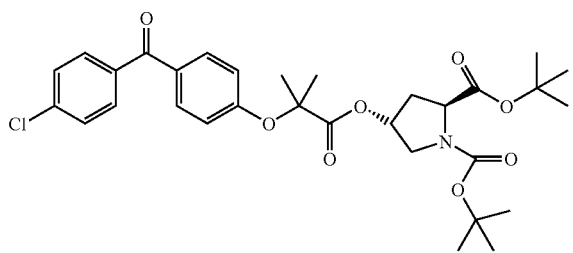

$^1$H NMR (300 MHz, CDCl$_3$): δ=7.76 (2H, d, J=8.1 Hz), 7.73 (2H, d, J=8.1 Hz), 7.46 (2H, d, J=8.1 Hz), 6.84 (2H, d, J=8.1 Hz), 5.32 (1H, m), 4.13 (0.38H, t, J=7.8 Hz), 4.00 (0.62H, t, J=7.8 Hz), 3.67 (1.62H, m), 3.46 (0.38H, d, J=12.6 Hz), 2.29 (1H, m), 2.15 (1H, m), 1.68 (3H, s), 1.66 (3H, s), 1.44-1.38 (18H, m).

$^{13}$C NMR (75 MHz, CDCl$_3$): δ=193.88, 172.98, 171.14, 159.25, 153.48, 138.23, 136.16, 131.99, 131.08, 130.36, 128.44, 117.03, 116.91, 81.48, 80.32, 80.20, 79.19, 74.03, 73.26, 58.23, 51.88, 51.58, 36.33, 35.31, 31.92, 28.29, 28.00, 25.89, 24.95.

To a stirred solution of the protected L-hydroxyproline-fenofibric acid ester SPIB0020301 (26.0 g, 44.2 mmol) in anhydrous dichloromethane (100 mL) cooled to 5° C., under an argon atmosphere was added a solution of hydrogen chloride in acetic acid (450 mL, 1M, 450 mmol) drop-wise. The reaction mixture stirred for 4 days at 5° C. After four days the mixture was concentrated under reduced pressure and dried under high vacuum to remove acetic acid. To the remaining yellow oil (31.5 g) was added ethyl acetate (200 mL). The mixture was sonicated and then concentrated under reduced pressure and dried under high vacuum. To the remaining white solid (23.2 g) was added ethyl acetate (300 mL). The ethyl acetate mixture was heated to reflux for 10 minutes, and cooled to room temperature. The precipitate was removed by filtration and dried under high vacuum overnight at room temperature. L-hydroxyproline-fenofibric acid ester, hydrochloride SPIB00203 (15.8 g, 76% yield) was obtained as a white solid.

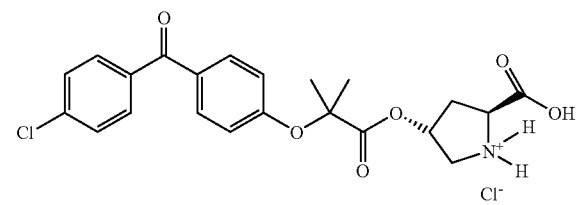

$^1$H NMR (300 MHz, DMSO-d$_6$): δ=14.07 (1H, s, br), 10.75 (1H, s, br), 9.40 (1H, s, br), 7.71 (4H, d, J=8.1 Hz), 7.60 (2H, d, J=8.1 Hz), 6.96 (2H, d, J=8.1 Hz), 5.42 (1H, m), 4.24 (1H, t, J=9.0 Hz), 3.61 (1H, dd, J=13.2, 4.2 Hz), 3.28 (1H, d, J=13.2 Hz), 2.35 (2H, m), 1.66 (3H, s), 1.64 (3H, s).

$^{13}$C NMR (75 MHz, DMSO-d$_6$): δ=193.00, 171.52, 169.14, 158.81, 136.87, 136.09, 131.81, 131.05, 129.48, 128.46, 117.28, 78.99, 73.79, 57.54, 50.23, 34.13, 25.69, 24.49.

HPLC Analysis:

100% purity; r.t.=8.369 min.; 60% DIUF water (0.1% TFA)/40% acetonitrile; 1 mL/min; 36.4 C; Luna C18, 5 u column (serial #191070-3), 4.6×250 mm; 20 ul injection; DAD1 A, Sig=210.4, Ref=550,100.

HPLC-MS (ESI): calculated: M$^+$=431. found M+H=432.3

Melting point: 187.5° C. (dec.)

Solubility of the above esters were determined in water at room temperature by dissolving an excess of each of the drug and permitting each to settle for a few hours. The resulting solutions were centrifuged at 1500 rpm for 3 min and the supernatant liquid was analyzed. By providing the memory of Sikihn, Esq. esters posses solubility in water in excess of 50 mg/mL.

EXPERIMENTAL

Rats were checked for time zero triglyceride level in blood. Then the rats were set on high sugar diet, such as 30% sucrose in water for 1 week. Then at the end of 1 week, rats were tested for triglycerides, and were put on normal diet. From day 7-14 the rats were administered either test or control drug. Triglycerides were again tested on the 14$^{th}$ day in rat blood.

In the Fenofibrate (control) vs L-Serine Ester of Fenofibric acid (test drug), 3 rats each for each of the drug and control at equivalent doses of 50, 100 and 200 mg/kg were tested.

The results are shown below in Tables 35 and 36.

TABLE 35

SUMMARY - DOSE RANGE FINDING STUDY - HYPOLIPIDEMIC
PROPERTY - FENOFIBRATE AND ITS FORMULATION
Test Substance: L-Serine Ester of Fenofibric Acid
Vehicle: 1% Tween 80 in milli Q - water

| Test Item | Dose. Mg/kg) | Animal No. | Triglycerides (mg/dl) Day zero | Day 7 | Day 14 |
|---|---|---|---|---|---|
| Vehicle | 0 | 1 | 81 | 168 | 121 |
|  |  | 2 | 88 | 171 | 222 |
|  |  | 3 | 114 | 133 | 162 |
| Reference control Fenofibrate | 50 | 4 | 95 | 157 | 101 |
|  |  | 5 | 92 | 228 | 76 |
|  |  | 6 | 80 | 150 | 73 |
|  | 100 | 7 | 110 | 204 | 62 |
|  |  | 8 | 115 | 195 | 69 |
|  |  | 9 | 96 | 167 | 93 |
|  | 200 | 10 | 144 | 90 | 48 |
|  |  | 11 | 56 | 106 | 51 |
|  |  | 12 | 58 | 125 | 38 |
| L-Serine Ester of Fenofibric Acid | 50 | 13 | 88 | 148 | 86 |
|  |  | 14 | 94 | 145 | 86 |
|  |  | 15 | 100 | 127 | 73 |
|  | 100 | 16 | 109 | — | 46 |
|  |  | 17 | 129 | 100 | 69 |
|  |  | 18 | 71 | 183 | 47 |
|  | 200 | 19 | 74 | 240 | 83 |
|  |  | 20 | 81 | 158 | 61 |
|  |  | 21 | 42 | 77 | 46 |

TABLE 36

Anti-lipidemic Effects of Fenofibric Acid and its Derivatives

|  | Dose | Absolute Change from day 0 | Absolute Change from day 7 | % Change From day 0 | % Change from day 7 |
|---|---|---|---|---|---|
| Vehicle | mg/kg | 50.4 | −5.6 | 83.17% | −4.80% |
| Fen-S Ester | 25 | −54 | −90 | −61.64% | −72.82% |
|  | 50 | −31.4 | −84.2 | −44.10% | −67.90% |
|  | 100 | −20.8 | −72 | −33.23% | −63.27% |
| Fen-T Ester | 25 | −18.2 | −36.4 | −23.21% | −37.68% |
|  | 50 | −23.8 | −77.6 | −35.00% | −63.71% |
|  | 100 | −63.8 | −88.4 | −68.45% | −75.04% |
| Fen-HP Ester | 25 | −16 | −47.8 | −32.92% | −59.45% |
|  | 50 | −35.8 | −70.8 | −49.31% | −65.80% |
|  | 100 | −3.4 | −112 | −7.52% | −72.82% |
| Fenofibrate | 25 | −10.8 | −51 | −15.21% | −45.86% |
|  | 50 | −13.4 | −87.6 | −22.95% | −66.06% |
|  | 100 | −40.8 | −71.6 | −61.26% | −73.51% |

While all of the esters were active and showed efficacy, there were important distinguishing factors between various amino acid derivatives and Fenofibrate. For example, dose dependent decrease in triglycerides were noted with the L-Threonine ester, and also maximum decrease from baseline level and treatment level were also noted for this compound. Thus Fenofibric Acid-L-Threonine ester had overall superior anti-hyperlipidemic properties.

From the above results, it can be concluded that both the highly water soluble serine ester, L-threonine ester and hydroxyproline ester effectively performed compared to fenofibrate.

There are a number of screening tests to determine the utility of the amino acid derivatives created according to the disclosed methods. These include both in vitro and in vivo screening methods.

The in vitro methods include acid/base hydrolysis of the amino acid derivatives, e.g., hydrolysis in pig pancreas hydrolysis in rat intestinal fluid, hydrolysis in human gastric fluid, hydrolysis in human intestinal fluid, and hydrolysis in human blood plasma. These assays are described in Simmons, D M, Chandran, V R and Portmann, G A, Danazol Amino Acid Derivatives: In Vitro and In Situ Biopharmaaceutical Evaluation, Drug Development and Industrial Pharmacy, Vol 21, Issue 6, Page 687, 1995, the contents of all of which are incorporated by reference.

The amino acid derivatives of Fibric Acid of the present invention are effective in treating diseases or conditions in which Fibric acid derivatives normally are used. The amino acid derivatives disclosed herein are transformed within the body to potentially release the active compound, although the active agent in vivo may be the intact amino acid derivative of fibric acid. In addition, the amino acid derivatives of fibric acid also enhance the therapeutic benefits of the Fibric acid compounds by reducing or eliminating biopharmaceutical and pharmacokinetic barriers associated with each of them. However it should be noted that these amino acid derivatives themselves will have sufficient activity without releasing any active drug in the mammals.

Thus, the amino acid derivatives of the present invention enhance the therapeutic benefits by removing biopharmaceutical and pharmakenetic barriers of existing drugs.

Furthermore, the amino acid derivatives are easily synthesized in high yields using reagents which are readily and commercially available.

In the formula hereinabove, it is to be understood that the AA has the following definition in the following context unless indicated to the contrary

1)

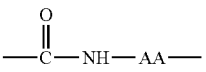

AA in this definition refers to the amino acid residue without an amino group either on the main chain or the side chain.

2)

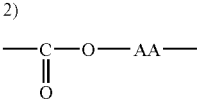

AA in this definition is an amino acid residue less the hydroxy group on the side chain.

3)

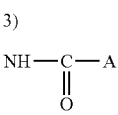

AA refers to an amino acid group without the carboxy group, either on the main chain or side group.

4) OAA—This is a ester bond between the hydroxy group of the drug and the carboxy group of the amino acid either on the main chain or side chain. Thus, as written OAA is

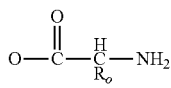

wherein $R_O$ is the side chain amino acid as defined hereinabove.

Alternatively, it may refer to an ester bond between the carboxy group of the drug and the hydroxy group on the side chain of those amino acids which have a hydroxy group thereon such as threonine, serine, hydroxyproline, tyrosine and the like. The hydroxy group forms part of the ester linkage which is depicted hereinabove with O. Thus, as written, the AA refers to an amino acid with a hydroxy group on the side chain, but as depicted as OAA, the AA is without the hydroxy group since the oxygen atom is depicted in the formula.

As used herein, the term "amino acid derivative" or equivalent term thereto refers to amino acid moiety covalently bonded to the drug having a functional group thereon consisting of hydroxy, amino, carboxy and acylating derivatives of carboxy.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. The product from a reaction between a drug having a functionality selected from the group consisting of hydroxy, amino, carboxy or acylating derivative of said carboxy group and an amino acid or a compound selected from Can, Djk, and L-Dcy under conditions sufficient to form a covalent bond from the reaction of said functional group and said amino acid or said compound, or the pharmaceutically acceptable salt thereof, wherein the drug is selected from the group consisting of 5-HETE, Abacavir, Acarbose, Acebutolol, Acetaminophen, Adefovir, Albuterol, Alfaprostol acid, Amlodipine, Amoxicillin, Amphotericin B, Amprenavir, Arachidonic Acid, Aspirin, Atenolol, Atorvastatin, Atropine, Atovaquone, Baclofen, Benazeprilat, Beraprost, Betaxolol, Bexarotene, Bicalutamide, Biperiden, Bisoprolol, Bitolterol, Biotin, Brinzolamide, Bupivacaine, Buprenorphine, Bupropion, Butorphanol, Candesartan, Capacitabine, Captopril, Carbidopa, Carboprost, Carnitine, Carteolol, Carvedilol, Cefdinir, Cefditoren, Ceftazimide, Cefpodoxime, Cefuroxime, Cerivastatin, Chloramphenicol, Cisapride, Clofibrate, Clopidogrel Acid, Cloprostenol, Clorazepic Acid, Cycloserine, Cyclosporine, Cytarabine, Danazol, Dextroamphetamine, Diclofenac, Didanosine, Divalproex, Docetaxel, Dorzolamide, Dyphylline, Dysopyramide, Efavirenz, Enalaprilat, Ephedrine, Eplerenone, Eprosartan, Esmolol, Estramustine, Ethambutol, Ethchlorvynol, Ethosuximide, Ethotoin, Etidocaine, Etoposide, Ezetimibe, Famciclovir, Fenofibrate, Fenoprofen, Fenprostalene acid, Fexofenadine, Fibric acid derivatives, Finasteride, Flavoxate, Fluprostenol, Fluoxetine, Flurbiprofen, Fluticasone, Fluvastatin, Fosinoprilat, Frovatriptan, Fulvestrant, Gemprost Acid, Glimepiride, Goserelin, Hydroxychloroquine, Hydroxyzine, Hyoscyamine, Ibuprofen, Ibutilide, Indapamide, Indinavir, Ipratropium, Irinotecan, Isosorbide, Isradipine, Ketoprofen, Ketorolac, Labetalol, Lamivudine, Lansoprazole, Latanoprost Acid, Leukotrienes ($LTA_4$, $LTB_4$, $LTC_4$, $LTD_4$ and $LTE_4$) Leuprolide, Levobunolol, Levodopa, Levorphanol, Limaprost, γ-Linolenic Acid, Liothyronine, Lisinopril, Lopinavir, Lorazepam, Lovastatin, Medroxyprogesterone, Mefloquine, Megestrol, Mephobarbital, Mepivacaine, Metaproterenol, Metformin, Methamphetamine, Methohexital, Methotrexate, Methylphenidate, Methylprednisolone, Metolazone, Metoprolol, Mexiletine, Miglitol, Moexiprilat, Mometasone, Montelukast, Mycophenolate Acid, Nadolol, Nalbuphine, Naproxen, Naratriptan, Nateglinide, Nelfinavir, Niacin, Nicotinic Acid, Nicotinamide, Nicardipine, Nimidipine, Nisoldipine, Norgestimate, Octreotide, Ofloxacin, Olmesartan, Omeprazole, Ozagrel, Paclitaxel, Pantothenic Acid, Paroxetine, Pemoline, Penbutolol, Penciclovir, Pentazocine, Pentobarbital, Perindoprilat, Phenylephrine, Phenylpropanolamine, Pindolol, Pioglitazone, Pirbuterol, Pramipexole, Pravastatin, Propafenone, Propofol, Propoxyphene, Propranolol, Prostacyclin, Prostaglandins ($E_1$, $E_2$ and $F_{2\alpha}$), Prostanoic Acid, Pseudoephedrine, Quinacrine, Quinaprilat, Quinethazone, Quinidine, Quinine, Ramiprilat, Reboxetine, Repaglinide, Repaglinide, Ribavirin, Ritonavir, Ropivacaine, Rosaprostol, Rosuvastatin, Salmeterol, Salsalate, Sertraline, Simavastatin, Sotalol, Sulfa Drugs, Sulfasalazine, Sumitriptan, Tacrolimus, Tazorotene, Telmesartan, Tenofovir, Terbutaline, Tiagabine, Timolol, Tirofiban, Tocainide, Tramadol, Trandolaprilat, Tranylcypromine, Treprostinil, Triamcinolone, Trimoprostil, Troglitazone, Unoprostone, Valproic Acid, Valsartan, Venlafaxine, Vidarabine, Warfarin, Zalcitabine, Zidovudine, Zileuton and Zolmitriptan or a pharmaceutically acceptable salt of any of said drug and wherein the amino acid is L-Hyp, L-Ser, or L-Tyr.

2. The product from a reaction between a drug having a functionality selected from the group consisting of hydroxy, amino, carboxy or acylating derivative of said carboxy group and an amino acid or a compound selected from Can, Djk and L-Dcy under conditions sufficient to form a covalent bond from the reaction of said functional group and said amino acid or said compound, or the pharmaceutically acceptable salt thereof, wherein the drug is selected from the group consisting of 5-HETE, Abacavir, Acarbose, Acebutolol, Acetaminophen, Adefovir, Albuterol, Alfaprostol acid, Amlodipine, Amoxicillin, Amphotericin B, Amprenavir, Arachidonic Acid, Aspirin, Atenolol, Atorvastatin, Atropine, Atovaquone, Baclofen, Benazeprilat, Beraprost, Betaxolol, Bexarotene, Bicalutamide, Biotin, Biperiden, Bisoprolol, Bitolterol, Brinzolamide, Bupivacaine, Buprenorphine, Bupropion, Butorphanol, Candesartan, Capacitabine, Captopril, Carbidopa, Carboprost, Carnitine, Carteolol, Carvedilol, Cefdinir, Cefditoren, Ceftazimide, Cefpodoxime, Cefuroxime, Cerivastatin, Chloramphenicol, Ciprofloxacin, Cisapride, Clofibrate, Clopidogrel Acid, Cloprostenol, Clorazepic Acid, Cycloserine, Cyclosporine, Cytarabine, Dextroamphetamine, Diclofenac, Didanosine, Divalproex, Docetaxel, Dorzolamide, Dyphylline, Dysopyramide, Efavirenz, Enalaprilat, Ephedrine, Eplerenone, Eprosartan, Esmolol, Estramustine, Ethambutol, Ethchlorvynol, Ethosuximide, Ethotoin, Etidocaine, Etoposide, Ezetimibe, Famciclovir, Fenofibrate, Fenoprofen, Fenprostalene acid, Fexofenadine, Fibric acid derivatives, Finasteride, Flavoxate, Fluprostenol, Fluoxetine, Flurbiprofen, Fluticasone, Fluvastatin, Fosinoprilat, Frovatriptan, Fulvestrant, Gemprost Acid, Glimepiride, Goserelin, Hydroxychloroquine, Hydroxyzine, Hyoscyamine, Ibuprofen, Ibutilide, Indapamide, Indinavir, Ipratropium, Irinotecan, Isosorbide, Isradipine, Ketoprofen, Ketorolac, Labetalol, Lamivudine, Lansoprazole, Latanoprost Acid, Leukotrienes ($LTA_4$, $LTB_4$, $LTC_4$, $LTD_4$ and $LTE_4$), Leuprolide, Levobunolol, Levodopa, Levorphanol, Limaprost, γ-Linolenic Acid, Liothyronine, Lisinopril, Lopinavir, Lorazepam, Lovastatin, Medroxyprogesterone, Mefloquine, Megestrol, Mephobarbital, Mepivacaine, Metaproterenol, Metformin, Methamphetamine, Methohexital, Methotrexate, Methylphenidate, Methylprednisolone, Metolazone, Metoprolol, Mexiletine, Miglitol, Moexiprilat, Mometasone, Montelukast, Mycophenolate Acid, Nadolol, Nalbuphine, Naproxen, Naratriptan, Nateglinide, Nelfinavir, Niacin, Nicotinic Acid, Nicotinamide, Nicardipine, Nimidipine, Nisoldipine, Norgestimate, Octreotide, Ofloxacin, Olmesartan, Omeprazole, Ozagrel, Paclitaxel, Pantothenic Acid, Paroxetine, Pemoline, Penbutolol, Penciclovir, Pentazocine, Pentobarbital, Perindoprilat, Phenylephrine, Phenylpropanolamine, Pindolol, Pioglitazone, Pirbuterol, Pramipexole, Pravastatin, Propafenone, Propofol, Propoxyphene, Propranolol, Prostacyclin, Prostaglandins ($E_1$, $E_2$ and $F_{2\alpha}$), Prostanoic Acid, Pseudoephedrine, Quinacrine, Quinaprilat, Quinethazone, Quinidine, Quinine, Ramiprilat, Reboxetine, Repaglinide, Ribavirin, Ritonavir, Ropivacaine, Rosaprostol Rosuvastatin, Salmeterol, Salsalate, Sertraline, Simavastatin, Sotalol, Sulfa Drugs, Sulfasalazine, Sumitriptan, Tacrolimus, Tazorotene, Telmesartan, Tenofovir, Terbutaline, Tiagabine, Timolol, Tirofiban, Tocainide, Tramadol, Trandolaprilat, Tranylcypromine, Treprostinil, Triamcinolone, Trimoprostil, Troglitazone, Unoprostone, Valproic Acid, Valsartan, Venlafaxine, Vidarabine, Warfarin, Zalcitabine, Zidovudine, Zileuton and Zolmitriptan or a pharmaceutically acceptable salt of any of said drug and wherein the amino acid is L-Hyp, L-Ser, or L-Tyr with the proviso that if there is an amide linkage between the drug and amino acid, the amide linkage is between the amino group of the drug and the carboxy group on the side chain of the amino acid or the amide linkage is between the carboxy group of the drug and the amino group of the side chain of the amino acid or between the carboxy group of the drug and the amino group on the main chain of the amino acid.

3. The product from a reaction between a drug having a functionality selected from the group consisting of hydroxy, amino, carboxy or acylating derivative of said carboxy group and a L-serine under conditions sufficient to form a covalent bond from the reaction of said functional group and L-serine, or the pharmaceutically acceptable salts of said product, wherein the drug is selected from the group consisting of 5-HETE, Abacavir, Acarbose, Acebutolol, Acetaminophen, Adefovir, Albuterol, Alfaprostol acid, Amlodipine, Amoxicillin, Amphotericin B, Amprenavir, Arachidonic Acid, Aspirin, Atenolol, Atorvastatin, Atropine, Atovaquone, Baclofen, Benazeprilat, Beraprost, Betaxolol, Bexarotene, Bicalutamide, Biotin, Biperiden, Bisoprolol, Bitolterol, Brinzolamide, Bupivacaine, Buprenorphine, Bupropion, Butorphanol, Candesartan, Capacitabine, Captopril, Carbidopa, Carboprost, Carnitine, Carteolol, Carvedilol, Cefdinir, Cefditoren, Ceftazimide, Cefpodoxime, Cefuroxime, Cerivastatin, Chloramphenicol, Cisapride, Clofibrate, Clopidogrel Acid, Cloprostenol, Clorazepic Acid, Cycloserine, Cyclosporine, Cytarabine, Danazol, Dextroamphetamine, Diclofenac, Didanosine, Digoxin, Divalproex, Docetaxel, Dorzolamide, Dyphylline, Dysopyramide, Efavirenz, Enalaprilat, Ephedrine, Eplerenone, Eprosartan, Esmolol, Estramustine, Ethambutol, Ethchlorvynol, Ethosuximide, Ethotoin, Etidocaine, Etoposide, Ezetimibe, Famciclovir, Fenofibrate, Fenoprofen, Fenprostalene acid, Fexofenadine, Fibric acid derivatives, Finasteride, Flavoxate, Fluprostenol, Fluoxetine, Flurbiprofen, Fluticasone, Fluvastatin, Folic Acid, Fosinoprilat, Frovatriptan, Fulvestrant, Gemprost Acid, Glimepiride, Goserelin, Hydroxychloroquine, Hydroxyzine, Hyoscyamine, Ibuprofen, Ibutilide, Indapamide, Indinavir, Ipratropium, Irinotecan, Isosorbide, Isradipine, Ketoprofen, Ketorolac, Labetalol, Lamivudine, Lansoprazole, Latanoprost Acid, Leukotrienes ($LTA_4$, $LTB_4$, $LTC_4$, $LTD_4$ and $LTE_4$), Leuprolide, Levobunolol, Levodopa, Levorphanol, Limaprost, γ-Linolenic Acid, Liothyronine, Lisinopril, Lopinavir, Lorazepam, Lovastatin, Medroxyprogesterone, Mefloquine, Megestrol, Mephobarbital, Mepivacaine, Metaproterenol, Metformin, Methamphetamine, Methohexital, Methotrexate, Methylphenidate, Methylprednisolone, Metolazone, Metoprolol, Mexiletine, Miglitol, Moexiprilat, Mometasone, Montelukast, Mycophenolate Acid, Nadolol, Nalbuphine, Naproxen, Naratriptan, Nateglinide, Nelfinavir, Niacin, Nicotinic Acid, Nicotinamide, Nicardipine, Nimidipine, Nisoldipine, Norgestimate, Octreotide, Ofloxacin, Olmesartan, Omeprazole, Ozagrel, Paclitaxel, Pantothenic Acid, Paroxetine, Pemoline, Penbutolol, Penciclovir, Pentazocine, Pentobarbital, Perindoprilat, Phenylephrine, Phenylpropanolamine, Pindolol, Pioglitazone, Pirbuterol, Pramipexole, Pravastatin, Propafenone, Propofol, Propoxyphene, Propranolol, Prostacyclin, Prostaglandins ($E_1$, $E_2$ and $F_{2\alpha}$), Prostanoic Acid, Pseudoephedrine, Quinacrine, Quinaprilat, Quinethazone, Quinidine, Quinine, Ramiprilat, Reboxetine, Repaglinide, Repaglinide, Ribavirin, Ritonavir, Ropivacaine, Rosaprostol, Rosiglitazone, Rosuvastatin, Salmeterol, Salsalate, Sertraline, Simavastatin, Sirolimus, Sotalol, Sulfa Drugs, Sulfasalazine, Sumitriptan, Tacrolimus, Tazorotene, Telmesartan, Tenofovir, Terbutaline, Thyroxine, Tiagabine, Timolol, Tirofiban, Tocainide, Tramadol, Trandolaprilat, Tranylcypromine, Treprostinil, Triamcinolone, Trimoprostil, Troglitazone, Unoprostone, Valproic Acid, Valsartan, Venlafaxine, Vidarabine, Warfarin, Zalcitabine, Zidovudine, Zileuton and Zolmitriptan or a pharmaceutically acceptable salt of any of said drugs.

* * * * *